(12) United States Patent
Kahraman et al.

(10) Patent No.: US 9,078,871 B2
(45) Date of Patent: Jul. 14, 2015

(54) ESTROGEN RECEPTOR MODULATORS AND USES THEREOF

(71) Applicant: SERAGON PHARMACEUTICALS, INC., San Diego, CA (US)

(72) Inventors: Mehmet Kahraman, La Jolla, CA (US); Steven P. Govek, San Diego, CA (US); Johnny Y. Nagasawa, San Diego, CA (US); Nicholas D. Smith, San Diego, CA (US)

(73) Assignee: SERAGON PHARMACEUTICALS, INC., San Diego, CA (US)

( * ) Notice: Subject to any disclaimer, the term of this patent is extended or adjusted under 35 U.S.C. 154(b) by 0 days.

(21) Appl. No.: 14/137,394

(22) Filed: Dec. 20, 2013

(65) Prior Publication Data
US 2014/0107095 A1    Apr. 17, 2014

Related U.S. Application Data

(62) Division of application No. 13/702,394, filed as application No. PCT/US2011/039669 on Jun. 8, 2011, now Pat. No. 8,703,810.

(60) Provisional application No. 61/353,531, filed on Jun. 10, 2010.

(51) Int. Cl.
| | |
|---|---|
| *A61K 31/4025* | (2006.01) |
| *C07D 405/10* | (2006.01) |
| *A61K 31/352* | (2006.01) |
| *A61K 45/06* | (2006.01) |
| *C07D 311/60* | (2006.01) |
| *C07D 405/12* | (2006.01) |
| *C07D 407/14* | (2006.01) |
| *C07D 487/08* | (2006.01) |
| *A61K 31/403* | (2006.01) |
| *A61K 31/4178* | (2006.01) |
| *A61K 31/439* | (2006.01) |
| *A61K 31/453* | (2006.01) |
| *A61K 31/5377* | (2006.01) |
| *A61K 31/55* | (2006.01) |
| *C07D 471/08* | (2006.01) |

(52) U.S. Cl.
CPC ............ *A61K 31/352* (2013.01); *A61K 31/403* (2013.01); *A61K 31/4025* (2013.01); *A61K 31/4178* (2013.01); *A61K 31/439* (2013.01); *A61K 31/453* (2013.01); *A61K 31/5377* (2013.01); *A61K 31/55* (2013.01); *A61K 45/06* (2013.01); *C07D 311/60* (2013.01); *C07D 405/12* (2013.01); *C07D 407/14* (2013.01); *C07D 471/08* (2013.01); *C07D 487/08* (2013.01)

(58) Field of Classification Search
CPC .......................... A61K 31/4025; C07D 405/10
USPC ........................ 548/517, 525; 514/408, 422
See application file for complete search history.

(56) References Cited

U.S. PATENT DOCUMENTS

| | | |
|---|---|---|
| 5,254,568 A | 10/1993 | Kapil et al. |
| 5,389,646 A | 2/1995 | Labroo |
| 5,395,842 A | 3/1995 | Labrie et al. |
| 5,407,947 A | 4/1995 | Bryant et al. |
| 5,416,098 A | 5/1995 | Labroo et al. |
| 5,446,061 A | 8/1995 | Bryant et al. |
| 5,446,071 A | 8/1995 | Grese |
| 5,637,598 A | 6/1997 | Grese |
| 5,686,465 A | 11/1997 | Labrie et al. |
| 5,840,735 A | 11/1998 | Labrie et al. |
| 5,980,938 A | 11/1999 | Berg et al. |
| 6,060,503 A | 5/2000 | Labrie et al. |
| 6,262,270 B1 | 7/2001 | Draper et al. |
| 6,326,392 B1 | 12/2001 | Gast et al. |
| 6,465,445 B1 | 10/2002 | Labrie |
| 6,638,727 B1 | 10/2003 | Hung et al. |
| 6,670,346 B1 | 12/2003 | Labrie |
| 6,774,122 B2 | 8/2004 | Evans et al. |
| 6,844,336 B2 | 1/2005 | Kuenzer et al. |
| 6,965,850 B2 | 11/2005 | Baxter et al. |
| 7,005,428 B1 | 2/2006 | Labrie |
| 7,456,160 B2 | 11/2008 | Evans et al. |
| 8,299,112 B2 | 10/2012 | Smith et al. |
| 8,703,810 B2 | 4/2014 | Kahraman et al. |
| 2002/0099013 A1 | 7/2002 | Piccariello et al. |
| 2002/0198179 A1 | 12/2002 | Labrie |
| 2003/0040510 A1 | 2/2003 | Labrie |

(Continued)

FOREIGN PATENT DOCUMENTS

| | | |
|---|---|---|
| EP | 0470310 | 2/1992 |
| EP | 0635264 | 1/1995 |

(Continued)

OTHER PUBLICATIONS

Ariazi, E., et al. "Estrogen Receptors as Therapeutic Targets in Breast Cancer." Current Topics in Medicinal Chemistry, (2006): 6, p. 195-216.
Bentrem, D., et al. "Molecular Mechanism of Action at Estrogen Receptor a of a New Clinically Relevant Antiestrogen (GW7604) Related to Tamoxifen." Endocronology (2001): 142(2), p. 838-846.
Bhattacharyya, R., et al. "Fulvestrant (ICI 182,780) down-regulates androgen receptor expression and diminishes androgenic responses in LNCaP human prostate cancer cells." Mol Cancer Ther (2006): 5(6), p. 1539-1549.
Blizzard, T., et al. "Estrogen receptor ligands. Part 7: Dihydrobenzoxathiin SERAMs with bicyclic amine side chains", Bioorganic & Medicinal Chemistry Letters 14 (2004) 3861-3864.
Blizzard, T., et al. "Estrogen receptor ligands. Part 8: Dihydrobenzoxathiin SERAMs with heteroatom-substituted side chains." Bioorganic & Medicinal Chemistry Letters (2004): 14 p. 3865-3868.

(Continued)

*Primary Examiner* — Golam M M Shameem
(74) *Attorney, Agent, or Firm* — Alex Andrus; Genetech, Inc.

(57) ABSTRACT

Described herein are compounds that are estrogen receptor modulators. Also described are pharmaceutical compositions and medicaments that include the compounds described herein, as well as methods of using such estrogen receptor modulators, alone and in combination with other compounds, for treating diseases or conditions that are mediated or dependent upon estrogen receptors.

22 Claims, No Drawings

(56) References Cited

U.S. PATENT DOCUMENTS

| | | |
|---|---|---|
| 2003/0059433 A1 | 3/2003 | Sirbasku |
| 2003/0065008 A1 | 4/2003 | Labrie |
| 2003/0072760 A1 | 4/2003 | Sirbasku |
| 2003/0162807 A1 | 8/2003 | Day et al. |
| 2004/0034017 A1 | 2/2004 | Kuenzer et al. |
| 2004/0082557 A1 | 4/2004 | Wajszczuk et al. |
| 2004/0248989 A1 | 12/2004 | Santti et al. |
| 2004/0259915 A1 | 12/2004 | Kanojia et al. |
| 2005/0277681 A1 | 12/2005 | Hanney et al. |
| 2007/0078114 A1 | 4/2007 | Hobden et al. |
| 2007/0270394 A1 | 11/2007 | El-Alfy et al. |
| 2008/0227814 A1 | 9/2008 | Dodge et al. |
| 2008/0311594 A1 | 12/2008 | Hoffman et al. |
| 2013/0116232 A1 | 5/2013 | Kahraman et al. |

FOREIGN PATENT DOCUMENTS

| | | |
|---|---|---|
| EP | 0652006 | 5/1995 |
| EP | 0693285 | 1/1996 |
| EP | 0712628 | 5/1996 |
| EP | 1118323 | 7/2001 |
| EP | 1120114 | 8/2001 |
| EP | 1125582 | 8/2001 |
| EP | 1149579 | 10/2001 |
| EP | 1167364 | 1/2002 |
| EP | 1177787 | 2/2002 |
| EP | 1192945 | 4/2002 |
| EP | 1199069 | 4/2002 |
| EP | 1226823 | 7/2002 |
| GB | 2374412 | 10/2002 |
| WO | WO 93-10741 | 6/1993 |
| WO | WO 96-26201 | 8/1996 |
| WO | WO 98-18776 | 5/1998 |
| WO | WO 99-02512 | 1/1999 |
| WO | WO 99-02513 | 1/1999 |
| WO | WO 99-07668 | 2/1999 |
| WO | WO 99-08682 | 2/1999 |
| WO | WO 99-24027 | 5/1999 |
| WO | WO 99-50658 | 10/1999 |
| WO | WO 99-63974 | 12/1999 |
| WO | WO 00-09493 | 2/2000 |
| WO | WO 00-37083 | 6/2000 |
| WO | WO 00-42841 | 7/2000 |
| WO | WO 00-61123 | 10/2000 |
| WO | WO 01-01969 | 1/2001 |
| WO | WO 01-26651 | 4/2001 |
| WO | WO 01-54699 | 8/2001 |
| WO | WO 01-63292 | 8/2001 |
| WO | WO 01-77057 | 10/2001 |
| WO | WO 02-13802 | 2/2002 |
| WO | WO 02-20020 | 3/2002 |
| WO | WO 02-30429 | 4/2002 |
| WO | WO 02-32373 | 4/2002 |
| WO | WO 02-32377 | 4/2002 |
| WO | WO 02-34237 | 5/2002 |
| WO | WO 02-072106 | 9/2002 |
| WO | WO 03-016270 | 2/2003 |
| WO | WO 03-026568 | 4/2003 |
| WO | WO 03-029268 | 4/2003 |
| WO | WO 03-032961 | 4/2003 |
| WO | WO 03-034987 | 5/2003 |
| WO | WO 03-063859 | 8/2003 |
| WO | WO 03-070253 | 8/2003 |
| WO | WO 03-076660 | 9/2003 |
| WO | WO 03-077919 | 9/2003 |
| WO | WO 03-086388 | 10/2003 |
| WO | WO 03-087073 | 10/2003 |
| WO | WO 03-091239 | 11/2003 |
| WO | WO 03-092588 | 11/2003 |
| WO | WO 04-000225 | 12/2003 |
| WO | WO 04-000801 | 12/2003 |
| WO | WO 2004-041277 | 5/2004 |
| WO | WO 2004-091488 | 10/2004 |
| WO | WO 2004-098618 | 11/2004 |
| WO | WO 2004-100874 | 11/2004 |
| WO | WO 2005-004807 | 1/2005 |
| WO | WO 2005-005380 | 1/2005 |
| WO | WO 2005-005606 | 1/2005 |
| WO | WO 2005-009949 | 2/2005 |
| WO | WO 2005-025572 | 3/2005 |
| WO | WO 2005-025579 | 3/2005 |
| WO | WO 2005-033056 | 4/2005 |
| WO | WO 2005-044988 | 5/2005 |
| WO | WO 2005-073190 | 8/2005 |
| WO | WO 2005-123130 | 12/2005 |
| WO | WO 2005-123193 | 12/2005 |
| WO | WO 2006-024689 | 3/2006 |
| WO | WO 2006-042409 | 4/2006 |
| WO | WO 2006-084937 | 8/2006 |
| WO | WO 2007-098090 | 8/2007 |
| WO | WO 2008-128792 | 10/2008 |
| WO | WO 2008-148582 | 12/2008 |
| WO | WO 2009-143309 | 11/2009 |
| WO | WO 2010-107474 A1 | 9/2010 |
| WO | WO 2010-145010 | 12/2010 |
| WO | WO 2011-159769 | 12/2011 |
| WO | WO 2011-161101 | 12/2011 |
| WO | WO 2012-084711 | 6/2012 |
| WO | WO 2013-090829 | 6/2013 |
| WO | WO 2013-090836 | 6/2013 |
| WO | WO 2013-090921 A1 | 6/2013 |

OTHER PUBLICATIONS

Blizzard, T., et al. "Estrogen receptor ligands. Part 9: Dihydrobenzoxathiin SERAMs with alkyl substituted pyrrolidine side chains and linkers." Bioorganic & Medicinal Chemistry Letters (2005): 15, p. 107-113.

Blizzard, T.A., "Selective estrogen modulator medicinal chemistry at Merck. A review", Curr Top Med Chem 2008; 8(9):792-812.

Blizzard. T., et al. "Estrogen receptor ligands. Part 13: Dihydrobenzoxathiin SERAMs with an optimized antagonist side chain." Bioorganic & Medicinal Chemistry Letters (2005): 15, p. 3912-3916.

Blizzard. T., et al. "Estrogen receptor ligands. Part 14: Application of novel antagonist side chains to existing platforms." Bioorganic & Medicinal Chemistry Letters (2005): 15, p. 5124-5128.

Connor, C., et al. "Circumventing Tamoxifen Resistance in Breast Cancers Using Antiestrogens That Induce Unique Conformational Changes in the Estrogen Receptor." Cancer Research(Apr. 1, 2001): 61, p. 2917-2922.

Dardes, R., et al. "Effects of a New Clinically Relevant Antiestrogen (GW5638) Related to Tamoxifen on Breast and Endometrial Cancer Growth in vivo." Clinical Cancer Research 1995 (Jun. 2002): 8, p. 1995-2001.

Dhar, J., et al. "Structure activity relationship of some 2,3-diaryl-2H-1-benzopyrans to their anti-implantation, estrogenic and antiestrogenic activities in rat." Contraception (1994): 49, p. 609-616.

Fan, M., et al. "Characterization of molecular and structural determinants of selective estrogen receptor downregulators." Breast Cancer Res Treat (2007): 103, p. 37-44.

Gauthier et al (2005): STN International HCAPLUS database, (Columbus, Ohio), Accession No. 2005:387736.

Gauthier et al—1 (2005): STN International HCAPLUS database, (Columbus, Ohio), Accession No. 2005:387736.

Gauthier, S., et al. "Synthesis and structure-activity relationships of analogs of EM-652 (acolbifene), a pure selective estrogen receptor modulator. Study of nitrogen substitution." Journal of Enzyme Inhibition and Medicinal Chemistry, Apr. 2005: 20(2), p. 165-177.

Hajela, K., et al. "Synthesis and post-coital contraceptive activity of a new series of substituted 2,3-diaryl-2H-1-benzopyrans." Eur J Med Chem (1997): 32, p. 135-142.

Hajela, K., et al. "Synthesis and post-coital contraceptive activity of ether and ester analogues 2,3-diaryl-2H-1-benzopyrans." Bioorganic & Medicinal Chemistry Letters (1995): 3(11), p. 1417-1421.

Jain, N., et al. "Identification and Structure-Activity Relationships of Chromene-Derived Selective Estrogen Receptor Modulators for Treatment of Postmenopausal Symptoms." J. Med. Chem. (2009): 52, p. 7544-7569.

(56) References Cited

OTHER PUBLICATIONS

Jain, N., et al. "Novel Chromene-Derived Selective Estrogen Receptor Modulators Useful for Alleviating Hot Flushes and Vaginal Dryness." Journal of Medicinal Chemistry (2006): 49(11), p. 3056-3059.

Katzenellenbogen, John A., "The 2010 Philip S. Portoghese Medicinal Chemistry Lectureship: Addressing the "Core Issue" in the Design of Estrogen Receptor Ligands", Journal of Medicinal Chemistry, Aug. 11, 2011;54(15):5271-82; doi1021/jm200801h.

Kim S., et al., Estrogen Receptor Ligands, 12, Synthesis of the Major Metabolites of an ERα-Selective, Dihydrobenzoxathiin Antagonist for Osteoporosis, Organic Letters (2005): vol. 7, No. 3 p. 411-414.

Kocanova, S., et al. "Ligands specify estrogen receptor alpha nuclear localization and degradation." . BMC Cell Biology (2010): 11(98), p. 1-13.

Labrie, F. et al., The combination of a novel selective estrogen receptor modulator with an estrogen protects the mammary gland and uterus in a rodent model: the future of postmenopausal women's health?, Endocrinology Nov. 2003;144(11):4700-6.

Li, X., et al. "Synthesis of Tetracyclic Heterocompounds as Selective Estrogen Receptor Modulators. Part 3. Development of an Acid-Catalyzed Racemization Process for (S)-2,8-(Dimethoxy)-5-{4-[2-(1-piperidinyl)ethoxy]-phenyl}-11,12-dihydro-5H-6,13-dioxabenzo[3,4]cyclohepta[1,2-a]naphthalene." Organic Process Research & Development (2009):13, p. 102-105.

Li, X., et al. "Synthesis of Tetracyclic Heterocompounds as Selective Estrogen Receptor Modulators. Part 2. Process Improvement for Scale-Up of 2,5,8-Substituted 11,12-Dihydro-5H-6,13-dioxabenzo[3,4]cyclohepta-[1,2-a]naphthalene Derivatives." Organic Process Research & Development (2007): 11, p. 731-738.

Liu et al., "Estrogen receptor ligands. Part 11: Synthesis and activity of ischromans and isothiochromans", Bioorganic & Medicinal Chemistry Letters 15 (2005) 715-718.

Macgregor, J., et al. "Basic Guide to the Mechanisms of the Antiestrogen Action." The American Society for Pharmacology and Experimental Therapeutics (1998): 50(2), p. 151-196.

McDonnell, D., "The Molecular Pharmacology of Estrogen Receptor Modulators: Implications for the Treatment of Breast Cancer." Clinical Cancer Research (Jan. 15, 2005): vol. 11, p. 871s-877s.

Paterni, I., et al., "Estrogen receptor ligands: a patent review update", Expert Opin. Ther. Patents (2013) 23(10):1-25.

PCT/US2011/039699 International Preliminary Report on Patentability dated Dec. 10, 2012.

PCT/US2011/039699 International Search Report and Written Opinion dated Feb. 29, 2012.

Reid, G., et al. "Cyclic, Proteasome-Mediated Turnover of Unliganded and Liganded ER on Responsive Promoters is an Integral Feature of Estrogen Signaling." Molecular Cell (Mar. 2003): vol. 11, p. 695-707.

Robertson, J., "ICI 182,780 (Fulvestrant™)—the first oestrogen receptor down-regulator—current clinical data." British Journal of Cancer (2001) 85(Suppl 2), p. 11-14.

Saeed, A., et al. "Structure-Activity Relationship of Antiestrogrens. Studies on 2,3-Diaryl-1-Benzopyrans."J Med Chem (1990): 33, p. 3210-3216.

Sanceau et al., "Synthesis and deuterium labelling of the pure selective estrogen receptor modulator (SERM) acolbifene glucuronides", J Label Compd Radiopharm 2007; 50: p. 197-206.

Science IP, The CAS Search Service, Dec. 21, 2009, p. 1-189.

Sharma, A., et al. "Structure Activity Relationship of Antiestrogens. Effect of the Side Chain and its position on the Activity of 2,3-Diaryl-2H-1-Benzopyrans." J Med Chem (1990): 33, p. 3216-3222.

Sharma, A., et al. "Structure Activity Relationship of Antiestrogens. Phenolic Analogues of 2,3-Diaryl-2H-1-Benzopyrans." J Med Chem (1990): 33, p. 3222-3229.

Song, Z., et al. "An efficient asymmetric synthesis of an estrogen receptor modulator by sulfoxide-directed borane reduction." PNAS (Apr. 20, 2004): 101(16), p. 5776-5781.

Tamrazi, A., et al. "Molecular Sensors of Estrogen Receptor Conformations and Dynamics." Molecular Endocrinology (2003): 17(12), p. 2593-2602.

Tan, Q., et al. "Estrogen receptor ligands. Part 10: Chromanes: old scaffolds for new SERAMs." Bioorganic & Medicinal Chemistry Letters (2005): 15, p. 1675-1681.

Tan, Q., et al. "Estrogen receptor ligands. Part 6: Synthesis and binding affinity of dihydrobenzoditiins", Bioorganic & Medicinal Chemistry Letters 14 (2004) p. 3753-3755.

Tripathi, S., et al. "Evaluation of Piperidinoethoxy Moiety as an Antiestrogenic Substituent in Non-steroidal Anti-Estrogens: : Fertility Regulation." Bioorganic & Medicinal Chemistry Letters (1997): 7(16), p. 2131-2136.

Venneman, G., "Non-Steroidal Subtype Selective Estrogens." Current Medicinal Chemistry, (2005): 12, p. 1077-1136.

Wardell, S., et al. "Research Resource: Transcriptional Profiling in a Cellular Model of Breast Cancer Reveals Functional and Mechanistic Differences Between Clinically Relevant SERM and Between SERM/Estrogen Complexes." Mol Endocrinol (Jul. 2012): 26(7), p. 1-14.

Weatherman, R., et al. "Differential SERM activation of the estrogen receptors (ERα and ERβ) at AP-1 sites." Chemistry & Biology (2001): 8, p. 427-436.

Welboren, W., et al. "Genomic actions of estrogen receptor α: what are the targets and how are they regulated?" Endocrine-Related Cancer (2009): 16, p. 1073-1089.

Wijayaratne, A., et al. "Comparative Analyses of Mechanistic Differences Among Antiestrogens." Endocrinology (1999) 140(12): 5828-5840.

Willson, T., et al. "3-[-4-(1,2-Diphenylbut-1-enyl)phenyl]acrylic acid: a non-steroidal estrogen with functional selectivity for bone over uterus in rats." J. Med. Chem. 37:1550-1552 (1994).

Willson, T., et al. "Dissection of the Molecular Mechanism of Action of GW5638, a Novel Estrogen Receptor Ligand, Provides Insights into the Role of Estrogen Receptor in Bone." Endocrinology (1997): 138, p. 3901-3911.

Wittman, B., et al. "Definition of Functionally Important Mechanistic Differences among Selective Estrogen Receptor Down-regulators." Cancer Res (2007):67(19), p. 9549-60.

Wu, Y., et al. "Structural Basis for an Unexpected Mode of SERM-Mediated ER Antagonism." Molecular Cell (May 13, 2005): vol. 18, p. 413-424.

Xu et al. "Discovery of estrogen receptor modulators: a review of virtual screening and SAR efforts", Expert Opin. Drug Discov. (2010) 5(1):21-31.

ESTROGEN RECEPTOR MODULATORS AND USES THEREOF

RELATED APPLICATIONS

This application is a division of U.S. application Ser. No. 13/702,394, filed Jan. 24, 2013, which was filed pursuant to 35 U.S.C. §371 as a United States National Phase Application of International Application No. PCT/US2011/039669, entitled "ESTROGEN RECEPTOR MODULATORS AND USES THEREOF", filed Jun. 8, 2011, which claims benefit of U.S. Provisional Application No. 61/353,531, entitled "ESTROGEN RECEPTOR MODULATORS AND USES THEREOF" filed on Jun. 10, 2010, all of which is are herein incorporated by reference in its their entirety.

FIELD OF THE INVENTION

Described herein are compounds, including pharmaceutically acceptable salts, solvates, metabolites, prodrugs thereof, methods of making such compounds, pharmaceutical compositions comprising such compounds, and methods of using such compounds to treat, prevent or diagnose diseases or conditions that are estrogen sensitive, estrogen receptor dependent or estrogen receptor mediated.

BACKGROUND OF THE INVENTION

The estrogen receptor ("ER") is a ligand-activated transcriptional regulatory protein that mediates induction of a variety of biological effects through its interaction with endogenous estrogens. Endogenous estrgoegns include 17β-estradiol and estrones. ER has been found to have two isoforms, ER-α and ER-β.

Estrogens and estrogen receptors are implicated in a number of diseases or conditions, such as breast cancer, lung cancer, ovarian cancer, colon cancer, prostate cancer, endometrial cancer, uterine cancer, as well as others diseases or conditions.

SUMMARY OF THE INVENTION

In one aspect, presented herein are compounds of Formula (I), (II), (III), (IV), (V), (VI), (VII), (VIII), (IX), (X), (XI), (XII), and (XIII) that diminish the effects of estrogens with estrogen receptors and/or lower the concentrations of estrogen receptors, and therefore, are useful as agents for the treatment or prevention of diseases or conditions in which the actions of estrogens and/or estrogen receptors are involved in the etiology or pathology of the disease or condition or contribute to at least one symptom of the disease or condition and wherein such actions of estrogens and/or estrogen receptors are undesirable. In some embodiments, compounds disclosed herein are estrogen receptor degrader compounds.

In one aspect, a compound of Formula (I), (II), (III), (IV), (V), (VI), (VII), (VIII), (IX), (X), (XI), (XII), or (XIII) is useful for the treatment of ER-related diseases or conditions including, but not limited to, ER-α dysfunction associated with cancer (bone cancer, breast cancer, lung cancer, colorectal cancer, endometrial cancer, prostate cancer, ovarian and uterine cancer), central nervous system (CNS) defects (alcoholism, migraine), cardiovascular system defects (aortic aneurysm, susceptibility to myocardial infarction, aortic valve sclerosis, cardiovascular disease, coronary artery disease, hypertension), hematological system defects (deep vein thrombosis), immune and inflammation diseases (Graves' Disease, arthritis, multiple sclerosis, cirrhosis), susceptibility to infection (hepatitis B, chronic liver disease), metabolic defects (bone density, cholestasis, hypospadias, obesity, osteoarthritis, osteopenia, osteoporosis), neurological defects (Alzheimer's disease, Parkinson's disease, migraine, vertigo), psychiatric defects (anorexia nervosa, attention deficity hyperactivity disorder (ADHD), dementia, major depressive disorder, psychosis) and reproductive defects (age of menarche, endometriosis, infertility).

In one aspect, described herein are compounds of Formula (I), (II), (III), (IV), (V), (VI), (VII), (VIII), (IX), (X), (XI), (XII), and (XIII), pharmaceutically acceptable salts, solvates, metabolites and prodrugs thereof. Compounds described herein are estrogen receptor modulators. In some embodiments, the compound of Formula (I), (II), (III), (IV), (V), (VI), (VII), (VIII), (IX), (X), (XI), (XII), or (XIII) is an estrogen receptor antagonist. In some embodiments, the compound of Formula (I), (II), (III), (IV), (V), (VI), (VII), (VIII), (IX), (X), (XI), (XII), or (XIII) is an estrogen receptor degrader. In some embodiments, the compound of Formula (I), (II), (III), (IV), (V), (VI), (VII), (VIII), (IX), (X), (XI), (XII), or (XIII) is an estrogen receptor antagonist as well as an estrogen receptor degrader. In some embodiments, the compound of Formula (I), (II), (III), (IV), (V), (VI), (VII), (VIII), (IX), (X), (XI), (XII), or (XIII) displays minimal or no estrogen receptor agonist activity. In some embodiments, in the context of treating cancers, the compound of Formula (I), (II), (III), (IV), (V), (VI), (VII), (VIII), (IX), (X), (XI), (XII), or (XIII) may offer improved therapeutic activity characterized by complete or longer-lasting tumor regression, a lower incidence or rate of development of resistance to treatment, and/or a reduction in tumor invasiveness.

In one aspect, provided herein is a compound of Formula (I), or a pharmaceutically acceptable salt, solvate, metabolite or prodrug thereof:

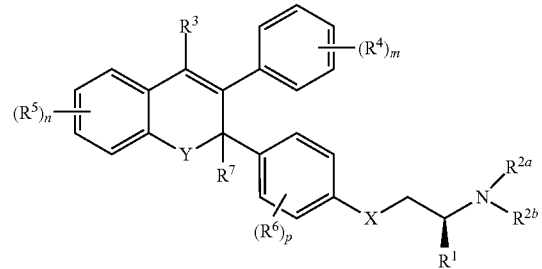

Formula (I)

wherein, $R^1$ is F, $C_1$-$C_6$alkyl, or $C_1$-$C_6$fluoroalkyl;

$R^{2a}$ is H or $R^{10}$;

$R^{2b}$ is —C(=O)$R^{10}$, —C(=O)O$R^{10}$, —C(=O)NH$R^{10}$, —S(=O)$_2R^{10}$, or $R^{10}$;

or $R^{2a}$ and $R^{2b}$ are taken together with the N atom to which they are attached to form a substituted or unsubstituted monocyclic heterocycloalkyl, a substituted or unsubstituted bicyclic heterocycloalkyl, a substituted or unsubstituted monocyclic heteroaryl, or a substituted or unsubstituted bicyclic heteroaryl;

$R^3$ is H, halogen, $C_1$-$C_4$alkyl, $C_3$-$C_6$cycloalkyl, or $C_1$-$C_4$fluoroalkyl;

each $R^4$ is independently selected from H, halogen, —CN, —OH, —O$R^9$, —S$R^9$, —S(=O)$R^{10}$, —S(=O)$_2R^{10}$, —C(=O)$R^{10}$, —C(=O)OH, —C(=O)O$R^{10}$, —C(=O)NHR¹⁰, —C(=O)N(R¹⁰)₂, substituted or unsubstituted C₁-C₆alkyl, substituted or unsubstituted C₁-C₆fluoroalkyl, substituted or unsubstituted C₁-C₆fluoroalkoxy, substituted or unsubstituted C₁-C₆alkoxy, and substituted or unsubstituted C₁-C₆heteroalkyl;

each R⁵ is independently selected from H, halogen, —CN, —OH, —OR⁹, —SR⁹, —S(=O)R¹⁰, —S(=O)₂R¹⁰, substituted or unsubstituted C₁-C₆alkyl, substituted or unsubstituted C₁-C₆fluoroalkyl, substituted or unsubstituted C₁-C₆fluoroalkoxy, substituted or unsubstituted C₁-C₆alkoxy, and substituted or unsubstituted C₁-C₆heteroalkyl;

each R⁶ is independently selected from H, halogen, —CN, —OH, —OR⁹, —SR⁹, —S(=O)R¹⁰, —S(=O)₂R¹⁰, substituted or unsubstituted C₁-C₆alkyl, substituted or unsubstituted C₁-C₆fluoroalkyl, substituted or unsubstituted C₁-C₆fluoroalkoxy, substituted or unsubstituted C₁-C₆alkoxy, and substituted or unsubstituted C₁-C₆heteroalkyl;

R⁷ is H or C₁-C₄alkyl;

each R⁹ is independently selected from H, —C(=O)R¹⁰, —C(=O)OR¹⁰, —C(=O)NHR¹⁰, substituted or unsubstituted C₁-C₆alkyl, substituted or unsubstituted C₁-C₆heteroalkyl, substituted or unsubstituted C₁-C₆fluoroalkyl, substituted or unsubstituted C₃-C₁₀cycloalkyl, substituted or unsubstituted C₂-C₁₀heterocycloalkyl, substituted or unsubstituted aryl, substituted or unsubstituted heteroaryl, —C₁-C₂alkylene-(substituted or unsubstituted C₃-C₁₀cycloalkyl), —C₁-C₂alkylene-(substituted or unsubstituted C₂-C₁₀heterocycloalkyl), —C₁-C₂alkylene-(substituted or unsubstituted aryl), and —C₁-C₂alkylene-(substituted or unsubstituted heteroaryl); or each R¹⁰ is independently selected from substituted or unsubstituted C₁-C₆alkyl, substituted or unsubstituted C₁-C₆heteroalkyl, substituted or unsubstituted C₁-C₆fluoroalkyl, substituted or unsubstituted C₃-C₁₀cycloalkyl, substituted or unsubstituted C₂-C₁₀heterocycloalkyl, substituted or unsubstituted aryl, substituted or unsubstituted heteroaryl, —C₁-C₂alkylene-(substituted or unsubstituted C₃-C₁₀cycloalkyl), —C₁-C₂alkylene-(substituted or unsubstituted C₂-C₁₀heterocycloalkyl), —C₁-C₂alkylene-(substituted or unsubstituted aryl), and —C₁-C₂alkylene-(substituted or unsubstituted heteroaryl);

Y is —O—, —S—, or —NR¹¹—; R¹¹ is H, —C(=O)R¹⁰, substituted or unsubstituted C₁-C₆alkyl, substituted or unsubstituted C₁-C₆fluoroalkyl, or substituted or unsubstituted C₁-C₆heteroalkyl;

X is —O—, —S—, —CH₂—, —NH— or —N(C₁-C₆alkyl)-;

m is 0, 1, 2, 3, 4 or 5;

n is 0, 1, 2, 3 or 4;

p is 0, 1, 2, 3 or 4.

For any and all of the embodiments, substituents are selected from among from a subset of the listed alternatives. For example, in some embodiments, R¹ is F, C₁-C₄alkyl, or C₁-C₄fluoroalkyl. In other embodiments, R¹ is C₁-C₄alkyl or C₁-C₄fluoroalkyl. In some embodiments, R¹ is —CH₃, —CH₂CH₃, —CF₃, or —CH₂CF₃. In some embodiments, R¹ is —CH₃ or —CF₃. In some embodiments, R¹ is —CH₃.

In some embodiments, R³ is H, halogen, C₁-C₄alkyl, C₃-C₆cycloalkyl, or C₁-C₄fluoroalkyl. In some embodiments, R³ is H, halogen, C₁-C₄alkyl, or C₁-C₄fluoroalkyl. In some embodiments, R³ is C₁-C₄alkyl, or C₁-C₄fluoroalkyl. In some embodiments, R³ is C₁-C₄alkyl. In some embodiments, R³ is C₁-C₄fluoroalkyl. In some embodiments, R³ is C₃-C₆cycloalkyl. In some embodiments, R³ is H. In some embodiments, R³ is halogen. In some embodiments, R¹ is H, halogen, —CH₃, —CH₂CH₃, cyclopropyl, cyclobutyl, cyclopentyl, cyclohexyl, —CF₃, or —CH₂CF₃. In some embodiments, R¹ is H, halogen, —CH₃, cyclopropyl, cyclobutyl, or —CF₃. In some embodiments, R¹ is —CH₃, cyclopropyl, cyclobutyl, or —CF₃. In some embodiments, R¹ is —CH₃. In some embodiments, R¹ is —CF₃. In some embodiments, R¹ is cyclopropyl, cyclobutyl, cyclopentyl, or cyclohexyl. In some embodiments, R¹ is cyclopropyl, or cyclobutyl.

In some embodiments, R¹ is C₁-C₄alkyl; R²ᵃ and R²ᵇ are taken together with the N atom to which they are attached to form a substituted or unsubstituted monocyclic heterocycloalkyl, a substituted or unsubstituted bicyclic heterocycloalkyl, a substituted or unsubstituted monocyclic heteroaryl, or a substituted or unsubstituted bicyclic heteroaryl; R³ is C₁-C₄alkyl or C₁-C₄fluoroalkyl; each R⁴ is independently selected from H, halogen, —CN, —OH, —OR⁹, —SR⁹, —S(=O)R¹⁰, —S(=O)₂R¹⁰, C₁-C₆alkyl, C₁-C₆fluoroalkyl, C₁-C₆fluoroalkoxy, C₁-C₆alkoxy, and C₁-C₆heteroalkyl; each R⁵ is independently selected from H, halogen, —CN, —OH, —OR⁹, C₁-C₆alkyl, C₁-C₆fluoroalkyl, C₁-C₆fluoroalkoxy, C₁-C₆alkoxy, and C₁-C₆heteroalkyl; each R⁶ is independently selected from H, halogen, —CN, —OH, C₁-C₆alkyl, C₁-C₆fluoroalkyl, C₁-C₆fluoroalkoxy, and C₁-C₆alkoxy; R⁷ is H or —CH₃; Y is —O— or —S—.

In some embodiments, the compound of Formula (I) has the structure of Formula (II):

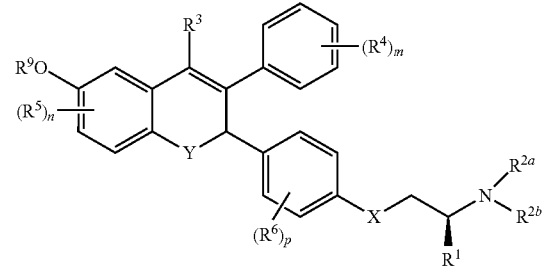

Formula (II)

wherein,

X is —O—, —S—, —CH₂—, —NH— or —N(CH₃)—;

each R⁵ is independently selected from H, halogen, —CN, —OH, C₁-C₆alkyl, C₁-C₆fluoroalkyl, C₁-C₆fluoroalkoxy, C₁-C₆alkoxy, and C₁-C₆heteroalkyl;

each R⁶ is independently selected from H, F, Cl, —OH, —CH₃, —CF₃, —OCF₃ and —OCH₃;

n is 0, 1, 2, or 3;

p is 0, 1, or 2.

In some embodiments, the compound of Formula (I) has the structure of Formula (III):

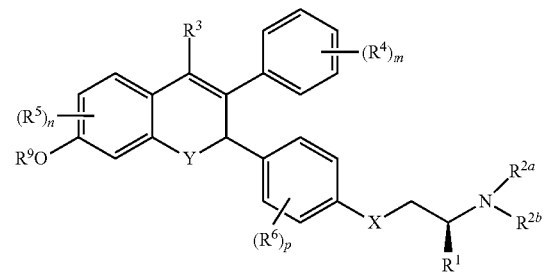

Formula (III)

wherein,

X is —O—, —S—, —CH$_2$—, —NH— or —N(CH$_3$)—;

each R$^5$ is independently selected from H, halogen, —CN, —OH, C$_1$-C$_6$alkyl, C$_1$-C$_6$fluoroalkyl, C$_1$-C$_6$fluoroalkoxy, C$_1$-C$_6$alkoxy, and C$_1$-C$_6$heteroalkyl;

each R$^6$ is independently selected from H, F, Cl, —OH, —CH$_3$, —CF$_3$, —OCF$_3$ and —OCH$_3$;

n is 0, 1, 2, or 3;

p is 0, 1, or 2.

In some embodiments, R$^{2a}$ and R$^{2b}$ are taken together with the N atom to which they are attached to form a substituted or unsubstituted monocyclic C$_2$-C$_6$heterocycloalkyl, a substituted or unsubstituted bicyclic C$_5$-C$_{10}$heterocycloalkyl, a substituted or unsubstituted monocyclic C$_1$-C$_5$heteroaryl, or a substituted or unsubstituted bicyclic C$_5$-C$_{10}$heteroaryl.

In some embodiments, R$^{2a}$ and R$^{2b}$ are taken together with the N atom to which they are attached to form a substituted or unsubstituted monocyclic heterocycloalkyl or a substituted or unsubstituted monocyclic heteroaryl.

In some embodiments, R$^{2a}$ and R$^{2b}$ are taken together with the N atom to which they are attached to form a substituted or unsubstituted monocyclic heterocycloalkyl.

In some embodiments, R$^{2a}$ and R$^{2b}$ are taken together with the N atom to which they are attached to form a substituted or unsubstituted azetidinyl, substituted or unsubstituted pyrrolidinyl, substituted or unsubstituted piperidinyl, substituted or unsubstituted azepanyl, substituted or unsubstituted morpholinyl, substituted or unsubstituted piperazinyl, substituted or unsubstituted 3-azabicyclo[3.1.0]hexan-3-yl, substituted or unsubstituted 3-azabicyclo[3.2.0]heptan-3-yl, substituted or unsubstituted 7-azabicyclo[2.2.1]heptan-7-yl, substituted or unsubstituted octahydrocyclopenta[c]pyrrolyl, substituted or unsubstituted octahydro-1H-isoindolyl, substituted or unsubstituted isoindolinyl, substituted or unsubstituted pyrazolyl, substituted or unsubstituted triazolyl, substituted or unsubstituted pyrrolyl, a substituted or unsubstituted imidazolyl, or substituted or unsubstituted isoindolyl.

In some embodiments, R$^{2a}$ and R$^{2b}$ are taken together with the N atom to which they are attached to form a substituted or unsubstituted azetidinyl, substituted or unsubstituted pyrrolidinyl, substituted or unsubstituted piperidinyl, substituted or unsubstituted azepanyl, substituted or unsubstituted morpholinyl, substituted or unsubstituted piperazinyl, substituted or unsubstituted 3-azabicyclo[3.1.0]hexan-3-yl, substituted or unsubstituted 3-azabicyclo[3.2.0]heptan-3-yl, substituted or unsubstituted octahydrocyclopenta[c]pyrrolyl, substituted or unsubstituted octahydro-1H-isoindolyl, substituted or unsubstituted isoindolinyl, substituted or unsubstituted pyrazolyl, substituted or unsubstituted triazolyl, substituted or unsubstituted pyrrolyl, a substituted or unsubstituted imidazolyl, or substituted or unsubstituted isoindolyl.

In some embodiments, R$^{2a}$ and R$^{2b}$ are taken together with the N atom to which they are attached to form a substituted or unsubstituted azetidinyl, substituted or unsubstituted pyrrolidinyl, substituted or unsubstituted piperidinyl, substituted or unsubstituted azepanyl, substituted or unsubstituted pyrazolyl, substituted or unsubstituted triazolyl, substituted or unsubstituted pyrrolyl, or a substituted or unsubstituted imidazolyl.

In some embodiments, R$^1$ is —CH$_3$; R$^3$ is —CH$_3$ or —CF$_3$; R$^{2a}$ and R$^{2b}$ are taken together with the N atom to which they are attached to form substituted or unsubstituted pyrrolidinyl or a substituted or unsubstituted piperidinyl.

In some embodiments, Y is —O—.

In some embodiments, X is —O—.

In some embodiments, R$^{2a}$ and R$^{2b}$ are taken together with the N atom to which they are attached to form a substituted or unsubstituted pyrrolidinyl.

In some embodiments, the compound of Formula (I) has the structure of Formula (IV):

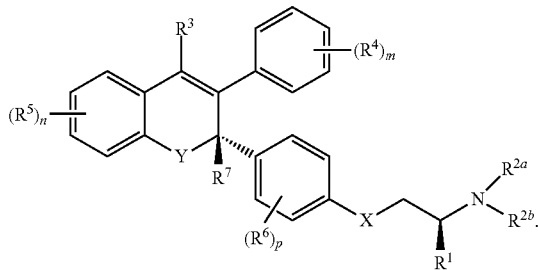

Formula (IV)

In some embodiments, the compound of Formula (I) has the structure of Formula (V):

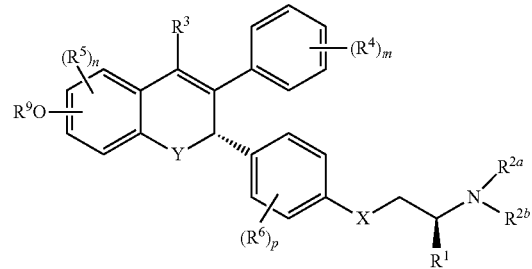

Formula (V)

wherein, n is 0, 1 or 2;

p is 0, 1 or 2.

In some embodiments, R$^1$ is —CH$_3$; R$^{2a}$ and R$^{2b}$ are taken together with the N atom to which they are attached to form a substituted or unsubstituted heterocycloalkyl; R$^3$ is —CH$_3$ or —CF$_3$; Y is —O—; X is —O—.

In some embodiments, R$^{2a}$ and R$^{2b}$ are taken together with the N atom to which they are attached to form a substituted or unsubstituted pyrrolidinyl or a substituted or unsubstituted piperidinyl.

In some embodiments, R$^1$ is —CH$_3$; R$^3$ is —CH$_3$ or —CF$_3$; R$^{2a}$ and R$^{2b}$ are taken together with the N atom to which they are attached to form R$^{2a}$ and R$^{2b}$ are taken together with the N atom to which they are attached to form

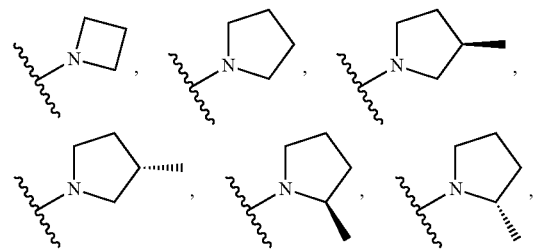

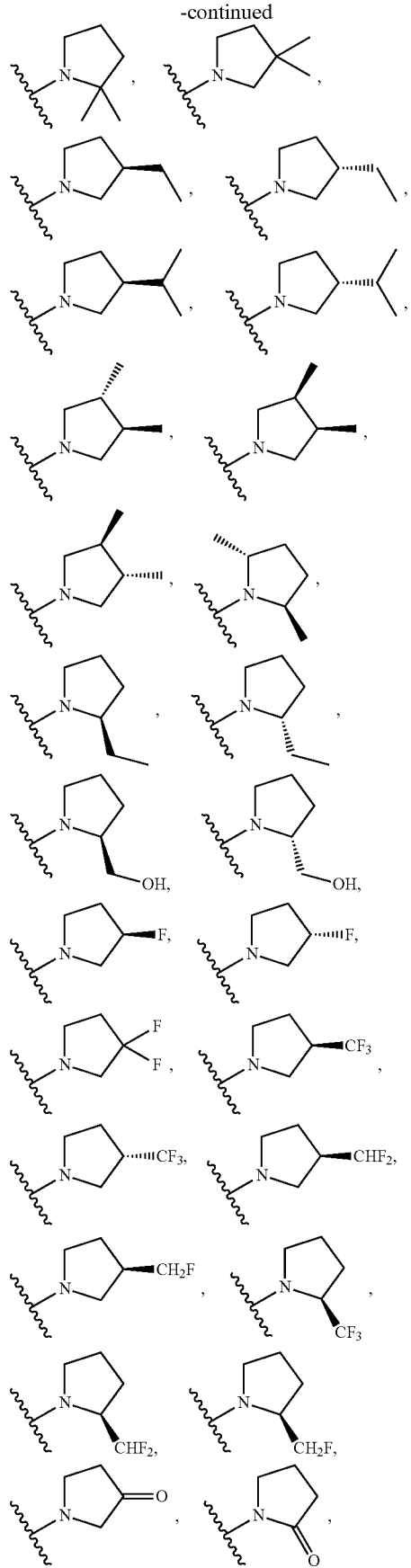
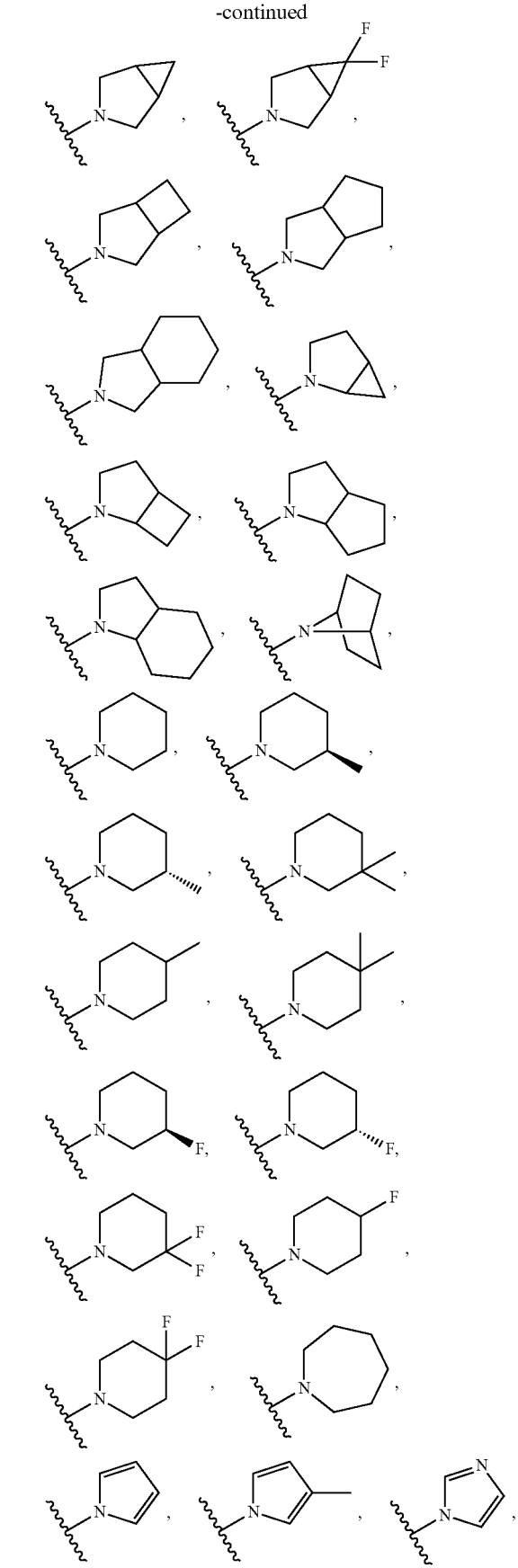

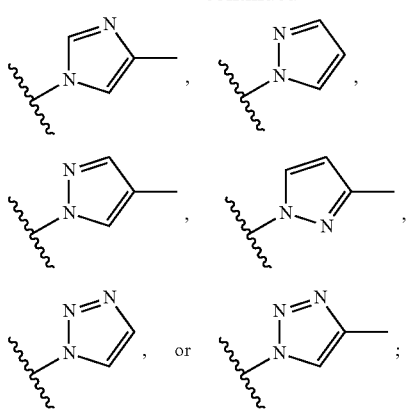

Y is —O— or —S—; X is —O—, —S—, —CH$_2$—, —NH— or —N(CH$_3$)—.

In some embodiments, R$^{2a}$ and R$^{2b}$ are taken together with the N atom to which they are attached to form

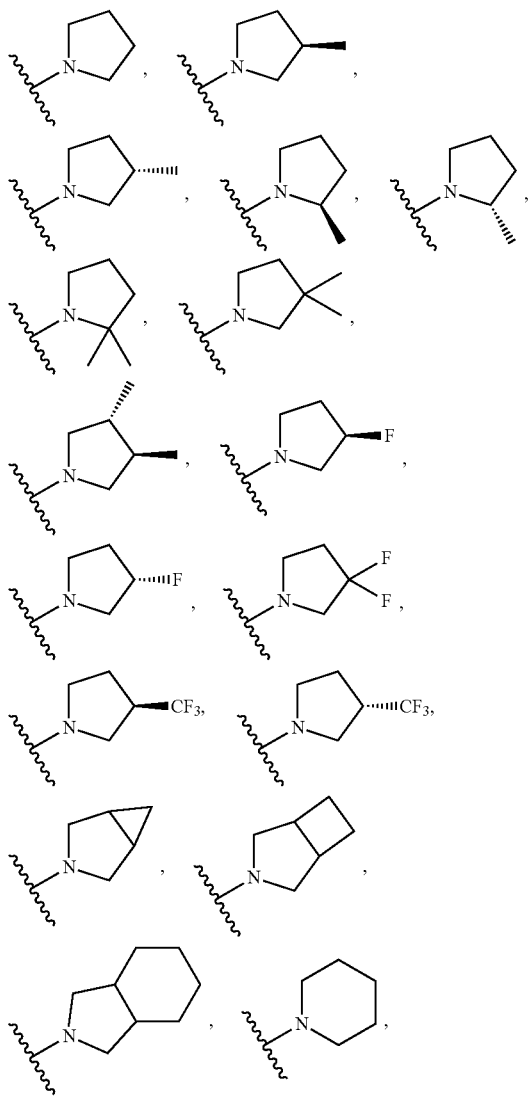

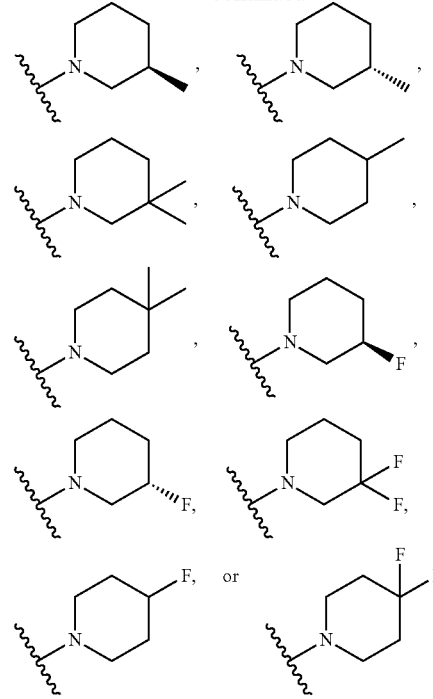

In some embodiments, R$^9$ is H; Y is —O—; X is —O—.
Also described herein is a compound of Formula (VI), or a pharmaceutically acceptable salt, or solvate thereof:

Formula (VI)

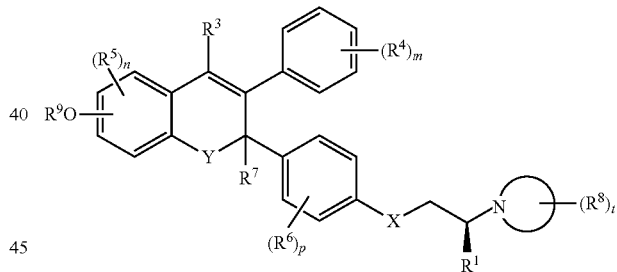

wherein,
R$^1$ is H, F, C$_1$-C$_4$alkyl, or C$_1$-C$_4$fluoroalkyl;
R$^3$ is H, halogen, C$_1$-C$_4$alkyl, C$_3$-C$_6$cycloalkyl, or C$_1$-C$_4$fluoroalkyl;
each R$^4$ is independently selected from H, halogen, —CN, —OH, —OR$^9$, —SR$^9$, —S(═O)R$^{10}$, —S(═O)$_2$R$^{10}$, —C(═O)R$^{10}$, —C(═O)OH, —C(═O)OR$^{10}$, —C(═O)NHR$^{10}$, —C(═O)N(R$^{10}$)$_2$, substituted or unsubstituted C$_1$-C$_6$alkyl, substituted or unsubstituted C$_1$-C$_6$fluoroalkyl, substituted or unsubstituted C$_1$-C$_6$fluoroalkoxy, substituted or unsubstituted C$_1$-C$_6$alkoxy, and substituted or unsubstituted C$_1$-C$_6$heteroalkyl;
each R$^5$ is independently selected from H, halogen, —CN, —OH, —OR$^9$, —SR$^9$, —S(═O)R$^{10}$, —S(═O)$_2$R$^{10}$, substituted or unsubstituted C$_1$-C$_6$alkyl, substituted or unsubstituted C$_1$-C$_6$fluoroalkyl, substituted or unsubstituted C$_1$-C$_6$fluoroalkoxy, substituted or unsubstituted C$_1$-C$_6$alkoxy, and substituted or unsubstituted C$_1$-C$_6$heteroalkyl;

each $R^6$ is independently selected from H, halogen, —CN, —OH, —OR$^9$, —SR$^9$, —S(=O)R$^{10}$, —S(=O)$_2$R$^{10}$, substituted or unsubstituted C$_1$-C$_6$alkyl, substituted or unsubstituted C$_1$-C$_6$fluoroalkyl, substituted or unsubstituted C$_1$-C$_6$fluoroalkoxy, substituted or unsubstituted C$_1$-C$_6$alkoxy, and substituted or unsubstituted C$_1$-C$_6$heteroalkyl;

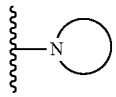

is a heterocycloalkyl or a heteroaryl;
$R^7$ is H or C$_1$-C$_4$alkyl;
each $R^8$ is independently selected from F, Cl, —CN, —OH, —OR$^9$, —SR$^9$, —S(=O)R$^{10}$, —S(=O)$_2$R$^{10}$, substituted or unsubstituted C$_1$-C$_6$alkyl, substituted or unsubstituted C$_1$-C$_6$fluoroalkyl, substituted or unsubstituted C$_1$-C$_6$fluoroalkoxy, substituted or unsubstituted C$_1$-C$_6$alkoxy, and substituted or unsubstituted C$_1$-C$_6$heteroalkyl;
or 1 $R^8$ is taken together with $R^1$ along with the intervening atoms joining $R^8$ to $R^1$ to form a 5-, 6-, or 7-membered ring;
each $R^9$ is independently selected from H, —C(=O)R$^{10}$, —C(=O)OR$^{10}$, —C(=O)NHR$^{10}$, substituted or unsubstituted C$_1$-C$_6$alkyl, substituted or unsubstituted C$_1$-C$_6$heteroalkyl, substituted or unsubstituted C$_1$-C$_6$fluoroalkyl, substituted or unsubstituted C$_3$-C$_{10}$cycloalkyl, substituted or unsubstituted C$_2$-C$_{10}$heterocycloalkyl, substituted or unsubstituted aryl, substituted or unsubstituted heteroaryl, —C$_1$-C$_2$alkylene-(substituted or unsubstituted C$_3$-C$_{10}$cycloalkyl), —C$_1$-C$_2$alkylene-(substituted or unsubstituted C$_2$-C$_{10}$heterocycloalkyl), —C$_1$-C$_2$alkylene-(substituted or unsubstituted aryl), and —C$_1$-C$_2$alkylene-(substituted or unsubstituted heteroaryl); or
each $R^{10}$ is independently selected from substituted or unsubstituted C$_1$-C$_6$alkyl, substituted or unsubstituted C$_1$-C$_6$heteroalkyl, substituted or unsubstituted C$_1$-C$_6$fluoroalkyl, substituted or unsubstituted C$_3$-C$_{10}$cycloalkyl, substituted or unsubstituted C$_2$-C$_{10}$heterocycloalkyl, substituted or unsubstituted aryl, substituted or unsubstituted heteroaryl, —C$_1$-C$_2$alkylene-(substituted or unsubstituted C$_3$-C$_{10}$cycloalkyl), —C$_1$-C$_2$alkylene-(substituted or unsubstituted C$_2$-C$_{10}$heterocycloalkyl), —C$_1$-C$_2$alkylene-(substituted or unsubstituted aryl), and —C$_1$-C$_2$alkylene-(substituted or unsubstituted heteroaryl);
Y is —O—, —S—, or —NR$^{11}$—; R$^{11}$ is H, —C(=O)R$^{10}$, substituted or unsubstituted C$_1$-C$_6$alkyl, substituted or unsubstituted C$_1$-C$_6$fluoroalkyl, or substituted or unsubstituted C$_1$-C$_6$heteroalkyl;
X is —O—, —S—, —CH$_2$—, —NH— or —N(C$_1$-C$_6$alkyl)-;
m is 0, 1, 2, 3 or 4; n is 0, 1, 2, or 3; p is 0, 1, 2, 3 or 4; t is 1, 2, 3 or 4.

In some embodiments, $R^1$ is H or C$_1$-C$_4$alkyl; $R^3$ is C$_1$-C$_4$alkyl or C$_1$-C$_4$fluoroalkyl; each $R^4$ is independently selected from H, halogen, —CN, —OH, —OR$^9$, —SR$^9$, —S(=O)R$^{10}$, —S(=O)$_2$R$^{10}$, C$_1$-C$_4$alkyl, C$_1$-C$_4$fluoroalkyl, C$_1$-C$_4$fluoroalkoxy, C$_1$-C$_4$alkoxy, and C$_1$-C$_4$heteroalkyl; each $R^5$ is independently selected from H, halogen, —OH, C$_1$-C$_4$alkyl, C$_1$-C$_4$fluoroalkyl, C$_1$-C$_4$fluoroalkoxy, C$_1$-C$_4$alkoxy, and C$_1$-C$_4$heteroalkyl; each $R^6$ is independently selected from H, halogen, —OH, C$_1$-C$_4$alkyl, C$_1$-C$_4$fluoroalkyl, C$_1$-C$_4$fluoroalkoxy, and C$_1$-C$_4$alkoxy; $R^7$ is H or —CH$_3$; Y is —O— or —S—; X is —O—, —S—, —CH$_2$—, —NH— or —N(CH$_3$)—; p is 0, 1, or 2.

In some embodiments, each $R^5$ is independently selected from H, F, Cl, —OH, —CH$_3$, —CF$_3$, —OCF$_3$ and —OCH$_3$; each $R^6$ is independently selected from H, F, Cl, —OH, —CH$_3$, —CF$_3$, —OCF$_3$ and —OCH$_3$; $R^7$ is H;

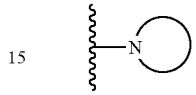

is azetidinyl, pyrrolidinyl, piperidinyl, azepanyl, morpholinyl, piperazinyl, 3-azabicyclo[3.1.0]hexan-3-yl, 3-azabicyclo[3.2.0]heptan-3-yl, octahydrocyclopenta[c]pyrrolyl, octahydro-1H-isoindolyl, isoindolinyl, pyrazolyl, triazolyl, pyrrolyl, imidazolyl, or isoindolyl; each $R^8$ is independently selected from F, Cl, —OH, C$_1$-C$_4$alkyl, C$_1$-C$_4$fluoroalkyl, C$_1$-C$_4$fluoroalkoxy, C$_1$-C$_4$alkoxy, and C$_1$-C$_4$heteroalkyl.

In some embodiments,

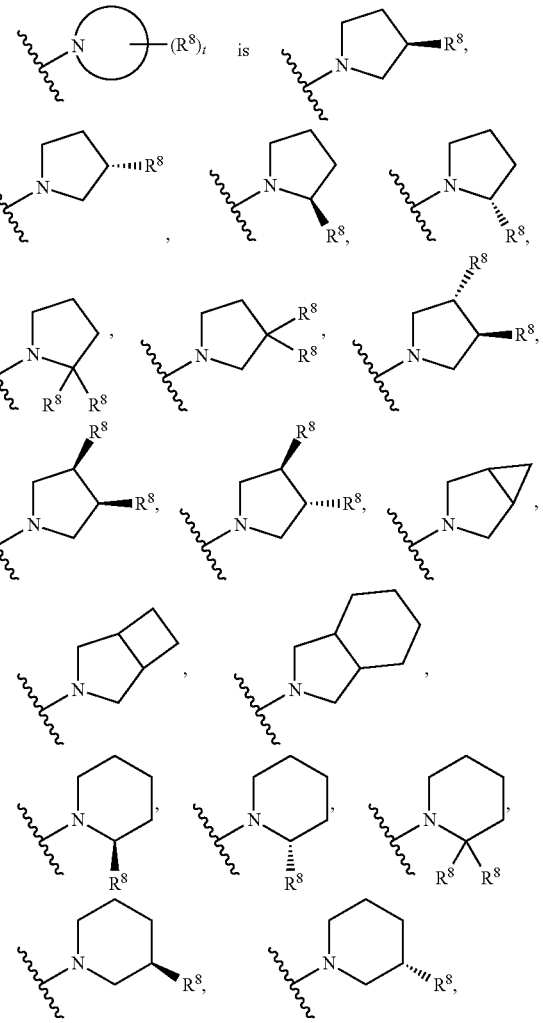

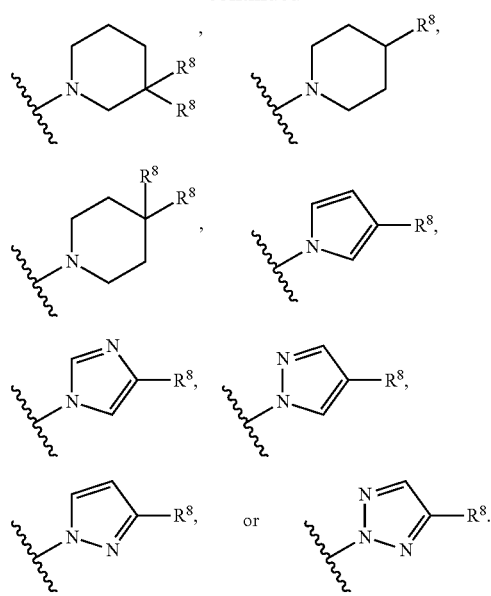
In some embodiments, each $R^8$ is independently selected from F, Cl, —OH, —CH$_3$, —CH$_2$CH$_3$, —CH(CH$_3$)$_2$, —CF$_3$, —CH$_2$CF$_3$, —OCF$_3$, —OCH$_2$CF$_3$, —OCH$_3$, —OCH$_2$CH$_3$, —CH$_2$OCH$_3$, —CH$_2$OCH$_2$CH$_3$, and —CH$_2$OH.
In some embodiments,
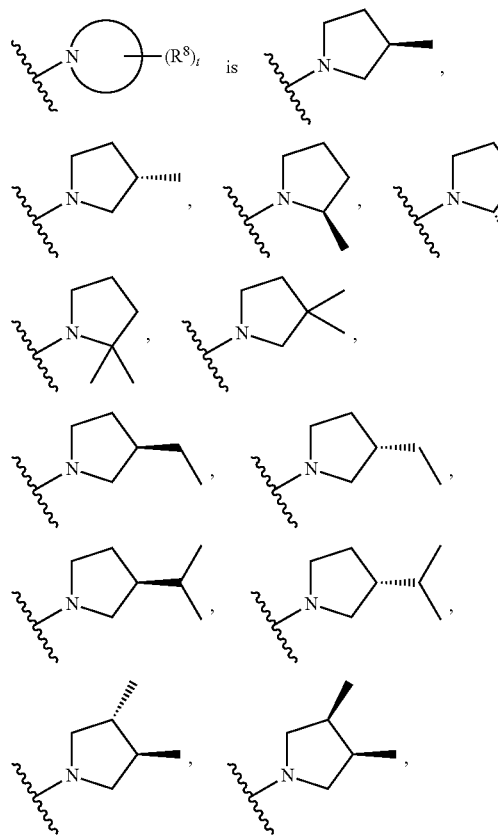
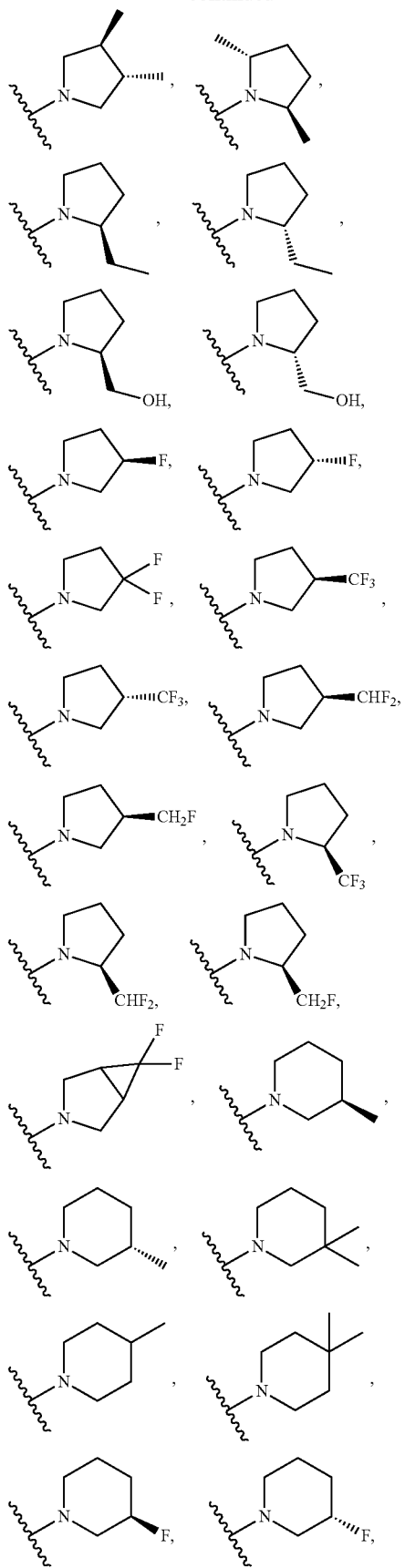

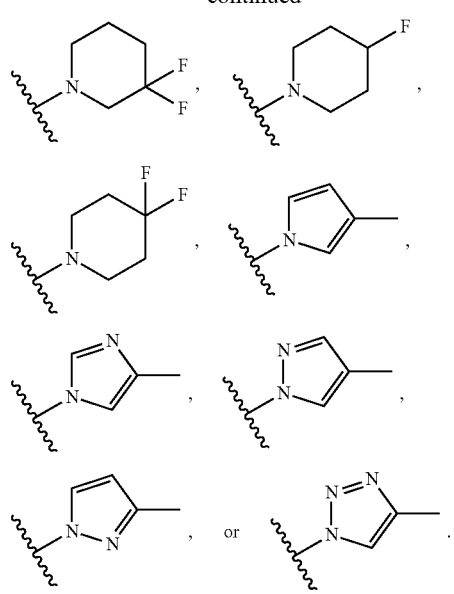
In some embodiments,
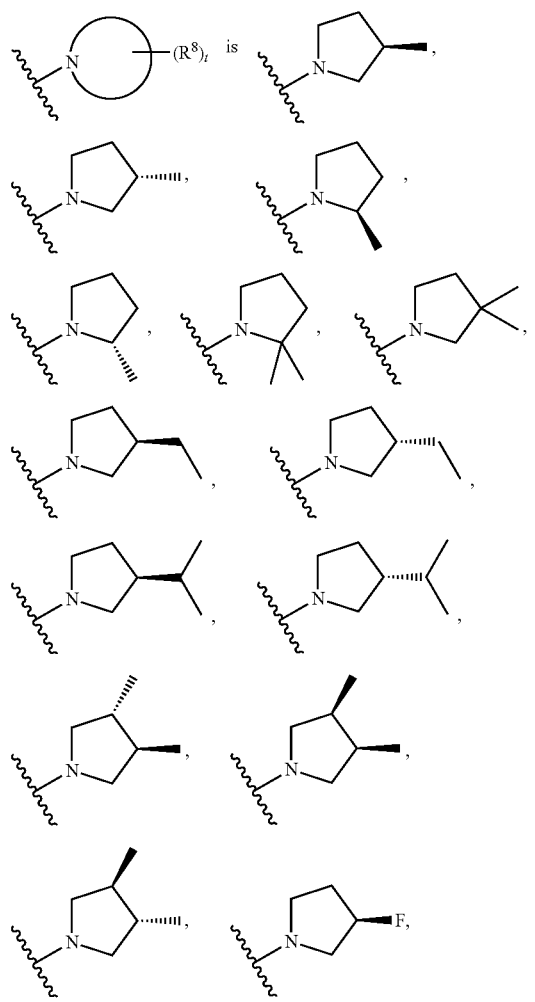
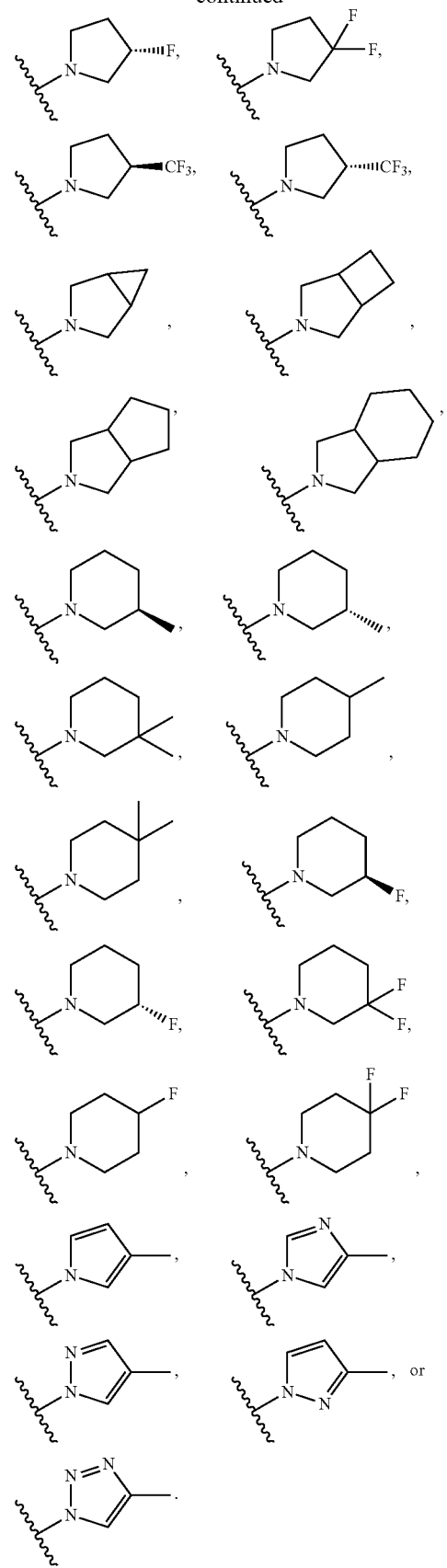

In some embodiments, the compound of Formula (VI) has the structure of Formula (VII):

Formula (VII)

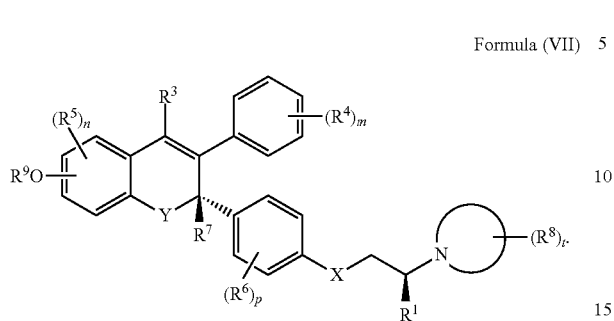

In some embodiments, the compound of Formula (VI) has the structure of Formula (VIII):

Formula (VIII)

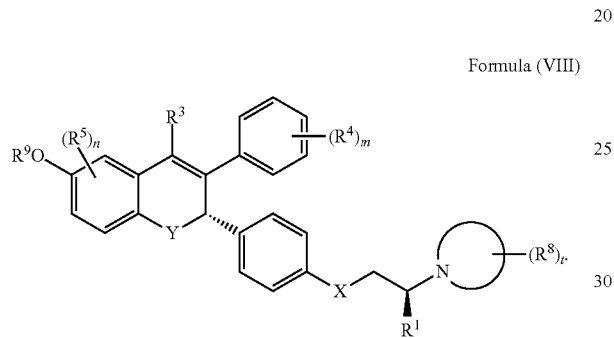

In some embodiments, the compound of Formula (VI) has the structure of Formula (IX):

Formula (IX)

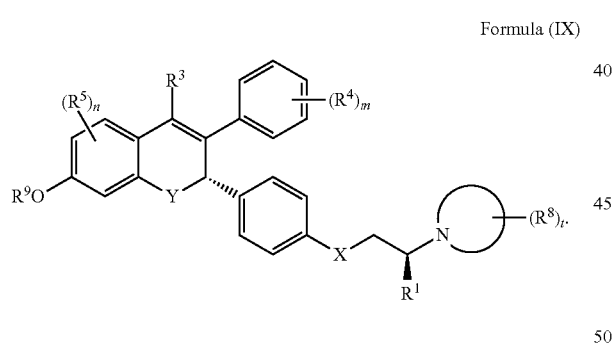

In some embodiments, the compound of Formula (VI) has the structure of Formula (X):

Formula (X)

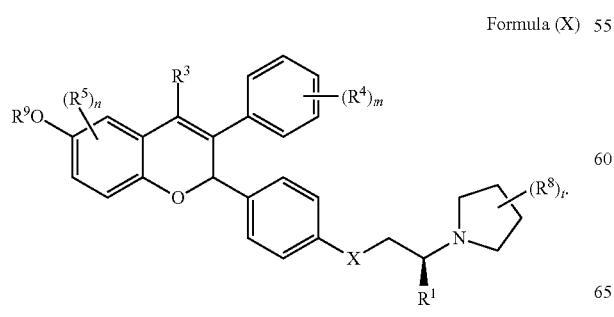

In some embodiments,

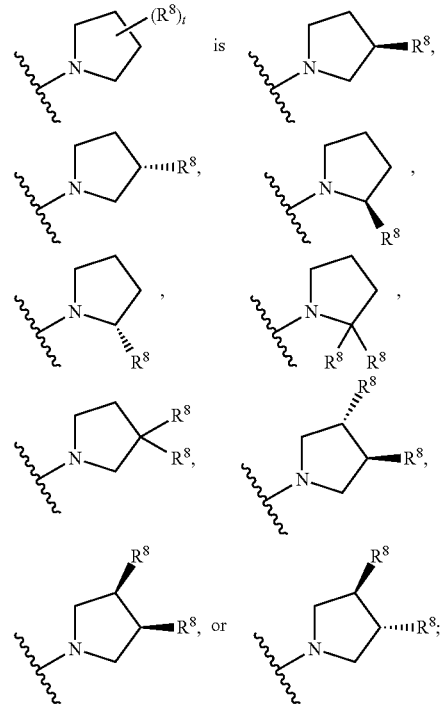

each $R^8$ is independently selected from F, Cl, —OH, —CH$_3$, —CH$_2$CH$_3$, —CH(CH$_3$)$_2$, —CF$_3$, —CH$_2$CF$_3$, —OCF$_3$, —OCH$_2$CF$_3$, —OCH$_3$, —OCH$_2$CH$_3$, —CH$_2$OCH$_3$, —CH$_2$OCH$_2$CH$_3$, and —CH$_2$OH.

In some embodiments, $R^1$ is H or —CH$_3$; $R^3$ is —CH$_3$ or —CF$_3$; $R^9$ is H; X is —O—.

Also described herein is a compound of Formula (IX), or a pharmaceutically acceptable salt, or solvate thereof:

Formula (XI)

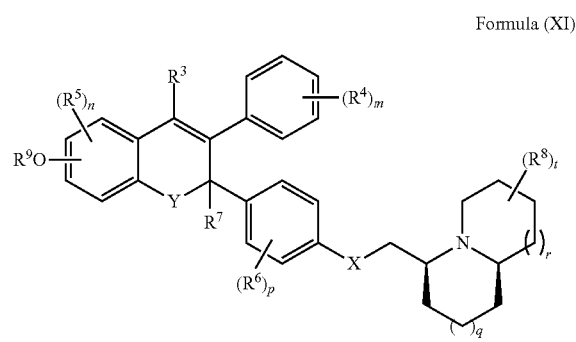

wherein,
$R^3$ is H, halogen, C$_1$-C$_4$alkyl, C$_3$-C$_6$cycloalkyl, or C$_1$-C$_4$fluoroalkyl;
each $R^4$ is independently selected from H, halogen, —CN, —OH, —OR$^9$, —SR$^9$, —S(=O)R$^{10}$, —S(=O)$_2$R$^{10}$, C$_1$-C$_6$alkyl, C$_1$-C$_6$fluoroalkyl, C$_1$-C$_6$fluoroalkoxy, C$_1$-C$_6$alkoxy, and C$_1$-C$_6$heteroalkyl;
each $R^5$ is independently selected from H, halogen, —CN, —OH, —OR$^9$, —SR$^9$, —S(=O)R$^{10}$, —S(=O)$_2$R$^{10}$, C$_1$-C$_6$alkyl, C$_1$-C$_6$fluoroalkyl, C$_1$-C$_6$fluoroalkoxy, C$_1$-C$_6$alkoxy, and C$_1$-C$_6$heteroalkyl;
each $R^6$ is independently selected from H, halogen, —CN, —OH, —OR$^9$, —SR$^9$, —S(=O)R$^{10}$, —S(=O)$_2$R$^{10}$, $C_1$-$C_6$alkyl, $C_1$-$C_6$fluoroalkyl, $C_1$-$C_6$fluoroalkoxy, $C_1$-$C_6$alkoxy, and $C_1$-$C_6$heteroalkyl;

$R^7$ is H or $C_1$-$C_4$alkyl;

each $R^8$ is independently selected from F, Cl, —CN, —OH, —$OR^9$, —$SR^9$, —$S(=O)R^{10}$, —$S(=O)_2R^{10}$, $C_1$-$C_6$alkyl, $C_1$-$C_6$fluoroalkyl, $C_1$-$C_6$fluoroalkoxy, $C_1$-$C_6$alkoxy, and $C_1$-$C_6$heteroalkyl;

each $R^9$ is independently selected from H, —$C(=O)R^{10}$, —$C(=O)OR^{10}$, —$C(=O)NHR^{10}$, $C_1$-$C_6$alkyl, $C_1$-$C_6$heteroalkyl, $C_1$-$C_6$fluoroalkyl, substituted or unsubstituted $C_3$-$C_{10}$cycloalkyl, substituted or unsubstituted $C_2$-$C_{10}$heterocycloalkyl, substituted or unsubstituted aryl, and substituted or unsubstituted heteroaryl; or each $R^{10}$ is independently selected from $C_1$-$C_6$alkyl, $C_1$-$C_6$heteroalkyl, $C_1$-$C_6$fluoroalkyl, substituted or unsubstituted $C_3$-$C_{10}$cycloalkyl, substituted or unsubstituted $C_2$-$C_{10}$heterocycloalkyl, substituted or unsubstituted aryl, and substituted or unsubstituted heteroaryl;

Y is —O—, or —S—;

X is —O—, —S—, —$CH_2$—, —NH— or —$N(C_1$-$C_6$alkyl)-;

m is 0, 1, 2, 3 or 4;

n is 0, 1, 2, or 3; p is 0, 1, 2, 3 or 4; q is 0, 1 or 2; r is 0, 1 or 2; t is 0, 1, 2, 3 or 4.

In some embodiments, $R^3$ is —$CH_3$ or —$CF_3$; each $R^5$ is independently selected from H, halogen, —OH, $C_1$-$C_4$alkyl, $C_1$-$C_4$fluoroalkyl, $C_1$-$C_4$fluoroalkoxy, and $C_1$-$C_4$alkoxy; each $R^6$ is independently selected from H, halogen, —OH, $C_1$-$C_4$alkyl, $C_1$-$C_4$fluoroalkyl, $C_1$-$C_4$fluoroalkoxy, and $C_1$-$C_4$alkoxy; $R^7$ is H; each $R^8$ is independently selected from F, Cl, —OH, $C_1$-$C_4$alkyl, $C_1$-$C_4$fluoroalkyl, $C_1$-$C_4$fluoroalkoxy, $C_1$-$C_4$alkoxy, and $C_1$-$C_4$heteroalkyl; Y is —O—; X is —O—; m is 0, 1, or 2; n is 0, 1, or 2; p is 0, 1, or 2; t is 0, 1, or 2.

Also described is a compound having the structure of Formula (XII), or a pharmaceutically acceptable salt, or solvate thereof:

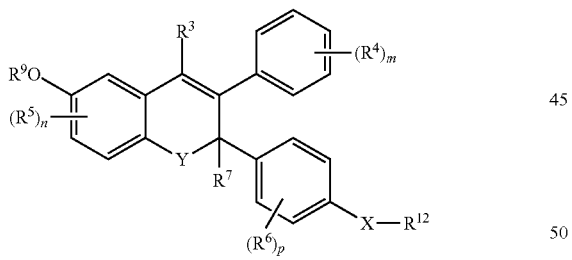

Formula (XII)

wherein, $R^3$ is H, halogen, $C_1$-$C_4$alkyl, $C_3$-$C_6$cycloalkyl, or $C_1$-$C_4$fluoroalkyl;

each $R^4$ is independently selected from H, halogen, —CN, —OH, —$OR^9$, —$SR^9$, —$S(=O)R^{10}$, —$S(=O)_2R^{10}$, —$C(=O)R^{10}$, —$C(=O)OH$, —$C(=O)OR^{10}$, —$C(=O)NHR^{10}$, —$C(=O)N(R^{10})_2$, substituted or unsubstituted $C_1$-$C_6$alkyl, substituted or unsubstituted $C_1$-$C_6$fluoroalkyl, substituted or unsubstituted $C_1$-$C_6$fluoroalkoxy, substituted or unsubstituted $C_1$-$C_6$alkoxy, and substituted or unsubstituted $C_1$-$C_6$heteroalkyl;

each $R^5$ is independently selected from H, halogen, —CN, —OH, —$OR^9$, —$SR^9$, —$S(=O)R^{10}$, —$S(=O)_2R^{10}$, substituted or unsubstituted $C_1$-$C_6$alkyl, substituted or unsubstituted $C_1$-$C_6$fluoroalkyl, substituted or unsubstituted $C_1$-$C_6$fluoroalkoxy, substituted or unsubstituted $C_1$-$C_6$alkoxy, and substituted or unsubstituted $C_1$-$C_6$heteroalkyl;

each $R^6$ is independently selected from H, halogen, —CN, —OH, —$OR^9$, —$SR^9$, —$S(=O)R^{10}$, —$S(=O)_2R^{10}$, substituted or unsubstituted $C_1$-$C_6$alkyl, substituted or unsubstituted $C_1$-$C_6$fluoroalkyl, substituted or unsubstituted $C_1$-$C_6$fluoroalkoxy, substituted or unsubstituted $C_1$-$C_6$alkoxy, and substituted or unsubstituted $C_1$-$C_6$heteroalkyl;

$R^7$ is H or $C_1$-$C_4$alkyl;

each $R^9$ is independently selected from H, —$C(=O)R^{10}$, —$C(=O)OR^{10}$, —$C(=O)NHR^{10}$, substituted or unsubstituted $C_1$-$C_6$alkyl, substituted or unsubstituted $C_1$-$C_6$heteroalkyl, substituted or unsubstituted $C_1$-$C_6$fluoroalkyl, substituted or unsubstituted $C_3$-$C_{10}$cycloalkyl, substituted or unsubstituted $C_2$-$C_{10}$heterocycloalkyl, substituted or unsubstituted aryl, substituted or unsubstituted heteroaryl, —$C_1$-$C_2$alkylene-(substituted or unsubstituted $C_3$-$C_{10}$cycloalkyl), —$C_1$-$C_2$alkylene-(substituted or unsubstituted $C_2$-$C_{10}$heterocycloalkyl), —$C_1$-$C_2$alkylene-(substituted or unsubstituted aryl), and —$C_1$-$C_2$alkylene-(substituted or unsubstituted heteroaryl); or each $R^{10}$ is independently selected from substituted or unsubstituted $C_1$-$C_6$alkyl, substituted or unsubstituted $C_1$-$C_6$heteroalkyl, substituted or unsubstituted $C_1$-$C_6$fluoroalkyl, substituted or unsubstituted $C_3$-$C_{10}$cycloalkyl, substituted or unsubstituted $C_2$-$C_{10}$heterocycloalkyl, substituted or unsubstituted aryl, substituted or unsubstituted heteroaryl, —$C_1$-$C_2$alkylene-(substituted or unsubstituted $C_3$-$C_{10}$cycloalkyl), —$C_1$-$C_2$alkylene-(substituted or unsubstituted $C_2$-$C_{10}$heterocycloalkyl), —$C_1$-$C_2$alkylene-(substituted or unsubstituted aryl), and —$C_1$-$C_2$alkylene-(substituted or unsubstituted heteroaryl);

$R^{12}$ is -L-$NR^{2a}R^{2b}$,

L is a substituted or unsubstituted $C_1$-$C_6$alkylene, where if L is substituted then L is substituted with $R^1$, where $R^1$ is F, $C_1$-$C_4$alkyl, or $C_1$-$C_4$fluoroalkyl;

$R^{2a}$ is H or $R^{10}$;

$R^{2b}$ is —$C(=O)R^{10}$, —$C(=O)OR^{10}$, —$C(=O)NHR^{10}$, —$S(=O)_2R^{10}$, or $R^{10}$; or $R^{2a}$ and $R^{2b}$ are taken together with the N atom to which they are attached to form a substituted or unsubstituted monocyclic heterocycloalkyl, a substituted or unsubstituted bicyclic heterocycloalkyl, a substituted or unsubstituted monocyclic heteroaryl, or a substituted or unsubstituted bicyclic heteroaryl;

Y is —O—, —S—, or —$NR^{11}$—; $R^{11}$ is H, —$C(=O)R^{10}$, substituted or unsubstituted $C_1$-$C_6$alkyl, substituted or unsubstituted $C_1$-$C_6$fluoroalkyl, or substituted or unsubstituted $C_1$-$C_6$heteroalkyl;

X is —O—, —S—, —$CH_2$—, —NH— or —$N(C_1$-$C_6$alkyl)-;

m is 0, 1, 2, 3, 4 or 5;

n is 0, 1, 2 or 3;

p is 0, 1, 2, 3 or 4.

In some embodiments, $R^3$ is H, —$CH_3$ or $CF_3$; each $R^4$ is independently selected from H, halogen, —CN, —OH, —$OR^9$, —$SR^9$, —$S(=O)R^{10}$, —$S(=O)_2R^{10}$, $C_1$-$C_6$alkyl, $C_1$-$C_6$fluoroalkyl, $C_1$-$C_6$fluoroalkoxy, $C_1$-$C_6$alkoxy, and $C_1$-$C_6$heteroalkyl; each $R^5$ is independently selected from H, halogen, —CN, —OH, —OR$^9$, C$_1$-C$_6$alkyl, C$_1$-C$_6$fluoroalkyl, C$_1$-C$_6$fluoroalkoxy, C$_1$-C$_6$alkoxy, and C$_1$-C$_6$heteroalkyl; each R$^6$ is independently selected from H, halogen, —CN, —OH, C$_1$-C$_6$alkyl, C$_1$-C$_6$fluoroalkyl, C$_1$-C$_6$fluoroalkoxy, and C$_1$-C$_6$alkoxy; R$^7$ is H or —CH$_3$; R$^{12}$ is -L-NR$^{2a}$R$^{2b}$, L is a substituted or unsubstituted ethylene, where if L is substituted then L is substituted with R$^1$, where R$^1$ is —CH$_3$, —CF$_3$, —CHF$_2$, —CH$_2$F; R$^{2a}$ is H or R$^{10}$; R$^{2b}$ is R$^{10}$; or R$^{2a}$ and R$^{2b}$ are taken together with the N atom to which they are attached to form a substituted or unsubstituted monocyclic heterocycloalkyl, a substituted or unsubstituted bicyclic heterocycloalkyl, a substituted or unsubstituted monocyclic heteroaryl, or a substituted or unsubstituted bicyclic heteroaryl; Y is —O—; X is —O—, —S—, —CH$_2$—, —NH— or —N(CH$_3$)—; m is 0, 1, 2, or 3; n is 0, 1, 2 or 3; p is 0 or 1.

In some embodiments, R$^3$ is —CH$_3$; R$^7$ is H; R$^{12}$ is

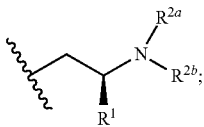

R$^{2a}$ is H, C$_1$-C$_6$alkyl, C$_3$-C$_{10}$cycloalkyl, substituted or unsubstituted aryl, or substituted or unsubstituted heteroaryl; R$^{2b}$ is C$_1$-C$_6$alkyl, C$_3$-C$_{10}$cycloalkyl, substituted or unsubstituted aryl, or substituted or unsubstituted heteroaryl; or R$^{2a}$ and R$^{2b}$ are taken together with the N atom to which they are attached to form a substituted or unsubstituted monocyclic heterocycloalkyl, a substituted or unsubstituted bicyclic heterocycloalkyl, a substituted or unsubstituted monocyclic heteroaryl, or a substituted or unsubstituted bicyclic heteroaryl; Y is —O—; X is —O—; p is 0.

Any combination of the groups described above for the various variables is contemplated herein. Throughout the specification, groups and substituents thereof can be chosen by one skilled in the field to provide stable moieties and compounds.

Compounds disclosed herein are estrogen receptor modulators. In some embodiments, compounds disclosed herein have high specificity for the estrogen receptor and have desirable, tissue-selective pharmacological activities. Desirable, tissue-selective pharmacological activities include, but are not limited to, ER antagonist activity in breast cells and no ER agonist activity in uterine cells. In some embodiments, compounds disclosed herein are estrogen receptor degraders that display full estrogen receptor antagonist activity with negligible or minimal estrogen receptor agonist activity.

In some embodiments, compounds disclosed herein are estrogen receptor degraders. In some embodiments, compounds disclosed herein are estrogen receptor antagonists. In some embodiments, compounds disclosed herein have minimal or negligible estrogen receptor agonist activity.

In some embodiments, presented herein are compounds selected from active metabolites, tautomers, pharmaceutically acceptable solvates, pharmaceutically acceptable salts or prodrugs of a compound of Formula (I), (II), (III), (IV), (V), (VI), (VII), (VIII), (IX), (X), (XI), (XII), or (XIII).

Also described are pharmaceutical compositions comprising a therapeutically effective amount of a compound of Formula (I), (II), (III), (IV), (V), (VI), (VII), (VIII), (IX), (X), (XI), (XII), or (XIII), or a pharmaceutically acceptable salt thereof. In some embodiments, the pharmaceutical composition also contains at least one pharmaceutically acceptable inactive ingredient. In some embodiments, the pharmaceutical composition is formulated for intravenous injection, subcutaneous injection, oral administration, or topical administration. In some embodiments, the pharmaceutical composition is a tablet, a pill, a capsule, a liquid, a suspension, a gel, a dispersion, a suspension, a solution, an emulsion, an ointment, or a lotion.

In some embodiments, the pharmaceutical composition further comprises one or more additional therapeutically active agents selected from: corticosteroids, anti-emetic agents, analgesics, anti-cancer agents, anti-inflammatories, kinase inhibitors, antibodies, HSP90 inhibitors, histone deacetylase (HDAC) inhibitors, poly ADP-ribose polymerase (PARP) inhibitors, and aromatase inhibitors.

In some embodiments, provided herein is a method comprising administering a compound of Formula (I), (II), (III), (IV), (V), (VI), (VII), (VIII), (IX), (X), (XI), (XII), or (XIII), or a pharmaceutically acceptable salt thereof, to a human with a diseases or condition that is estrogen sensitive, estrogen receptor meditated or estrogen receptor dependent. In some embodiments, the human is already being administered one or more additional therapeutically active agents other than a compound of Formula (I), (II), (III), (IV), (V), (VI), (VII), (VIII), (IX), (X), (XI), (XII), or (XIII), or a pharmaceutically acceptable salt thereof. In some embodiments, the method further comprises administering one or more additional therapeutically active agents other than a compound of Formula (I), (II), (III), (IV), (V), (VI), (VII), (VIII), (IX), (X), (XI), (XII), or (XIII), or a pharmaceutically acceptable salt thereof.

In some embodiments, the one or more additional therapeutically active agents other than a compound of Formula (I), (II), (III), (IV), (V), (VI), (VII), (VIII), (IX), (X), (XI), (XII), or (XIII), or a pharmaceutically acceptable salt thereof, are selected from: corticosteroids, anti-emetic agents, analgesics, anti-cancer agents, anti-inflammatories, kinase inhibitors, antibodies, HSP90 inhibitors, histone deacetylase (HDAC) inhibitors, and aromatase inhibitors.

Pharmaceutical formulations described herein are administered to a mammal in a variety of ways, including but not limited to, oral, parenteral (e.g., intravenous, subcutaneous, intramuscular), buccal, topical or transdermal administration routes. The pharmaceutical formulations described herein include, but are not limited to, aqueous liquid dispersions, self-emulsifying dispersions, solid solutions, liposomal dispersions, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

In some embodiments, the compounds of Formula (I), (II), (III), (IV), (V), (VI), (VII), (VIII), (IX), (X), (XI), (XII), or (XIII), or a pharmaceutically acceptable salt thereof, are administered orally.

In some embodiments, the compounds of Formula (I), (II), (III), (IV), (V), (VI), (VII), (VIII), (IX), (X), (XI), (XII), or (XIII), or a pharmaceutically acceptable salt thereof, are administered systemically.

In some embodiments, the compounds of Formula (I), (II), (III), (IV), (V), (VI), (VII), (VIII), (IX), (X), (XI), (XII), or (XIII) are administered intravenously.

In some embodiments, the compounds of Formula (I), (II), (III), (IV), (V), (VI), (VII), (VIII), (IX), (X), (XI), (XII), or (XIII), or a pharmaceutically acceptable salt thereof, are administered subcutaneously.

In some embodiments, the compounds of Formula (I), (II), (III), (IV), (V), (VI), (VII), (VIII), (IX), (X), (XI), (XII), or (XIII), or a pharmaceutically acceptable salt thereof, are administered topically. In such embodiments, the compound of Formula (I), (II), (III), (IV), (V), (VI), (VII), (VIII), (IX), (X), (XI), (XII), or (XIII), or a pharmaceutically acceptable salt thereof, is formulated into a variety of topically administrable compositions, such as solutions, suspensions, lotions, gels, pastes, shampoos, scrubs, rubs, smears, medicated sticks, medicated bandages, balms, creams or ointments. In some embodiments, the compounds of Formula (I), (II), (III), (IV), (V), (VI), (VII), (VIII), (IX), (X), (XI), (XII), or (XIII), or a pharmaceutically acceptable salt thereof, are administered topically to the skin of mammal.

In another aspect is the use of a compound of Formula (I), (II), (III), (IV), (V), (VI), (VII), (VIII), (IX), (X), (XI), (XII), or (XIII), or a pharmaceutically acceptable salt thereof, in the manufacture of a medicament for treating a disease, disorder or conditions in which the activity of estrogen receptors contributes to the pathology and/or symptoms of the disease or condition. In one aspect, the disease or condition is any of the diseases or conditions specified herein.

In any of the aforementioned aspects are further embodiments in which the effective amount of the compound of Formula (I), (II), (III), (IV), (V), (VI), (VII), (VIII), (IX), (X), (XI), (XII), or (XIII), or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) adminstered non-systemically or locally to the mammal.

In any of the aforementioned aspects are further embodiments comprising single administrations of the effective amount of the compound, including further embodiments in which (i) the compound is administered once; (ii) the compound is administered to the mammal multiple times over the span of one day; (iii) continually; or (iv) continuously.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

Also provided is a method of reducing ER activation in a mammal comprising administering to the mammal at least one compound having the structure of Formula (I), (II), (III), (IV), (V), (VI), (VII), (VIII), (IX), (X), (XI), (XII), or (XIII), or a pharmaceutically acceptable salt thereof. In some embodiments, the method comprises reducing ER activation in breast cells, lung cells, ovarian cells, colon cells, prostate cells, endometrial cells, or uterine cells in the mammal. In some embodiments, the method comprises reducing ER activation in breast cells, ovarian cells, colon cells, prostate cells, endometrial cells, or uterine cells in the mammal. In some embodiments, the method of reducing ER activation in the mammal comprises reducing the binding of estrogens to estrogen receptors in the mammal. In some embodiments, the method of reducing ER activation in the mammal comprises reducing ER concentrations in the mammal.

In one aspect is the use of a compound of Formula (I), (II), (III), (IV), (V), (VI), (VII), (VIII), (IX), (X), (XI), (XII), or (XIII), or a pharmaceutically acceptable salt thereof, in the manufacture of a medicament for the treatment of diseases or conditions that are estrogen sensitive, estrogen receptor dependent or estrogen receptor mediated. In some embodiments, the disease or condition is breast cancer, lung cancer, ovarian cancer, colon cancer, prostate cancer, endometrial cancer, or uterine cancer. In some embodiments, the disease or condition is described herein.

In some cases disclosed herein is the use of a compound of Formula (I), (II), (III), (IV), (V), (VI), (VII), (VIII), (IX), (X), (XI), (XII), or (XIII), or a pharmaceutically acceptable salt thereof, in the treatment or prevention of diseases or conditions that are estrogen sensitive, estrogen receptor dependent or estrogen receptor mediated. In some embodiments, the disease or condition is described herein.

In any of the embodiments disclosed herein, the mammal is a human.

In some embodiments, compounds provided herein are used to diminish, reduce, or eliminate the activity of estrogen receptors.

Articles of manufacture, which include: packaging material; a compound of Formula (I), (II), (III), (IV), (V), (VI), (VII), (VIII), (IX), (X), (XI), (XII), or (XIII), or a pharmaceutically acceptable salt, active metabolite, prodrug, or pharmaceutically acceptable solvate thereof, or composition thereof, within the packaging material; and a label that indicates that the compound or pharmaceutically acceptable salt, active metabolite, prodrug, or pharmaceutically acceptable solvate thereof, or composition thereof, or composition thereof, is used for reducing, diminishing or eliminating the effects of estrogen receptors, or for the treatment, prevention or amelioration of one or more symptoms of a disease or condition that would benefit from a reduction or elimination of estrogen receptor activity, are provided.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description

DETAILED DESCRIPTION OF THE INVENTION

Estrogen receptor alpha (ER-α; NR3A1) and estrogen receptor beta (ER-β; NR3A2) are steroid hormone receptors, which are members of the large nuclear receptor superfamily. Nuclear receptors share a common modular structure, which minimally includes a DNA binding domain (DBD) and a ligand binding domain (LBD). Steroid hormone receptors are soluble, intracellular proteins that act as ligand-regulated transcription factors. Vertebrates contain five closely related steroid hormone receptors (estrogen receptor, androgen receptor, progesterone receptor, glucocorticoid receptor, mineralcorticoid receptor), which regulate a wide spectrum of reproductive, metabolic and developmental activities. The activities of ER are controlled by the binding of endogenous estrogens, including 17β-estradiol and estrones.

The ER-α gene is located on 6q25.1 and encodes a 595 AA protein. The ER-β gene resides on chromosome 14q23.3 and produces a 530 AA protein. However, due to alternative splicing and translation start sites, each of these genes can give rise to multiple isoforms. In addition to the DNA binding domain (called C domain) and ligand binding domain (E domain) these receptors contain an N-terminal (A/B) domain, a hinge (D) domain that links the C and E domains, and a C-terminal extension (F domain) (Gronemeyer and Laudet; Protein Profile 2: 1173-1308, 1995). While the C and E domains of ER-α and ER-β are quite conserved (95% and 55% amino acid identity, respectively), conservation of the A/B, D and F domains is poor (below 30% amino acid identity). Both receptors are involved in the regulation and development of the female reproductive tract but also play various roles in the central nervous system, cardiovascular systems and bone metabolism.

The ligand binding pocket of steroid hormone receptors is deeply buried within the ligand binding domain. Upon binding, the ligand becomes part of the hydrophobic core of this domain. Consequently most steroid hormone receptors are instable in the absence of hormone and require assistance from chaperones, such as Hsp90, in order to maintain hormone-binding competency. The interaction with Hsp90 also controls nuclear translocation of these receptors. Ligand-binding stabilizes the receptor and initiates sequential conformational changes that release the chaperones, alter the interactions between the various receptor domains and remodel protein interaction surfaces that allow these receptors to translocate into the nucleus, bind DNA and engage in interactions with chromatin remodeling complexes and the transcriptional machinery. Although ER can interact with Hsp90, this interaction is not required for hormone binding and, dependent on the cellular context, apo-ER can be both cytoplasmic and nuclear. Biophysical studies indicated that DNA binding rather than ligand binding contributes to the stability of the receptor (Greenfield et al., Biochemistry 40: 6646-6652, 2001).

ER can interact with DNA either directly by binding to a specific DNA sequence motif called estrogen response element (ERE) (classical pathway), or indirectly via protein-protein interactions (nonclassical pathway) (Welboren et al., Endocrine-Related Cancer 16: 1073-1089, 2009). In the non-classical pathway, ER has been shown to tether to other transcription factors including SP-1, AP-1 and NF-κB. These interactions appear to play critical roles in the ability of ER to regulate cell proliferation and differentiation.

Both types of ER DNA interactions can result in gene activation or repression dependent on the transcriptional coregulators that are recruited by the respective ER-ERE complex (Klinge, Steroid 65: 227-251, 2000). The recruitment of coregulators is primarily mediated by two protein interaction surfaces, the AF2 and AF1. AF2 is located in the ER E-domain and its conformation is directly regulated by the ligand (Brzozowski et al., Nature 389: 753-758, 1997). Full agonists appear to promote the recruitment of co-activators, whereas weak agonists and antagonists facilitate the binding of co-repressors. The regulation of protein with the AF1 is less well understood but can be controlled by serine phosphorylation (Ward and Weigel, Biofactors 35: 528-536, 2009). One of the involved phosphorylation sites (S118) appears to control the transcriptional activity of ER in the presence of antagonists such as tamoxifen, which plays an important role in the treatment of breast cancer. While full agonists appear to arrest ER in certain conformation, weak agonists tend to maintain ER in equilibrium between different conformations, allowing cell-dependent differences in co-regulator repertoires to modulate the activity of ER in a cell-dependent manner (Tamrazi et al., Mol. Endocrinol. 17: 2593-2602, 2003). Interactions of ER with DNA are dynamic and include, but are not limited to, the degradation of ER by the proteasome (Reid et al., Mol Cell 11: 695-707, 2003). The degradation of ER with ligands provides an attractive treatment strategy for disease or conditions that estrogen-sensitive and/or resistant to available anti-hormonal treatments.

ER signaling is crucial for the development and maintenance of female reproductive organs including breasts, ovulation and thickening of the endometrium. ER signaling also has a role in bone mass, lipid metabolism, cancers, etc. About 70% of breast cancers express ER-α (ER-α positive) and are dependent on estrogens for growth and survival. Other cancers also are thought to be dependent on ER-α signaling for growth and survival, such as for example ovarian and endometrial cancers. The ER-α antagonist tamoxifen has been used to treat early and advanced ER-α positive breast cancer in both pre- and post-menopausal women. Fulvestrant (Faslodex™) a steroid-based ER antagonist is used to treat breast cancer in women which has have progressed despite therapy with tamoxifen. Steroidal and non-steroidal aromatase inhibitors are also used to treat cancers in humans. In some embodiments, the steroidal and non-steroidal aromatase inhibitors block the production of estrogen from androstenedione and testosterone in post-menopausal women, thereby blocking ER dependent growth in the cancers. In addition to these anti-hormonal agents, progressive ER positive breast cancer is treated in some cases with a variety of other chemotherapeutics, such as for example, the anthracylines, platins, taxanes. In some cases, ER positive breast cancers that harbor genetic amplication of the ERB-B/HER2 tyrosine kinase receptor are treated with the monoclonal antibody trastuzumab (Herceptin™) or the small molecule pan-ERB-B inhibitor lapatinib. Despite this battery of anti-hormonal, chemotherapeutic and small-molecule and antibody-based targeted therapies, many women with ER-α positive breast develop progressive metastatic disease and are in need of new therapies. Importantly, the majority of ER positive tumors that progress on existing anti-hormonal, as well as and other therapies, are thought to remain dependent on ER-α for growth and survival. Thus, there is a need for new ER-α targeting agents that have activity in the setting of metastatic disease and acquired resistance. In one aspect, described herein are compounds that are selective estrogen receptor modulators (SERMs). In specific embodiments, the SERMs described herein are selective estrogen receptor degraders (SERDs). In some embodiments, in cell-based assays the compounds described herein result in a reduction in steady state ER-α levels (i.e. ER degradation) and are useful in the treatment of estrogen sensitive diseases or conditions and/or diseases or conditions that have developed resistant to anti-hormonal therapies.

Given the central role of ER-α in breast cancer development and progression, compounds disclosed herein are useful in the treatment of breast cancer, either alone or in combination with other agent agents that can modulate other critical pathways in breast cancer, including but not limited to those that target IGF1R, EGFR, erB-B2 and 3 the PI3K/AKT/mTOR axis, HSP90, PARP or histone deacetylases.

Given the central role of ER-α in breast cancer development and progression, compounds disclosed herein are useful in the treatment of breast cancer, either alone or in combination with other agent used to treat breast cancer, including but not limited to aromatase inhibitors, anthracylines, platins, nitrogen mustard alkylating agents, taxanes. Illustrative agent used to treat breast cancer, include, but are not limited to, paclitaxel, anastrozole, exemestane, cyclophosphamide, epirubicin, fulvestrant, letrozole, gemcitabine, trastuzumab, pegfilgrastim, filgrastim, tamoxifen, docetaxel, toremifene, vinorelbine, capecitabine, ixabepilone, as well as others described herein.

ER-related diseases or conditions include ER-α dysfunction is associated with cancer (bone cancer, breast cancer, lung cancer, colorectal cancer, endometrial cancer, prostate cancer, ovarian and uterine cancer), central nervous system (CNS) defects (alcoholism, migraine), cardiovascular system defects (aortic aneurysm, susceptibility to myocardial infarction, aortic valve sclerosis, cardiovascular disease, coronary artery disease, hypertension), hematological system defects (deep vein thrombosis), immune and inflammation diseases (Graves' Disease, arthritis, multiple sclerosis, cirrhosis), susceptibility to infection (hepatitis B, chronic liver disease), metabolic defects (bone density, cholestasis, hypospadias, obesity, osteoarthritis, osteopenia, osteoporosis), neurological defects (Alzheimer's disease, Parkinson's disease, migraine, vertigo), psychiatric defects (anorexia nervosa, attention deficit hyperactivity disorder (ADHD), dementia, major depressive disorder, psychosis) and reproductive defects (age of menarche, endometriosis, infertility.

In some embodiments, compounds disclosed herein are used in the treatment of an estrogen receptor dependent or estrogen receptor mediated disease or condition in mammal.

In some embodiments, the estrogen receptor dependent or estrogen receptor mediated disease or condition is selected from cancer, central nervous system (CNS) defects, cardiovascular system defects, hematological system defects, immune and inflammation diseases, susceptibility to infection, metabolic defects, neurological defects, psychiatric defects and reproductive defects.

In some embodiments, the estrogen receptor dependent or estrogen receptor mediated disease or condition is selected from bone cancer, breast cancer, lung cancer, colorectal cancer, endometrial cancer, prostate cancer, ovarian cancer, uterine cancer, alcoholism, migraine, aortic aneurysm, susceptibility to myocardial infarction, aortic valve sclerosis, cardiovascular disease, coronary artery disease, hypertension, deep vein thrombosis, Graves' Disease, arthritis, multiple sclerosis, cirrhosis, hepatitis B, chronic liver disease, bone density, cholestasis, hypospadias, obesity, osteoarthritis, osteopenia, osteoporosis, Alzheimer's disease, Parkinson's disease, migraine, vertigo, anorexia nervosa, attention deficit hyperactivity disorder (ADHD), dementia, major depressive disorder, psychosis, age of menarche, endometriosis, and infertility.

In some embodiments, compounds disclosed herein are used to treat cancer in a mammal. In some embodiments, the cancer is breast cancer, ovarian cancer, endometrial cancer, prostate cancer, or uterine cancer. In some embodiments, the cancer is breast cancer, lung cancer, ovarian cancer, endometrial cancer, prostate cancer, or uterine cancer. In some embodiments, the cancer is breast cancer. In some embodiments, the cancer is a hormone dependent cancer. In some embodiments, the cancer is an estrogen receptor dependent cancer. In some embodiments, the cancer is an estrogen-sensitive cancer. In some embodiments, the cancer is resistant to anti-hormonal treatment. In some embodiments, the cancer is an estrogen-sensitive cancer or an estrogen receptor dependent cancer that is resistant to anti-hormonal treatment. In some embodiments, the cancer is a hormone-sensitive cancer or a hormone receptor dependent cancer that is resistant to anti-hormonal treatment. In some embodiments, anti-hormonal treatment includes treatment with at least one agent selected from tamoxifen, fulvestrant, steroidal aromatase inhibitors, and non-steroidal aromatase inhibitors-resistant.

In some embodiments, compounds disclosed herein are used to treat hormone receptor positive metastatic breast cancer in a postmenopausal woman with disease progression following anti-estrogen therapy.

In some embodiments, compounds disclosed herein are used to treat a hormonal dependent benign or malignant disease of the breast or reproductive tract in a mammal. In some embodiments, the benign or malignant disease is breast cancer.

In some embodiments, the compound used in any of the methods described herein is an estrogen receptor degrader; is an estrogen receptor antagonist; has minimal or negligible estrogen receptor agonist activity; or combinations thereof.

In some embodiments, methods of treatment with compounds described herein include a treatment regimen that includes administering radiation therapy to the mammal.

In some embodiments, methods of treatment with compounds described herein include administering the compound prior to or following surgery.

In some embodiments, methods of treatment with compounds described herein include administering to the mammal at least one additional anti-cancer agent.

In some embodiments, compounds disclosed herein are used to treat cancer in a mammal, wherein the mammal is chemotherapy-naïve.

In some embodiments, compounds disclosed herein are used to treat cancer in a mammal, wherein the mammal is being treated for cancer with at least one anti-cancer agent. In one embodiment, the cancer is a hormone refractory cancer.

Compounds

Compounds of Formula (I), (II), (III), (IV), (V), (VI), (VII), (VIII), (IX), (X), (XI), (XII), and (XIII), including pharmaceutically acceptable salts, prodrugs, active metabolites and pharmaceutically acceptable solvates thereof, are estrogen receptor modulators. In specific embodiments, the compounds described herein are estrogen receptor degraders. In specific embodiments, the compounds described herein are estrogen receptor antagonists. In specific embodiments, the compounds described herein are estrogen receptor degraders and estrogen receptor antagonists with minimal or no estrogen receptor agonist activity.

In some embodiments, compounds disclosed herein are estrogen receptor degraders and estrogen receptor antagonists that exhibit: no estrogen receptor agonism; and/or anti-proliferative activity against breast cancer, ovarian cancer, endometrial cancer, cervical cancer cell lines; and/or maximal anti-proliferative efficacy against breast cancer, ovarian cancer, endometrial cancer, cervical cell lines in-vitro; and/or minimal agonism in the human endometrial (Ishikawa) cell line; and/or no agonism in the human endometrial (Ishikawa) cell line; and/or no agonism in the immature rat uterine assay in-vivo; and/or inverse agonism in the immature rat uterine assay in-vivo; and/or anti-tumor activity in breast cancer, ovarian cancer, endometrial cancer, cervical cancer cell lines in xenograft assays in-vivo or other rodent models of these cancers.

In one aspect, provided herein is a compound of Formula (I), or a pharmaceutically acceptable salt, solvate, metabolite or prodrug thereof:

Formula (I)

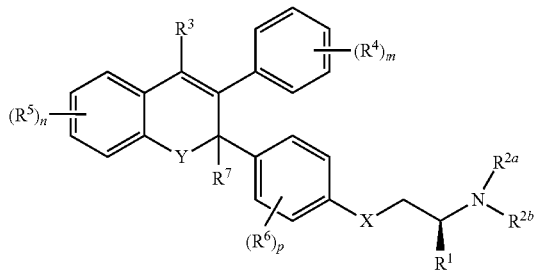

wherein,
$R^1$ is F, $C_1$-$C_6$alkyl, or $C_1$-$C_6$fluoroalkyl;
$R^{2a}$ is selected from H or $R^{10}$;
$R^{2b}$ is selected from —C(=O)$R^{10}$, —C(=O)O$R^{10}$, —C(=O)NH$R^{10}$, —S(=O)$_2R^{10}$, or $R^{10}$;
or
$R^{2a}$ and $R^{2b}$ are taken together with the N atom to which they are attached to form a substituted or unsubstituted monocyclic heterocycloalkyl, a substituted or unsubstituted bicyclic heterocycloalkyl, a substituted or unsubstituted monocyclic heteroaryl, or a substituted or unsubstituted bicyclic heteroaryl;
$R^3$ is H, halogen, $C_1$-$C_4$alkyl, $C_3$-$C_6$cycloalkyl, or $C_1$-$C_4$fluoroalkyl;
each $R^4$ is independently selected from H, halogen, —CN, —OH, —O$R^9$, —S$R^9$, —S(=O)$R^{10}$, —S(=O)$_2R^{10}$, —C(=O)$R^{10}$, —C(=O)OH, —C(=O)O$R^{10}$, —C(=O)NH$R^{10}$, —C(=O)N($R^{10}$)$_2$, substituted or unsubstituted $C_1$-$C_6$alkyl, substituted or unsubstituted $C_1$-$C_6$fluoroalkyl, substituted or unsubstituted $C_1$-$C_6$fluoroalkoxy, substituted or unsubstituted $C_1$-$C_6$alkoxy, and substituted or unsubstituted $C_1$-$C_6$heteroalkyl;
each $R^5$ is independently selected from H, halogen, —CN, —OH, —O$R^9$, —S$R^9$, —S(=O)$R^{10}$, —S(=O)$_2R^{10}$, substituted or unsubstituted $C_1$-$C_6$alkyl, substituted or unsubstituted $C_1$-$C_6$fluoroalkyl, substituted or unsubstituted $C_1$-$C_6$fluoroalkoxy, substituted or unsubstituted $C_1$-$C_6$alkoxy, and substituted or unsubstituted $C_1$-$C_6$heteroalkyl;
each $R^6$ is independently selected from H, halogen, —CN, —OH, —O$R^9$, —S$R^9$, —S(=O)$R^{10}$, —S(=O)$_2R^{10}$, substituted or unsubstituted $C_1$-$C_6$alkyl, substituted or unsubstituted $C_1$-$C_6$fluoroalkyl, substituted or unsubstituted $C_1$-$C_6$fluoroalkoxy, substituted or unsubstituted $C_1$-$C_6$alkoxy, and substituted or unsubstituted $C_1$-$C_6$heteroalkyl;
$R^7$ is H or $C_1$-$C_4$alkyl;
each $R^9$ is independently selected from H, —C(=O)$R^{10}$, —C(=O)O$R^{10}$, —C(=O)NH$R^{10}$, substituted or unsubstituted $C_1$-$C_6$alkyl, substituted or unsubstituted $C_1$-$C_6$heteroalkyl, substituted or unsubstituted $C_1$-$C_6$fluoroalkyl, substituted or unsubstituted $C_3$-$C_{10}$cycloalkyl, substituted or unsubstituted $C_2$-$C_{10}$heterocycloalkyl, substituted or unsubstituted aryl, substituted or unsubstituted heteroaryl, —$C_1$-$C_2$alkylene-(substituted or unsubstituted $C_3$-$C_{10}$cycloalkyl), —$C_1$-$C_2$alkylene-(substituted or unsubstituted $C_2$-$C_{10}$heterocycloalkyl), —$C_1$-$C_2$alkylene-(substituted or unsubstituted aryl), and —$C_1$-$C_2$alkylene-(substituted or unsubstituted heteroaryl); or each $R^{10}$ is independently selected from substituted or unsubstituted $C_1$-$C_6$alkyl, substituted or unsubstituted $C_1$-$C_6$heteroalkyl, substituted or unsubstituted $C_1$-$C_6$fluoroalkyl, substituted or unsubstituted $C_3$-$C_{10}$cycloalkyl, substituted or unsubstituted $C_2$-$C_{10}$heterocycloalkyl, substituted or unsubstituted aryl, substituted or unsubstituted heteroaryl, —$C_1$-$C_2$alkylene-(substituted or unsubstituted $C_3$-$C_{10}$cycloalkyl), —$C_1$-$C_2$alkylene-(substituted or unsubstituted $C_2$-$C_{10}$heterocycloalkyl), —$C_1$-$C_2$alkylene-(substituted or unsubstituted aryl), and —$C_1$-$C_2$alkylene-(substituted or unsubstituted heteroaryl);
Y is —O—, —S—, or —N$R^{11}$—; $R^{11}$ is H, —C(=O)$R^{10}$, substituted or unsubstituted $C_1$-$C_6$alkyl, substituted or unsubstituted $C_1$-$C_6$fluoroalkyl, or substituted or unsubstituted $C_1$-$C_6$heteroalkyl;
X is —O—, —S—, —CH$_2$—, —NH— or —N($C_1$-$C_6$alkyl)-;
m is 0, 1, 2, 3, 4 or 5;
n is 0, 1, 2, 3 or 4;
p is 0, 1, 2, 3 or 4.

For any and all of the embodiments, substituents are selected from among from a subset of the listed alternatives. For example, in some embodiments, $R^1$ is F, $C_1$-$C_4$alkyl, or $C_1$-$C_4$fluoroalkyl. In other embodiments, $R^1$ is $C_1$-$C_4$alkyl or $C_1$-$C_4$fluoroalkyl. In some embodiments, $R^1$ is —CH$_3$, —CH$_2$CH$_3$, —CF$_3$, or —CH$_2$CF$_3$.

In some embodiments, $R^3$ is H, halogen, $C_1$-$C_4$alkyl, $C_3$-$C_6$cycloalkyl, or $C_1$-$C_4$fluoroalkyl. In some embodiments, $R^3$ is H, halogen, $C_1$-$C_4$alkyl, or $C_1$-$C_4$fluoroalkyl. In some embodiments, $R^3$ is $C_1$-$C_4$alkyl, or $C_1$-$C_4$fluoroalkyl. In some embodiments, $R^3$ is $C_1$-$C_4$alkyl. In some embodiments, $R^3$ is $C_1$-$C_4$fluoroalkyl. In some embodiments, $R^3$ is $C_3$-$C_6$cycloalkyl. In some embodiments, $R^3$ is H. In some embodiments, $R^3$ is halogen. In some embodiments, $R^1$ is H, halogen, —CH$_3$, —CH$_2$CH$_3$, cyclopropyl, cyclobutyl, cyclopentyl, cyclohexyl, —CF$_3$, or —CH$_2$CF$_3$. In some embodiments, $R^1$ is H, halogen, —CH$_3$, cyclopropyl, cyclobutyl, or —CF$_3$. In some embodiments, $R^1$ is —CH$_3$, cyclopropyl, cyclobutyl, or —CF$_3$. In some embodiments, $R^1$ is —CH$_3$. In some embodiments, $R^1$ is —CF$_3$. In some embodiments, $R^1$ is cyclopropyl, cyclobutyl, cyclopentyl, or cyclohexyl. In some embodiments, $R^1$ is cyclopropyl, or cyclobutyl.

In some embodiments, $R^7$ is H or —CH$_3$. In some embodiments, $R^7$ is H.

In some embodiments, each $R^4$ is independently selected from H, halogen, —CN, —OH, —O$R^9$, —S$R^9$, —S(=O)$R^{10}$, —S(=O)$_2R^{10}$, substituted or unsubstituted $C_1$-$C_6$alkyl, substituted or unsubstituted $C_1$-$C_6$fluoroalkyl, substituted or unsubstituted $C_1$-$C_6$fluoroalkoxy, substituted or unsubstituted $C_1$-$C_6$alkoxy, and substituted or unsubstituted $C_1$-$C_6$heteroalkyl.

In some embodiments, n is 0, 1, 2, 3 or 4. In some embodiments, n is 0, 1, 2 or 3. In some embodiments, n is 0, 1 or 2. In some embodiments, n is 0 or 1. In some embodiments, n is 1, 2, 3 or 4. In some embodiments, n is 1, 2 or 3. In some embodiments, n is 1 or 2. In some embodiments, n is 1, 2, 3 or 4, and at least one $R^5$ is —OH or —O$R^9$. In some embodiments, n is 1, 2 or 3, and at least one $R^5$ is —OH. In some embodiments, n is 1 or 2, and at least one $R^5$ is —OH.

In some embodiments, p is 0, 1, 2, 3 or 4. In some embodiments, p is 0, 1, 2 or 3. In some embodiments, p is 0, 1 or 2. In some embodiments, p is 0 or 1. In some embodiments, p is 0.

In some embodiments, m is 0, 1, 2, 3, 4 or 5. In some embodiments, m is 0, 1, 2, 3 or 4. In some embodiments, m is 0, 1, 2 or 3. In some embodiments, m is 0, 1 or 2.

In some embodiments, m is 0 or 1. In some embodiments, m is 0, 1, 2, 3, 4 or 5. In some embodiments, each $R^4$ is independently selected from H, halogen, —CN, —OH, —OR$^9$, —SR$^9$, —S(═O)R$^{10}$, —S(═O)$_2$R$^{10}$, C$_1$-C$_6$alkyl, C$_1$-C$_6$fluoroalkyl, C$_1$-C$_6$fluoroalkoxy, C$_1$-C$_6$alkoxy, and C$_1$-C$_6$heteroalkyl. In some embodiments, each $R^4$ is independently halogen, —CN, —OH, —S(═O)$_2$CH$_3$, —S(═O)$_2$CH$_2$CH$_3$, —CH$_3$, —CH$_2$CH$_3$, —CHCH$_2$, —C≡CH, —CF$_3$, —CH$_2$OH, —OCF$_3$, —OCH$_3$, or —OCH$_2$CH$_3$.

In some embodiments,

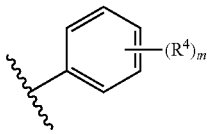

is phenyl, 2-fluorophenyl, 3-fluorophenyl, 4-fluorophenyl, 2,3-difluorophenyl, 2,4-difluorophenyl, 2,5-difluorophenyl, 2,6-difluorophenyl, 3,4-difluorophenyl, 2-chlorophenyl, 3-chlorophenyl, 4-chlorophenyl, 2,3-dichlorophenyl, 2,4-dichlorophenyl, 2,5-dichlorophenyl, 2,6-dichlorophenyl, 2-bromophenyl, 3-bromophenyl, 4-bromophenyl, 2-methylphenyl, 3-methylphenyl, 4-methylphenyl, 2-ethylphenyl, 3-ethylphenyl, 4-ethylphenyl, 2-ethenylphenyl, 3-ethenylphenyl, 4-ethenylphenyl, 2-ethynylphenyl, 3-ethynylphenyl, 4-ethynylphenyl, 2-methoxyphenyl, 3-methoxyphenyl, 4-methoxyphenyl, 2-trifluoromethylphenyl, 3-trifluoromethylphenyl, 4-trifluoromethylphenyl, 2-fluoro-4-methoxyphenyl, 2-cyanophenyl, 3-cyanophenyl, 4-cyanophenyl, 2-fluoro-3-chlorophenyl, 2-fluoro-4-chlorophenyl, 2-fluoro-5-chlorophenyl, 2-fluoro-6-chlorophenyl, 2-chloro-3-fluorophenyl, 2-chloro-4-fluorophenyl, 2-chloro-5-fluorophenyl, 2-chloro-6-fluorophenyl, 2-methyl-3-chlorophenyl, 2-methyl-4-chlorophenyl, 2-methyl-5-chlorophenyl, 2-methyl-6-chlorophenyl, 2-methyl-3-fluorophenyl, 2-methyl-4-fluorophenyl, 2-methyl-5-fluorophenyl, 2-methyl-6-fluorophenyl, 3-methyl-4-fluorophenyl, 2-trifluoromethyl-3-chlorophenyl, 2-trifluoromethyl-4-chlorophenyl, 2-trifluoromethyl-5-chlorophenyl, 2-trifluoromethyl-6-chlorophenyl, 2-hydroxyphenyl, 3-hydroxyphenyl, 4-hydroxyphenyl, 3-hydroxy-2-methylphenyl, 3-hydroxy-4-methylphenyl, 4-hydroxy-2-methylphenyl, 4-hydroxy-3-methylphenyl, 3-fluoro-5-hydroxyphenyl, 2-fluoro-3-hydroxyphenyl, 2-fluoro-4-hydroxyphenyl, 2-fluoro-5-hydroxyphenyl, 3-fluoro-4-hydroxyphenyl, 4-fluoro-3-hydroxyphenyl, 3,5-difluoro-4-hydroxyphenyl, 2,4-difluoro-3-hydroxyphenyl, 3,4-difluoro-5-hydroxyphenyl, 3-hydroxy-4-(trifluoromethyl)phenyl, 4-hydroxy-3-(trifluoromethyl)phenyl, 2-hydroxymethylphenyl, 3-hydroxymethylphenyl, 4-hydroxymethylphenyl, 2-methylsulfonylphenyl, 3-methylsulfonylphenyl, or 4-methylsulfonylphenyl.

In some embodiments,

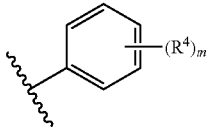

is 3-hydroxyphenyl. In some embodiments,

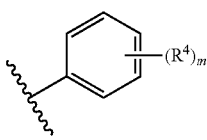

is 4-hydroxyphenyl.

In some embodiments, $R^1$ is C$_1$-C$_4$alkyl; $R^2$ is H or —CH$_3$; $R^{2a}$ and $R^{2b}$ are taken together with the N atom to which they are attached to form a substituted or unsubstituted monocyclic heterocycloalkyl, a substituted or unsubstituted bicyclic heterocycloalkyl, a substituted or unsubstituted monocyclic heteroaryl, or a substituted or unsubstituted bicyclic heteroaryl; $R^3$ is C$_1$-C$_4$alkyl or C$_1$-C$_4$fluoroalkyl; each $R^4$ is independently selected from H, halogen, —CN, —OH, —OR$^9$, —SR$^9$, —S(═O)R$^{10}$, —S(═O)$_2$R$^{10}$, C$_1$-C$_6$alkyl, C$_1$-C$_6$fluoroalkyl, C$_1$-C$_6$fluoroalkoxy, C$_1$-C$_6$alkoxy, and C$_1$-C$_6$heteroalkyl; each $R^5$ is independently selected from H, halogen, —CN, —OH, —OR$^9$, C$_1$-C$_6$alkyl, C$_1$-C$_6$fluoroalkyl, C$_1$-C$_6$fluoroalkoxy, C$_1$-C$_6$alkoxy, and C$_1$-C$_6$heteroalkyl; each $R^6$ is independently selected from H, halogen, —CN, —OH, C$_1$-C$_6$alkyl, C$_1$-C$_6$fluoroalkyl, C$_1$-C$_6$fluoroalkoxy, and C$_1$-C$_6$alkoxy; Y is —O— or —S—.

In some embodiments, the compound of Formula (I) has the structure of Formula (II):

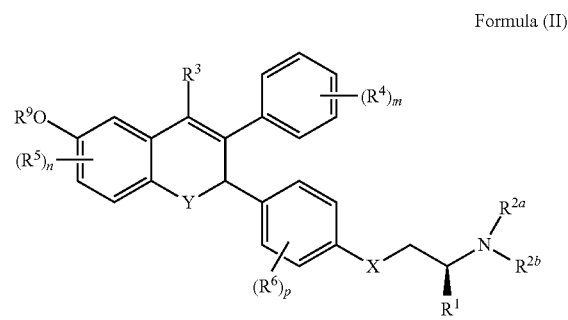

Formula (II)

wherein,
X is —O—, —S—, —CH$_2$—, —NH— or —N(CH$_3$)—;
each $R^5$ is independently selected from H, halogen, —CN, —OH, C$_1$-C$_6$alkyl, C$_1$-C$_6$fluoroalkyl, C$_1$-C$_6$fluoroalkoxy, C$_1$-C$_6$alkoxy, and C$_1$-C$_6$heteroalkyl;
each $R^6$ is independently selected from H, F, Cl, —OH, —CH$_3$, —CF$_3$, —OCF$_3$ and —OCH$_3$;
n is 0, 1, 2, or 3; p is 0, 1, or 2.

In some embodiments, the compound of Formula (I) has the structure of Formula (III):

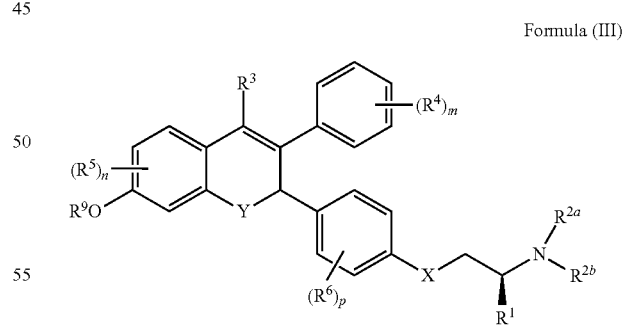

Formula (III)

wherein
X is —O—, —S—, —CH$_2$—, —NH— or —N(CH$_3$)—;
each $R^5$ is independently selected from H, halogen, —CN, —OH, C$_1$-C$_6$alkyl, C$_1$-C$_6$fluoroalkyl, C$_1$-C$_6$fluoroalkoxy, C$_1$-C$_6$alkoxy, and C$_1$-C$_6$heteroalkyl;
each $R^6$ is independently selected from H, F, Cl, —OH, —CH$_3$, —CF$_3$, —OCF$_3$ and —OCH$_3$;
n is 0, 1, 2, or 3; p is 0, 1, or 2.

In some embodiments, $R^{2a}$ and $R^{2b}$ are taken together with the N atom to which they are attached to form a substituted or unsubstituted monocyclic heterocycloalkyl, a substituted or unsubstituted bicyclic heterocycloalkyl, a substituted or unsubstituted monocyclic heteroaryl, or a substituted or unsubstituted bicyclic heteroaryl.

In some embodiments, $R^{2a}$ and $R^{2b}$ are taken together with the N atom to which they are attached to form a substituted or unsubstituted monocyclic heterocycloalkyl or a substituted or unsubstituted monocyclic heteroaryl.

In some embodiments, $R^{2a}$ and $R^{2b}$ are taken together with the N atom to which they are attached to form a substituted or unsubstituted monocyclic heterocycloalkyl.

In some embodiments, $R^{2a}$ and $R^{2b}$ are taken together with the N atom to which they are attached to form a substituted or unsubstituted azetidinyl, substituted or unsubstituted pyrrolidinyl, substituted or unsubstituted piperidinyl, substituted or unsubstituted azepanyl, substituted or unsubstituted morpholinyl, substituted or unsubstituted piperazinyl, substituted or unsubstituted 3-azabicyclo[3.1.0]hexan-3-yl, substituted or unsubstituted 3-azabicyclo[3.2.0]heptan-3-yl, substituted or unsubstituted 7-azabicyclo[2.2.1]heptan-7-yl, substituted or unsubstituted octahydrocyclopenta[c]pyrrolyl, substituted or unsubstituted octahydro-1H-isoindolyl, substituted or unsubstituted isoindolinyl, substituted or unsubstituted pyrazolyl, substituted or unsubstituted triazolyl, substituted or unsubstituted pyrrolyl, a substituted or unsubstituted imidazolyl, or substituted or unsubstituted isoindolyl.

In some embodiments, $R^{2a}$ and $R^{2b}$ are taken together with the N atom to which they are attached to form a substituted or unsubstituted azetidinyl, substituted or unsubstituted pyrrolidinyl, substituted or unsubstituted piperidinyl, substituted or unsubstituted azepanyl, substituted or unsubstituted morpholinyl, substituted or unsubstituted piperazinyl, substituted or unsubstituted 3-azabicyclo[3.1.0]hexan-3-yl, substituted or unsubstituted 3-azabicyclo[3.2.0]heptan-3-yl, substituted or unsubstituted octahydrocyclopenta[c]pyrrolyl, substituted or unsubstituted octahydro-1H-isoindolyl, substituted or unsubstituted isoindolinyl, substituted or unsubstituted pyrazolyl, substituted or unsubstituted triazolyl, substituted or unsubstituted pyrrolyl, a substituted or unsubstituted imidazolyl, or substituted or unsubstituted isoindolyl.

In some embodiments, $R^{2a}$ and $R^{2b}$ are taken together with the N atom to which they are attached to form a substituted or unsubstituted azetidinyl, substituted or unsubstituted pyrrolidinyl, substituted or unsubstituted piperidinyl, substituted or unsubstituted azepanyl, substituted or unsubstituted pyrazolyl, substituted or unsubstituted triazolyl, substituted or unsubstituted pyrrolyl, or a substituted or unsubstituted imidazolyl.

In some embodiments, $R^{2a}$ and $R^{2b}$ are taken together with the N atom to which they are attached to form a substituted or unsubstituted azetidinyl, substituted or unsubstituted pyrrolidinyl, substituted or unsubstituted piperidinyl, or substituted or unsubstituted azepanyl.

In some embodiments, $R^{2a}$ and $R^{2b}$ are taken together with the N atom to which they are attached to form a substituted or unsubstituted pyrrolidinyl, or a substituted or unsubstituted piperidinyl.

In some embodiments, $R^{2a}$ and $R^{2b}$ are taken together with the N atom to which they are attached to form a substituted or unsubstituted pyrazolyl, substituted or unsubstituted triazolyl, substituted or unsubstituted pyrrolyl, or a substituted or unsubstituted imidazolyl.

In some embodiments, $R^1$ is —$CH_3$; $R^3$ is —$CH_3$ or —$CF_3$; $R^{2a}$ and $R^{2b}$ are taken together with the N atom to which they are attached to form substituted or unsubstituted pyrrolidinyl or a substituted or unsubstituted piperidinyl.

In some embodiments, Y is —O— or —S—. In some embodiments, Y is —O—.

In some embodiments, X is —O—, —S—, —$CH_2$—, —NH— or —N($CH_3$)—. In some embodiments, X is —O—.

In some embodiments, $R^{2a}$ and $R^{2b}$ are taken together with the N atom to which they are attached to form a substituted or unsubstituted pyrrolidinyl.

In some embodiments, the compound of Formula (I) has the structure of Formula (IV):

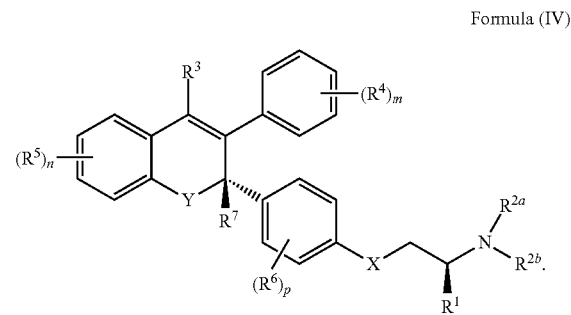

Formula (IV)

In some embodiments, the compound of Formula (I) has the structure of Formula (V):

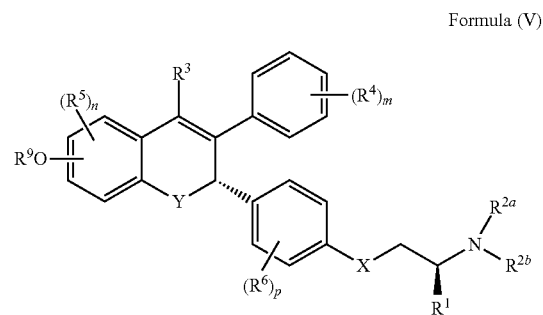

Formula (V)

wherein,
n is 0, 1 or 2; p is 0, 1 or 2.

In some embodiments, $R^1$ is —$CH_3$; $R^{2a}$ and $R^{2b}$ are taken together with the N atom to which they are attached to form a substituted or unsubstituted heterocycloalkyl; $R^3$ is —$CH_3$ or —$CF_3$; Y is —O—; X is —O—.

In some embodiments, $R^{2a}$ and $R^{2b}$ substituted or unsubstituted pyrrolidinyl or a substituted or unsubstituted piperidinyl.

In some embodiments, $R^{2a}$ and $R^{2b}$ are taken together with the N atom to which they are attached to form

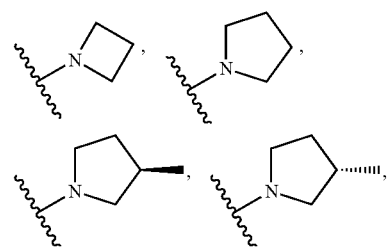

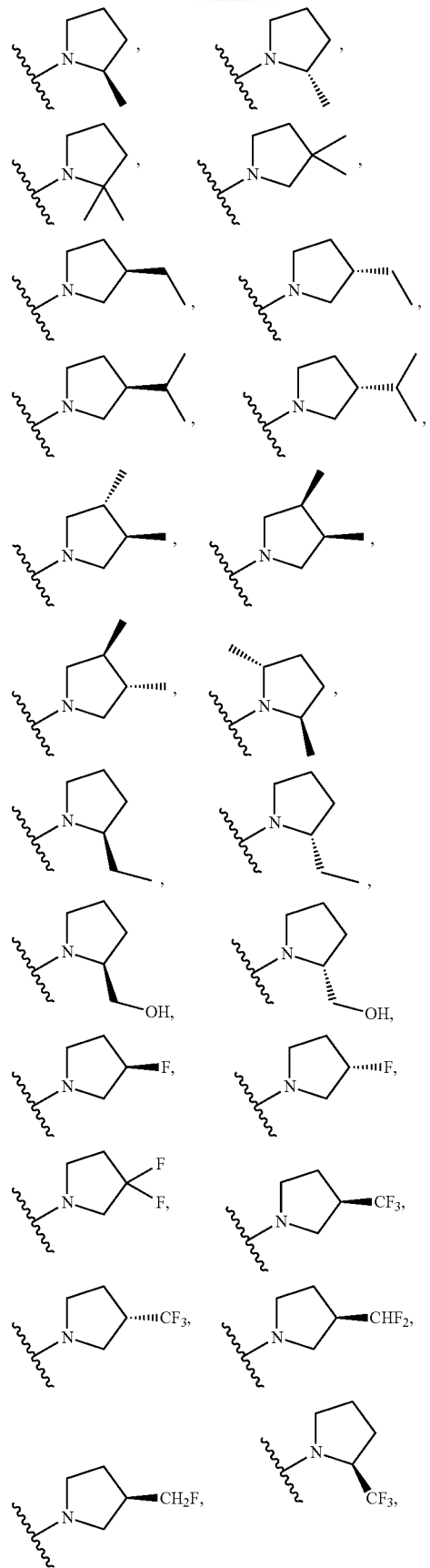
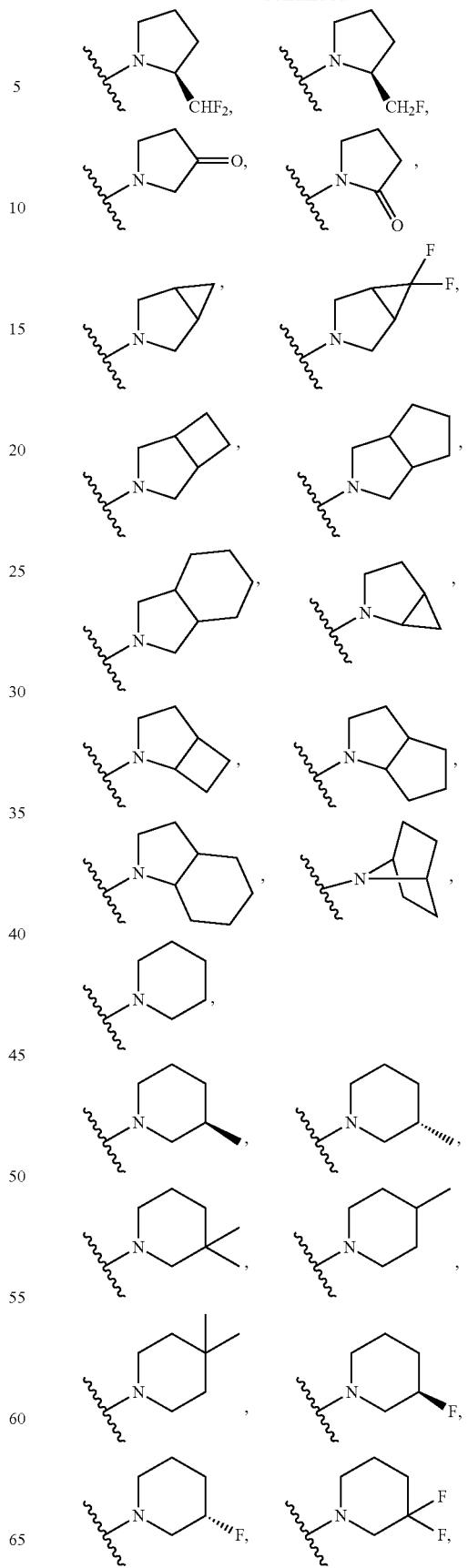

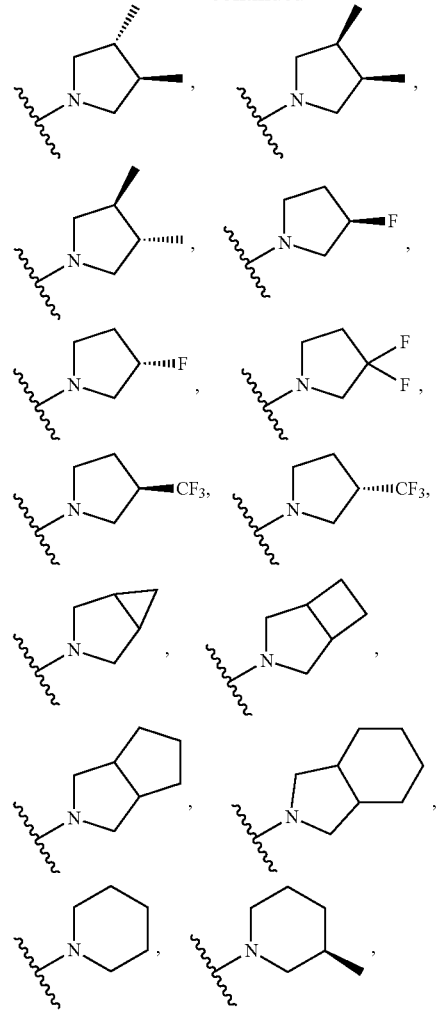
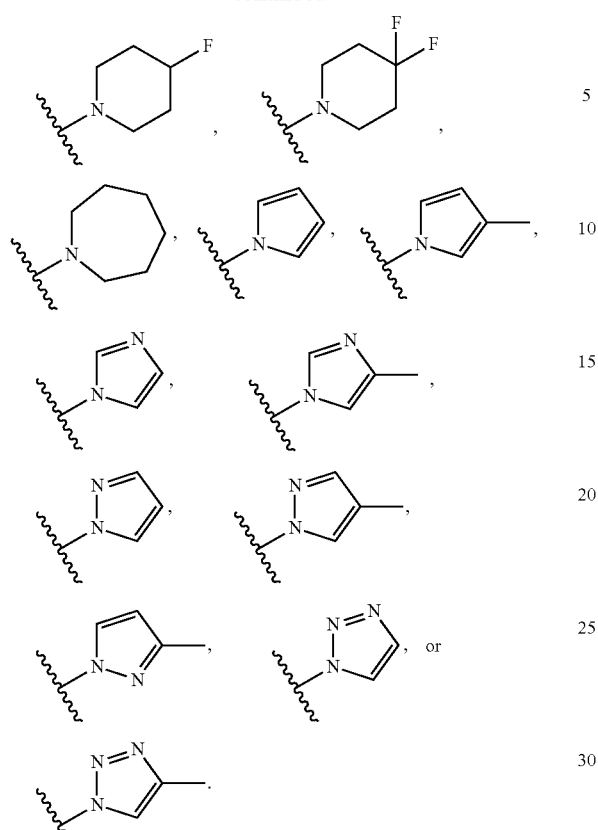
In some embodiments, $R^1$ is —$CH_3$; $R^3$ is —$CH_3$ or —$CF_3$; $R^{2a}$ and $R^{2b}$ are taken together with the N atom to which they are attached to form
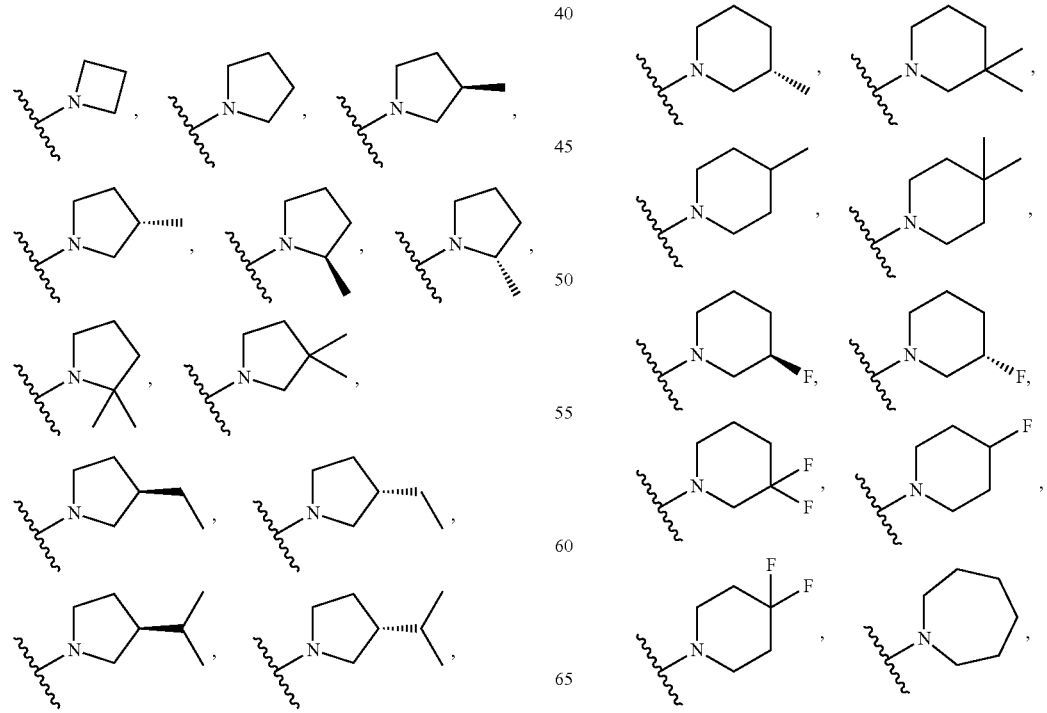

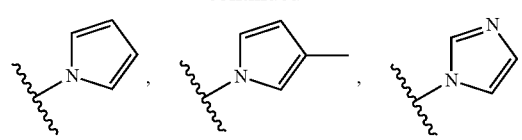
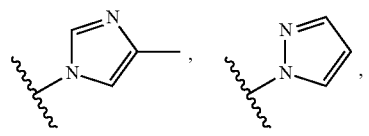
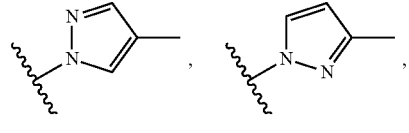
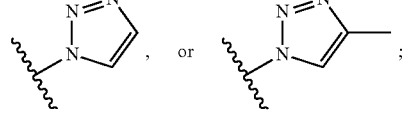
Y is —O— or —S—; X is —O—, —S—, —NH— or —N(CH₃)—.
In some embodiments, $R^{2a}$ and $R^{2b}$ are taken together with the N atom to which they are attached to form
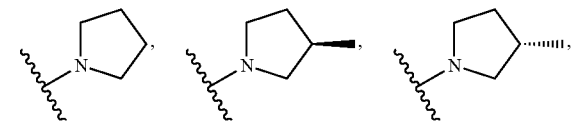
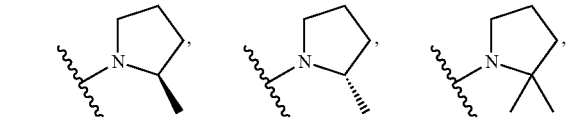
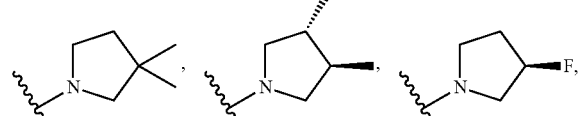
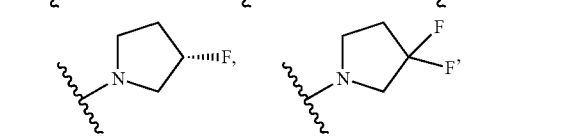
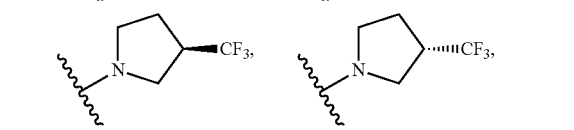
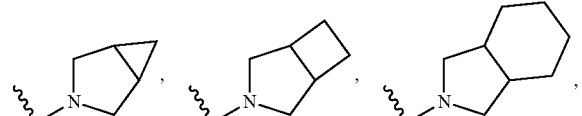
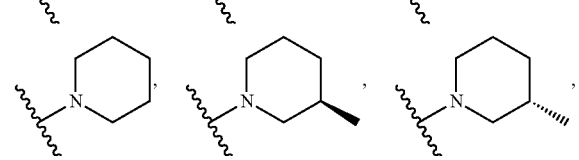
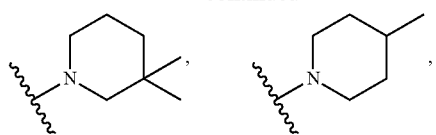
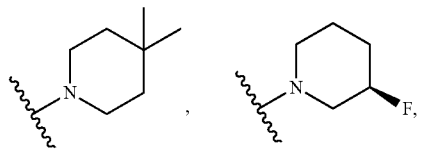
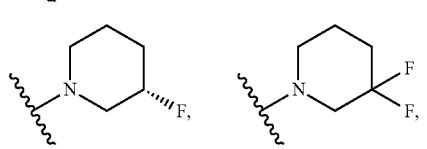
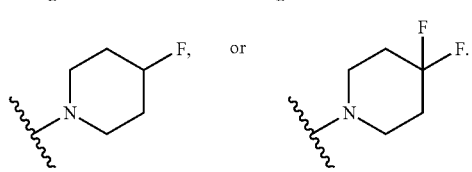
In some embodiments, $R^{2a}$ and $R^{2b}$ are taken together with the N atom to which they are attached to form
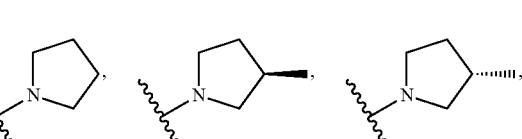
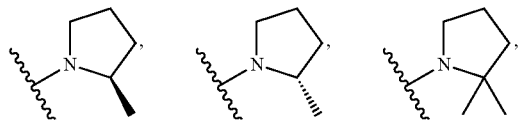
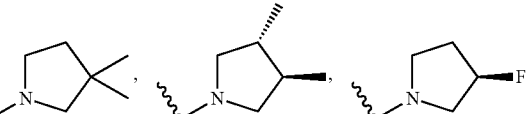
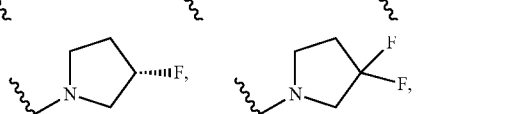
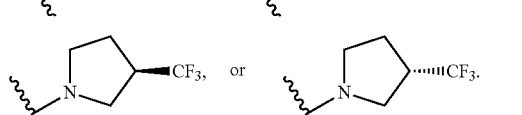
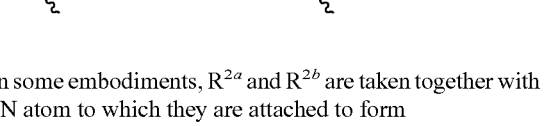
In some embodiments, $R^{2a}$ and $R^{2b}$ are taken together with the N atom to which they are attached to form
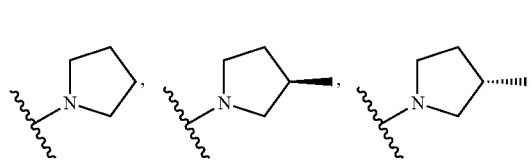

-continued

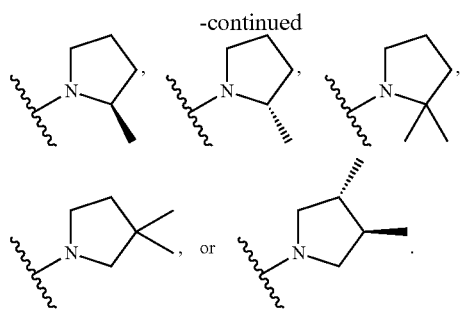

In some embodiments, $R^9$ is H; Y is —O—; X is —O—.

Also described is a compound having the structure of Formula (XIII), or a pharmaceutically acceptable salt, or solvate thereof:

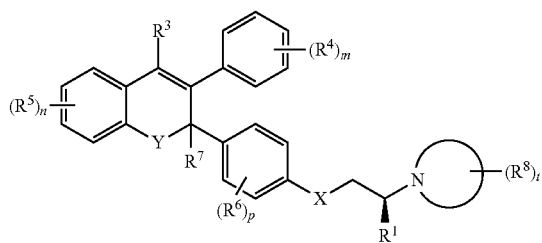

Formula (XIII)

wherein,
$R^1$ is H, F, $C_1$-$C_4$alkyl, or $C_1$-$C_4$fluoroalkyl;
$R^3$ is H, halogen, $C_1$-$C_4$alkyl, $C_3$-$C_6$cycloalkyl, or $C_1$-$C_4$fluoroalkyl;
each $R^4$ is independently selected from H, halogen, —CN, —OH, —OR$^9$, —SR$^9$, —S(=O)R$^{10}$, —S(=O)$_2$R$^{10}$, —C(=O)R$^{10}$, —C(=O)OH, —C(=O)OR$^{10}$, —C(=O)NHR$^{10}$, —C(=O)N(R$^{10}$)$_2$, substituted or unsubstituted $C_1$-$C_6$alkyl, substituted or unsubstituted $C_1$-$C_6$fluoroalkyl, substituted or unsubstituted $C_1$-$C_6$fluoroalkoxy, substituted or unsubstituted $C_1$-$C_6$alkoxy, and substituted or unsubstituted $C_1$-$C_6$heteroalkyl;
each $R^5$ is independently selected from H, halogen, —CN, —OH, —OR$^9$, —SR$^9$, —S(=O)R$^{10}$, —S(=O)$_2$R$^{10}$, substituted or unsubstituted $C_1$-$C_6$alkyl, substituted or unsubstituted $C_1$-$C_6$fluoroalkyl, substituted or unsubstituted $C_1$-$C_6$fluoroalkoxy, substituted or unsubstituted $C_1$-$C_6$alkoxy, and substituted or unsubstituted $C_1$-$C_6$heteroalkyl;
each $R^6$ is independently selected from H, halogen, —CN, —OH, —OR$^9$, —SR$^9$, —S(=O)R$^{10}$, —S(=O)$_2$R$^{10}$, substituted or unsubstituted $C_1$-$C_6$alkyl, substituted or unsubstituted $C_1$-$C_6$fluoroalkyl, substituted or unsubstituted $C_1$-$C_6$fluoroalkoxy, substituted or unsubstituted $C_1$-$C_6$alkoxy, and substituted or unsubstituted $C_1$-$C_6$heteroalkyl;
$R^7$ is H or $C_1$-$C_4$alkyl;

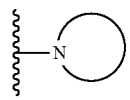

is a heterocycloalkyl or a heteroaryl;
each $R^8$ is independently selected from F, Cl, —CN, —OH, —OR$^9$, —SR$^9$, —S(=O)R$^{10}$, —S(=O)$_2$R$^{10}$, substituted or unsubstituted $C_1$-$C_6$alkyl, substituted or unsubstituted $C_1$-$C_6$fluoroalkyl, substituted or unsubstituted $C_1$-$C_6$fluoroalkoxy, substituted or unsubstituted $C_1$-$C_6$alkoxy, and substituted or unsubstituted $C_1$-$C_6$heteroalkyl;
or 1 $R^8$ is taken together with $R^1$ along with the intervening atoms joining $R^8$ to $R^1$ to form a 5-, 6-, or 7-membered ring;
each $R^9$ is independently selected from H, —C(=O)R$^{10}$, —C(=O)OR$^{10}$, —C(=O)NHR$^{10}$, substituted or unsubstituted $C_1$-$C_6$alkyl, substituted or unsubstituted $C_1$-$C_6$heteroalkyl, substituted or unsubstituted $C_1$-$C_6$fluoroalkyl, substituted or unsubstituted $C_3$-$C_{10}$cycloalkyl, substituted or unsubstituted $C_2$-$C_{10}$heterocycloalkyl, substituted or unsubstituted aryl, substituted or unsubstituted heteroaryl, —$C_1$-$C_2$alkylene-(substituted or unsubstituted $C_3$-$C_{10}$cycloalkyl), —$C_1$-$C_2$alkylene-(substituted or unsubstituted $C_2$-$C_{10}$heterocycloalkyl), —$C_1$-$C_2$alkylene-(substituted or unsubstituted aryl), and —$C_1$-$C_2$alkylene-(substituted or unsubstituted heteroaryl); or
each $R^{10}$ is independently selected from substituted or unsubstituted $C_1$-$C_6$alkyl, substituted or unsubstituted $C_1$-$C_6$heteroalkyl, substituted or unsubstituted $C_1$-$C_6$fluoroalkyl, substituted or unsubstituted $C_3$-$C_{10}$cycloalkyl, substituted or unsubstituted $C_2$-$C_{10}$heterocycloalkyl, substituted or unsubstituted aryl, substituted or unsubstituted heteroaryl, —$C_1$-$C_2$alkylene-(substituted or unsubstituted $C_3$-$C_{10}$cycloalkyl), —$C_1$-$C_2$alkylene-(substituted or unsubstituted $C_2$-$C_{10}$heterocycloalkyl), —$C_1$-$C_2$alkylene-(substituted or unsubstituted aryl), and —$C_1$-$C_2$alkylene-(substituted or unsubstituted heteroaryl);
Y is —O—, —S—, or —NR$^{11}$—; R$^{11}$ is H, —C(=O)R$^{10}$, substituted or unsubstituted $C_1$-$C_6$alkyl, substituted or unsubstituted $C_1$-$C_6$fluoroalkyl, or substituted or unsubstituted $C_1$-$C_6$heteroalkyl;
X is —O—, —S—, —CH$_2$—, —NH— or —N($C_1$-$C_6$alkyl)-;
m is 0, 1, 2, 3 or 4;
n is 0, 1, 2, 3 or 4;
p is 0, 1, 2, 3 or 4;
t is 1, 2, 3 or 4.

In some embodiments, the compound of Formula (XIII) has the structure of Formula (VI), or a pharmaceutically acceptable salt, or solvate thereof:

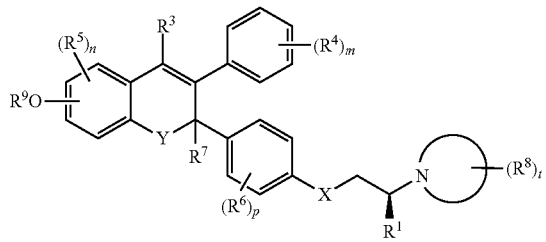

Formula (VI)

wherein,
$R^1$ is H, F, $C_1$-$C_4$alkyl, or $C_1$-$C_4$fluoroalkyl;
$R^3$ is H, halogen, $C_1$-$C_4$alkyl, $C_3$-$C_6$cycloalkyl, or $C_1$-$C_4$fluoroalkyl;

each $R^4$ is independently selected from H, halogen, —CN, —OH, —OR$^9$, —SR$^9$, —S(=O)R$^{10}$, —S(=O)$_2$R$^{10}$, —C(=O)R$^{10}$, —C(=O)OH, —C(=O)OR$^{10}$, —C(=O)NHR$^{10}$, —C(=O)N(R$^{10}$)$_2$, substituted or unsubstituted $C_1$-$C_6$alkyl, substituted or unsubstituted $C_1$-$C_6$fluoroalkyl, substituted or unsubstituted $C_1$-$C_6$fluoroalkoxy, substituted or unsubstituted $C_1$-$C_6$alkoxy, and substituted or unsubstituted $C_1$-$C_6$heteroalkyl;

each $R^5$ is independently selected from H, halogen, —CN, —OH, —OR$^9$, —SR$^9$, —S(=O)R$^{10}$, —S(=O)$_2$R$^{10}$, substituted or unsubstituted $C_1$-$C_6$alkyl, substituted or unsubstituted $C_1$-$C_6$fluoroalkyl, substituted or unsubstituted $C_1$-$C_6$fluoroalkoxy, substituted or unsubstituted $C_1$-$C_6$alkoxy, and substituted or unsubstituted $C_1$-$C_6$heteroalkyl;

each $R^6$ is independently selected from H, halogen, —CN, —OH, —OR$^9$, —SR$^9$, —S(=O)R$^{10}$, —S(=O)$_2$R$^{10}$, substituted or unsubstituted $C_1$-$C_6$alkyl, substituted or unsubstituted $C_1$-$C_6$fluoroalkyl, substituted or unsubstituted $C_1$-$C_6$fluoroalkoxy, substituted or unsubstituted $C_1$-$C_6$alkoxy, and substituted or unsubstituted $C_1$-$C_6$heteroalkyl;

$R^7$ is H or $C_1$-$C_4$alkyl;

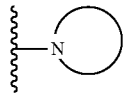

is a heterocycloalkyl or a heteroaryl;

each $R^8$ is independently selected from F, Cl, —CN, —OH, —OR$^9$, —SR$^9$, —S(=O)R$^{10}$, —S(=O)$_2$R$^{10}$, substituted or unsubstituted $C_1$-$C_6$alkyl, substituted or unsubstituted $C_1$-$C_6$fluoroalkyl, substituted or unsubstituted $C_1$-$C_6$fluoroalkoxy, substituted or unsubstituted $C_1$-$C_6$alkoxy, and substituted or unsubstituted $C_1$-$C_6$heteroalkyl;

or 1 $R^8$ is taken together with $R^1$ along with the intervening atoms joining $R^8$ to $R^1$ to form a 5-, 6-, or 7-membered ring;

each $R^9$ is independently selected from H, —C(=O)R$^{10}$, —C(=O)OR$^{10}$, —C(=O)NHR$^{10}$, substituted or unsubstituted $C_1$-$C_6$alkyl, substituted or unsubstituted $C_1$-$C_6$heteroalkyl, substituted or unsubstituted $C_1$-$C_6$fluoroalkyl, substituted or unsubstituted $C_3$-$C_{10}$cycloalkyl, substituted or unsubstituted $C_2$-$C_{10}$heterocycloalkyl, substituted or unsubstituted aryl, substituted or unsubstituted heteroaryl, —$C_1$-$C_2$alkylene-(substituted or unsubstituted $C_3$-$C_{10}$cycloalkyl), —$C_1$-$C_2$alkylene-(substituted or unsubstituted $C_2$-$C_{10}$heterocycloalkyl), —$C_1$-$C_2$alkylene-(substituted or unsubstituted aryl), and —$C_1$-$C_2$alkylene-(substituted or unsubstituted heteroaryl); or each $R^{10}$ is independently selected from substituted or unsubstituted $C_1$-$C_6$alkyl, substituted or unsubstituted $C_1$-$C_6$heteroalkyl, substituted or unsubstituted $C_1$-$C_6$fluoroalkyl, substituted or unsubstituted $C_3$-$C_{10}$cycloalkyl, substituted or unsubstituted $C_2$-$C_{10}$heterocycloalkyl, substituted or unsubstituted aryl, substituted or unsubstituted heteroaryl, —$C_1$-$C_2$alkylene-(substituted or unsubstituted $C_3$-$C_{10}$cycloalkyl), —$C_1$-$C_2$alkylene-(substituted or unsubstituted $C_2$-$C_{10}$heterocycloalkyl), —$C_1$-$C_2$alkylene-(substituted or unsubstituted aryl), and —$C_1$-$C_2$alkylene-(substituted or unsubstituted heteroaryl);

Y is —O—, —S—, or —NR$^{11}$—; R$^{11}$ is H, —C(=O)R$^{10}$, substituted or unsubstituted $C_1$-$C_6$alkyl, substituted or unsubstituted $C_1$-$C_6$fluoroalkyl, or substituted or unsubstituted $C_1$-$C_6$heteroalkyl;

X is —O—, —S—, —CH$_2$—, —NH— or —N($C_1$-$C_6$alkyl)-;

m is 0, 1, 2, 3 or 4;
n is 0, 1, 2, or 3;
p is 0, 1, 2, 3 or 4;
t is 1, 2, 3 or 4.

In some embodiments, each $R^4$ is independently selected from H, halogen, —CN, —OH, —OR$^9$, —SR$^9$, —S(=O)R$^{10}$, —S(=O)$_2$R$^{10}$, substituted or unsubstituted $C_1$-$C_6$alkyl, substituted or unsubstituted $C_1$-$C_6$fluoroalkyl, substituted or unsubstituted $C_1$-$C_6$fluoroalkoxy, substituted or unsubstituted $C_1$-$C_6$alkoxy, and substituted or unsubstituted $C_1$-$C_6$heteroalkyl.

In some embodiments, $R^1$ is H or $C_1$-$C_4$alkyl; $R^3$ is $C_1$-$C_4$alkyl or $C_1$-$C_4$fluoroalkyl; each $R^4$ is independently selected from H, halogen, —CN, —OH, —OR$^9$, —SR$^9$, —S(=O)R$^{10}$, —S(=O)$_2$R$^{10}$, $C_1$-$C_4$alkyl, $C_1$-$C_4$fluoroalkyl, $C_1$-$C_4$fluoroalkoxy, $C_1$-$C_4$alkoxy, and $C_1$-$C_4$heteroalkyl; each $R^5$ is independently selected from H, halogen, —OH, $C_1$-$C_4$alkyl, $C_1$-$C_4$fluoroalkyl, $C_1$-$C_4$fluoroalkoxy, $C_1$-$C_4$alkoxy, and $C_1$-$C_4$heteroalkyl; each $R^6$ is independently selected from H, halogen, —OH, $C_1$-$C_4$alkyl, $C_1$-$C_4$fluoroalkyl, $C_1$-$C_4$fluoroalkoxy, and $C_1$-$C_4$alkoxy; $R^7$ is H or —CH$_3$; Y is —O— or —S—; X is —O—, —S—, —CH$_2$—, —NH— or —N(CH$_3$)—; p is 0, 1, or 2.

In some embodiments, each $R^5$ is independently selected from H, F, Cl, —OH, —CH$_3$, —CF$_3$, —OCF$_3$ and —OCH$_3$. In some embodiments, each $R^5$ is independently selected from H, F, Cl, —OH, —CH$_3$ and —CF$_3$. In some embodiments, each $R^5$ is independently selected from H, F, Cl, —CH$_3$ and —CF$_3$.

In some embodiments, each $R^6$ is independently selected from H, F, Cl, —OH, —CH$_3$, —CF$_3$, —OCF$_3$ and —OCH$_3$. In some embodiments, each $R^6$ is independently selected from H, F, Cl, —OH, —CH$_3$, and —CF$_3$. In some embodiments, each $R^6$ is H.

In some embodiments, p is 0, 1, or 2. In some embodiments, p is 0 or 1. In some embodiments, p is 0.

In some embodiments, $R^2$ is H; each $R^5$ is independently selected from H, F, Cl, —OH, —CH$_3$, —CF$_3$, —OCF$_3$ and —OCH$_3$; each $R^6$ is independently selected from H, F, Cl, —OH, —CH$_3$, —CF$_3$, —OCF$_3$ and —OCH$_3$;

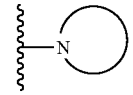

is azetidinyl, pyrrolidinyl, piperidinyl, azepanyl, morpholinyl, piperazinyl, 3-azabicyclo[3.1.0]hexan-3-yl, 3-azabicyclo[3.2.0]heptan-3-yl, octahydrocyclopenta[c]pyrrolyl, octahydro-1H-isoindolyl, isoindolinyl, pyrazolyl, triazolyl, pyrrolyl, imidazolyl, or isoindolyl.

In some embodiments,

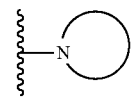

is azetidinyl, pyrrolidinyl, piperidinyl, azepanyl, morpholinyl, piperazinyl, 3-azabicyclo[3.1.0]hexan-3-yl, 3-azabicyclo[3.2.0]heptan-3-yl, octahydrocyclopenta[c]pyrrolyl, octahydro-1H-isoindolyl, isoindolinyl, pyrazolyl, triazolyl, pyrrolyl, imidazolyl, or isoindolyl. In some embodiments,

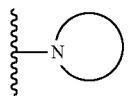

is azetidinyl, pyrrolidinyl, piperidinyl, azepanyl, morpholinyl, or piperazinyl. In some embodiments,

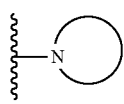

is pyrrolidinyl or piperidinyl. In some embodiments,

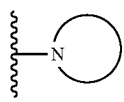

is pyrrolidinyl.

In some embodiments, each $R^8$ is independently selected from F, Cl, —OH, $C_1$-$C_4$alkyl, $C_1$-$C_4$fluoroalkyl, $C_1$-$C_4$fluoroalkoxy, $C_1$-$C_4$alkoxy, and $C_1$-$C_4$heteroalkyl.

In some embodiments,

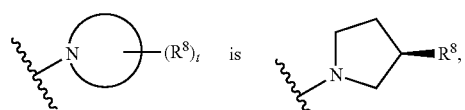

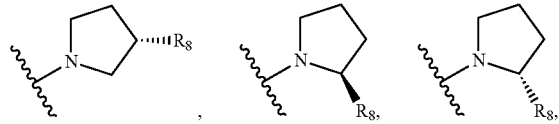

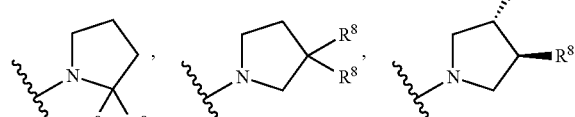

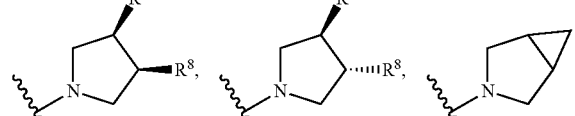

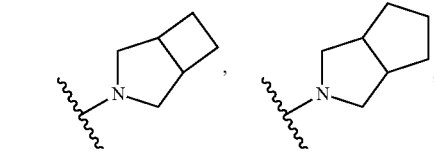

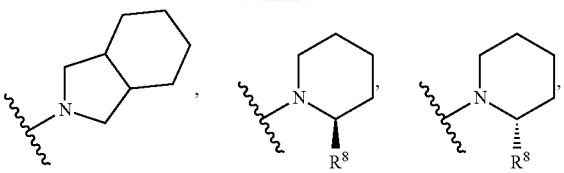

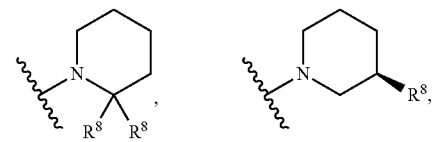

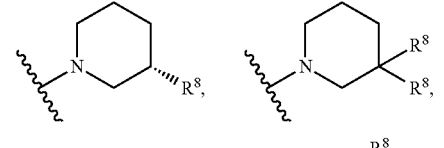

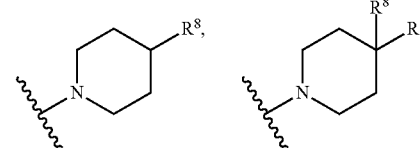

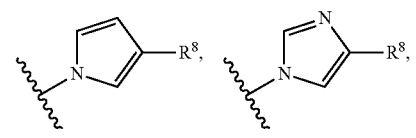

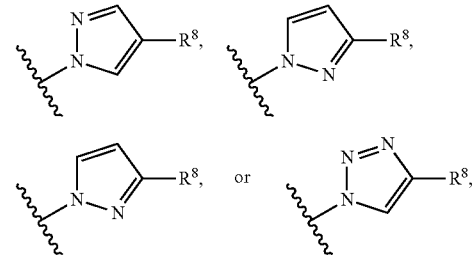

In some embodiments,

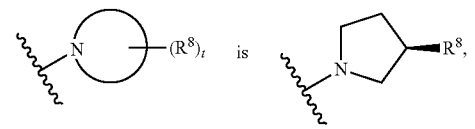

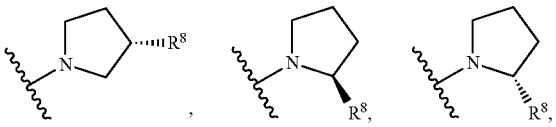

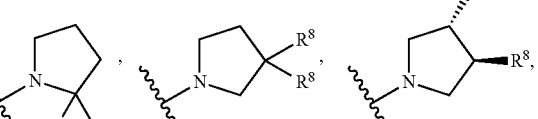

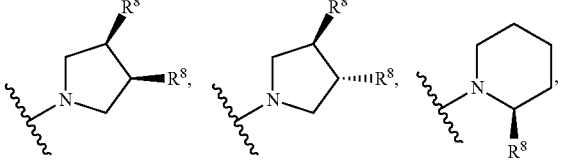

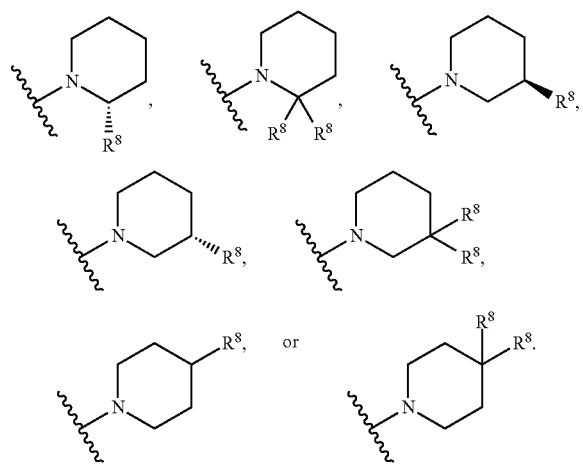
In some embodiments,
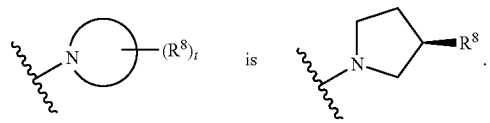
In some embodiments, each R⁸ is independently selected from F, Cl, —OH, —CH₃, —CH₂CH₃, —CH(CH₃)₂, —CF₃, —CH₂CF₃, —OCF₃, —OCH₂CF₃, —OCH₃, —OCH₂CH₃, —CH₂OCH₃, —CH₂OCH₂CH₃, and —CH₂OH. In some embodiments, each R⁸ is —CH₃.
In some embodiments,
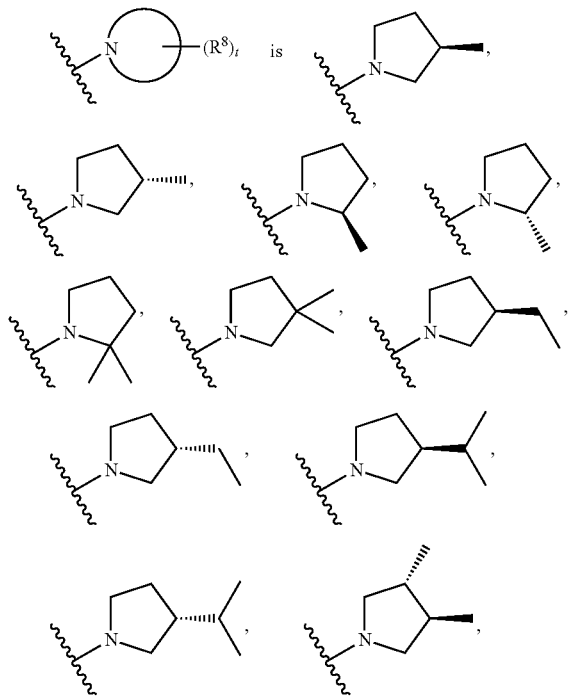
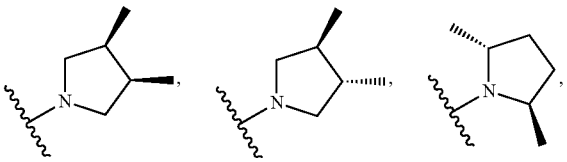
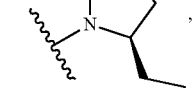
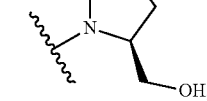
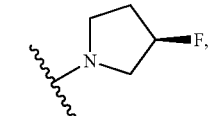
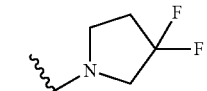
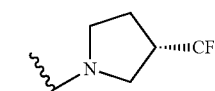
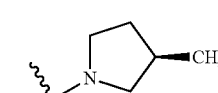
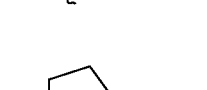
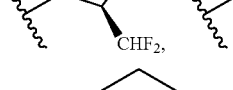
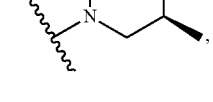
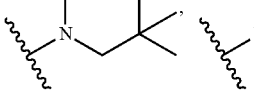
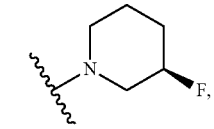
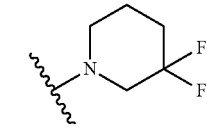

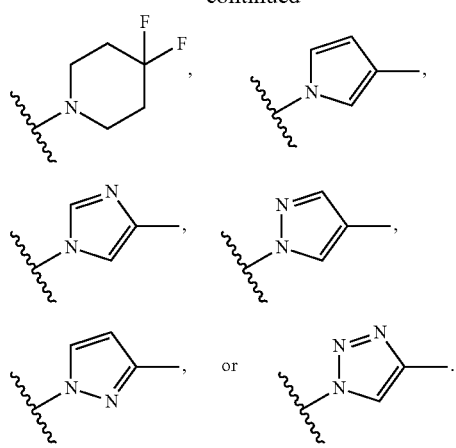
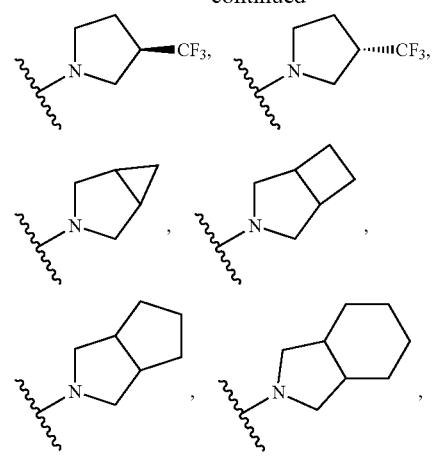
In some embodiments,
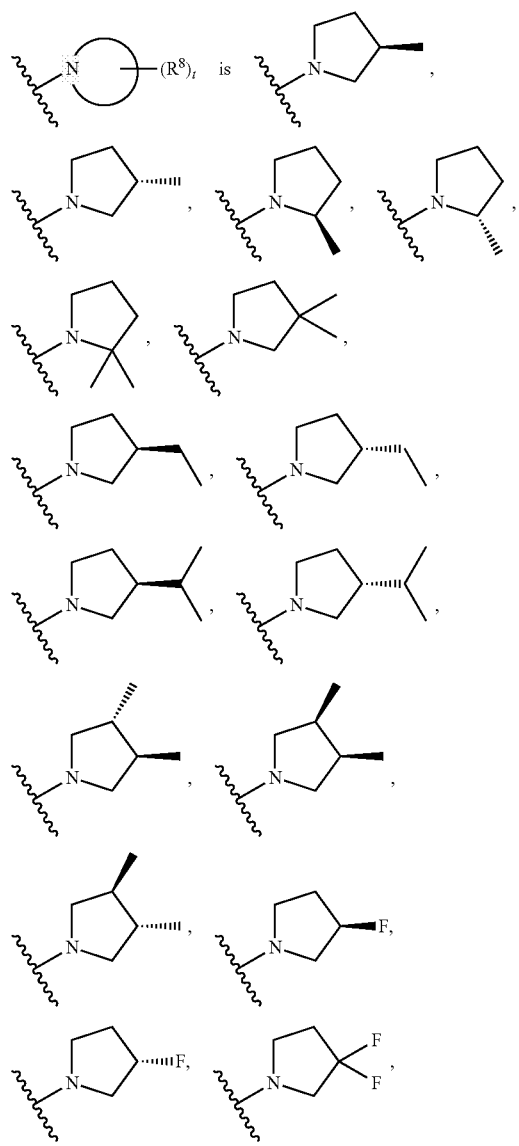

In some embodiments, the compound of Formula (VI) has the structure of Formula (VII):

Formula (VII)

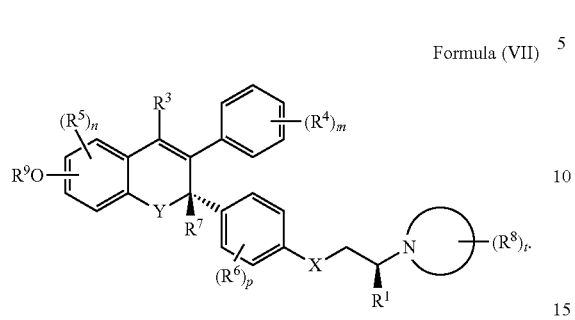

In some embodiments, the compound of Formula (VI) has the structure of Formula (VIII):

Formula (VIII)

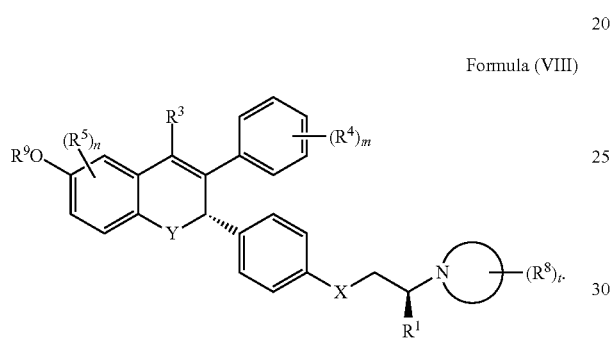

In some embodiments, the compound of Formula (VI) has the structure of Formula (IX):

Formula (IX)

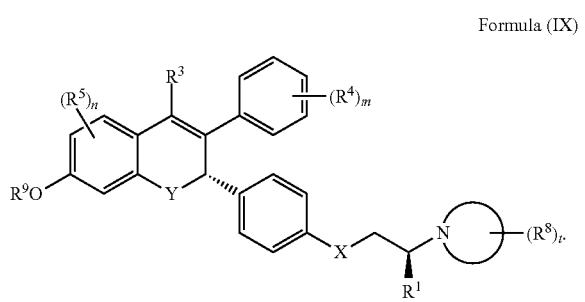

In some embodiments, the compound of Formula (VI) has the structure of Formula (X):

Formula (X)

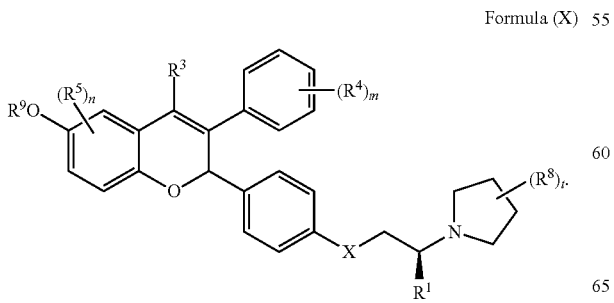

In some embodiments,

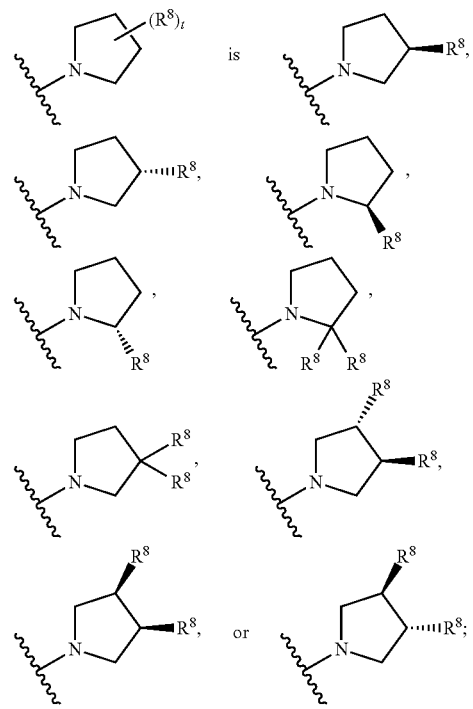

is independently selected from F, Cl, —OH, —CH₃, —CH₂CH₃, —CH(CH₃)₂, —CF₃, —CH₂CF₃, —OCF₃, —OCH₂CF₃, —OCH₃, —OCH₂CH₃, —CH₂OCH₃, —CH₂OCH₂CH₃, and —CH₂OH.

In some embodiments,

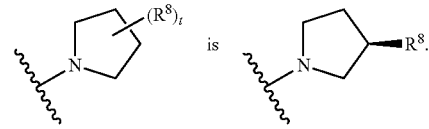

In some embodiments, R¹ is H or —CH₃; R³ is —CH₃ or —CF₃; R⁷ is H. In some embodiments, R¹ is H or —CH₃; R³ is —CH₃ or —CF₃; R⁷ is H; X is —O—. In some embodiments, R¹ is H or —CH₃; R³ is —CH₃ or —CF₃; R⁷ is H; X is —O—; Y is —O—.

In some embodiments, R¹ is —CH₃; R³ is —CH₃ or —CF₃; R⁷ is H.

Also described is a compound having the structure of Formula (XI), or a pharmaceutically acceptable salt, or solvate thereof:

Formula (XI)

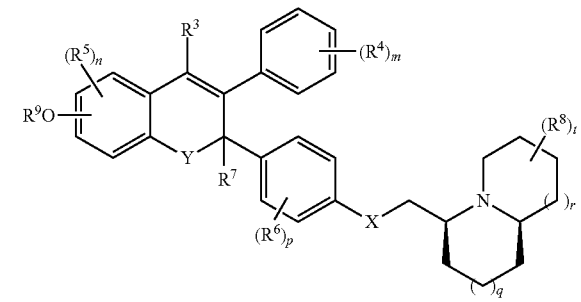

wherein,
R³ is H, halogen, $C_1$-$C_4$alkyl, $C_3$-$C_6$cycloalkyl, or $C_1$-$C_4$fluoroalkyl;
each R⁴ is independently selected from H, halogen, —CN, —OH, —OR⁹, —SR⁹, —S(=O)R¹⁰, —S(=O)₂R¹⁰, $C_1$-$C_6$alkyl, $C_1$-$C_6$fluoroalkyl, $C_1$-$C_6$fluoroalkoxy, $C_1$-$C_6$alkoxy, and $C_1$-$C_6$heteroalkyl;
each R⁵ is independently selected from H, halogen, —CN, —OH, —OR⁹, —SR⁹, —S(=O)R¹⁰, —S(=O)₂R¹⁰, $C_1$-$C_6$alkyl, $C_1$-$C_6$fluoroalkyl, $C_1$-$C_6$fluoroalkoxy, $C_1$-$C_6$alkoxy, and $C_1$-$C_6$heteroalkyl;
each R⁶ is independently selected from H, halogen, —CN, —OH, —OR⁹, —SR⁹, —S(=O)R¹⁰, —S(=O)₂R¹⁰, $C_1$-$C_6$alkyl, $C_1$-$C_6$fluoroalkyl, $C_1$-$C_6$fluoroalkoxy, $C_1$-$C_6$alkoxy, and $C_1$-$C_6$heteroalkyl;
R⁷ is H or $C_1$-$C_4$alkyl;
each R⁸ is independently selected from F, Cl, —CN, —OH, —OR⁹, —SR⁹, —S(=O)R¹⁰, —S(=O)₂R¹⁰, $C_1$-$C_6$alkyl, $C_1$-$C_6$fluoroalkyl, $C_1$-$C_6$fluoroalkoxy, $C_1$-$C_6$alkoxy, and $C_1$-$C_6$heteroalkyl;
each R⁹ is independently selected from H, —C(=O)R¹⁰, —C(=O)OR¹⁰, —C(=O)NHR¹⁰, $C_1$-$C_6$alkyl, $C_1$-$C_6$heteroalkyl, $C_1$-$C_6$fluoroalkyl, substituted or unsubstituted $C_3$-$C_{10}$cycloalkyl, substituted or unsubstituted $C_2$-$C_{10}$heterocycloalkyl, substituted or unsubstituted aryl, and substituted or unsubstituted heteroaryl; or
each R¹⁰ is independently selected from $C_1$-$C_6$alkyl, $C_1$-$C_6$heteroalkyl, $C_1$-$C_6$fluoroalkyl, substituted or unsubstituted $C_3$-$C_{10}$cycloalkyl, substituted or unsubstituted $C_2$-$C_{10}$heterocycloalkyl, substituted or unsubstituted aryl, and substituted or unsubstituted heteroaryl;
Y is —O—, or —S—;
X is —O—, —S—, —CH₂—, —NH— or —N($C_1$-$C_6$alkyl)-;
m is 0, 1, 2, 3 or 4; n is 0, 1, 2, or 3; p is 0, 1, 2, 3 or 4; q is 0, 1 or 2; r is 0, 1 or 2; t is 0, 1, 2, 3 or 4.
In some embodiments, R³ is —CH₃ or —CF₃; each R⁵ is independently selected from H, halogen, —OH, $C_1$-$C_4$alkyl, $C_1$-$C_4$fluoroalkyl, $C_1$-$C_4$fluoroalkoxy, and $C_1$-$C_4$alkoxy; each R⁶ is independently selected from H, halogen, —OH, $C_1$-$C_4$alkyl, $C_1$-$C_4$fluoroalkyl, $C_1$-$C_4$fluoroalkoxy, and $C_1$-$C_4$alkoxy; R⁷ is H; each R⁸ is independently selected from F, Cl, —OH, $C_1$-$C_4$alkyl, $C_1$-$C_4$fluoroalkyl, $C_1$-$C_4$fluoroalkoxy, $C_1$-$C_4$alkoxy, and $C_1$-$C_4$heteroalkyl; Y is —O—; X is —O—; m is 0, 1, or 2; n is 0, 1, or 2; p is 0, 1, or 2; t is 0, 1, or 2.
In some embodiments, q is 1.
Also described is a compound having the structure of Formula (XII), or a pharmaceutically acceptable salt, or solvate thereof:

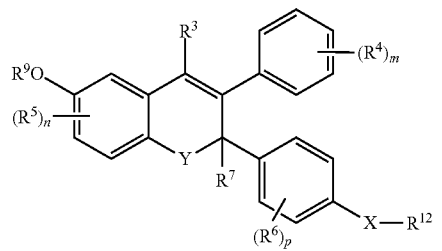

Formula (XII)

wherein,
R³ is H, halogen, $C_1$-$C_4$alkyl, $C_3$-$C_6$cycloalkyl, or $C_1$-$C_4$fluoroalkyl;
each R⁴ is independently selected from H, halogen, —CN, —OH, —OR⁹, —SR⁹, —S(=O)R¹⁰, —S(=O)₂R¹⁰, —C(=O)R¹⁰, —C(=O)OH, —C(=O)OR¹⁰, —C(=O)NHR¹⁰, —C(=O)N(R¹⁰)₂, substituted or unsubstituted $C_1$-$C_6$alkyl, substituted or unsubstituted $C_1$-$C_6$fluoroalkyl, substituted or unsubstituted $C_1$-$C_6$fluoroalkoxy, substituted or unsubstituted $C_1$-$C_6$alkoxy, and substituted or unsubstituted $C_1$-$C_6$heteroalkyl;
each R⁵ is independently selected from H, halogen, —CN, —OH, —OR⁹, —SR⁹, —S(=O)R¹⁰, —S(=O)₂R¹⁰, substituted or unsubstituted $C_1$-$C_6$alkyl, substituted or unsubstituted $C_1$-$C_6$fluoroalkyl, substituted or unsubstituted $C_1$-$C_6$fluoroalkoxy, substituted or unsubstituted $C_1$-$C_6$alkoxy, and substituted or unsubstituted $C_1$-$C_6$heteroalkyl;
each R⁶ is independently selected from H, halogen, —CN, —OH, —OR⁹, —SR⁹, —S(=O)R¹⁰, —S(=O)₂R¹⁰, substituted or unsubstituted $C_1$-$C_6$alkyl, substituted or unsubstituted $C_1$-$C_6$fluoroalkyl, substituted or unsubstituted $C_1$-$C_6$fluoroalkoxy, substituted or unsubstituted $C_1$-$C_6$alkoxy, and substituted or unsubstituted $C_1$-$C_6$heteroalkyl;
R⁷ is H or $C_1$-$C_4$alkyl;
each R⁹ is independently selected from H, —C(=O)R¹⁰, —C(=O)OR¹⁰, —C(=O)NHR¹⁰, substituted or unsubstituted $C_1$-$C_6$alkyl, substituted or unsubstituted $C_1$-$C_6$heteroalkyl, substituted or unsubstituted $C_1$-$C_6$fluoroalkyl, substituted or unsubstituted $C_3$-$C_{10}$cycloalkyl, substituted or unsubstituted $C_2$-$C_{10}$heterocycloalkyl, substituted or unsubstituted aryl, substituted or unsubstituted heteroaryl, —$C_1$-$C_2$alkylene-(substituted or unsubstituted $C_3$-$C_{10}$cycloalkyl), —$C_1$-$C_2$alkylene-substituted or unsubstituted $C_2$-$C_{10}$heterocycloalkyl), —$C_1$-$C_2$alkylene-(substituted or unsubstituted aryl), and —$C_1$-$C_2$alkylene-(substituted or unsubstituted heteroaryl); or
each R¹⁰ is independently selected from substituted or unsubstituted $C_1$-$C_6$alkyl, substituted or unsubstituted $C_1$-$C_6$heteroalkyl, substituted or unsubstituted $C_1$-$C_6$fluoroalkyl, substituted or unsubstituted $C_3$-$C_{10}$cycloalkyl, substituted or unsubstituted $C_2$-$C_{10}$heterocycloalkyl, substituted or unsubstituted aryl, substituted or unsubstituted heteroaryl, —$C_1$-$C_2$alkylene-(substituted or unsubstituted $C_3$-$C_{10}$cycloalkyl), —$C_1$-$C_2$alkylene-(substituted or unsubstituted $C_2$-$C_{10}$heterocycloalkyl), —$C_1$-$C_2$alkylene-(substituted or unsubstituted aryl), and —$C_1$-$C_2$alkylene-(substituted or unsubstituted heteroaryl);
R¹² is -L-NR²ᵃR²ᵇ,
L is a substituted or unsubstituted $C_1$-$C_6$alkylene, where if L is substituted then L is substituted with R¹, where R¹ is F, $C_1$-$C_4$alkyl, or $C_1$-$C_4$fluoroalkyl;
R²ᵃ is H or R¹⁰;
R²ᵇ is —C(=O)R¹⁰, —C(=O)OR¹⁰, —C(=O)NHR¹⁰, —S(=O)₂R¹⁰, or R¹⁰;
or
R²ᵃ and R²ᵇ are taken together with the N atom to which they are attached to form a substituted or unsubstituted monocyclic heterocycloalkyl, a substituted or unsubstituted bicyclic heterocycloalkyl, a substituted or unsubstituted monocyclic heteroaryl, or a substituted or unsubstituted bicyclic heteroaryl;

Y is —O—, —S—, or —NR$^{11}$—; R$^{11}$ is H, —C(=O)R$^{10}$, substituted or unsubstituted C$_1$-C$_6$alkyl, substituted or unsubstituted C$_1$-C$_6$fluoroalkyl, or substituted or unsubstituted C$_1$-C$_6$heteroalkyl;

X is —O—, —S—, —CH$_2$—, —NH— or —N(C$_1$-C$_6$alkyl)-;

m is 0, 1, 2, 3, 4 or 5;

n is 0, 1, 2 or 3;

p is 0, 1, 2, 3 or 4.

In some embodiments, R$^3$ is H, —CH$_3$ or CF$_3$; each R$^4$ is independently selected from H, halogen, —CN, —OH, —OR$^9$, —SR$^9$, —S(=O)R$^{10}$, —S(=O)$_2$R$^{10}$, C$_1$-C$_6$alkyl, C$_1$-C$_6$fluoroalkyl, C$_1$-C$_6$fluoroalkoxy, C$_1$-C$_6$alkoxy, and C$_1$-C$_6$heteroalkyl; each R$^5$ is independently selected from H, halogen, —CN, —OH, —OR$^9$, C$_1$-C$_6$alkyl, C$_1$-C$_6$fluoroalkyl, C$_1$-C$_6$fluoroalkoxy, C$_1$-C$_6$alkoxy, and C$_1$-C$_6$heteroalkyl; each R$^6$ is independently selected from H, halogen, —CN, —OH, C$_1$-C$_6$alkyl, C$_1$-C$_6$fluoroalkyl, C$_1$-C$_6$fluoroalkoxy, and C$_1$-C$_6$alkoxy; R$^7$ is H or —CH$_3$; R$^{12}$ is -L-NR$^{2a}$R$^{2b}$, L is a substituted or unsubstituted ethylene, where if L is substituted then L is substituted with R$^1$, where R$^1$ is —CH$_3$, —CF$_3$, —CHF$_2$, —CH$_2$F; R$^{2a}$ is H or R$^{10}$; R$^{2b}$ is R$^{10}$; or R$^{2a}$ and R$^{2b}$ are taken together with the N atom to which they are attached to form a substituted or unsubstituted monocyclic heterocycloalkyl, a substituted or unsubstituted bicyclic heterocycloalkyl, a substituted or unsubstituted monocyclic heteroaryl, or a substituted or unsubstituted bicyclic heteroaryl; Y is —O—; X is —O—, —S—, —CH$_2$—, —NH— or —N(CH$_3$)—; m is 0, 1, 2, or 3; n is 0, 1, 2 or 3; p is 0 or 1.

In some embodiments, L is a substituted or unsubstituted ethylene or propylene, where if L is substituted then L is substituted with R$^1$. In some embodiments, L is a substituted or unsubstituted ethylene, where if L is substituted then L is substituted with R$^1$.

In some embodiments, R$^{12}$ is —CH$_2$CH$_2$—NR$^{2a}$R$^{2b}$ or —CH$_2$CH(R$^1$)—NR$^{2a}$R$^{2b}$. In some embodiments, R$^{12}$ is —CH$_2$CH$_2$—NR$^{2a}$R$^{2b}$. In some embodiments, R$^{12}$ is —CH$_2$CH(R$^1$)—NR$^{2a}$R$^{2b}$.

In some embodiments, R$^{12}$ is —CH$_2$CH$_2$—NR$^{2a}$R$^{2b}$ or

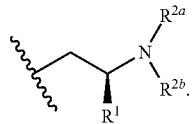

In some embodiments, R$^{12}$ is R$^{12}$ is

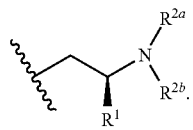

In some embodiments, R$^3$ is —CH$_3$; R$^7$ is H; R$^{12}$ is

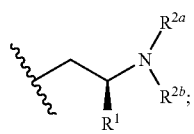

R$^{2a}$ is H, C$_1$-C$_6$alkyl, C$_3$-C$_{10}$cycloalkyl, substituted or unsubstituted aryl, or substituted or unsubstituted heteroaryl; R$^{2b}$ is C$_1$-C$_6$alkyl, C$_3$-C$_{10}$cycloalkyl, substituted or unsubstituted aryl, or substituted or unsubstituted heteroaryl; or R$^{2a}$ and R$^{2b}$ are taken together with the N atom to which they are attached to form a substituted or unsubstituted monocyclic heterocycloalkyl, a substituted or unsubstituted bicyclic heterocycloalkyl, a substituted or unsubstituted monocyclic heteroaryl, or a substituted or unsubstituted bicyclic heteroaryl; Y is —O—; X is —O—; p is 0.

In some embodiments, R$^{2a}$ and R$^{2b}$ are taken together with the N atom to which they are attached to form a heterocycle as described herein.

In some embodiments, R$^{2a}$ and R$^{2b}$ are taken together with the N atom to which they are attached to form

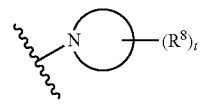

as described herein.

In some embodiments, R$^{2a}$ and R$^{2b}$ are taken together with the N atom to which they are attached to form

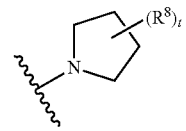

as described herein.

In some embodiments, the compound of Formula (XII) has the structure:

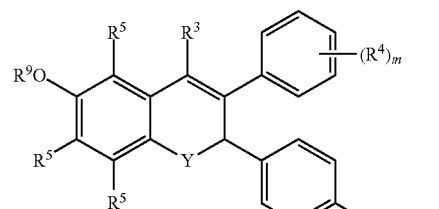

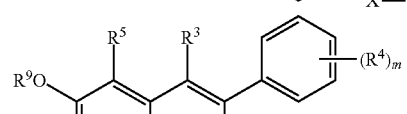

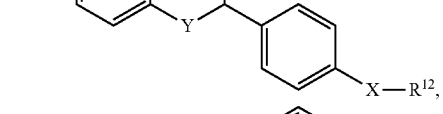

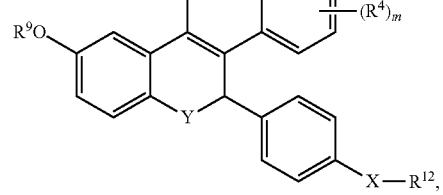

-continued

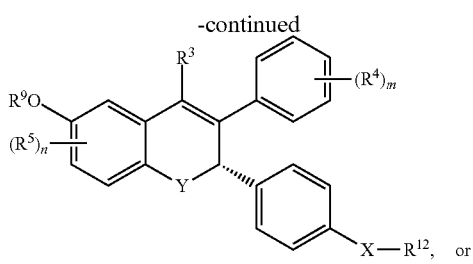

In some embodiments, each R⁹ is independently selected from H, —C(=O)R¹⁰, —C(=O)OR¹⁰, —C(=O)NHR¹⁰, $C_1$-$C_6$alkyl, $C_1$-$C_6$heteroalkyl, $C_1$-$C_6$fluoroalkyl, substituted or unsubstituted $C_3$-$C_{10}$cycloalkyl, substituted or unsubstituted $C_2$-$C_{10}$heterocycloalkyl, substituted or unsubstituted aryl, substituted or unsubstituted heteroaryl, —$C_1$-$C_2$alkylene-(substituted or unsubstituted $C_3$-$C_{10}$cycloalkyl), —$C_1$-$C_2$alkylene-(substituted or unsubstituted $C_2$-$C_{10}$heterocycloalkyl), —$C_1$-$C_2$alkylene-(substituted or unsubstituted aryl), and —$C_1$-$C_2$alkylene-(substituted or unsubstituted heteroaryl). In some embodiments, each R⁹ is independently selected from H, —C(=O)R¹⁰, —C(=O)OR¹⁰, —C(=O)NHR¹⁰, $C_1$-$C_6$alkyl, $C_1$-$C_6$heteroalkyl, $C_1$-$C_6$fluoroalkyl, substituted or unsubstituted $C_3$-$C_{10}$cycloalkyl, substituted or unsubstituted $C_2$-$C_{10}$heterocycloalkyl, substituted or unsubstituted phenyl, substituted or unsubstituted heteroaryl. In some embodiments, each R⁹ is independently selected from H and $C_1$-$C_6$alkyl.

In some embodiments, each R¹⁰ is independently selected from $C_1$-$C_6$alkyl, $C_1$-$C_6$heteroalkyl, $C_1$-$C_6$fluoroalkyl, substituted or unsubstituted $C_3$-$C_{10}$cycloalkyl, substituted or unsubstituted $C_2$-$C_{10}$heterocycloalkyl, substituted or unsubstituted aryl, substituted or unsubstituted heteroaryl, —$C_1$-$C_2$alkylene-(substituted or unsubstituted $C_3$-$C_{10}$cycloalkyl), —$C_1$-$C_2$alkylene-(substituted or unsubstituted $C_2$-$C_{10}$heterocycloalkyl), —$C_1$-$C_2$alkylene-(substituted or unsubstituted aryl), and —$C_1$-$C_2$alkylene-(substituted or unsubstituted heteroaryl). In some embodiments, each R¹⁰ is independently selected from $C_1$-$C_6$alkyl, $C_1$-$C_6$heteroalkyl, $C_1$-$C_6$fluoroalkyl, substituted or unsubstituted $C_3$-$C_{10}$cycloalkyl, substituted or unsubstituted $C_2$-$C_{10}$heterocycloalkyl, substituted or unsubstituted aryl, substituted or unsubstituted heteroaryl. In some embodiments, each R¹⁰ is $C_1$-$C_6$alkyl.

Any combination of the groups described above for the various variables is contemplated herein. Throughout the specification, groups and substituents thereof are chosen by one skilled in the field to provide stable moieties and compounds.

Compounds of Formula (I), (II), (III), (IV), (V), (VI), (VII), (VIII), (IX), (X), (XI), (XII), or (XIII), include, but are not limited to, compounds in the following table:

| Example | Structure | Compound Name |
|---|---|---|
| 1 | 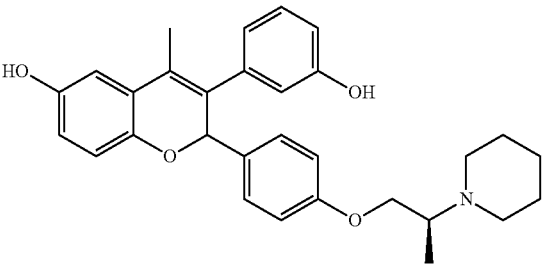 [SMILES: CC1=C(c2cccc(O)c2)C(c2ccc(OC[C@H](C)N3CCCCC3)cc2)Oc2ccc(O)cc21] | 3-(3-Hydroxyphenyl)-4-methyl-2-(4-((S)-2-(piperidin-1-yl)propoxy)phenyl)-2H-chromen-6-ol |
| 2 | 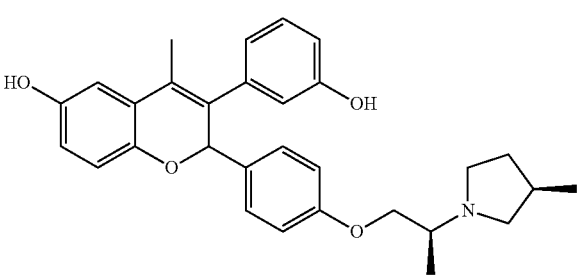 | 3-(3-Hydroxyphenyl)-4-methyl-2-(4-((S)-2-((R)-3-methylpyrrolidin-1-yl)propoxy)phenyl)-2H-chromen-6-ol |

| Example | Structure | Compound Name |
|---|---|---|
| 2a | 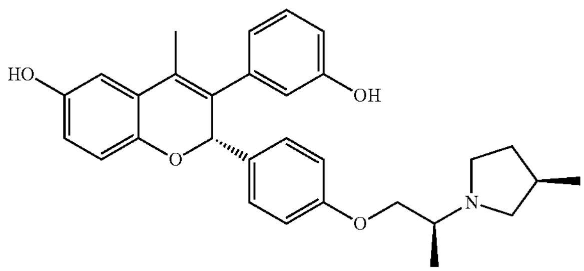 [SMILES: CC1=C(c2cccc(O)c2)[C@H](c2ccc(OC[C@H](C)N3CC[C@@H](C)C3)cc2)Oc2ccc(O)cc21] | (S)-3-(3-Hydroxyphenyl)-4-methyl-2-(4-((S)-2-((R)-3-methylpyrrolidin-1-yl)propoxy)phenyl)-2H-chromen-6-ol |
| 2b | 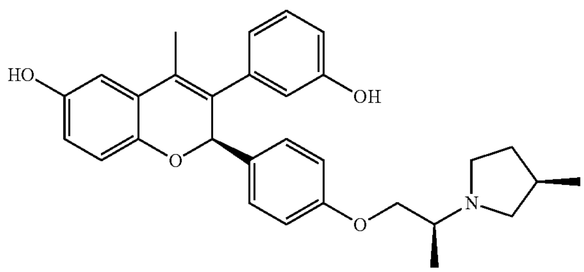 [SMILES: CC1=C(c2cccc(O)c2)[C@@H](c2ccc(OC[C@H](C)N3CC[C@@H](C)C3)cc2)Oc2ccc(O)cc21] | (R)-3-(3-Hydroxyphenyl)-4-methyl-2-(4-((S)-2-((R)-3-methylpyrrolidin-1-yl)propoxy)phenyl)-2H-chromen-6-ol |
| 3 | 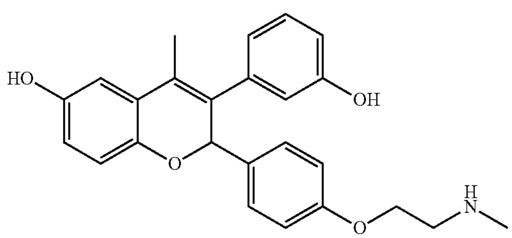 [SMILES: CNCCOc1ccc(C2Oc3ccc(O)cc3C(C)=C2c2cccc(O)c2)cc1] | 3-(3-Hydroxyphenyl)-4-methyl-2-(4-(2-(methylamino)ethoxy)phenyl)-2H-chromen-6-ol |
| 4 | 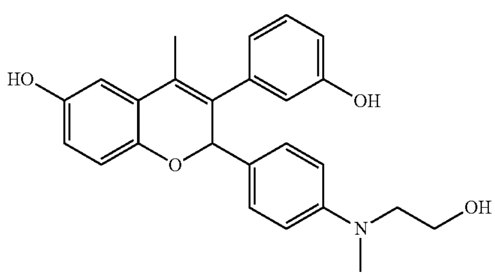 [SMILES: CC1=C(c2cccc(O)c2)C(c2ccc(N(C)CCO)cc2)Oc2ccc(O)cc21] | 2-(4-((2-Hydroxyethyl)(methyl)amino)phenyl)-3-(3-hydroxyphenyl)-4-methyl-2H-chromen-6-ol |
| 5 | 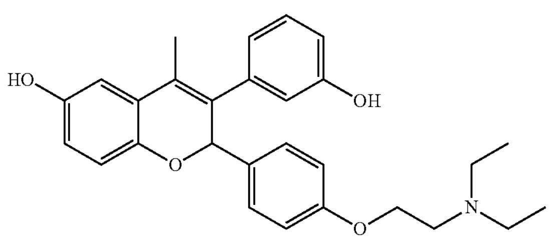 [SMILES: CCN(CC)CCOc1ccc(C2Oc3ccc(O)cc3C(C)=C2c2cccc(O)c2)cc1] | 2-(4-(2-(Diethylamino)ethoxy)phenyl)-3-(3-hydroxyphenyl)-4-methyl-2H-chromen-6-ol |
| 6 | 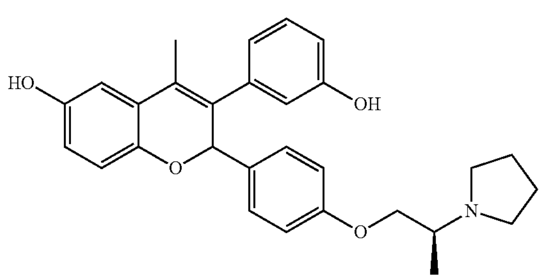 | 3-(3-Hydroxyphenyl)-4-methyl-2-(4-((S)-2-(pyrrolidin-1-yl)propoxy)phenyl)-2H-chromen-6-ol |

-continued

| Example | Structure | Compound Name |
|---|---|---|
| 7 | 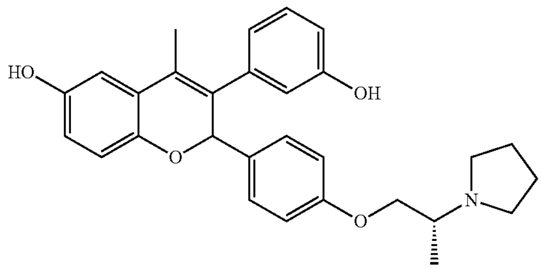 [SMILES: CC1=C(c2cccc(O)c2)C(c2ccc(OC[C@@H](C)N3CCCC3)cc2)Oc2ccc(O)cc21] | 3-(3-Hydroxyphenyl)-4-methyl-2-(4-((R)-2-(pyrrolidin-1-yl)propoxy)phenyl)-2H-chromen-6-ol |
| 8 | 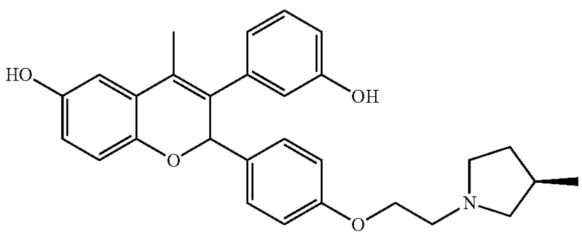 [SMILES: CC1=C(c2cccc(O)c2)C(c2ccc(OCCN3CC[C@@H](C)C3)cc2)Oc2ccc(O)cc21] | 3-(3-Hydroxyphenyl)-4-methyl-2-(4-(2-((R)-3-methylpyrrolidin-1-yl)ethoxy)phenyl)-2H-chromen-6-ol |
| 9 | 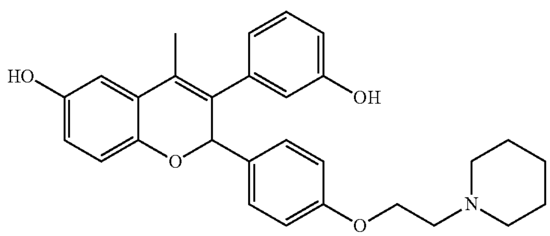 [SMILES: CC1=C(c2cccc(O)c2)C(c2ccc(OCCN3CCCCC3)cc2)Oc2ccc(O)cc21] | 3-(3-Hydroxyphenyl)-4-methyl-2-(4-(2-piperidylethoxy)phenyl)-2H-chromen-6-ol |
| 10 | 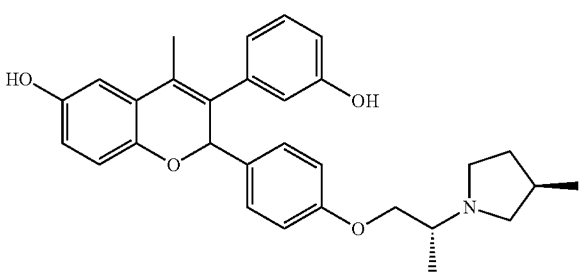 [SMILES: CC1=C(c2cccc(O)c2)C(c2ccc(OC[C@@H](C)N3CC[C@@H](C)C3)cc2)Oc2ccc(O)cc21] | 3-(3-Hydroxyphenyl)-4-methyl-2-(4-((R)-2-((R)-3-methylpyrrolidin-1-yl)propoxy)phenyl)-2H-chromen-6-ol |
| 11 | 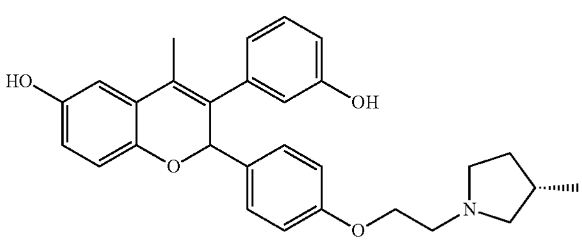 [SMILES: CC1=C(c2cccc(O)c2)C(c2ccc(OCCN3CC[C@H](C)C3)cc2)Oc2ccc(O)cc21] | 3-(3-Hydroxyphenyl)-4-methyl-2-(4-(2-((S)-3-methylpyrrolidin-1-yl)ethoxy)phenyl)-2H-chromen-6-ol |
| 12 | 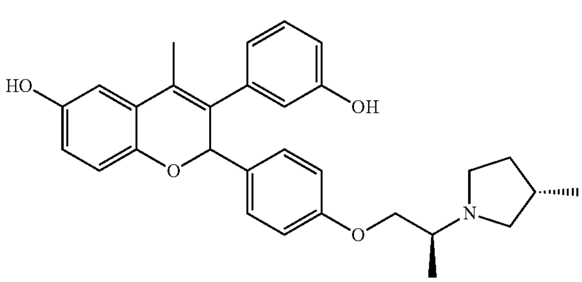 [SMILES: CC1=C(c2cccc(O)c2)C(c2ccc(OC[C@H](C)N3CC[C@H](C)C3)cc2)Oc2ccc(O)cc21] | 3-(3-Hydroxyphenyl)-4-methyl-2-(4-((S)-2-((S)-3-methylpyrrolidin-1-yl)propoxy)phenyl)-2H-chromen-6-ol |

-continued

| Example | Structure | Compound Name |
|---|---|---|
| 13 | 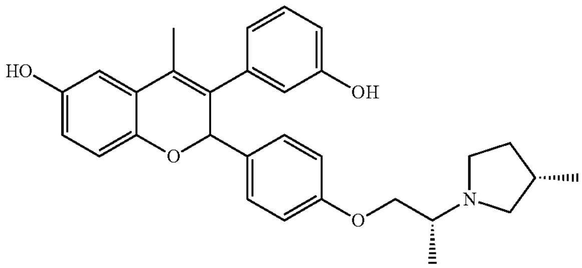 [SMILES: CC1=C(c2cccc(O)c2)C(c2ccc(OC[C@@H](C)N3CC[C@H](C)C3)cc2)Oc2ccc(O)cc21] | 3-(3-Hydroxyphenyl)-4-methyl-2-(4-((R)-2-((S)-3-methylpyrrolidin-1-yl)propoxy)phenyl)-2H-chromen-6-ol |
| 14 | 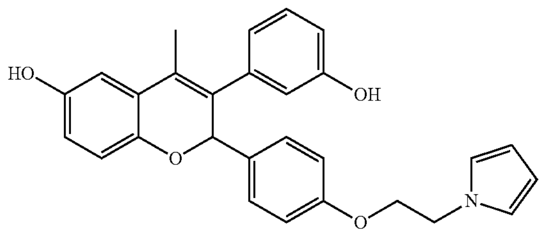 [SMILES: CC1=C(c2cccc(O)c2)C(c2ccc(OCCn3cccc3)cc2)Oc2ccc(O)cc21] | 3-(3-Hydroxyphenyl)-4-methyl-2-(4-(2-pyrrolylethoxy)phenyl)-2H-chromen-6-ol |
| 15 | 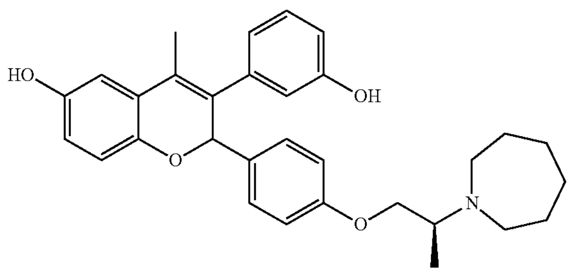 [SMILES: CC1=C(c2cccc(O)c2)C(c2ccc(OC[C@H](C)N3CCCCCC3)cc2)Oc2ccc(O)cc21] | 2-(4-((S)-2-(Azepan-1-yl)propoxy)phenyl)-3-(3-hydroxyphenyl)-4-methyl-2H-chromen-6-ol |
| 16 | 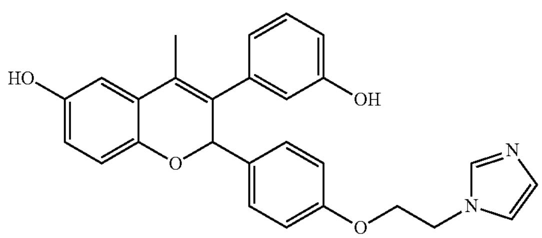 [SMILES: CC1=C(c2cccc(O)c2)C(c2ccc(OCCn3ccnc3)cc2)Oc2ccc(O)cc21] | 3-(3-Hydroxyphenyl)-2-(4-(2-imidazolylethoxy)phenyl)-4-methyl-2H-chromen-6-ol |
| 17 | 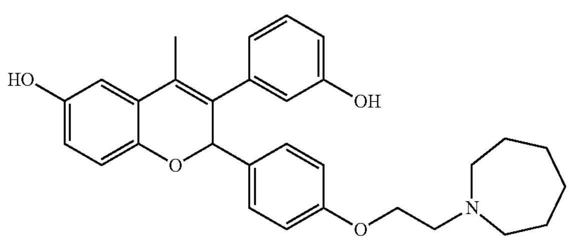 [SMILES: CC1=C(c2cccc(O)c2)C(c2ccc(OCCN3CCCCCC3)cc2)Oc2ccc(O)cc21] | 2-(4-(2-(Azepan-1-yl)ethoxy)phenyl)-3-(3-hydroxyphenyl)-4-methyl-2H-chromen-6-ol |
| 18 | 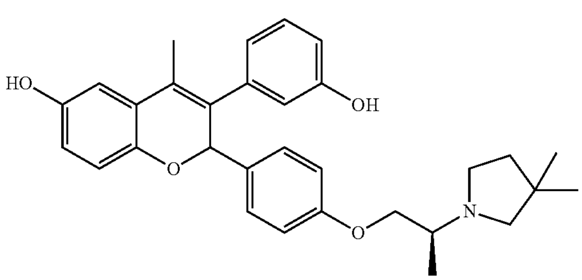 [SMILES: CC1=C(c2cccc(O)c2)C(c2ccc(OC[C@H](C)N3CCC(C)(C)C3)cc2)Oc2ccc(O)cc21] | 2-(4-((S)-2-(3,3-Dimethylpyrrolidin-1-yl)propoxy)phenyl)-3-(3-hydroxyphenyl)-4-methyl-2H-chromen-6-ol |

-continued

| Example | Structure | Compound Name |
|---|---|---|
| 19 | 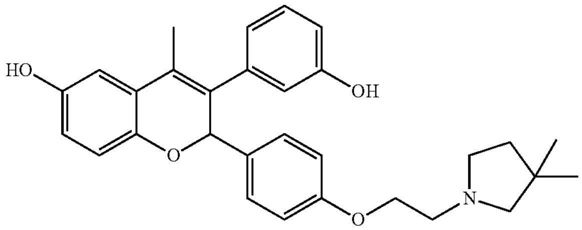 [SMILES: CC1=C(c2cccc(O)c2)C(c2ccc(OCCN3CCC(C)(C)C3)cc2)Oc2ccc(O)cc21] | 2-(4-(2-(3,3-Dimethylpyrrolidin-1-yl)ethoxy)phenyl)-3-(3-hydroxyphenyl)-4-methyl-2H-chromen-6-ol |
| 20 | 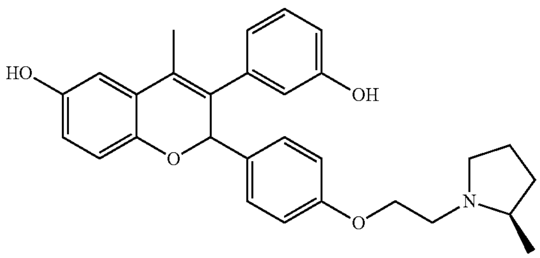 [SMILES: CC1=C(c2cccc(O)c2)C(c2ccc(OCCN3CCC[C@H]3C)cc2)Oc2ccc(O)cc21] | 3-(3-Hydroxyphenyl)-4-methyl-2-(4-(2-((R)-2-methylpyrrolidin-1-yl)ethoxy)phenyl)-2H-chromen-6-ol |
| 21 | 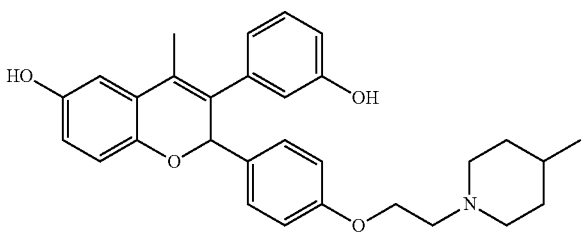 [SMILES: CC1=C(c2cccc(O)c2)C(c2ccc(OCCN3CCC(C)CC3)cc2)Oc2ccc(O)cc21] | 3-(3-Hydroxyphenyl)-4-methyl-2-(4-(2-(4-methylpiperidin-1-yl)ethoxy)phenyl)-2H-chromen-6-ol |
| 22 | 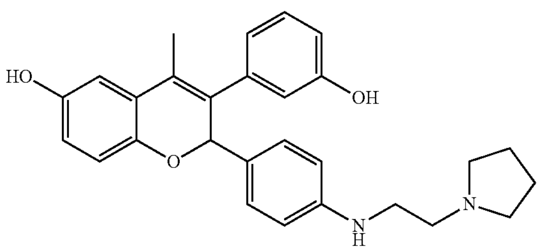 [SMILES: CC1=C(c2cccc(O)c2)C(c2ccc(NCCN3CCCC3)cc2)Oc2ccc(O)cc21] | 3-(3-Hydroxyphenyl)-4-methyl-2-(4-((2-(pyrrolidin-1-yl)ethyl)amino)phenyl)-2H-chromen-6-ol |
| 23 | 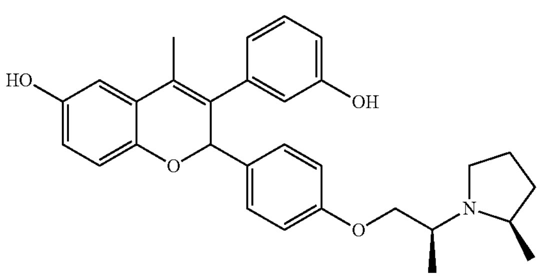 [SMILES: CC1=C(c2cccc(O)c2)C(c2ccc(OC[C@H](C)N3CCC[C@H]3C)cc2)Oc2ccc(O)cc21] | 3-(3-Hydroxyphenyl)-4-methyl-2-(4-((S)-2-((R)-2-methylpyrrolidin-1-yl)propoxy)phenyl)-2H-chromen-6-ol |
| 24 | 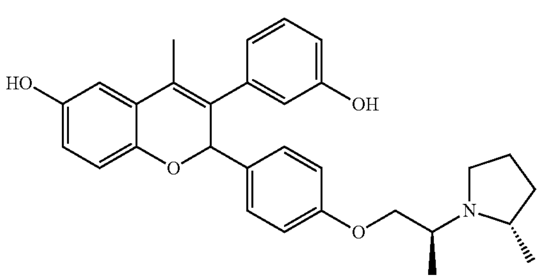 [SMILES: CC1=C(c2cccc(O)c2)C(c2ccc(OC[C@H](C)N3CCC[C@@H]3C)cc2)Oc2ccc(O)cc21] | 3-(3-Hydroxyphenyl)-4-methyl-2-(4-((S)-2-((S)-2-methylpyrrolidin-1-yl)propoxy)phenyl)-2H-chromen-6-ol |

| Example | Structure | Compound Name |
|---|---|---|
| 25 | 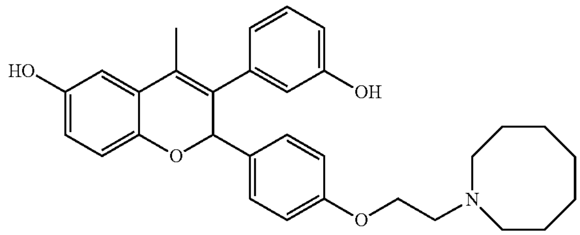 [SMILES: CC1=C(c2cccc(O)c2)C(c2ccc(OCCN3CCCCCCC3)cc2)Oc2ccc(O)cc21] | 2-(4-(2-(Azocan-1-yl)ethoxy)phenyl)-3-(3-hydroxyphenyl)-4-methyl-2H-chromen-6-ol |
| 26 | 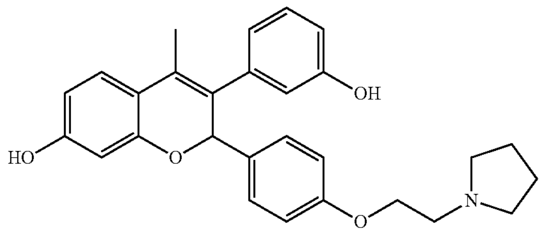 [SMILES: CC1=C(c2cccc(O)c2)C(c2ccc(OCCN3CCCC3)cc2)Oc2cc(O)ccc21] | 3-(3-Hydroxyphenyl)-4-methyl-2-(4-(2-(pyrrolidin-1-yl)ethoxy)phenyl)-2H-chromen-7-ol |
| 27 | 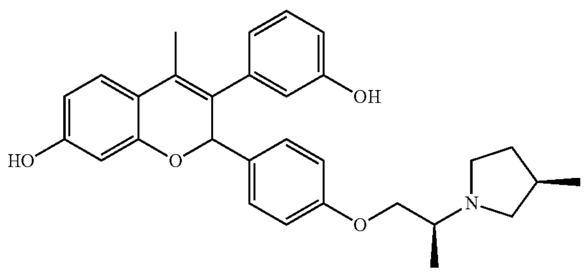 [SMILES: CC1=C(c2cccc(O)c2)C(c2ccc(OC[C@H](C)N3CC[C@@H](C)C3)cc2)Oc2cc(O)ccc21] | 3-(3-Hydroxyphenyl)-4-methyl-2-(4-((S)-2-((R)-3-methylpyrrolidin-1-yl)propoxy)phenyl)-2H-chromen-7-ol |
| 28 | 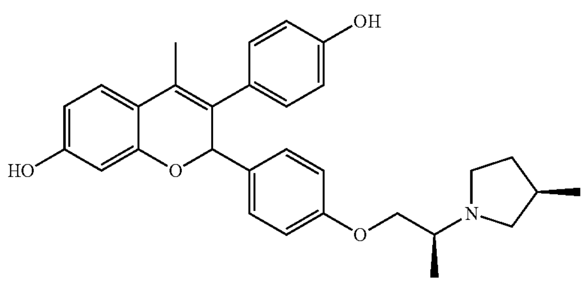 [SMILES: CC1=C(c2ccc(O)cc2)C(c2ccc(OC[C@H](C)N3CC[C@@H](C)C3)cc2)Oc2cc(O)ccc21] | 3-(4-Hydroxyphenyl)-4-methyl-2-(4-((S)-2-((R)-3-methylpyrrolidin-1-yl)propoxy)phenyl)-2H-chromen-7-ol |
| 29 | 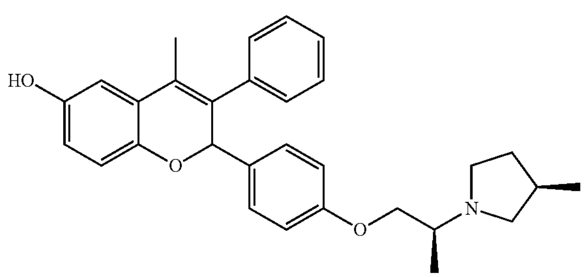 [SMILES: CC1=C(c2ccccc2)C(c2ccc(OC[C@H](C)N3CC[C@@H](C)C3)cc2)Oc2ccc(O)cc21] | 4-Methyl-2-(4-((S)-2-((R)-3-methylpyrrolidin-1-yl)propoxy)phenyl)-3-phenyl-2H-chromen-6-ol |
| 30 | 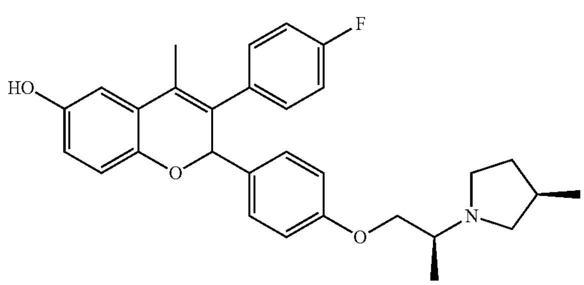 [SMILES: CC1=C(c2ccc(F)cc2)C(c2ccc(OC[C@H](C)N3CC[C@@H](C)C3)cc2)Oc2ccc(O)cc21] | 3-(4-Fluorophenyl)-4-methyl-2-(4-((S)-2-((R)-3-methylpyrrolidin-1-yl)propoxy)phenyl)-2H-chromen-6-ol |

| Example | Structure | Compound Name |
|---|---|---|
| 30a | 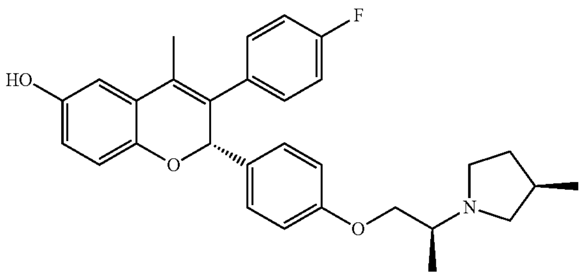 | (S)-3-(4-Fluorophenyl)-4-methyl-2-(4-((S)-2-((R)-3-methylpyrrolidin-1-yl)propoxy)phenyl)-2H-chromen-6-ol |
| 30b | 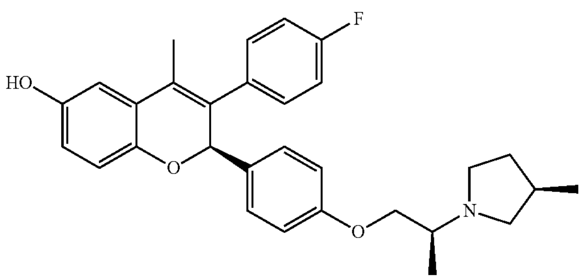 [SMILES: CC1=C(c2ccc(F)cc2)[C@@H](c2ccc(OC[C@H](C)N3CC[C@@H](C)C3)cc2)Oc2ccc(O)cc21] | (R)-3-(4-Fluorophenyl)-4-methyl-2-(4-((S)-2-((R)-3-methylpyrrolidin-1-yl)propoxy)phenyl)-2H-chromen-6-ol |
| 31 | 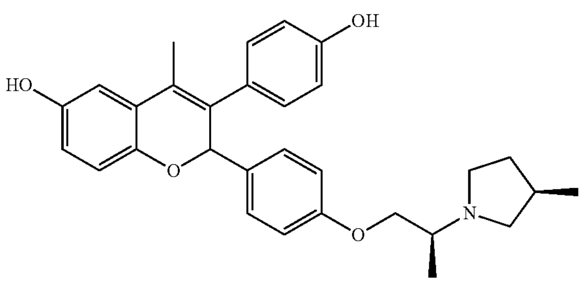 | 3-(4-Hydroxyphenyl)-4-methyl-2-(4-((S)-2-((R)-3-methylpyrrolidin-1-yl)propoxy)phenyl)-2H-chromen-6-ol |
| 32 | 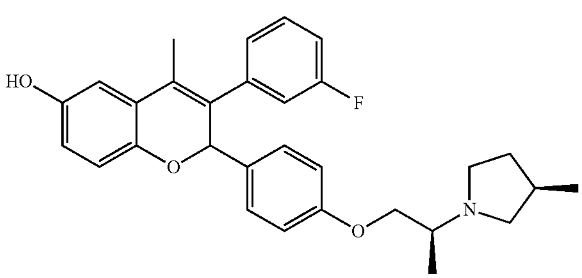 [SMILES: CC1=C(c2cccc(F)c2)C(c2ccc(OC[C@H](C)N3CC[C@@H](C)C3)cc2)Oc2ccc(O)cc21] | 3-(3-Fluorophenyl)-4-methyl-2-(4-((S)-2-((R)-3-methylpyrrolidin-1-yl)propoxy)phenyl)-2H-chromen-6-ol |
| 33 | 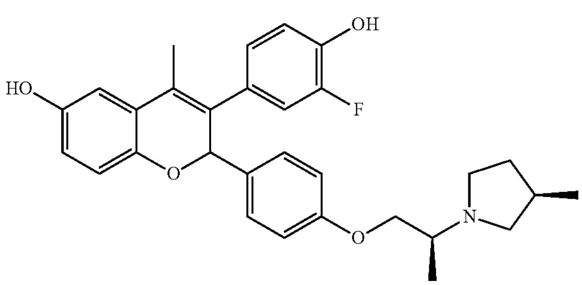 | 3-(3-Fluoro-4-hydroxyphenyl)-4-methyl-2-(4-((S)-2-((R)-3-methylpyrrolidin-1-yl)propoxy)phenyl)-2H-chromen-6-ol |

| Example | Structure | Compound Name |
|---|---|---|
| 34 | 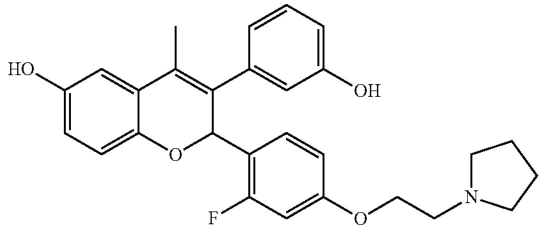 [SMILES: CC1=C(c2cccc(O)c2)C(c2ccc(OCCN3CCCC3)cc2F)Oc2ccc(O)cc21] | 2-(2-Fluoro-4-(2-(pyrrolidin-1-yl)ethoxy)phenyl)-3-(3-hydroxyphenyl)-4-methyl-2H-chromen-6-ol |
| 35 | 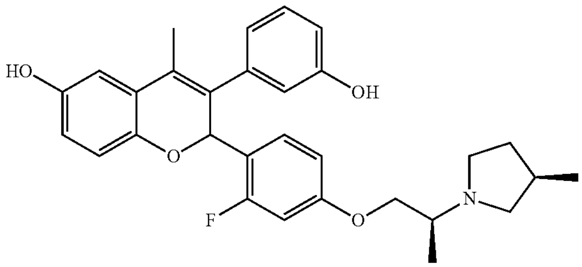 [SMILES: CC1=C(c2cccc(O)c2)C(c2ccc(OC[C@H](C)N3CC[C@@H](C)C3)cc2F)Oc2ccc(O)cc21] | 2-(2-Fluoro-4-((S)-2-((R)-3-methylpyrrolidin-1-yl)propoxy)phenyl)-3-(3-hydroxyphenyl)-4-methyl-2H-chromen-6-ol |
| 36 | 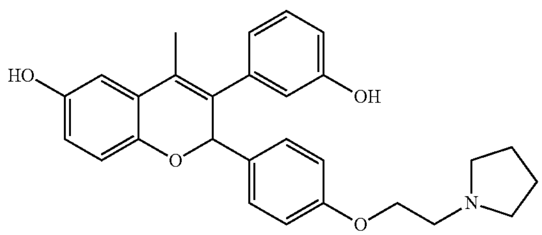 [SMILES: CC1=C(c2cccc(O)c2)C(c2ccc(OCCN3CCCC3)cc2)Oc2ccc(O)cc21] | 3-(3-Hydroxyphenyl)-4-methyl-2-(4-(2-(pyrrolidin-1-yl)ethoxy)phenyl)-2H-chromen-6-ol |
| 37 | 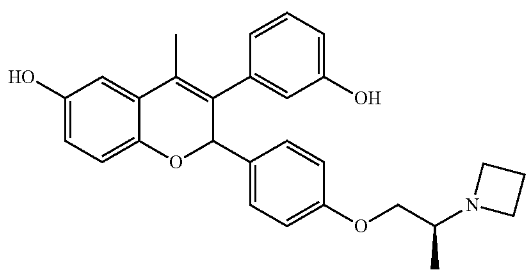 [SMILES: CC1=C(c2cccc(O)c2)C(c2ccc(OC[C@H](C)N3CCC3)cc2)Oc2ccc(O)cc21] | 2-(4-((S)-2-(Azetidin-1-yl)propoxy)phenyl)-3-(3-hydroxyphenyl)-4-methyl-2H-chromen-6-ol |
| 38 | 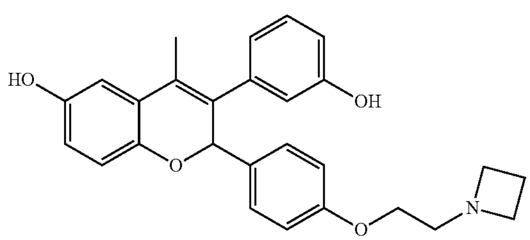 [SMILES: CC1=C(c2cccc(O)c2)C(c2ccc(OCCN3CCC3)cc2)Oc2ccc(O)cc21] | 2-(4-(2-(Azetidin-1-yl)ethoxy)phenyl)-3-(3-hydroxyphenyl)-4-methyl-2H-chromen-6-ol |
| 39 | 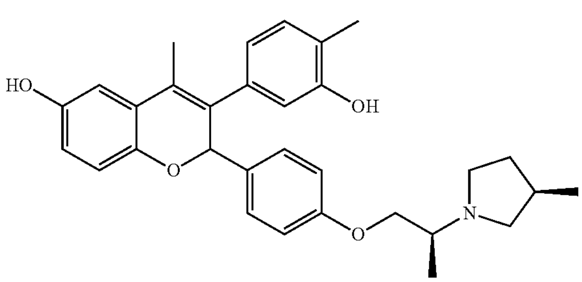 [SMILES: CC1=C(c2ccc(C)c(O)c2)C(c2ccc(OC[C@H](C)N3CC[C@@H](C)C3)cc2)Oc2ccc(O)cc21] | 3-(3-Hydroxy-4-methylphenyl)-4-methyl-2-(4-((S)-2-((R)-3-methylpyrrolidin-1-yl)propoxy)phenyl)-2H-chromen-6-ol |

-continued

| Example | Structure | Compound Name |
|---|---|---|
| 40 | 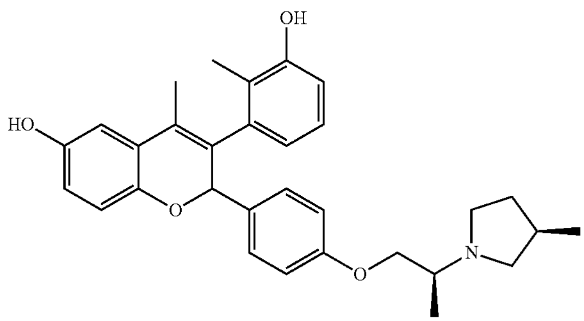 [SMILES: CC1=C(c2cccc(O)c2C)C(c2ccc(OC[C@H](C)N3CC[C@@H](C)C3)cc2)Oc2ccc(O)cc21] | 3-(3-Hydroxy-2-methylphenyl)-4-methyl-2-(4-((S)-2-((R)-3-methylpyrrolidin-1-yl)propoxy)phenyl)-2H-chromen-6-ol |
| 41 | 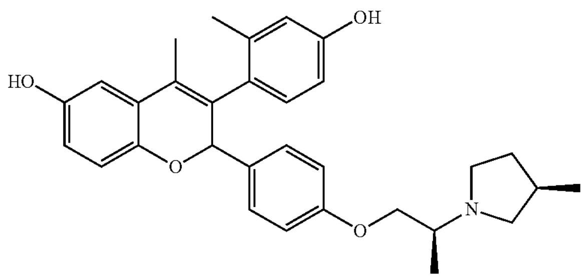 | 3-(4-Hydroxy-2-methylphenyl)-4-methyl-2-(4-((S)-2-((R)-3-methylpyrrolidin-1-yl)propoxy)phenyl)-2H-chromen-6-ol |
| 42 | 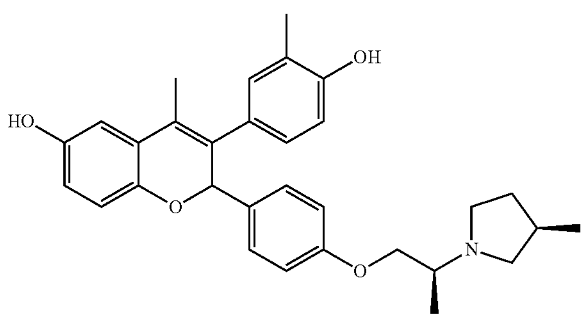 [SMILES: CC1=C(c2ccc(O)c(C)c2)C(c2ccc(OC[C@H](C)N3CC[C@@H](C)C3)cc2)Oc2ccc(O)cc21] | 3-(4-Hydroxy-3-methylphenyl)-4-methyl-2-(4-((S)-2-((R)-3-methylpyrrolidin-1-yl)propoxy)phenyl)-2H-chromen-6-ol |
| 43 | 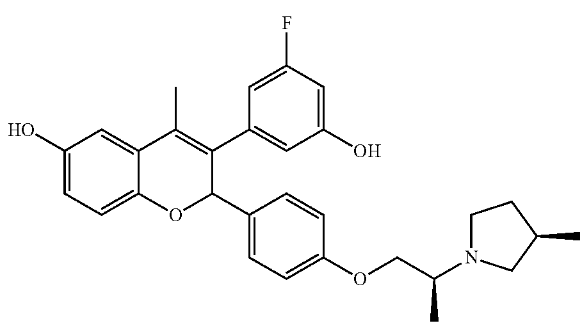 [SMILES: CC1=C(c2cc(O)cc(F)c2)C(c2ccc(OC[C@H](C)N3CC[C@@H](C)C3)cc2)Oc2ccc(O)cc21] | 3-(3-Fluoro-5-hydroxyphenyl)-4-methyl-2-(4-((S)-2-((R)-3-methylpyrrolidin-1-yl)propoxy)phenyl)-2H-chromen-6-ol |
| 44 | 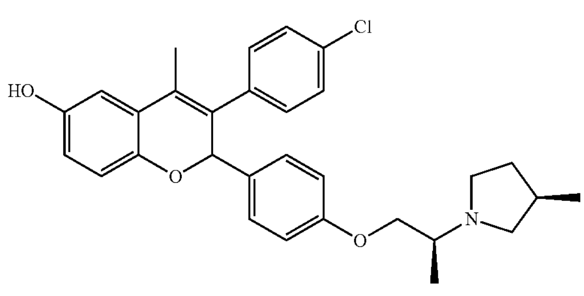 [SMILES: CC1=C(c2ccc(Cl)cc2)C(c2ccc(OC[C@H](C)N3CC[C@@H](C)C3)cc2)Oc2ccc(O)cc21] | 3-(4-Chlorophenyl)-4-methyl-2-(4-((S)-2-((R)-3-methylpyrrolidin-1-yl)propoxy)phenyl)-2H-chromen-6-ol |

-continued

| Example | Structure | Compound Name |
|---|---|---|
| 45 | 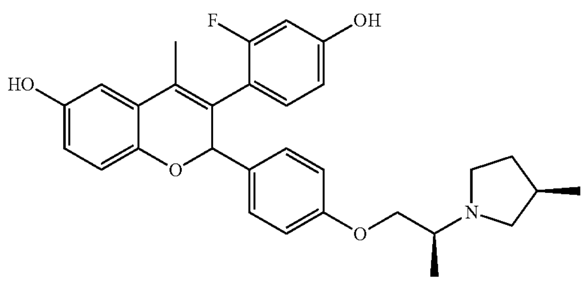 [SMILES: CC1=C(c2ccc(O)cc2F)C(c2ccc(OC[C@H](C)N3CC[C@@H](C)C3)cc2)Oc2ccc(O)cc21] | 3-(2-Fluoro-4-hydroxyphenyl)-4-methyl-2-(4-((S)-2-((R)-3-methylpyrrolidin-1-yl)propoxy)phenyl)-2H-chromen-6-ol |
| 46 | 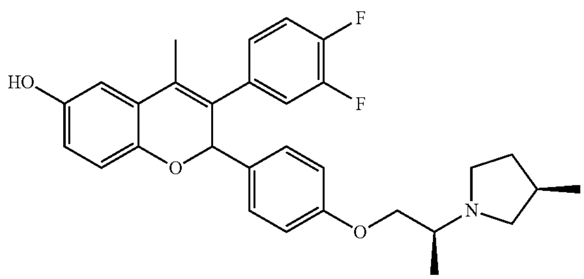 [SMILES: CC1=C(c2ccc(F)c(F)c2)C(c2ccc(OC[C@H](C)N3CC[C@@H](C)C3)cc2)Oc2ccc(O)cc21] | 3-(3,4-Difluorophenyl)-4-methyl-2-(4-((S)-2-((R)-3-methylpyrrolidin-1-yl)propoxy)phenyl)-2H-chromen-6-ol |
| 47 | 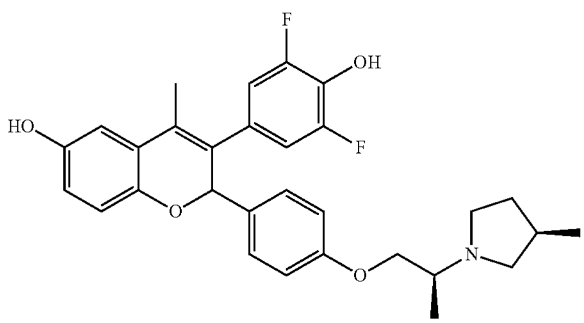 [SMILES: CC1=C(c2cc(F)c(O)c(F)c2)C(c2ccc(OC[C@H](C)N3CC[C@@H](C)C3)cc2)Oc2ccc(O)cc21] | 3-(3,5-Difluoro-4-hydroxyphenyl)-4-methyl-2-(4-((S)-2-((R)-3-methylpyrrolidin-1-yl)propoxy)phenyl)-2H-chromen-6-ol |
| 48 | 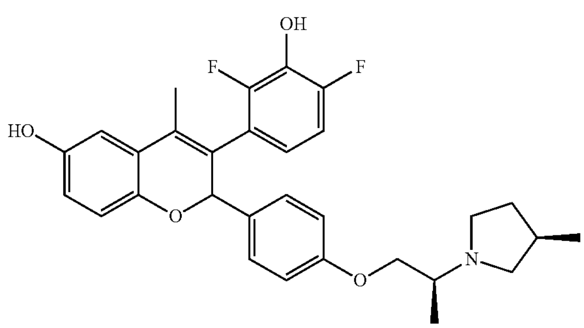 [SMILES: CC1=C(c2ccc(F)c(O)c2F)C(c2ccc(OC[C@H](C)N3CC[C@@H](C)C3)cc2)Oc2ccc(O)cc21] | 3-(2,4-Difluoro-3-hydroxyphenyl)-4-methyl-2-(4-((S)-2-((R)-3-methylpyrrolidin-1-yl)propoxy)phenyl)-2H-chromen-6-ol |
| 49 | 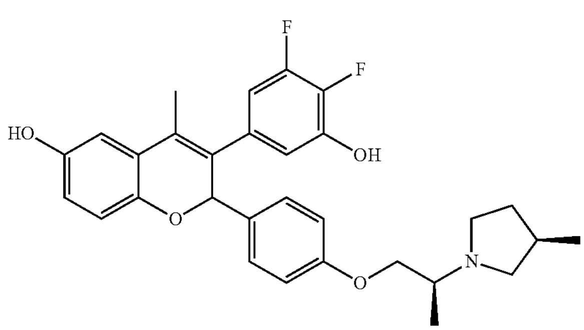 [SMILES: CC1=C(c2cc(O)c(F)c(F)c2)C(c2ccc(OC[C@H](C)N3CC[C@@H](C)C3)cc2)Oc2ccc(O)cc21] | 3-(3,4-Difluoro-5-hydroxyphenyl)-4-methyl-2-(4-((S)-2-((R)-3-methylpyrrolidin-1-yl)propoxy)phenyl)-2H-chromen-6-ol |

-continued

| Example | Structure | Compound Name |
| --- | --- | --- |
| 50 | 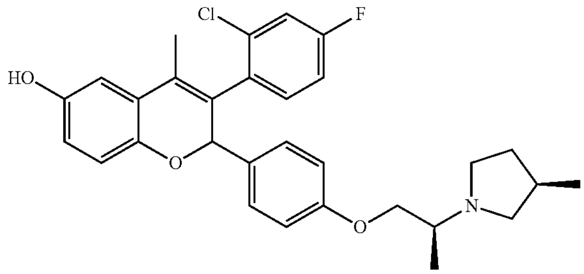 | 3-(2-Chloro-4-fluorophenyl)-4-methyl-2-(4-((S)-2-((R)-3-methylpyrrolidin-1-yl)propoxy)phenyl)-2H-chromen-6-ol |
| 51 | 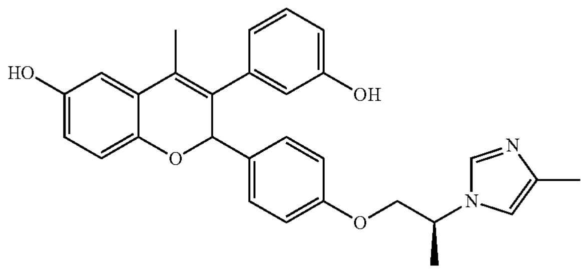 [SMILES: CC1=C(c2cccc(O)c2)C(c2ccc(OC[C@H](C)n3cnc(C)c3)cc2)Oc2ccc(O)cc21] | 3-(3-Hydroxyphenyl)-4-methyl-2-(4-((S)-2-(4-methyl-1H-imidazol-1-yl)propoxy)phenyl)-2H-chromen-6-ol |
| 52 | 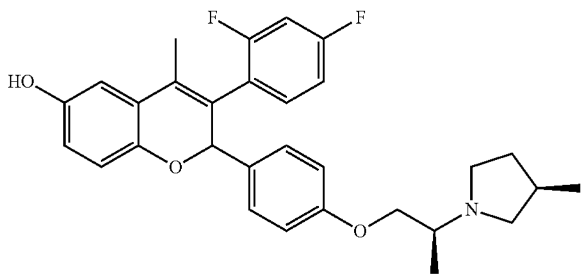 | 3-(2,4-Difluorophenyl)-4-methyl-2-(4-((S)-2-((R)-3-methylpyrrolidin-1-yl)propoxy)phenyl)-2H-chromen-6-ol |
| 53 | 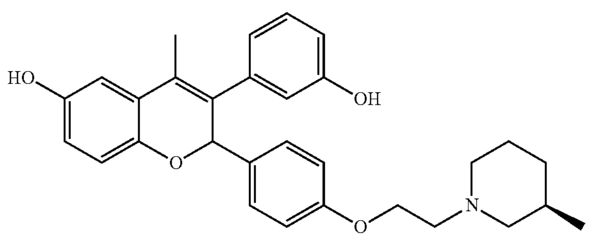 [SMILES: CC1=C(c2cccc(O)c2)C(c2ccc(OCCN3CCC[C@@H](C)C3)cc2)Oc2ccc(O)cc21] | 3-(3-Hydroxyphenyl)-4-methyl-2-(4-(2-((R)-3-methylpiperidin-1-yl)ethoxy)phenyl)-2H-chromen-6-ol |
| 54 | 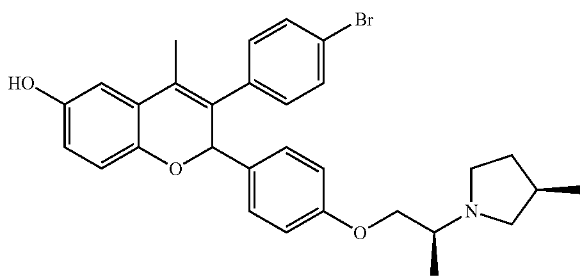 [SMILES: CC1=C(c2ccc(Br)cc2)C(c2ccc(OC[C@H](C)N3CC[C@@H](C)C3)cc2)Oc2ccc(O)cc21] | 3-(4-Bromophenyl)-4-methyl-2-(4-((S)-2-((R)-3-methylpyrrolidin-1-yl)propoxy)phenyl)-2H-chromen-6-ol |
| 55 | 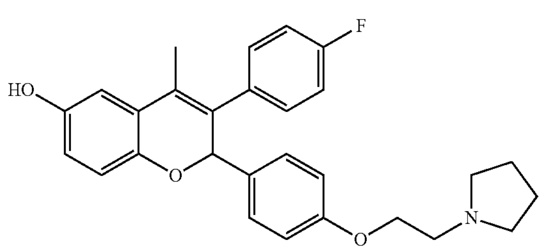 [SMILES: CC1=C(c2ccc(F)cc2)C(c2ccc(OCCN3CCCC3)cc2)Oc2ccc(O)cc21] | 3-(4-Fluorophenyl)-4-methyl-2-(4-(2-(pyrrolidin-1-yl)ethoxy)phenyl)-2H-chromen-6-ol |

| Example | Structure | Compound Name |
|---|---|---|
| 56 | 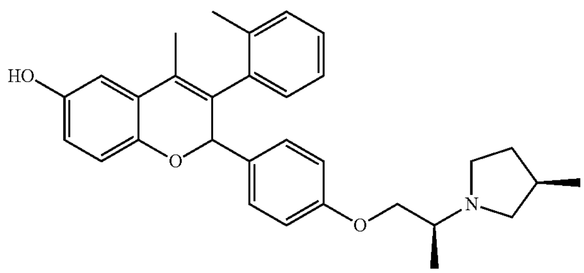 [SMILES: CC1=C(c2ccccc2C)C(c2ccc(OC[C@H](C)N3CC[C@@H](C)C3)cc2)Oc2ccc(O)cc21] | 4-Methyl-2-(4-((S)-2-((R)-3-methylpyrrolidin-1-yl)propoxy)phenyl)-3-(o-tolyl)-2H-chromen-6-ol |
| 57 | 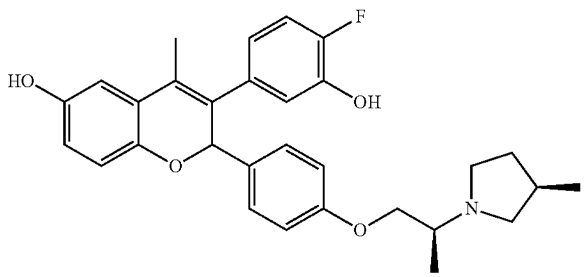 [SMILES: CC1=C(c2ccc(F)c(O)c2)C(c2ccc(OC[C@H](C)N3CC[C@@H](C)C3)cc2)Oc2ccc(O)cc21] | 3-(4-Fluoro-3-hydroxyphenyl)-4-methyl-2-(4-((S)-2-((R)-3-methylpyrrolidin-1-yl)propoxy)phenyl)-2H-chromen-6-ol |
| 58 | 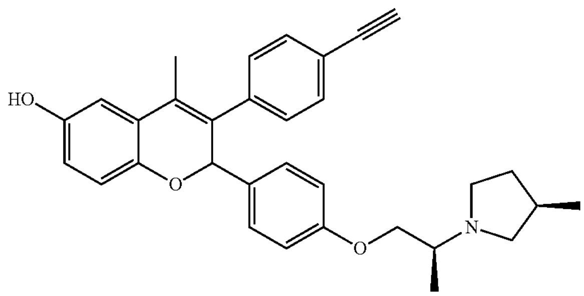 [SMILES: C#Cc1ccc(C2=C(C)c3cc(O)ccc3OC2c2ccc(OC[C@H](C)N3CC[C@@H](C)C3)cc2)cc1] | 3-(4-Ethynylphenyl)-4-methyl-2-(4-((S)-2-((R)-3-methylpyrrolidin-1-yl)propoxy)phenyl)-2H-chromen-6-ol |
| 59 | 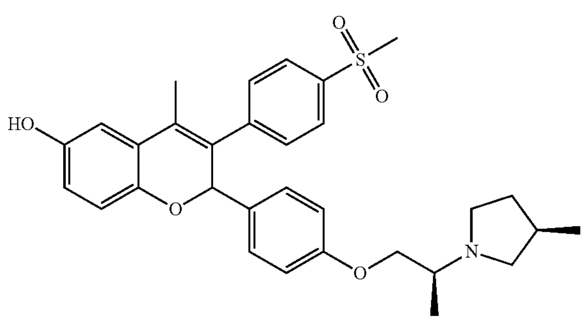 [SMILES: CC1=C(c2ccc(S(C)(=O)=O)cc2)C(c2ccc(OC[C@H](C)N3CC[C@@H](C)C3)cc2)Oc2ccc(O)cc21] | 4-Methyl-2-(4-((S)-2-((R)-3-methylpyrrolidin-1-yl)propoxy)phenyl)-3-(4-(methylsulfonyl)phenyl)-2H-chromen-6-ol |
| 60 | 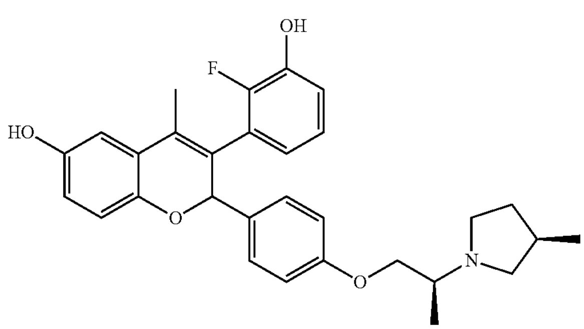 [SMILES: CC1=C(c2cccc(O)c2F)C(c2ccc(OC[C@H](C)N3CC[C@@H](C)C3)cc2)Oc2ccc(O)cc21] | 3-(2-Fluoro-3-hydroxyphenyl)-4-methyl-2-(4-((S)-2-((R)-3-methylpyrrolidin-1-yl)propoxy)phenyl)-2H-chromen-6-ol |

| Example | Structure | Compound Name |
|---|---|---|
| 61 | 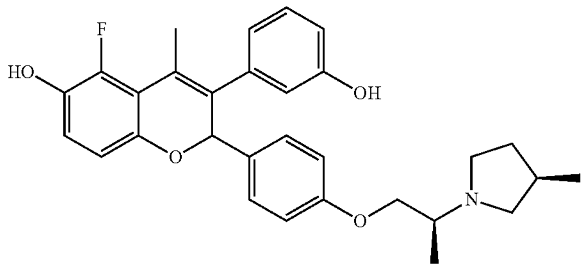 [SMILES: CC1=C(c2cccc(O)c2)C(c2ccc(OC[C@H](C)N3CC[C@@H](C)C3)cc2)Oc2ccc(O)c(F)c21] | 5-Fluoro-3-(3-hydroxyphenyl)-4-methyl-2-(4-((S)-2-((R)-3-methylpyrrolidin-1-yl)propoxy)phenyl)-2H-chromen-6-ol |
| 62 | 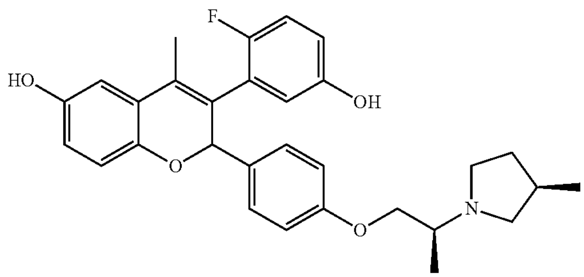 [SMILES: CC1=C(c2cc(O)ccc2F)C(c2ccc(OC[C@H](C)N3CC[C@@H](C)C3)cc2)Oc2ccc(O)cc21] | 3-(2-Fluoro-5-hydroxyphenyl)-4-methyl-2-(4-((S)-2-((R)-3-methylpyrrolidin-1-yl)propoxy)phenyl)-2H-chromen-6-ol |
| 63 | 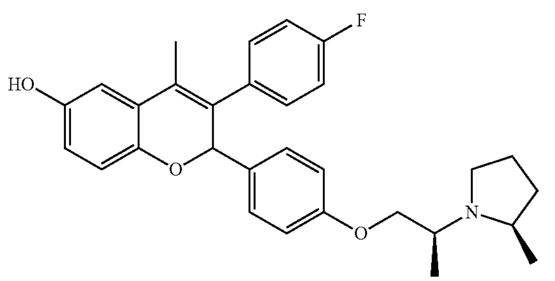 [SMILES: CC1=C(c2ccc(F)cc2)C(c2ccc(OC[C@H](C)N3CCC[C@H]3C)cc2)Oc2ccc(O)cc21] | 3-(4-Fluorophenyl)-4-methyl-2-(4-((S)-2-((R)-2-methylpyrrolidin-1-yl)propoxy)phenyl)-2H-chromen-6-ol |
| 64 | 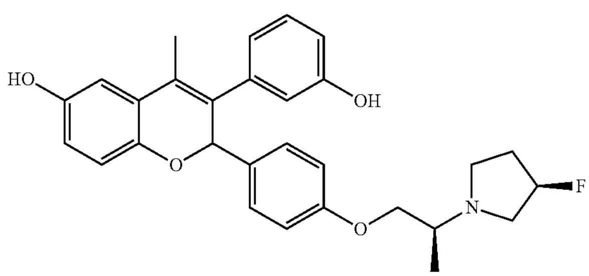 [SMILES: CC1=C(c2cccc(O)c2)C(c2ccc(OC[C@H](C)N3CC[C@@H](F)C3)cc2)Oc2ccc(O)cc21] | 2-(4-((S)-2-((R)-3-Fluoropyrrolidin-1-yl)propoxy)phenyl)-3-(3-hydroxyphenyl)-4-methyl-2H-chromen-6-ol |
| 65 | 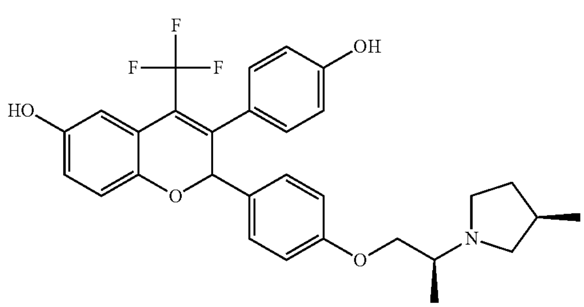 [SMILES: C[C@@H]1CCN([C@@H](C)COc2ccc(C3Oc4ccc(O)cc4C(C(F)(F)F)=C3c3ccc(O)cc3)cc2)C1] | 3-(4-Hydroxyphenyl)-2-(4-((S)-2-((R)-3-methylpyrrolidin-1-yl)propoxy)phenyl)-4-(trifluoromethyl)-2H-chromen-6-ol |

| Example | Structure | Compound Name |
|---|---|---|
| 66 | 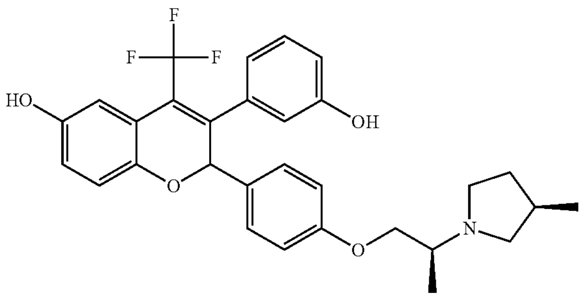 [SMILES: C[C@@H]1CCN([C@@H](C)COc2ccc(C3Oc4ccc(O)cc4C(C(F)(F)F)=C3c3cccc(O)c3)cc2)C1] | 3-(3-Hydroxyphenyl)-2-(4-((S)-2-((R)-3-methylpyrrolidin-1-yl)propoxy)phenyl)-4-(trifluoromethyl)-2H-chromen-6-ol |
| 67 | 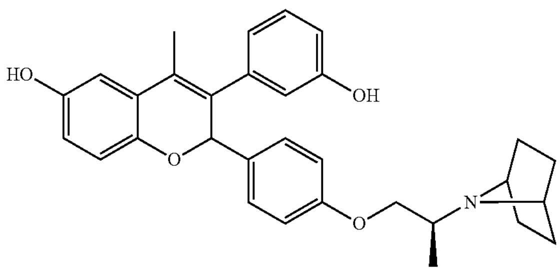 [SMILES: CC1=C(c2cccc(O)c2)C(c2ccc(OC[C@H](C)N3C4CCC3CC4)cc2)Oc2ccc(O)cc21] | 2-(4-((S)-2-(7-Azabicyclo[2.2.1]heptan-7-yl)propoxy)phenyl)-3-(3-hydroxyphenyl)-4-methyl-2H-chromen-6-ol |
| 68 | 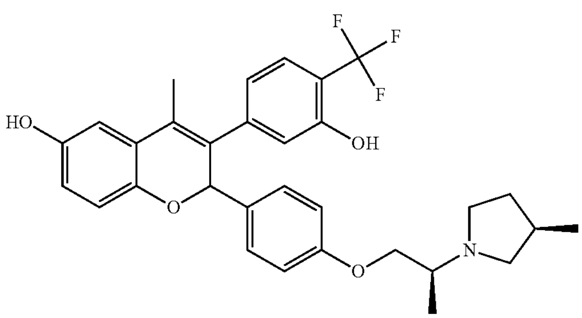 [SMILES: CC1=C(c2ccc(C(F)(F)F)c(O)c2)C(c2ccc(OC[C@H](C)N3CC[C@@H](C)C3)cc2)Oc2ccc(O)cc21] | 3-(3-Hydroxy-4-(trifluoromethyl)phenyl)-4-methyl-2-(4-((S)-2-((R)-3-methylpyrrolidin-1-yl)propoxy)phenyl)-2H-chromen-6-ol |
| 69 | 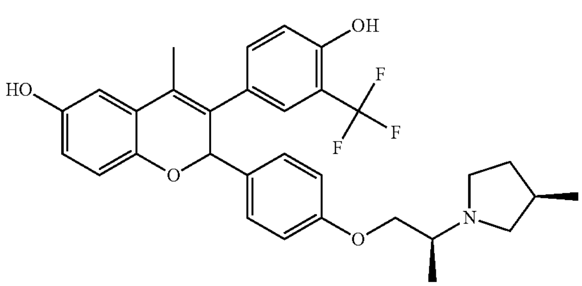 [SMILES: CC1=C(c2ccc(O)c(C(F)(F)F)c2)C(c2ccc(OC[C@H](C)N3CC[C@@H](C)C3)cc2)Oc2ccc(O)cc21] | 3-(4-Hydroxy-3-(trifluoromethyl)phenyl)-4-methyl-2-(4-((S)-2-((R)-3-methylpyrrolidin-1-yl)propoxy)phenyl)-2H-chromen-6-ol |
| 70 | 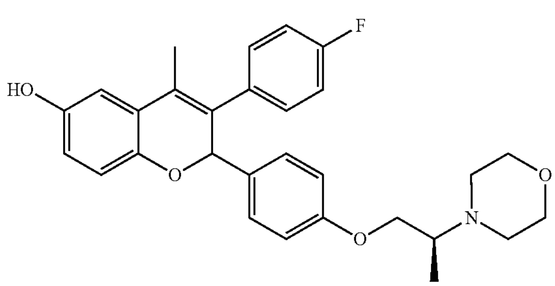 [SMILES: CC1=C(c2ccc(F)cc2)C(c2ccc(OC[C@H](C)N3CCOCC3)cc2)Oc2ccc(O)cc21] | 3-(4-Fluorophenyl)-4-methyl-2-(4-((S)-2-morpholinopropoxy)phenyl)-2H-chromen-6-ol |

| Example | Structure | Compound Name |
|---|---|---|
| 71 | 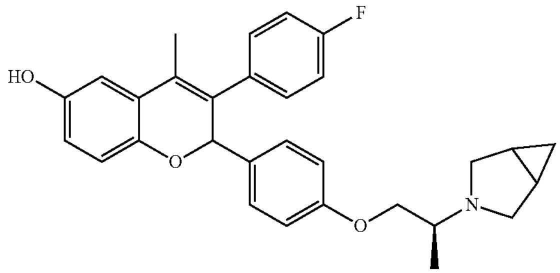 [SMILES: CC1=C(c2ccc(F)cc2)C(c2ccc(OC[C@H](C)N3CC4CC4C3)cc2)Oc2ccc(O)cc21] | 2-(4-((2S)-2-(3-Azabicyclo[3.1.0]hexan-3-yl)propoxy)phenyl)-3-(4-fluorophenyl)-4-methyl-2H-chromen-6-ol |

In some embodiments, a pharmaceutically acceptable salt of a compound of Formula (I), (II), (III), (IV), (V), (VI), (VII), (VIII), (IX), (X), (XI), (XII), or (XIII) includes a pharmaceutically acceptable salt of any one of the compound in the preceding table of compounds.

Synthesis of Compounds

Compounds of Formula (I), (II), (III), (IV), (V), (VI), (VII), (VIII), (IX), (X), (XI), (XII), or (XIII) described herein are synthesized using standard synthetic techniques or using methods known in the art in combination with methods described herein. In additions, solvents, temperatures and other reaction conditions presented herein may vary.

The starting material used for the synthesis of the compounds of Formula (I), (II), (III), (IV), (V), (VI), (VII), (VIII), (IX), (X), (XI), (XII), and (XIII) are either synthesized or obtained from commercial sources, such as, but not limited to, Sigma-Aldrich, Fluka, Acros Organics, Alfa Aesar, and the like. The compounds described herein, and other related compounds having different substituents are synthesized using techniques and materials described herein or otherwise known, including those found in March, ADVANCED ORGANIC CHEMISTRY 4$^{th}$ Ed., (Wiley 1992); Carey and Sundberg, ADVANCED ORGANIC CHEMISTRY 4$^{th}$ Ed., Vols. A and B (Plenum 2000, 2001), and Green and Wuts, PROTECTIVE GROUPS IN ORGANIC SYNTHESIS 3$^{rd}$ Ed., (Wiley 1999). General methods for the preparation of compounds can be modified by the use of appropriate reagents and conditions for the introduction of the various moieties found in the formulae as provided herein.

In some embodiments, the compounds of Formula (I), (II), (III), (IV), (V), (VI), (VII), (VIII), (IX), (X), (XI), (XII), and (XIII) are prepared as outlined in the following Schemes.

Scheme 1:

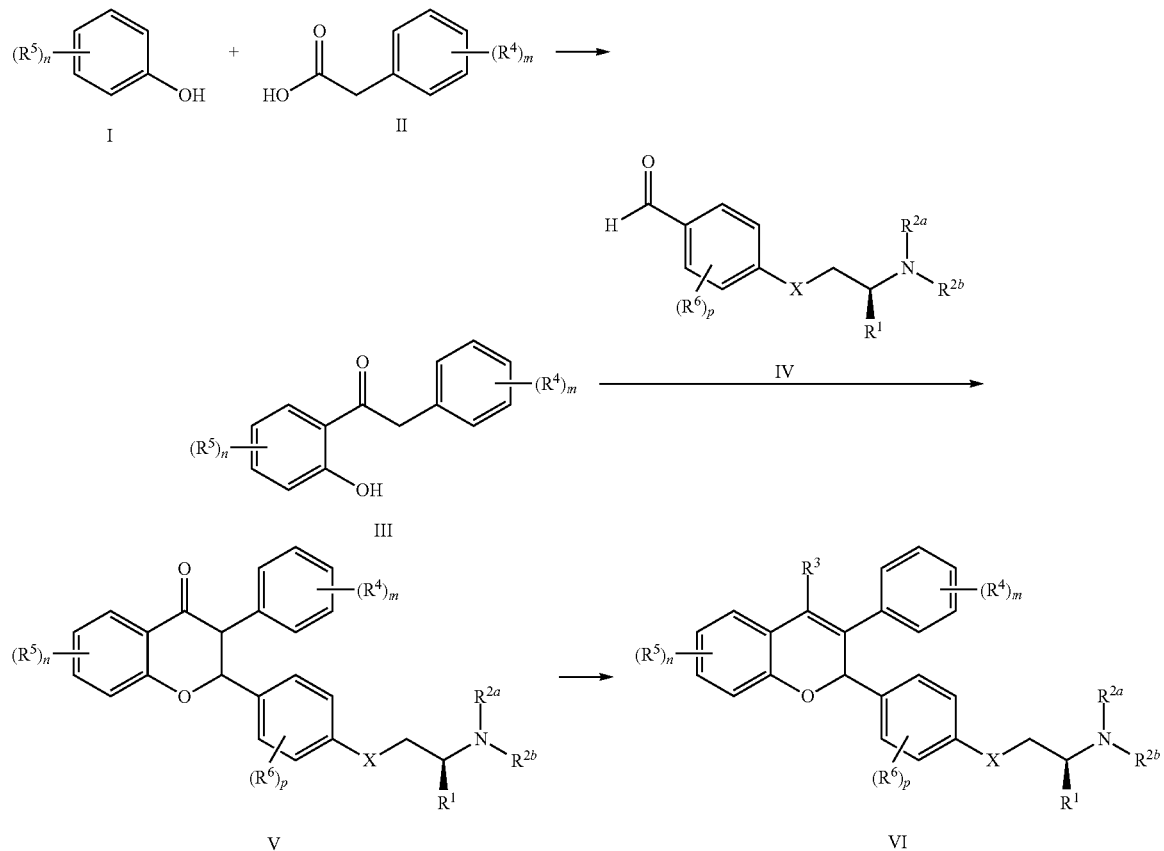

Treatment of phenols of structure I with phenylacetic acids of structure II in the presence of a suitable Lewis Acid in a suitable solvent provides ketones of structure III. In some embodiments the suitable Lewis Acid is BF$_3$-Et$_2$O. In some embodiments, the suitable solvent is toluene. In some embodiments, the reaction is heated. In some embodiments, the reaction is heated to 90° C. for 2 hours. Ketones of structure III are reacted with benzaldehydes of structure IV in the presence of a suitable base and suitable solvent to provide compounds of structure V. In some embodiments, the suitable base is piperidine and 1,8-diazabicyclo[5.4.0]undec-7-ene (DBU). In some embodiments, the suitable solvent is s-butanol and/or i-propanol. In some embodiments, ketones of structure III are reacted with benzaldehydes of structure IV in the presence of piperidine, DBU in s-butanol at reflux for 3 hours and then i-propanol is added and the reaction is stirred at room temperature for 1-3 days. Compounds of structure V are treated with suitable organometallic reagents to provide tertiary alcohols that are then dehydrated to provide chromenes of structure VI. In some embodiments, the suitable organometallic reagent is R$^3$—Li or R$^3$—MgCl. In some embodiments, the suitable organometallic reagent is methyl lithium, methyl magnesium chloride or methyl magnesium bromide. In some embodiments, compounds of structure V are dissolved in tetrahydrofuran and treated with methyl lithium at −78° C. to room temperature for 1 hour or methyl magnesium chloride at 0° C. to room temperature for 2 hours. The tertiary alcohol that is produced is then treated with acetic acid/water to eliminate to the chromene.

In some embodiments, compounds are prepared as outlined in Scheme 2.

Scheme 2:

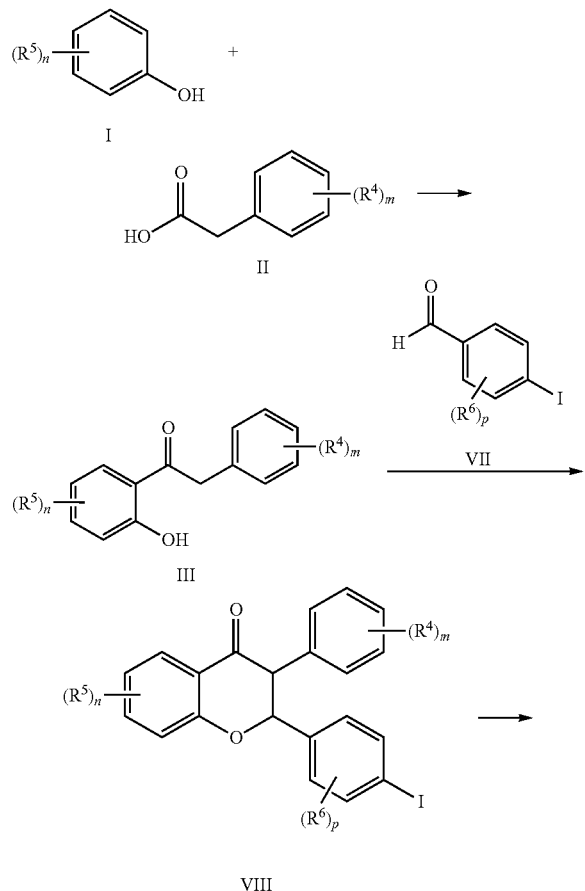

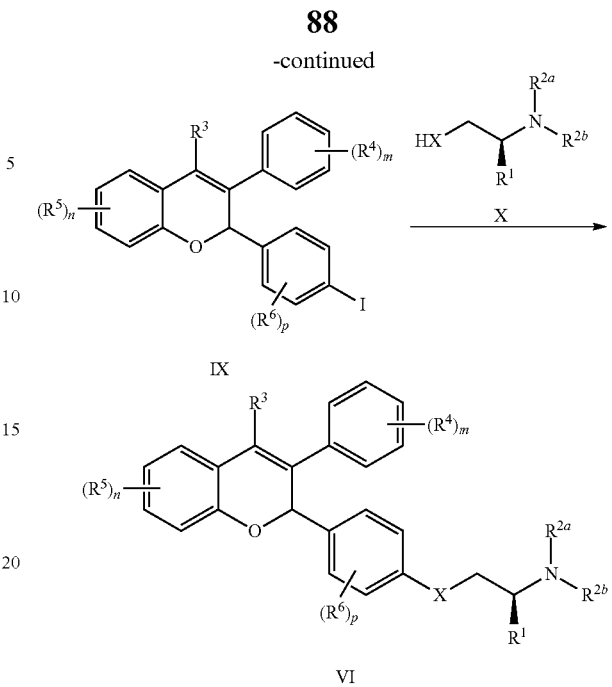

In some embodiments, ketones of structure III are prepared as outlined in Scheme 1 and then reacted with 4-halobenzaldehydes of structure VII in the presence of a suitable base and suitable solvent to provide compounds of structure VIII. In some embodiments, the suitable base is piperidine and 1,8-diazabicyclo[5.4.0]undec-7-ene (DBU). In some embodiments, the suitable solvent(s) is s-butanol and i-propanol. Compounds of structure VIII are then treated with suitable organometallic reagents, followed by dehydration of the tertiary alcohol to provide chromenes of structure IX. In some embodiments, the suitable organometallic reagent is R$^3$—Li or MgCl—R$^3$. In some embodiments, compounds of structure VIII are reacted with CsF and CF$_3$TMS in a suitable solvent at room temperature, followed by deprotection of the TMS protecting group and then dehydration of the resulting tertiary alcohol to provide chromenes of structure IX where R$^3$ is —CF$_3$. Chromenes of structure IX are then reacted with amino compounds of structure X under Ullmann reaction conditions to provide chromenes of structure VI. Ullmann reaction conditions include the use of copper salts. In some embodiments, the Ullmann reaction conditions include the use of CuI, Cs$_2$CO$_3$, and butyronitrile with heating to about 125° C. In some embodiments, the Ullmann reaction conditions include the use of CuI, bipyridine, and K$_2$CO$_3$ with heating to about 140° C. In some other embodiments, Ullmann reaction conditions include the use of CuI, potassium carbonate, and butyronitrile with heating to about 125° C. for about 5 days.

In some embodiments, ketones of structure III are prepared as outlined in Scheme 3:

Scheme 3:

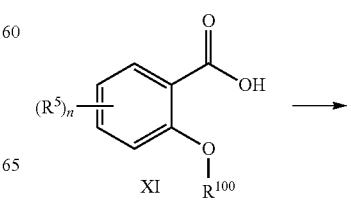

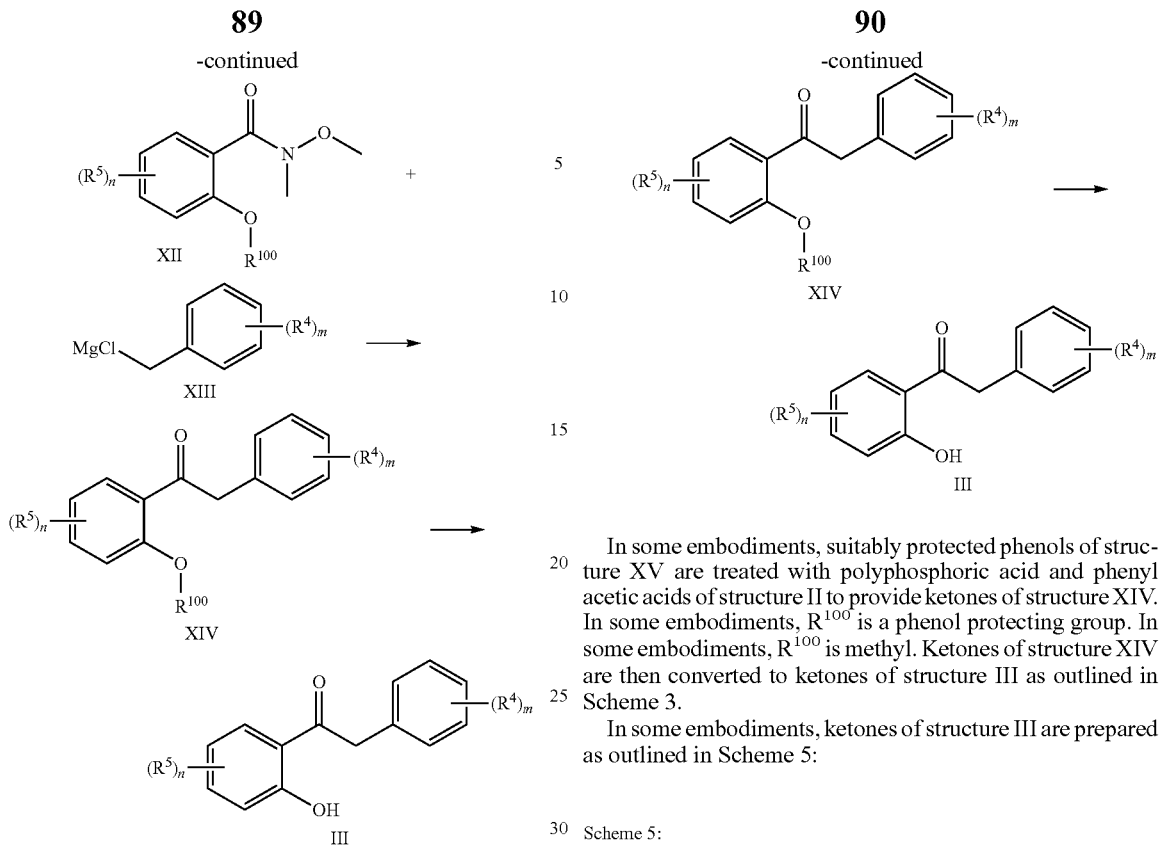

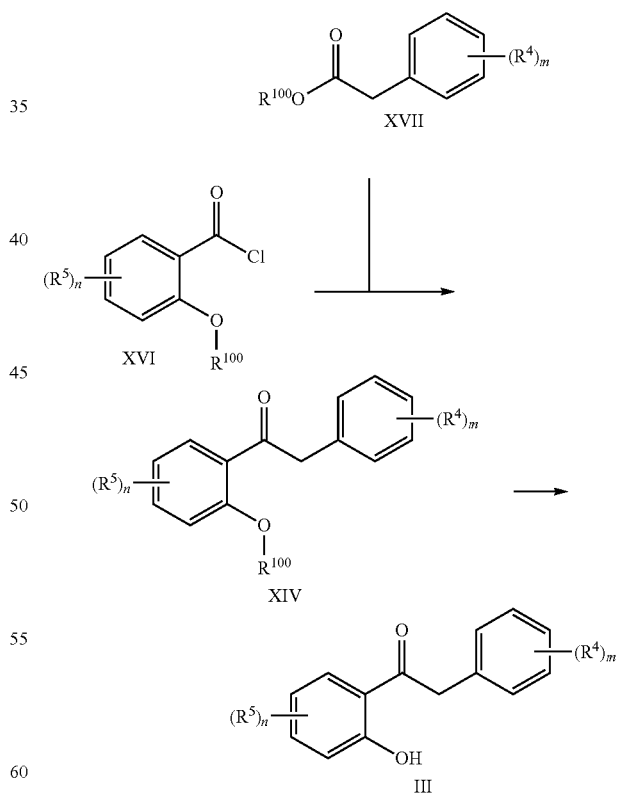

In some embodiments, suitably protected phenols of structure XV are treated with polyphosphoric acid and phenyl acetic acids of structure II to provide ketones of structure XIV. In some embodiments, $R^{100}$ is a phenol protecting group. In some embodiments, $R^{100}$ is methyl. Ketones of structure XIV are then converted to ketones of structure III as outlined in Scheme 3.

In some embodiments, ketones of structure III are prepared as outlined in Scheme 5:

Benzoic acid compounds of structure XI are converted to Weinreb amides of structure XII. In some embodiments, benzoic acid compounds of structure XI are treated with oxalyl chloride, dimethylformamide (DMF), dichloromethane (DCM), at room temperature for 2 hours followed by treatments with triethylamine (Et$_3$N), N,O-dimethylhydroxylamine-HCl, DCM, at 0° C. to rt for 1 hour to provide Weinreb amides of structure XII. Weinreb amides of structure XII are then treated with suitable organometallics reagents of structure XIII to provide ketones of structure XIV. In some embodiments, $R^{100}$ is a phenol protecting group. In some embodiments, $R^{100}$ is methyl. In some embodiments, when $R^{100}$ is methyl then ketones of structure XIV are treated with BBr$_3$, DCM, −78° C. to 0° C. for about 30 minutes to provide ketones of structure III.

In some embodiments, ketones of structure III are prepared as outlined in Scheme 4:

Scheme 4:

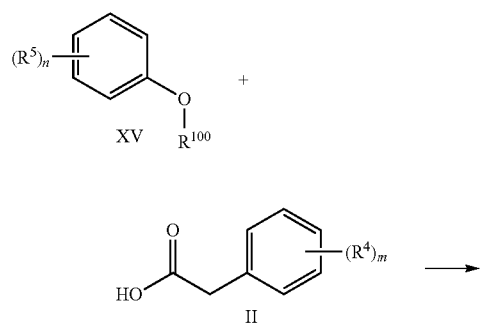

Alkyl esters of phenylacetic acids, such as compounds of structure XVII, are treated with a suitable base and then reacted with acid chlorides of structure XVI to provide keto-esters that are decarboxylated to provide ketones of structure XIV. In some embodiments, $R^{100}$ is alkyl. In some embodiments, $R^{100}$ is methyl. In some embodiments, the suitable base is lithium bis(trimethylsilyl)amide (LiHMDS). In some embodiments, compounds of structure XVII are treated with LiHMDS in tetrahydrofuran at −78° C. for about 15 minutes and then reacted with acid chlorides of structure XVI at −78° C. for about 1 hour. In some embodiments, decarboxylation of the keto-ester is accomplished using Krapcho decarboxylation condition. In some embodiments, Krapcho decarboxylation conditions include dimethylsulfoxide, brine with heating to about 150° C. for about 5 hours. Other decarboxylation conditions include the use of concentrated hydrochloric acid in ethanol at 130° C. for about 3 hours. $R^{100}$ is then removed from ketones of structure XIV as described in Scheme 3 to provide ketones of structure III.

In some embodiments, when $R^{2a}$ and $R^{2b}$ are taken together with the N atom to which they are attached to form a substituted or unsubstituted heterocycle, the substituted or unsubstituted heterocycle is prepared as outlined in Scheme 6.

provide imides of structure XXIII. Imides of structure XXIII are then reduced to provide amines of structure XXII.

In one aspect, compounds of Formula (I), (II), (III), (IV), (V), (VI), (VII), (VIII), (IX), (X), (XI), (XII), or (XIII) are synthesized as outlined in the Examples.

Throughout the specification, groups and substituents thereof are chosen by one skilled in the field to provide stable moieties and compounds.

A detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

Further Forms of Compounds

In one aspect, compounds of Formula (I), (II), (III), (IV), (V), (VI), (VII), (VIII), (IX), (X), (XI), (XII), or (XIII) possess one or more stereocenters and each stereocenter exists Scheme 6:

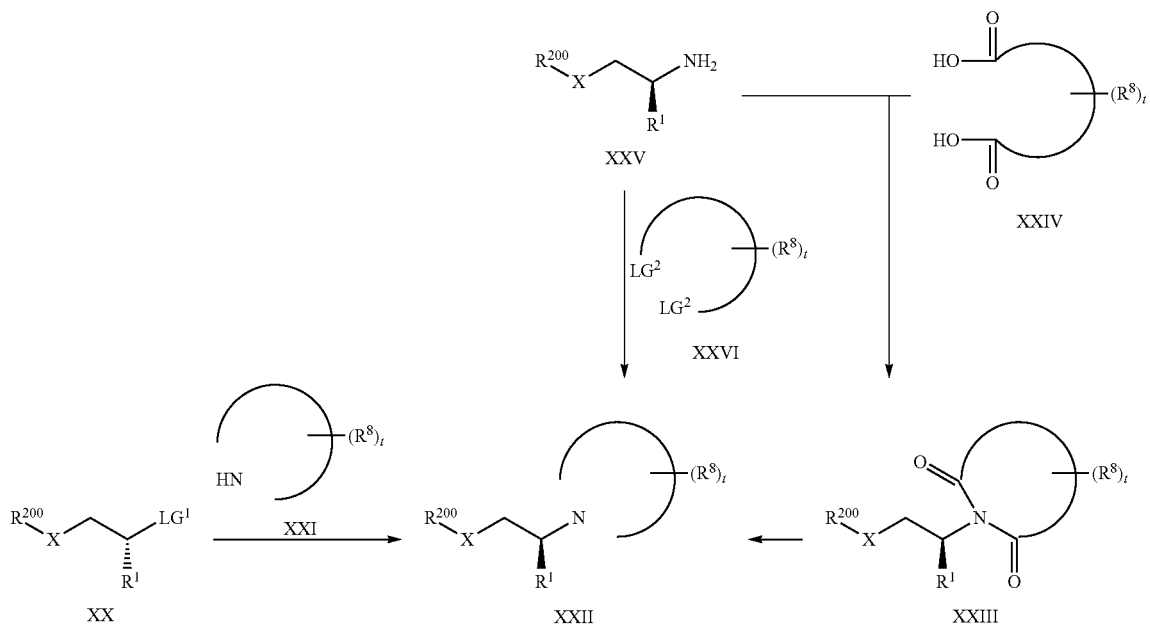

In some embodiments, substituted or unsubstituted heterocycles of structure XXI are reacted with compounds of structure XX, where $LG^1$ is a leaving group, to provide compounds of structure XXII. In some embodiments, substituted or unsubstituted heterocycles of structure XXI are reacted with compounds of structure XX: in the presence of triethylamine, dichloromethane, at room temperature; or in the presence of $K_2CO_3$, acetonitrile, room temperature. In some embodiments, $R^{200}$ is a suitable protecting group for X. In some embodiments, X is oxygen.

Alternatively, reaction of amines of structure XXV with activated alkanes of structure XXVI, where $LG^2$ is a suitable leaving group, provides compounds of structure XXII. Suitable leaving groups include, chloro, bromo, iodo, tosylate, mesylate, and triflate.

Alternatively, reaction of diacids of structure XXIV, where $LG^3$ is —OH, with acetic anhydride at about 85° C. for about 30 minutes provides an anhydride which is then treated with amines of structure XXV followed by acetic anhydride to independently in either the R or S configuration. The compounds presented herein include all diastereomeric, enantiomeric, and epimeric forms as well as the appropriate mixtures thereof. The compounds and methods provided herein include all cis, trans, syn, anti, entgegen (E), and zusammen (Z) isomers as well as the appropriate mixtures thereof. In certain embodiments, compounds of Formula (I), (II), (III), (IV), (V), (VI), (VII), (VIII), (IX), (X), (XI), (XII), and (XIII) are prepared as their individual stereoisomers by reacting a racemic mixture of the compound with an optically active resolving agent to form a pair of diastereoisomeric compounds/salts, separating the diastereomers and recovering the optically pure enantiomers. In some embodiments, resolution of enantiomers is carried out using covalent diastereomeric derivatives of the compounds described herein. In another embodiment, diastereomers are separated by separation/resolution techniques based upon differences in solubility. In other embodiments, separation of stereoisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In some embodiments, stereoisomers are obtained by stereoselective synthesis.

The methods and compositions described herein include the use of amorphous forms as well as crystalline forms (also known as polymorphs). In one aspect, compounds described herein are in the form of pharmaceutically acceptable salts. As well, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

In some embodiments, compounds described herein are prepared as prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. In some embodiments, the design of a prodrug increases the effective water solubility. An example, without limitation, of a prodrug is a compound described herein, which is administered as an ester (the "prodrug") but then is metabolically hydrolyzed to provide the active entity. In some embodiments, the active entity is a phenolic compound as described herein (e.g. compound of Formula (I), (II), (III), (IV), (V), (VI), (VII), (VIII), (IX), (X), (XI), (XII), or (XIII)). A further example of a prodrug might be a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

Prodrugs of the compounds described herein include, but are not limited to, esters, ethers, carbonates, thiocarbonates, N-acyl derivatives, N-acyloxyalkyl derivatives, quaternary derivatives of tertiary amines, N-Mannich bases, Schiff bases, amino acid conjugates, phosphate esters, and sulfonate esters. See for example Design of Prodrugs, Bundgaard, A. Ed., Elseview, 1985 and Method in Enzymology, Widder, K. et al., Ed.; Academic, 1985, vol. 42, p. 309-396; Bundgaard, H. "Design and Application of Prodrugs" in A Textbook of Drug Design and Development, Krosgaard-Larsen and H. Bundgaard, Ed., 1991, Chapter 5, p. 113-191; and Bundgaard, H., Advanced Drug Delivery Review, 1992, 8, 1-38, each of which is incorporated herein by reference. In some embodiments, a hydroxyl group in the compounds disclosed herein is used to form a prodrug, wherein the hydroxyl group is incorporated into an acyloxyalkyl ester, alkoxycarbonyloxyalkyl ester, alkyl ester, aryl ester, phosphate ester, sugar ester, ether, and the like.

Prodrug forms of the herein described compounds, wherein the prodrug is metabolized in vivo to produce a compound of Formula (I), (II), (III), (IV), (V), (VI), (VII), (VIII), (IX), (X), (XI), (XII), or (XIII) as set forth herein are included within the scope of the claims. In some cases, some of the herein-described compounds may be a prodrug for another derivative or active compound.

In some embodiments, sites on the aromatic ring portion of compounds of Formula (I), (II), (III), (IV), (V), (VI), (VII), (VIII), (IX), (X), (XI), (XII), and (XIII) are susceptible to various metabolic reactions. Incorporation of appropriate substituents on the aromatic ring structures will reduce, minimize or eliminate this metabolic pathway. In specific embodiments, the appropriate substituent to decrease or eliminate the susceptibility of the aromatic ring to metabolic reactions is, by way of example only, a halogen, deuterium or an alkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as, for example, $^{2}H$, $^{3}H$, $^{13}C$, $^{14}C$, $^{15}N$, $^{18}O$, $^{17}O$, $^{35}S$, $^{18}F$, $^{36}Cl$. In one aspect, isotopically-labeled compounds described herein, for example those into which radioactive isotopes such as $^{3}H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements.

In additional or further embodiments, the compounds described herein are metabolized upon administration to an organism in need to produce a metabolite that is then used to produce a desired effect, including a desired therapeutic effect.

"Pharmaceutically acceptable," as used herein, refers a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

The term "pharmaceutically acceptable salt" refers to a formulation of a compound that does not cause significant irritation to an organism to which it is administered and does not abrogate the biological activity and properties of the compound. In some embodiments, pharmaceutically acceptable salts are obtained by reacting a compound of Formula (I), (II), (III), (IV), (V), (VI), (VII), (VIII), (IX), (X), (XI), (XII), or (XIII) with acids. Pharmaceutically acceptable salts are also obtained by reacting a compound of Formula (I), (II), (III), (IV), (V), (VI), (VII), (VIII), (IX), (X), (XI), (XII), or (XIII) with a base to form a salt.

Compounds described herein may be formed as, and/or used as, pharmaceutically acceptable salts. The type of pharmaceutical acceptable salts, include, but are not limited to: (1) acid addition salts, formed by reacting the free base form of the compound with a pharmaceutically acceptable: inorganic acid to form a salt such as, for example, a hydrochloric acid salt, a hydrobromic acid salt, a sulfuric acid salt, a phosphoric acid salt, a metaphosphoric acid salt, and the like; or with an organic acid to form a salt such as, for example, an acetic acid salt, a propionic acid salt, a hexanoic acid salt, a cyclopentanepropionic acid salt, a glycolic acid salt, a pyruvic acid salt, a lactic acid salt, a malonic acid salt, a succinic acid salt, a malic acid salt, a maleic acid salt, a fumaric acid salt, a trifluoroacetic acid salt, a tartaric acid salt, a citric acid salt, a benzoic acid salt, a 3-(4-hydroxybenzoyl)benzoic acid salt, a cinnamic acid salt, a mandelic acid salt, a methanesulfonic acid salt, an ethanesulfonic acid salt, a 1,2-ethanedisulfonic acid salt, a 2-hydroxyethanesulfonic acid salt, a benzenesulfonic acid salt, a toluenesulfonic acid salt, a 2-naphthalenesulfonic acid salt, a 4-methylbicyclo-[2.2.2]oct-2-ene-1-carboxylic acid salt, a glucoheptonic acid salt, a 4,4'-methylenebis-(3-hydroxy-2-ene-1-carboxylic acid) salt, a 3-phenylpropionic acid salt, a trimethylacetic acid salt, a tertiary butylacetic acid salt, a lauryl sulfuric acid salt, a gluconic acid salt, a glutamic acid salt, a hydroxynaphthoic acid salt, a salicylic acid salt, a stearic acid salt, a muconic acid salt, a butyric acid salt, a phenylacetic acid salt, a phenylbutyric acid salt, a valproic acid salt, and the like; (2) salts formed when an acidic proton present in the parent compound is replaced by a metal ion, e.g., an alkali metal ion (e.g. a lithium salt, a sodium salt, or a potassium salt), an alkaline earth ion (e.g. a magnesium salt, or a calcium salt), or an aluminum ion (e.g. an aluminum salt). In some cases, compounds described herein may coordinate with an organic base to form a salt, such as, but not limited to, an ethanolamine salt, a diethanolamine salt, a triethanolamine salt, a tromethamine salt, a N-methylglucamine salt, a dicyclohexylamine salt, or a tris(hydroxymethyl)methylamine salt. In other cases, compounds described herein may form salts with amino acids such as, but not limited to, an arginine salt, a lysine salt, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

It should be understood that a reference to a pharmaceutically acceptable salt includes the solvent addition forms. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms.

CERTAIN TERMINOLOGY

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. In this application, the use of "or" or "and" means "and/or" unless stated otherwise. Furthermore, use of the term "including" as well as other forms, such as "include", "includes," and "included," is not limiting. The section headings used herein are for organizational purposes only and are not to be construed as limiting the subject matter described.

An "alkyl" group refers to an aliphatic hydrocarbon group. The alkyl group is saturated or unsaturated. The alkyl moiety, whether saturated or unsaturated, may be branched or straight chain. The "alkyl" group may have 1 to 6 carbon atoms (whenever it appears herein, a numerical range such as "1 to 6" refers to each integer in the given range; e.g., "1 to 6 carbon atoms" means that the alkyl group may consist of 1 carbon atom, 2 carbon atoms, 3 carbon atoms, etc., up to and including 6 carbon atoms, although the present definition also covers the occurrence of the term "alkyl" where no numerical range is designated). In one aspect the alkyl is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, sec-butyl, tertiary butyl, pentyl, neopentyl, hexyl, allyl, vinyl, acetylene, but-2-enyl, but-3-enyl, and the like.

The term "alkylene" refers to a divalent alkyl radical. Any of the above mentioned monovalent alkyl groups may be an alkylene by abstraction of a second hydrogen atom from the alkyl. Typical alkylene groups include, but are not limited to, —$CH_2$—, —$CH(CH_3)$—, —$C(CH_3)_2$—, —$CH_2CH_2$—, —$CH_2CH_2CH_2$— and the like.

An "alkoxy" group refers to a (alkyl)O— group, where alkyl is as defined herein.

The term "alkylamine" refers to the —$N(alkyl)_xH_y$ group, where x and y are selected from the group x=1, y=1 and x=2, y=0.

The term "aromatic" refers to a planar ring having a delocalized π-electron system containing $4n+2\pi$ electrons, where n is an integer. Aromatics are optionally substituted. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

The term "carbocyclic" or "carbocycle" refers to a ring or ring system where the atoms forming the backbone of the ring are all carbon atoms. The term thus distinguishes carbocyclic from heterocyclic rings in which the ring backbone contains at least one atom which is different from carbon.

As used herein, the term "aryl" refers to an aromatic ring wherein each of the atoms forming the ring is a carbon atom. Aryl groups are optionally substituted. In one aspect, an aryl is a phenyl or a naphthalenyl. In one aspect, an aryl is a phenyl. In one aspect, an aryl is a $C_6$-$C_{10}$aryl. Depending on the structure, an aryl group can be a monoradical or a diradical (i.e., an arylene group).

The term "cycloalkyl" refers to a monocyclic or polycyclic aliphatic, non-aromatic radical, wherein each of the atoms forming the ring (i.e. skeletal atoms) is a carbon atom. Cycloalkyls may be saturated, or partially unsaturated. Cycloalkyls may be fused with an aromatic ring, and the point of attachment is at a carbon that is not an aromatic ring carbon atom. Cycloalkyl groups include groups having from 3 to 10 ring atoms. In some embodiments, cycloalkyl groups are selected from among cyclopropyl, cyclobutyl, cyclopentyl, cyclopentenyl, cyclohexyl, cyclohexenyl, cycloheptyl, and cyclooctyl. Cycloalkyl groups may be substituted or unsubstituted. Depending on the structure, a cycloalkyl group can be a monoradical or a diradical (i.e., an cycloalkylene group, such as, but not limited to, cyclopropan-1,1-diyl, cyclobutan-1,1-diyl, cyclopentan-1,1-diyl, cyclohexan-1,1-diyl, cyclohexan-1,4-diyl, cycloheptan-1,1-diyl, and the like). In one aspect, a cycloalkyl is a $C_3$-$C_6$cycloalkyl.

The term "halo" or, alternatively, "halogen" or "halide" means fluoro, chloro, bromo or iodo.

The term "fluoroalkyl" refers to an alkyl in which one or more hydrogen atoms are replaced by a fluorine atom. In one aspect, a fluoralkyl is a $C_1$-$C_6$fluoroalkyl.

The term "heteroalkyl" refers to an alkyl group in which one or more skeletal atoms of the alkyl are selected from an atom other than carbon, e.g., oxygen, nitrogen (e.g. —NH—, —N(alkyl)-, sulfur, or combinations thereof. In one aspect, a heteroalkyl is a $C_1$-$C_6$heteroalkyl.

The term "heterocycle" or "heterocyclic" refers to heteroaromatic rings (also known as heteroaryls) and heterocycloalkyl rings (also known as heteroalicyclic groups) containing one to four heteroatoms in the ring(s), where each heteroatom in the ring(s) is selected from O, S and N, wherein each heterocyclic group has from 4 to 10 atoms in its ring system, and with the proviso that the any ring does not contain two adjacent O or S atoms. Non-aromatic heterocyclic groups (also known as heterocycloalkyls) include groups having only 3 atoms in their ring system, but aromatic heterocyclic groups must have at least 5 atoms in their ring system. The heterocyclic groups include benzo-fused ring systems. An example of a 3-membered heterocyclic group is aziridinyl. An example of a 4-membered heterocyclic group is azetidinyl. An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups may be C-attached (or C-linked) or N-attached where such is possible. For instance, a group derived from pyrrole may be pyrrol-1-yl (N-attached) or pyrrol-3-yl (C-attached). Further, a group derived from imidazole may be imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles may be substituted with one or two oxo (=O) moieties, such as pyrrolidin-2-one.

The terms "heteroaryl" or, alternatively, "heteroaromatic" refers to an aryl group that includes one or more ring heteroatoms selected from nitrogen, oxygen and sulfur. Illustrative examples of heteroaryl groups include the following moieties:

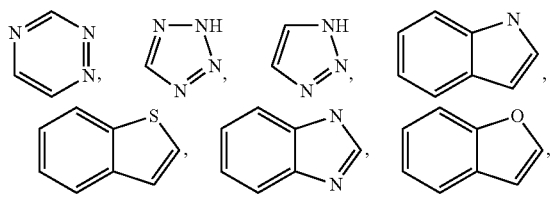

and the like. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. In some embodiments, a heteroaryl contains 0-3 N atoms in the ring. In some embodiments, a heteroaryl contains 1-3 N atoms in the ring. In some embodiments, a heteroaryl contains 0-3 N atoms, 0-1 O atoms, and 0-1 S atoms in the ring. In some embodiments, a heteroaryl is a monocyclic or bicyclic heteroaryl. In some embodiments, heteroaryl is a $C_1$-$C_9$heteroaryl. In some embodiments, monocyclic heteroaryl is a $C_1$-$C_5$heteroaryl. In some embodiments, monocyclic heteroaryl is a 5-membered or 6-membered heteroaryl. In some embodiments, bicyclic heteroaryl is a $C_6$-$C_9$heteroaryl. Depending on the structure, a heteroaryl group can be a monoradical or a diradical (i.e., a heteroarylene group).

A "heterocycloalkyl" or "heteroalicyclic" group refers to a cycloalkyl group that includes at least one heteroatom selected from nitrogen, oxygen and sulfur. The radicals may be fused with an aryl or heteroaryl. In some embodiments, the heterocycloalkyl is selected from oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, and indolinyl. The term heteroalicyclic also includes all ring forms of the carbohydrates, including but not limited to the monosaccharides, the disaccharides and the oligosaccharides. In one aspect, a heterocycloalkyl is a $C_2$-$C_{10}$heterocycloalkyl. In another aspect, a heterocycloalkyl is a $C_4$-$C_{10}$heterocycloalkyl. In some embodiments, a heterocycloalkyl contains 0-2 N atoms in the ring.

In some embodiments, a heterocycloalkyl contains 0-2 N atoms, 0-2 O atoms and 0-1 S atoms in the ring.

The term "bond" or "single bond" refers to a chemical bond between two atoms, or two moieties when the atoms joined by the bond are considered to be part of larger substructure. In one aspect, when a group described herein is a bond, the referenced group is absent thereby allowing a bond to be formed between the remaining identified groups.

The term "moiety" refers to a specific segment or functional group of a molecule. Chemical moieties are often recognized chemical entities embedded in or appended to a molecule.

The term "optionally substituted" or "substituted" means that the referenced group may be substituted with one or more additional group(s) individually and independently selected from alkyl, cycloalkyl, aryl, heteroaryl, heteroalicyclic, hydroxy, alkoxy, aryloxy, alkylthio, arylthio, alkylsulfoxide, arylsulfoxide, alkylsulfone, arylsulfone, cyano, halo, nitro, haloalkyl, fluoroalkyl, fluoroalkoxy, and amino, including mono- and di-substituted amino groups, and the protected derivatives thereof. In some embodiments, optional substituents are independently selected from halogen, —CN, —$NH_2$, —$NH(CH_3)$, —$N(CH_3)_2$, —OH, —$CO_2H$, —$CO_2$alkyl, —C(=O)$NH_2$, —C(=O)NH(alkyl), —C(=O)N(alkyl)$_2$, —S(=O)$_2NH_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some embodiments, optional substituents are independently selected from halogen, —CN, —$NH_2$, —OH, —$NH(CH_3)$, —$N(CH_3)_2$, —$CH_3$, —$CH_2CH_3$, —$CF_3$, —$OCH_3$, and —$OCF_3$. In some embodiments, substituted groups are substituted with one or two of the preceding groups. In some embodiments, an optional substituent on an aliphatic carbon atom (acyclic or cyclic, saturated or unsaturated carbon atoms, excluding aromatic carbon atoms) includes oxo (=O).

In certain embodiments, the compounds presented herein possess one or more stereocenters and each center independently exists in either the R or S configuration. The compounds presented herein include all diastereomeric, enantiomeric, and epimeric forms as well as the appropriate mixtures thereof. Stereoisomers are obtained, if desired, by methods such as, stereoselective synthesis and/or the separation of stereoisomers by chiral chromatographic columns.

The methods and formulations described herein include the use of N-oxides (if appropriate), crystalline forms (also known as polymorphs), or pharmaceutically acceptable salts of compounds having the structure of Formula (I), (II), (III), (IV), (V), (VI), (VII), (VIII), (IX), (X), (XI), (XII), or (XIII), as well as active metabolites of these compounds having the same type of activity. In some situations, compounds may exist as tautomers. All tautomers are included within the scope of the compounds presented herein. In specific embodiments, the compounds described herein exist in solvated forms with pharmaceutically acceptable solvents such as water, ethanol, and the like. In other embodiments, the compounds described herein exist in unsolvated form.

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an antagonist. In some embodiments, a modulator is a degrader.

"Selective estrogen receptor modulator" or "SERM" as used herein, refers to a molecule that differentially modulates the activity of estrogen receptors in different tissues. For example, in some embodiments, a SERM displays ER antagonist activity in some tissues and ER agonist activity in other tissues. In some embodiments, a SERM displays ER antagonist activity in some tissues and minimal or no ER agonist activity in other tissues. In some embodiments, a SERM displays ER antagonist activity in breast tissues, ovarian tissues, endometrial tissues, and/or cervical tissues but minimal or no ER agonist activity in uterine tissues.

The term "antagonist" as used herein, refers to a small-molecule agent that binds to a nuclear hormone receptor and subsequently decreases the agonist induced transcriptional activity of the nuclear hormone receptor.

The term "agonist" as used herein, refers to a small-molecule agent that binds to a nuclear hormone receptor and subsequently increases nuclear hormone receptor transcriptional activity in the absence of a known agonist.

The term "inverse agonist" as used herein, refers to a small-molecule agent that binds to a nuclear hormone receptor and subsequently decreases the basal level of nuclear hormone receptor transcriptional activity that is present in the absence of a known agonist.

The term "degrader" as used herein, refers to a small molecule agent that binds to a nuclear hormone receptor and subsequently lowers the steady state protein levels of said receptor. In some embodiments, a degrader as described herein lowers steady state estrogen receptor levels by at least 10%, at least 20%, at least 30%, at least 40%, at least 50%, at least 60%, at least 65%, at least 70%, at least 75%, at least 80%, at least 85%, at least 90% or at least 95%. In some embodiments, a degrader as described herein lowers steady state estrogen receptor levels by at least 65%. In some embodiments, a degrader as described herein lowers steady state estrogen receptor levels by at least 85%.

The term "selective estrogen receptor degrader" or "SERD" as used herein, refers to a small molecule agent that preferentially binds to estrogen receptors versus other receptors and subsequently lowers the steady state estrogen receptor levels.

The term "ER-dependent", as used herein, refers to diseases or conditions that would not occur, or would not occur to the same extent, in the absence of estrogen receptors.

The term "ER-mediated", as used herein, refers to diseases or conditions that might occur in the absence of estrogen receptors but can occur in the presence of estrogen receptors.

The term "ER-sensitive", as used herein, refers to diseases or conditions that would not occur, or would not occur to the same extent, in the absence of estrogens.

The term "cancer" as used herein refers to an abnormal growth of cells which tend to proliferate in an uncontrolled way and, in some cases, to metastasize (spread). The types of cancer include, but is not limited to, solid tumors (such as those of the bladder, bowel, brain, breast, endometrium, heart, kidney, lung, uterus, lymphatic tissue (lymphoma), ovary, pancreas or other endocrine organ (thyroid), prostate, skin (melanoma or basal cell cancer) or hematological tumors (such as the leukemias and lymphomas) at any stage of the disease with or without metastases.

Additional non-limiting examples of cancers include, acute lymphoblastic leukemia, acute myeloid leukemia, adrenocortical carcinoma, anal cancer, appendix cancer, astrocytomas, atypical teratoid/rhabdoid tumor, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-Cell lymphoma, embryonal tumors, endometrial cancer, ependymoblastoma, ependymoma, esophageal cancer, ewing sarcoma family of tumors, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, hodgkin lymphoma, hypopharyngeal cancer, intraocular melanoma, islet cell tumors (endocrine pancreas), Kaposi sarcoma, kidney cancer, Langerhans cell histiocytosis, laryngeal cancer, leukemia, Acute lymphoblastic leukemia, acute myeloid leukemia, chronic lymphocytic leukemia, chronic myelogenous leukemia, hairy cell leukemia, liver cancer, lung cancer, non-small cell lung cancer, small cell lung cancer, Burkitt lymphoma, cutaneous T-cell lymphoma, Hodgkin lymphoma, non-Hodgkin lymphoma, lymphoma, Waldenström macroglobulinemia, medulloblastoma, medulloepithelioma, melanoma, mesothelioma, mouth cancer, chronic myelogenous leukemia, myeloid leukemia, multiple myeloma, nasopharyngeal cancer, neuroblastoma, non-Hodgkin lymphoma, non-small cell lung cancer, oral cancer, oropharyngeal cancer, osteosarcoma, malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, retinoblastoma, rhabdomyosarcoma, salivary gland cancer, sarcoma, Ewing sarcoma family of tumors, sarcoma, kaposi, Sézary syndrome, skin cancer, small cell Lung cancer, small intestine cancer, soft tissue sarcoma, squamous cell carcinoma, stomach (gastric) cancer, supratentorial primitive neuroectodermal tumors, T-cell lymphoma, testicular cancer, throat cancer, thymoma and thymic carcinoma, thyroid cancer, urethral cancer, uterine cancer, uterine sarcoma, vaginal cancer, vulvar cancer, Waldenström macroglobulinemia, Wilms tumor.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound of Formula (I), (II), (III), (IV), (V), (VI), (VII), (VIII), (IX), (X), (XI), (XII), or (XIII), or a pharmaceutically acceptable salt thereof, and a co-agent, are both administered to a patient simultaneously in the form of a single entity or dosage. The term "non-fixed combination" means that the active ingredients, e.g. a compound of Formula (I), (II), (III), (IV), (V), (VI), (VII), (VIII), (IX), (X), (XI), (XII), or (XIII), or a pharmaceutically acceptable salt thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "kit" and "article of manufacture" are used as synonyms.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ-specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

Pharmaceutical Compositions/Formulations

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

Provided herein are pharmaceutical compositions that include a compound of Formula (I), (II), (III), (IV), (V), (VI), (VII), (VIII), (IX), (X), (XI), (XII), or (XIII), or a pharmaceutically acceptable salt thereof, and at least one pharmaceutically acceptable inactive ingredient. In some embodiments, the compounds described herein are administered as pharmaceutical compositions in which a compound of Formula (I), (II), (III), (IV), (V), (VI), (VII), (VIII), (IX), (X), (XI), (XII), or (XIII), or a pharmaceutically acceptable salt thereof, is mixed with other active ingredients, as in combination therapy. In other embodiments, the pharmaceutical compositions include other medicinal or pharmaceutical agents, carriers, adjuvants, preserving, stabilizing, wetting or emulsifying agents, solution promoters, salts for regulating the osmotic pressure, and/or buffers. In yet other embodiments, the pharmaceutical compositions include other therapeutically valuable substances.

A pharmaceutical composition, as used herein, refers to a mixture of a compound of Formula (I), (II), (III), (IV), (V), (VI), (VII), (VIII), (IX), (X), (XI), (XII), or (XIII), or a pharmaceutically acceptable salt thereof, with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, antifoaming agents, antioxidants, preservatives, or one or more combination thereof. The pharmaceutical composition facilitates administration of the compound to a mammal.

A therapeutically effective amount can vary widely depending on the severity of the disease, the age and relative health of the subject, the potency of the compound used and other factors. The compounds can be used singly or in combination with one or more therapeutic agents as components of mixtures.

The pharmaceutical formulations described herein are administered to a subject by appropriate administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

Pharmaceutical compositions including a compound of Formula (I), (II), (III), (IV), (V), (VI), (VII), (VIII), (IX), (X), (XI), (XII), or (XIII), or a pharmaceutically acceptable salt thereof, are manufactured in a conventional manner, such as, by way of example only, by means of conventional mixing, dissolving, granulating, dragee-making, levigating, emulsifying, encapsulating, entrapping or compression processes.

The pharmaceutical compositions will include at least one compound of Formula (I), (II), (III), (IV), (V), (VI), (VII), (VIII), (IX), (X), (XI), (XII), or (XIII) as an active ingredient in free-acid or free-base form, or in a pharmaceutically acceptable salt form. In addition, the methods and pharmaceutical compositions described herein include the use of N-oxides (if appropriate), crystalline forms, amorphous phases, as well as active metabolites of these compounds having the same type of activity. In some embodiments, compounds described herein exist in unsolvated form or in solvated forms with pharmaceutically acceptable solvents such as water, ethanol, and the like. The solvated forms of the compounds presented herein are also considered to be disclosed herein.

The pharmaceutical compositions described herein, which include a compound of Formula (I), (II), (III), (IV), (V), (VI), (VII), (VIII), (IX), (X), (XI), (XII), or (XIII), or a pharmaceutically acceptable salt thereof, are formulated into any suitable dosage form, including but not limited to, aqueous oral dispersions, liquids, gels, syrups, elixirs, slurries, suspensions, solid oral dosage forms, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

Pharmaceutical preparations that are administered orally include push-fit capsules made of gelatin, as well as soft, sealed capsules made of gelatin and a plasticizer, such as glycerol or sorbitol. The push-fit capsules contain the active ingredients in admixture with filler such as lactose, binders such as starches, and/or lubricants such as talc or magnesium stearate and, optionally, stabilizers. In some embodiments, the push-fit capsules do not include any other ingredient besides the capsule shell and the active ingredient. In soft capsules, the active compounds are dissolved or suspended in suitable liquids, such as fatty oils, liquid paraffin, or liquid polyethylene glycols. In some embodiments, stabilizers are added.

All formulations for oral administration are in dosages suitable for such administration.

In one aspect, solid oral soage forms are prepared by mixing a compound of Formula (I), (II), (III), (IV), (V), (VI), (VII), (VIII), (IX), (X), (XI), (XII), or (XIII), or a pharmaceutically acceptable salt thereof, with one or more of the following: antioxidants, flavoring agents, and carrier materials such as binders, suspending agents, disintegration agents, filling agents, surfactants, solubilizers, stabilizers, lubricants, wetting agents, and diluents.

In some embodiments, the solid dosage forms disclosed herein are in the form of a tablet, (including a suspension tablet, a fast-melt tablet, a bite-disintegration tablet, a rapid-disintegration tablet, an effervescent tablet, or a caplet), a pill, a powder, a capsule, solid dispersion, solid solution, bioerodible dosage form, controlled release formulations, pulsatile release dosage forms, multiparticulate dosage forms, beads, pellets, granules. In other embodiments, the pharmaceutical formulation is in the form of a powder. In still other embodiments, the pharmaceutical formulation is in the form of a tablet. In other embodiments, pharmaceutical formulation is in the form of a capsule.

In some embodiments, solid dosage forms, e.g., tablets, effervescent tablets, and capsules, are prepared by mixing particles of a compound of Formula (I), (II), (III), (IV), (V), (VI), (VII), (VIII), (IX), (X), (XI), (XII), or (XIII), or a pharmaceutically acceptable salt thereof, with one or more pharmaceutical excipients to form a bulk blend composition. The bulk blend is readily subdivided into equally effective unit dosage forms, such as tablets, pills, and capsules.

In some embodiments, the individual unit dosages include film coatings. These formulations are manufactured by conventional formulation techniques.

Conventional formulation techniques include, e.g., one or a combination of methods: (1) dry mixing, (2) direct compression, (3) milling, (4) dry or non-aqueous granulation, (5) wet granulation, or (6) fusion. Other methods include, e.g., spray drying, pan coating, melt granulation, granulation, fluidized bed spray drying or coating (e.g., wurster coating), tangential coating, top spraying, tableting, extruding and the like.

In some embodiments, tablets will include a film surrounding the final compressed tablet. In some embodiments, the film coating can provide a delayed release of the compound of Formula (I), (II), (III), (IV), (V), (VI), (VII), (VIII), (IX), (X), (XI), (XII), or (XIII), or a pharmaceutically acceptable salt thereof, from the formulation. In other embodiments, the film coating aids in patient compliance (e.g., Opadry® coatings or sugar coating). Film coatings including Opadry® typically range from about 1% to about 3% of the tablet weight.

A capsule may be prepared, for example, by placing the bulk blend of the formulation of the compound described above, inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule is swallowed whole or the capsule is opened and the contents sprinkled on food prior to eating.

In various embodiments, the particles of the compound of Formula (I), (II), (III), (IV), (V), (VI), (VII), (VIII), (IX), (X), (XI), (XII), or (XIII), or a pharmaceutically acceptable salt thereof, and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In still other embodiments, effervescent powders are also prepared. Effervescent salts have been used to disperse medicines in water for oral administration.

In some embodiments, the pharmaceutical solid oral dosage forms are formulated to provide a controlled release of the active compound. Controlled release refers to the release of the active compound from a dosage form in which it is incorporated according to a desired profile over an extended period of time. Controlled release profiles include, for example, sustained release, prolonged release, pulsatile release, and delayed release profiles. In contrast to immediate release compositions, controlled release compositions allow delivery of an agent to a subject over an extended period of time according to a predetermined profile. Such release rates can provide therapeutically effective levels of agent for an extended period of time and thereby provide a longer period of pharmacologic response while minimizing side effects as compared to conventional rapid release dosage forms. Such longer periods of response provide for many inherent benefits that are not achieved with the corresponding short acting, immediate release preparations.

In some embodiments, the solid dosage forms described herein are formulated as enteric coated delayed release oral dosage forms, i.e., as an oral dosage form of a pharmaceutical composition as described herein which utilizes an enteric coating to affect release in the small intestine or large intestine. In one aspect, the enteric coated dosage form is a compressed or molded or extruded tablet/mold (coated or uncoated) containing granules, powder, pellets, beads or particles of the active ingredient and/or other composition components, which are themselves coated or uncoated. In one aspect, the enteric coated oral dosage form is in the form of a capsule containing pellets, beads or granules.

Conventional coating techniques such as spray or pan coating are employed to apply coatings. The coating thickness must be sufficient to ensure that the oral dosage form remains intact until the desired site of topical delivery in the intestinal tract is reached.

In other embodiments, the formulations described herein are delivered using a pulsatile dosage form. A pulsatile dosage form is capable of providing one or more immediate release pulses at predetermined time points after a controlled lag time or at specific sites. Exemplary pulsatile dosage forms and methods of their manufacture are disclosed in U.S. Pat. Nos. 5,011,692, 5,017,381, 5,229,135, 5,840,329 and 5,837,284. In one embodiment, the pulsatile dosage form includes at least two groups of particles, (i.e. multiparticulate) each containing the formulation described herein. The first group of particles provides a substantially immediate dose of the active compound upon ingestion by a mammal. The first group of particles can be either uncoated or include a coating and/or sealant. In one aspect, the second group of particles comprises coated particles. The coating on the second group of particles provides a delay of from about 2 hours to about 7 hours following ingestion before release of the second dose. Suitable coatings for pharmaceutical compositions are described herein or in the art.

In some embodiments, pharmaceutical formulations are provided that include particles of a compound of Formula (I), (II), (III), (IV), (V), (VI), (VII), (VIII), (IX), (X), (XI), (XII), or (XIII), or a pharmaceutically acceptable salt thereof, and at least one dispersing agent or suspending agent for oral administration to a subject. The formulations may be a powder and/or granules for suspension, and upon admixture with water, a substantially uniform suspension is obtained.

In one aspect, liquid formulation dosage forms for oral administration are in the form of aqueous suspensions selected from the group including, but not limited to, pharmaceutically acceptable aqueous oral dispersions, emulsions, solutions, elixirs, gels, and syrups. See, e.g., Singh et al., Encyclopedia of Pharmaceutical Technology, 2nd Ed., pp. 754-757 (2002). In addition to the particles of the compound of Formula (I), the liquid dosage forms include additives, such as: (a) disintegrating agents; (b) dispersing agents; (c) wetting agents; (d) at least one preservative, (e) viscosity enhancing agents, (f) at least one sweetening agent, and (g) at least one flavoring agent. In some embodiments, the aqueous dispersions can further include a crystalline inhibitor.

Buccal formulations that include a compound of Formula (I), (II), (III), (IV), (V), (VI), (VII), (VIII), (IX), (X), (XI), (XII), or (XIII), or a pharmaceutically acceptable salt thereof, are administered using a variety of formulations known in the art. For example, such formulations include, but are not limited to, U.S. Pat. Nos. 4,229,447, 4,596,795, 4,755,386, and 5,739,136. In addition, the buccal dosage forms described herein can further include a bioerodible (hydrolysable) polymeric carrier that also serves to adhere the dosage form to the buccal mucosa. For buccal or sublingual administration, the compositions may take the form of tablets, lozenges, or gels formulated in a conventional manner.

In some embodiments, compounds of Formula (I), (II), (III), (IV), (V), (VI), (VII), (VIII), (IX), (X), (XI), (XII), and (XIII), or a pharmaceutically acceptable salt thereof, are prepared as transdermal dosage forms. In one embodiment, the transdermal formulations described herein include at least three components: (1) a formulation of a compound of Formula (I), (II), (III), (IV), (V), (VI), (VII), (VIII), (IX), (X), (XI), or (XIII), or a pharmaceutically acceptable salt thereof; (2) a penetration enhancer; and (3) an aqueous adjuvant. In some embodiments the transdermal formulations include additional components such as, but not limited to, gelling agents, creams and ointment bases, and the like. In some embodiments, the transdermal formulation further includes a woven or non-woven backing material to enhance absorption and prevent the removal of the transdermal formulation from the skin. In other embodiments, the transdermal formulations described herein can maintain a saturated or supersaturated state to promote diffusion into the skin.

In one aspect, formulations suitable for transdermal administration of compounds described herein employ transdermal delivery devices and transdermal delivery patches and can be lipophilic emulsions or buffered, aqueous solutions, dissolved and/or dispersed in a polymer or an adhesive. In one aspect, such patches are constructed for continuous, pulsatile, or on demand delivery of pharmaceutical agents. Still further, transdermal delivery of the compounds described herein can be accomplished by means of iontophoretic patches and the like. In one aspect, transdermal patches provide controlled delivery of the active compound. In one aspect, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

In one aspect, a compound of Formula (I), (II), (III), (IV), (V), (VI), (VII), (VIII), (IX), (X), (XI), (XII), or (XIII), or a pharmaceutically acceptable salt thereof, is formulated into a pharmaceutical composition suitable for intramuscular, subcutaneous, or intravenous injection. In one aspect, formulations suitable for intramuscular, subcutaneous, or intravenous injection include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles include water, ethanol, polyols (propyleneglycol, polyethylene-glycol, glycerol, cremophor and the like), vegetable oils and organic esters, such as ethyl oleate. In some embodiments, formulations suitable for subcutaneous injection contain additives such as preserving, wetting, emulsifying, and dispensing agents. Prolonged absorption of the injectable pharmaceutical form can be brought about by the use of agents delaying absorption, such as aluminum monostearate and gelatin.

For intravenous injections, compounds described herein are formulated in aqueous solutions, preferably in physiologically compatible buffers such as Hank's solution, Ringer's solution, or physiological saline buffer.

For transmucosal administration, penetrants appropriate to the barrier to be permeated are used in the formulation. Such penetrants are generally known in the art. For other parenteral injections, appropriate formulations include aqueous or non-aqueous solutions, preferably with physiologically compatible buffers or excipients. Such excipients are known.

Parenteral injections may involve bolus injection or continuous infusion. Formulations for injection may be presented in unit dosage form, e.g., in ampoules or in multi-dose containers, with an added preservative. The pharmaceutical composition described herein may be in a form suitable for parenteral injection as a sterile suspensions, solutions or emulsions in oily or aqueous vehicles, and may contain formulatory agents such as suspending, stabilizing and/or dispersing agents. In one aspect, the active ingredient is in powder form for constitution with a suitable vehicle, e.g., sterile pyrogen-free water, before use.

In certain embodiments, delivery systems for pharmaceutical compounds may be employed, such as, for example, liposomes and emulsions. In certain embodiments, compositions provided herein can also include an mucoadhesive polymer, selected from among, for example, carboxymethylcellulose, carbomer (acrylic acid polymer), poly (methylmethacrylate), polyacrylamide, polycarbophil, acrylic acid/butyl acrylate copolymer, sodium alginate and dextran.

In some embodiments, the compounds described herein may be administered topically and can be formulated into a variety of topically administrable compositions, such as solutions, suspensions, lotions, gels, pastes, medicated sticks, balms, creams or ointments. Such pharmaceutical compounds can contain solubilizers, stabilizers, tonicity enhancing agents, buffers and preservatives.

Methods of Dosing and Treatment Regimens

In one embodiment, the compounds of Formula (I), (II), (III), (IV), (V), (VI), (VII), (VIII), (IX), (X), (XI), (XII), and (XIII), or a pharmaceutically acceptable salt thereof, are used in the preparation of medicaments for the treatment of diseases or conditions in a mammal that would benefit from a reduction of estrogen receptor activity. Methods for treating any of the diseases or conditions described herein in a mammal in need of such treatment, involves administration of pharmaceutical compositions that include at least one compound of Formula (I), (II), (III), (IV), (V), (VI), (VII), (VIII), (IX), (X), (XI), (XII), or (XIII), or a pharmaceutically acceptable salt thereof, or a pharmaceutically acceptable salt, active metabolite, prodrug, or pharmaceutically acceptable solvate thereof, in therapeutically effective amounts to said mammal.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like.

When used in a patient, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of the disease being treated and is currently in remission, a pharmaceutical composition comprising a compound of Formula (I), (II), (III), (IV), (V), (VI), (VII), (VIII), (IX), (X), (XI), (XII), or (XIII), or a pharmaceutically acceptable salt thereof, in order to prevent a return of the symptoms of the disease or condition.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

In certain embodiments wherein a patient's status does improve, the dose of drug being administered may be temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but can nevertheless be determined according to the particular circumstances surrounding the case, including, e.g., the specific agent being administered, the route of administration, the condition being treated, and the subject or host being treated.

In general, however, doses employed for adult human treatment are typically in the range of 0.01 mg-5000 mg per day. In one aspect, doses employed for adult human treatment are from about 1 mg to about 1000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the compound of Formula (I), (II), (III), (IV), (V), (VI), (VII), (VIII), (IX), (X), (XI), (XII), or (XIII), or a pharmaceutically acceptable salt thereof, described herein are from about 0.01 to about 10 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{50}$ and the $ED_{50}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

Combination Treatments

In certain instances, it is appropriate to administer at least one compound of Formula (I), (II), (III), (IV), (V), (VI), (VII), (VIII), (IX), (X), (XI), (XII), or (XIII), or a pharmaceutically acceptable salt thereof, in combination with one or more other therapeutic agents.

In one embodiment, the therapeutic effectiveness of one of the compounds described herein is enhanced by administration of an adjuvant (i.e., by itself the adjuvant may have minimal therapeutic benefit, but in combination with another therapeutic agent, the overall therapeutic benefit to the patient is enhanced). Or, in some embodiments, the benefit experienced by a patient is increased by administering one of the compounds described herein with another therapeutic agent (which also includes a therapeutic regimen) that also has therapeutic benefit.

In one specific embodiment, a compound of Formula (I), (II), (III), (IV), (V), (VI), (VII), (VIII), (IX), (X), (XI), (XII), or (XIII), or a pharmaceutically acceptable salt thereof, is co-administered with a second therapeutic agent, wherein the compound of Formula (I), (II), (III), (IV), (V), (VI), (VII), (VIII), (IX), (X), (XI), (XII), or (XIII), or a pharmaceutically acceptable salt thereof, and the second therapeutic agent modulate different aspects of the disease, disorder or condition being treated, thereby providing a greater overall benefit than administration of either therapeutic agent alone.

In any case, regardless of the disease, disorder or condition being treated, the overall benefit experienced by the patient may simply be additive of the two therapeutic agents or the patient may experience a synergistic benefit.

In certain embodiments, different therapeutically-effective dosages of the compounds disclosed herein will be utilized in formulating pharmaceutical composition and/or in treatment regimens when the compounds disclosed herein are administered in combination with one or more additional agent, such as an additional therapeutically effective drug, an adjuvant or the like. Therapeutically-effective dosages of drugs and other agents for use in combination treatment regimens can be determined by means similar to those set forth hereinabove for the actives themselves. Furthermore, the methods of prevention/treatment described herein encompasses the use of metronomic dosing, i.e., providing more frequent, lower doses in order to minimize toxic side effects. In some embodiments, a combination treatment regimen encompasses treatment regimens in which administration of a compound of Formula (I), (II), (III), (IV), (V), (VI), (VII), (VIII), (IX), (X), (XI), (XII), or (XIII), or a pharmaceutically acceptable salt thereof, is initiated prior to, during, or after treatment with a second agent described herein, and continues until any time during treatment with the second agent or after termination of treatment with the second agent. It also includes treatments in which a compound of Formula (I), (II), (III), (IV), (V), (VI), (VII), (VIII), (IX), (X), (XI), (XII), or (XIII), or a pharmaceutically acceptable salt thereof, and the second agent being used in combination are administered simultaneously or at different times and/or at decreasing or increasing intervals during the treatment period. Combination treatment further includes periodic treatments that start and stop at various times to assist with the clinical management of the patient.

It is understood that the dosage regimen to treat, prevent, or ameliorate the condition(s) for which relief is sought, is modified in accordance with a variety of factors (e.g. the disease, disorder or condition from which the subject suffers; the age, weight, sex, diet, and medical condition of the subject). Thus, in some instances, the dosage regimen actually employed varies and, in some embodiments, deviates from the dosage regimens set forth herein.

For combination therapies described herein, dosages of the co-administered compounds vary depending on the type of co-drug employed, on the specific drug employed, on the disease or condition being treated and so forth. In additional embodiments, when co-administered with one or more other therapeutic agents, the compound provided herein is administered either simultaneously with the one or more other therapeutic agents, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

The compounds of Formula (I), (II), (III), (IV), (V), (VI), (VII), (VIII), (IX), (X), (XI), (XII), and (XIII), or a pharmaceutically acceptable salt thereof, as well as combination therapies, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject. For example, in specific embodiments, a compound described herein or a formulation containing the compound is administered for at least 2 weeks, about 1 month to about 5 years.

Exemplary Agent for Use in Combination Therapy

In some embodiments, methods for treatment of estrogen receptor-dependent or estrogen receptor-mediated conditions or diseases, such as proliferative disorders, including cancer, comprises administration to a mammal a compound of Formula (I), (II), (III), (IV), (V), (VI), (VII), (VIII), (IX), (X), (XI), (XII), or (XIII), or a pharmaceutically acceptable salt thereof, in combination with at least one additional therapeutic agent.

In some embodiments, a compound of Formula (I), (II), (III), (IV), (V), (VI), (VII), (VIII), (IX), (X), (XI), (XII), or (XIII), or a pharmaceutically acceptable salt thereof, in combination with hormone blocking therapy, chemotherapy, radiation therapy, monoclonal antibodies, or combinations thereof.

Hormone blocking therapy includes the use of agents that block the production of estrogens or block the estrogen receptors. In some embodiments, hormone blocking therapy includes the use of estrogen receptor modulators and/or aromatase inhibitors. Estrogen receptor modulators include triphenylethylene derivatives (e.g. tamoxifen, toremifene, droloxifene, 3-hydroxytamoxifen, idoxifene, TAT-59 (a phosphorylated derivative of 4-hydroxytamoxifen) and GW5638 (a carboxylic acid derivative of tamoxifen)); non-steroidal estrogen receptor modulators (e.g. raloxifene, LY353381 (SERM3) and LY357489); steroidal estrogen receptor modulators (e.g. ICI-182,780). Aromatase inhibitors include steroidal aromatase inhibitors and non-steroidal aromatase inhibitors. Steroidal aromatase inhibitors include, but are not limited to, such exemestane. Non-steroidal aromatase inhibitors include, but are not limited to, as anastrozole, and letrozole.

Chemotherapy includes the use of anti-cancer agents.

Monoclonal antibodies include, but are not limited to, trastuzumab (Herceptin).

In some embodiments, the at least one additional therapeutic agent for use in combination with the compounds of Formula (I), (II), (III), (IV), (V), (VI), (VII), (VIII), (IX), (X), (XI), (XII), or (XIII), or a pharmaceutically acceptable salt thereof, include one or more of the following: abiraterone; abarelix; adriamycin; aactinomycin; acivicin; aclarubicin; acodazole hydrochloride; acronine; adozelesin; aldesleukin; alemtuzumab; allopurinol; alitretinoin; altretamine; ambomycin; ametantrone acetate; aminoglutethimide; aminolevulinic acid; amifostine; amsacrine; anastrozole; anthramycin; aprepitant; arsenic trioxide; asparaginase; asperlin; azacitidine; azetepa; azotomycin; batimastat; bendamustine hydrochloride; benzodepa; bevacizumab; bexarotene; bicalutamide; bisantrene hydrochloride; bisnafide dimesylate; bizelesin; bleomycin; bleomycin sulfate; bortezomib; brequinar sodium; bropirimine; busulfan; cactinomycin; calusterone; caracemide; carbetimer; carboplatin; carmustine; carubicin hydrochloride; carzelesin; capecitabine; cedefingol; cetuximab; chlorambucil; cirolemycin; cisplatin; cladribine; clofarabine; crisnatol mesylate; cyclophosphamide; cytarabine; dacarbazine; dasatinib; daunorubicin hydrochloride; dactinomycin; darbepoetin alfa; decitabine; degarelix; denileukin diftitox; dexormaplatin; dexrazoxane hydrochloride; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; eltrombopag olamine; enloplatin; enpromate; epipropidine; epirubicin hydrochloride; epoetin alfa; erbulozole; erlotinib hydrochloride; esorubicin hydrochloride; estramustine; estramustine phosphate sodium; etanidazole; etoposide; etoposide phosphate; etoprine; everolimus; exemestane; fadrozole hydrochloride; fazarabine; fenretinide; filgrastim; floxuridine; fludarabine phosphate; fluorouracil; flurocitabine; fosquidone; fostriecin sodium; fulvestrant; gefitinib; gemcitabine; gemcitabine hydrochloride; gemcitabine-cisplatin; gemtuzumab ozogamicin; goserelin acetate; histrelin acetate; hydroxyurea; idarubicin hydrochloride; ifosfamide; iimofosine; ibritumomab tiuxetan; idarubicin; ifosfamide; imatinib mesylate; imiquimod; interleukin II (including recombinant interleukin II, or rIL2), interferon alfa-2a; interferon alfa-2b; interferon alfa-n1; interferon alfa-n3; interferon beta-1 a; interferon gamma-1 b; iproplatin; irinotecan hydrochloride; ixabepilone; lanreotide acetate; lapatinib; lenalidomide; letrozole; leuprolide acetate; leucovorin calcium; leuprolide acetate; levamisole; liposomal cytarabine; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; methoxsalen; metoprine; meturedepa; mitindomide; mitocarcin; mitocromin; mitogillin; mitomalcin; mitomycin C; mitosper; mitotane; mitoxantrone hydrochloride; mycophenolic acid; nandrolone phenpropionate; nelarabine; nilotinib; nocodazoie; nofetumomab; nogalamycin; ofatumumab; oprelvekin; ormaplatin; oxaliplatin; oxisuran; paclitaxel; palifermin; palonosetron hydrochloride; pamidronate; pegfilgrastim; pemetrexed disodium; pentostatin; panitumumab; pazopanib hydrochloride; pemetrexed disodium; plerixafor; pralatrexate; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; quinacrine; raloxifene hydrochloride; rasburicase; recombinant HPV bivalent vaccine; recombinant HPV quadrivalent vaccine; riboprine; rogletimide; rituximab; romidepsin; romiplostim; safingol; safingol hydrochloride; sargramostim; semustine; simtrazene; sipuleucel-T; sorafenib; sparfosate sodium; sparsomycin; spirogermanium hydrochloride; spiromustine; spiroplatin; streptonigrin; streptozocin; sulofenur; sunitinib malate; talisomycin; tamoxifen citrate; tecogalan sodium; tegafur; teloxantrone hydrochloride; temozolomide; temoporfin; temsirolimus; teniposide; teroxirone; testolactone; thalidomide; thiamiprine; thioguanine; thiotepa; tiazofurin; tirapazamine; topotecan hydrochloride; toremifene; tositumomab and I 131 Iodine tositumomab; trastuzumab; trestolone acetate; tretinoin; triciribine phosphate; trimetrexate; trimetrexate glucuronate; triptorelin; tubulozole hydrochloride; uracil mustard; uredepa; valrubicin; vapreotide; verteporfin; vinblastine; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorinostat; vorozole; zeniplatin; zinostatin; zoledronic acid; or zorubicin hydrochloride.

In some embodiments, the at least one additional chemotherapeutic agent is selected from, by way of example only, alemtuzumab, arsenic trioxide, asparaginase (pegylated or non-), bevacizumab, cetuximab, platinum-based compounds such as cisplatin, cladribine, daunorubicin/doxorubicin/idarubicin, irinotecan, fludarabine, 5-fluorouracil, gemtuzumab, methotrexate, taxol, temozolomide, thioguanine, or classes of drugs including hormones (an antiestrogen, an antiandrogen, or gonadotropin releasing hormone analogues, interferons such as alpha interferon, nitrogen mustards such as busulfan or melphalan or mechlorethamine, retinoids such as tretinoin, topoisomerase inhibitors such as irinotecan or topotecan, tyrosine kinase inhibitors such as gefinitinib or imatinib, or agents to treat signs or symptoms induced by such therapy including allopurinol, filgrastim, granisetron/ondansetron/palonosetron, dronabinol.

In one aspect, the compound of Formula (I), (II), (III), (IV), (V), (VI), (VII), (VIII), (IX), (X), (XI), (XII), or (XIII), or a pharmaceutically acceptable salt thereof, is administered or formulated in combination with one or more anti-cancer agents. In some embodiments, one or more of the anti-cancer agents are proapoptotic agents. Examples of anti-cancer agents include, but are not limited to, any of the following: gossypol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib, geldanamycin, 17-N-Allylamino-17-Demethoxygeldanamycin (17-AAG), flavopiridol, LY294002, bortezomib, trastuzumab, BAY 11-7082, PKC412, or PD184352, paclitaxel, and analogs of paclitaxel. Compounds that have the basic taxane skeleton as a common structure feature, have also been shown to have the ability to arrest cells in the G2-M phases due to stabilized microtubules and may be useful for treating cancer in combination with the compounds described herein.

Further examples of anti-cancer agents for use in combination with the compounds of Formula (I), (II), (III), (IV), (V), (VI), (VII), (VIII), (IX), (X), (XI), (XII), or (XIII), or a pharmaceutically acceptable salt thereof, include inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; mTOR inhibitors; and antibodies (e.g., rituxan).

Further examples of anti-cancer agents for use in combination with the compounds of Formula (I), (II), (III), (IV), (V), (VI), (VII), (VIII), (IX), (X), (XI), (XII), or (XIII), or a pharmaceutically acceptable salt thereof, include aromatase inhibitors. Aromatase inhibitors include steroidal aromatase inhibitors and non-steroidal aromatase inhibitors. Steroidal aromatase inhibitors include, but are not limited to, exemestane. Non-steroidal aromatase inhibitors include, but are not limited to, anastrozole, and letrozole.

Yet other anticancer agents for use in combination with the compounds of Formula (I), (II), (III), (IV), (V), (VI), (VII), (VIII), (IX), (X), (XI), (XII), or (XIII), or a pharmaceutically acceptable salt thereof, include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, ete.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

Examples of natural products for use in combination with the compounds of Formula (I), (II), (III), (IV), (V), (VI), (VII), (VIII), (IX), (X), (XI), (XII), or (XIII), or a pharmaceutically acceptable salt thereof, include but are not limited to vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents for use in combination with the compounds of Formula (I), (II), (III), (IV), (V), (VI), (VII), (VIII), (IX), (X), (XI), (XII), or (XIII), or a pharmaceutically acceptable salt thereof, include, but are not limited to, nitrogen mustards (e.g., mechloroethamine, cyclophosphamide, chlorambucil, meiphalan, etc.), ethylenimine and methylmelamines (e.g., hexamethlymelamine, thiotepa), alkyl sulfonates (e.g., busulfan), nitrosoureas (e.g., carmustine, lomusitne, semustine, streptozocin, etc.), or triazenes (decarbazine, ete.).

In some embodiments, compounds of Formula (I), (II), (III), (IV), (V), (VI), (VII), (VIII), (IX), (X), (XI), (XII), or (XIII), or a pharmaceutically acceptable salt thereof, are used to treat cancer in combination with: a second antiestrogen (e.g., tamoxifen), an antiandrogen (e.g., bicalutamide, flutamide), a gonadotropin releasing hormone analog (e.g., leuprolide).

Other agents that can be used in the methods and compositions described herein for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Examples of anti-cancer agents which act by arresting cells in the G2-M phases due to stabilized microtubules include without limitation the following marketed drugs and drugs in development: Erbulozole, Dolastatin 10, Mivobulin isethionate, Vincristine, NSC-639829, Discodermolide, ABT-751, Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride, Epothilones (such as Epothilone A, Epothilone B, Epothilone C, Epothilone D, Epothilone E, Epothilone F, Epothilone B N-oxide, Epothilone A N-oxide, 16-aza-epothilone B, 21-aminoepothilone B, 21-hydroxyepothilone D, 26-fluoroepothilone, Auristatin PE, Soblidotin, Vincristine sulfate, Cryptophycin 52, Vitilevuamide, Tubulysin A, Canadensol, Centaureidin, Oncocidin A1 Fijianolide B, Laulimalide, Narcosine, Nascapine, Hemiasterlin, Vanadocene acetylacetonate, Indanocine Eleutherobins (such as Desmethyleleutherobin, Desaetyleleutherobin, Isoeleutherobin A, and Z-Eleutherobin), Caribaeoside, Caribaeolin, Halichondrin B, Diazonamide A, Taccalonolide A, Diozostatin, (−)-Phenylahistin, Myoseverin B, Resverastatin phosphate sodium.

In one aspect, a compound of Formula (I), (II), (III), (IV), (V), (VI), (VII), (VIII), (IX), (X), (XI), (XII), or (XIII), or a pharmaceutically acceptable salt thereof, is co-administered with thrombolytic agents (e.g., alteplase anistreplase, streptokinase, urokinase, or tissue plasminogen activator), heparin, tinzaparin, warfarin, dabigatran (e.g., dabigatran etexilate), factor Xa inhibitors (e.g., fondaparinux, draparinux, rivaroxaban, DX-9065a, otamixaban, LY517717, or YM150), ticlopidine, clopidogrel, CS-747 (prasugrel, LY640315), ximelagatran, or BIBR 1048.

In some embodiments, a compound of Formula (I), (II), (III), (IV), (V), (VI), (VII), (VIII), (IX), (X), (XI), (XII), or (XIII), or a pharmaceutically acceptable salt thereof, is used in combination with anti-emetic agents to treat nausea or emesis, which may result from the use of a compound of Formula (I), (II), (III), (IV), (V), (VI), (VII), (VIII), (IX), (X), (XI), or (XIII), or a pharmaceutically acceptable salt thereof, anti-cancer agent(s) and/or radiation therapy.

Anti-emetic agents include, but are not limited to: neurokinin-1 receptor antagonists, 5HT3 receptor antagonists (such as ondansetron, granisetron, tropisetron, palonosetron, and zatisetron), $GABA_B$ receptor agonists (such as baclofen), corticosteroids (such as dexamethasone, prednisone, prednisolone, or others), dopamine antagonists (such as, but not limited to, domperidone, droperidol, haloperidol, chlorpromazine, promethazine, prochlorperazine, metoclopramide), antihistamines (H1 histamine receptor antagonists, such as but not limited to, cyclizine, diphenhydramine, dimenhydrinate, meclizine, promethazine, hydroxyzine), cannabinoids (such as but not limited to, cannabis, marinol, dronabinol), and others (such as, but not limited to, trimethobenzamide; ginger, emetrol, propofol).

In some embodiments, a compound of Formula (I), (II), (III), (IV), (V), (VI), (VII), (VIII), (IX), (X), (XI), (XII), or (XIII), or a pharmaceutically acceptable salt thereof, is used in combination with an agent useful in the treatment of anemia. Such an anemia treatment agent is, for example, a continuous eythropoiesis receptor activator (such as epoetin-α).

In some embodiments, a compound of Formula (I), (II), (III), (IV), (V), (VI), (VII), (VIII), (IX), (X), (XI), (XII), or (XIII), or a pharmaceutically acceptable salt thereof, is used in combination with an agent useful in the treatment of neutropenia. Examples of agents useful in the treatment of neutropenia include, but are not limited to, a hematopoietic growth factor which regulates the production and function of neutrophils such as a human granulocyte colony stimulating factor, (G-CSF). Examples of a G-CSF include filgrastim.

In some embodiments, a compound of Formula (I), (II), (III), (IV), (V), (VI), (VII), (VIII), (IX), (X), (XI), (XII), or (XIII), or a pharmaceutically acceptable salt thereof, is administered with corticosteroids. Corticosteroids, include, but are not limited to: betamethasone, prednisone, alclometasone, aldosterone, amcinonide, beclometasone, betamethasone, budesonide, ciclesonide, clobetasol, clobetasone, clocortolone, cloprednol, cortisone, cortivazol, deflazacort, deoxycorticosterone, desonide, desoximetasone, desoxycortone, dexamethasone, diflorasone, diflucortolone, difluprednate, fluclorolone, fludrocortisone, fludroxycortide, flumetasone, flunisolide, fluocinolone acetonide, fluocinonide, fluocortin, fluocortolone, fluorometholone, fluperolone, fluprednidene, fluticasone, formocortal, halcinonide, halometasone, hydrocortisone/cortisol, hydrocortisone aceponate, hydrocortisone buteprate, hydrocortisone butyrate, loteprednol, medrysone, meprednisone, methylprednisolone, methylprednisolone aceponate, mometasone furoate, parametasone, prednicarbate, prednisone/prednisolone, rimexolone, tixocortol, triamcinolone, and ulobetasol.

In one embodiment, a compound of Formula (I), (II), (III), (IV), (V), (VI), (VII), (VIII), (IX), (X), (XI), (XII), or (XIII), or a pharmaceutically acceptable salt thereof, is administered to a mammal in combination with a non-steroidal anti-inflammatory drug (NSAID). NSAIDs include, but are not limited to: aspirin, salicylic acid, gentisic acid, choline magnesium salicylate, choline salicylate, choline magnesium salicylate, choline salicylate, magnesium salicylate, sodium salicylate, diflunisal, carprofen, fenoprofen, fenoprofen calcium, flurobiprofen, ibuprofen, ketoprofen, nabutone, ketolorac, ketorolac tromethamine, naproxen, oxaprozin, diclofenac, etodolac, indomethacin, sulindac, tolmetin, meclofenamate, meclofenamate sodium, mefenamic acid, piroxicam, meloxicam, COX-2 specific inhibitors (such as, but not limited to, celecoxib, rofecoxib, valdecoxib, parecoxib, etoricoxib, lumiracoxib, CS-502, JTE-522, L-745,337 and NS398).

In some embodiments, a compound of Formula (I), (II), (III), (IV), (V), (VI), (VII), (VIII), (IX), (X), (XI), (XII), or (XIII), or a pharmaceutically acceptable salt thereof, is coadministered with an analgesic.

In some embodiments, a compound of Formula (I), (II), (III), (IV), (V), (VI), (VII), (VIII), (IX), (X), (XI), (XII), or (XIII), or a pharmaceutically acceptable salt thereof, is used in combination with radiation therapy (or radiotherapy). Radiation therapy is the treatment of cancer and other diseases with ionizing radiation. Radiation therapy can be used to treat localized solid tumors, such as cancers of the skin, tongue, larynx, brain, breast, prostate, colon, uterus and/or cervix. It can also be used to treat leukemia and lymphoma (cancers of the blood-forming cells and lymphatic system, respectively).

A technique for delivering radiation to cancer cells is to place radioactive implants directly in a tumor or body cavity. This is called internal radiotherapy (brachytherapy, interstitial irradiation, and intracavitary irradiation are types of internal radiotherapy.) Using internal radiotherapy, the radiation dose is concentrated in a small area, and the patient stays in the hospital for a few days. Internal radiotherapy is frequently used for cancers of the tongue, uterus, prostate, colon, and cervix.

The term "radiotherapy" or "ionizing radiation" include all forms of radiation, including but not limited to α, β, and γ radiation and ultraviolet light.

Kits/Articles of Manufacture

For use in the therapeutic applications described herein, kits and articles of manufacture are also described herein. Such kits can comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers are formed from any acceptable material including, e.g., glass or plastic.

For example, the container(s) can comprise one or more compounds described herein, optionally in a composition or in combination with another agent as disclosed herein. The container(s) optionally have a sterile access port (for example the container can be an intravenous solution bag or a vial having a stopper pierceable by a hypodermic injection needle). Such kits optionally comprising a compound with an identifying description or label or instructions relating to its use in the methods described herein.

A kit will typically comprise one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

EXAMPLES

These examples are provided for illustrative purposes only and not to limit the scope of the claims provided herein.

Synthesis of Compounds

Intermediate 1

N,2,5-Trimethoxy-N-methylbenzamide

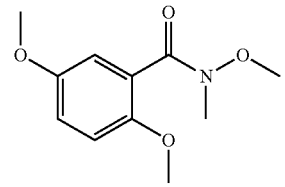 [SMILES: COc1ccc(OC)c(C(=O)N(C)OC)c1]

To a solution of 2,5-dimethoxybenzoic acid (6.00 g, 33.0 mmol) in DCM (100 mL) was added oxalyl chloride (3.6 mL, 41.3 mmol) and then DMF (0.2 mL). The solution was stirred at room temperature for 2 h, and the solvent was removed under reduced pressure. The crude material was placed under vacuum for 30 min to remove all of the oxalyl chloride. To a mixture of the residue and N, O-dimethylhydroxylamine hydrochloride (4.03 g, 41.32 mmol) in DCM (100 mL) at 0° C., triethylamine (6.8 mL, 48.78 mmol) was added dropwise. The solution was stirred at 0° C. for 30 min and then at room temperature for additional 30 min. The reaction was diluted with DCM (50 mL), washed (2×100 mL $H_2O$, 100 mL brine), dried over $Na_2SO_4$, and concentrated under reduced pressure. The crude material was purified on a silica gel column to yield N,2,5-trimethoxy-N-methylbenzamide (7.32 g, 99%) as clear oil which solidified over time. $^1$H NMR (CDCl$_3$): δ 7.90 (m, 3H), 3.82 (s, 3H), 3.79 (s, 3H), 3.58 (br s, 3H), 3.32 (br s, 3H).

Intermediate 2

1-(2-Hydroxy-5-((tetrahydro-2H-pyran-2-yl)oxy) phenyl)-2-(3-((tetrahydro-2H-pyran-2-yl)oxy)phenyl)ethanone

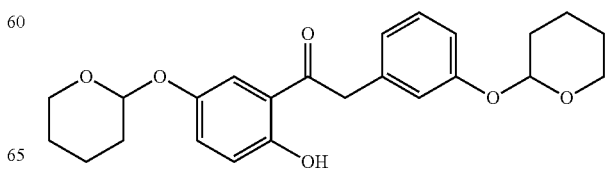

Step 1: 1-(2,5-Dimethoxyphenyl)-2-(3-methoxyphenyl)ethanone

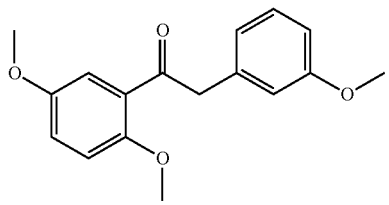 [SMILES: COc1cccc(CC(=O)c2cc(OC)ccc2OC)c1]

To a mixture of magnesium (2.88 g, 118 mmol) and iodine (1 crystal) in THF (30 mL) was added a 5 mL portion of a solution of 3-methoxybenzyl chloride (12.8 mL, 88.1 mmol) in THF (60 mL). The reaction mixture was stirred until the color disappeared and the remaining solution of 3-methoxybenzyl chloride was added dropwise over 45 min. The mixture was heated at 60° C. for 1 h, cooled to 0° C., and then added over 30 min to a solution of Intermediate 1 (6.65 g 29.6 mmol) in THF (70 mL) at 0° C. The reaction was stirred for 30 min at 0° C. and quenched with brine (50 mL). The mixture was extracted with ethyl acetate (3×100 mL), and the combined organic extracts were washed (50 mL brine), dried over $Na_2SO_4$, and concentrated under reduced pressure to give 1-(2,5-dimethoxyphenyl)-2-(3-methoxyphenyl)ethanone (7.99 g, 95%) as a white solid. $^1$H NMR (CDCl$_3$): δ 7.25 (m, 2H), 7.01 (dd, 1H), 6.92 (d, 1H), 6.83 (m, 3H), 4.30 (s, 2H), 3.90 (s, 3H), 3.82 (s, 3H), 3.79 (s, 3H).

Note: For other compounds synthesized using this reaction, the time, temperature, solvent, concentration, and equivalents can vary depending on the Grignard reagent utilized. This reaction can be quenched with HCl and may need to be purified by silica gel chromatography.

Step 2: 1-(2,5-Dihydroxyphenyl)-2-(3-hydroxyphenyl)ethanone

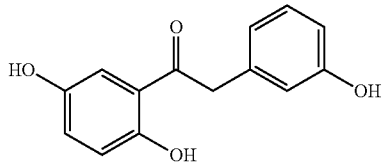 [SMILES: O=C(Cc1cccc(O)c1)c1cc(O)ccc1O]

To a solution of 1-(2,5-dimethoxyphenyl)-2-(3-methoxyphenyl)ethanone (3.35 g, 11.7 mmol) in DCM (50 mL) at −78° C., BBr$_3$ (1M in DCM, 48.0 mL, 48.0 mmol) was added dropwise. The reaction mixture was warmed to 0° C., stirred for 30 min, re-cooled to −78° C., and then quenched with methanol (15 mL). The reaction mixture was warmed to room temperature, concentrated under reduced pressure and purified on a silica gel column to give 1-(2,5-dihydroxyphenyl)-2-(3-hydroxyphenyl)ethanone (1.78 g, 62%) as a yellow solid. $^1$H NMR (DMSO-d$_6$): δ 11.24 (s, 1H), 9.34 (s, 1H), 9.20 (s, 1H), 7.26 (m, 1H), 7.10 (t, 1H), 6.98 (dd, 1H), 6.83 (d, 1H), 6.70 (m, 3H), 4.24 (s, 2H).

Note: For this compound or other compounds synthesized using this reaction, an alternate work-up procedure can be employed: after the quench with methanol, the reaction mixture was washed (sat'd NaHCO$_3$ and brine), dried over Na$_2$SO$_4$, concentrated under reduced pressure, and then purified on a silica gel column.

Step 3: 1-(2-Hydroxy-5-((tetrahydro-2H-pyran-2-yl)oxy)phenyl)-2-(3-((tetrahydro-2H-pyran-2-yl)oxy)phenyl)ethanone

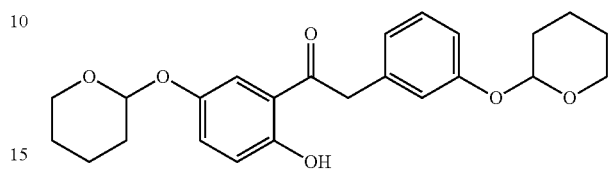

To a mixture of 1-(2,5-dihydroxyphenyl)-2-(3-hydroxyphenyl)ethanone (1.50 g, 6.15 mmol) and pyridinium p-toluene sulfonate (320 mg, 1.27 mmol) in DCM (40 mL) was added 3,4-dihydro-2H-pyran (2.65 g, 30.8 mmol) in DCM (6 mL). The reaction mixture was stirred at room temperature for 1 h and diluted with DCM (100 mL). The solution was washed (2×50 mL sat'd NaHCO$_3$, 50 mL brine), dried over Na$_2$SO$_4$ and concentrated under reduced pressure. The crude material was purified on a silica gel column to give 1-(2-hydroxy-5-((tetrahydro-2H-pyran-2-yl)oxy)phenyl)-2-(3-((tetrahydro-2H-pyran-2-yl)oxy)phenyl)ethanone (2.42 g, 96%) as yellow oil which solidified over time. $^1$H NMR (CDCl$_3$): δ 11.88 (s, 1H), 7.60 (m, 1H), 7.30 (m, 2H), 7.00 (m, 2H), 6.92 (m, 2H), 5.42 (m, 1H), 5.28 (m, 1H), 4.25 (s, 2H), 3.92 (m, 2H), 3.62 (m, 2H), 1.55-2.07 (m, 12H).

Intermediate 3

2-(4-Iodophenyl)-4-methyl-6-((tetrahydro-2H-pyran-2-yl)oxy)-3-(3-((tetrahydro-2H-pyran-2-yl)oxy)phenyl)-2H-chromene

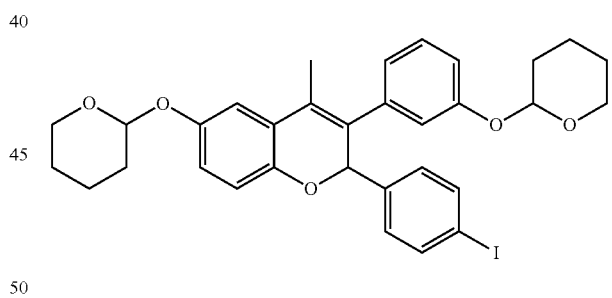

Step 1: 2-(4-Iodophenyl)-6-((tetrahydro-2H-pyran-2-yl)oxy)-3-(3-((tetrahydro-2H-pyran-2-yl)oxy)phenyl)chroman-4-one

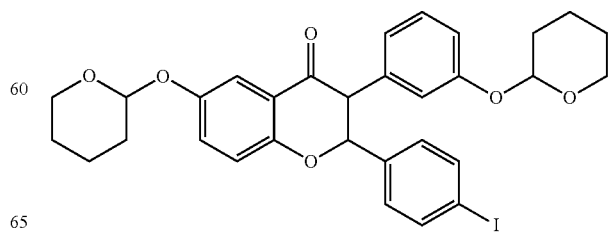

A solution of Intermediate 2 (2.41 g, 5.84 mmol), 4-iodobenzaldehyde (1.37 g, 5.91 mmol), piperidine (166 mg, 1.95 mmol), and DBU (301 mg, 1.98 mmol) in s-butanol (10 mL) was heated at reflux. Using a Dean-Stark trap, half (5 mL) of the solvent was collected over 45 min, and the reaction was kept at reflux without further concentration for additional 45 min. The reaction mixture was cooled to 90° C., i-propanol (10 mL) was added, and the reaction was allowed to cool to room temperature and stirred overnight. The resulting precipitate was collected by filtration to yield 2-(4-iodophenyl)-6-((tetrahydro-2H-pyran-2-yl)oxy)-3-(3-((tetrahydro-2H-pyran-2-yl)oxy)phenyl)chroman-4-one (3.17 g, 87%) as a white solid. $^1$H NMR (DMSO-d$_6$): δ 7.63 (d, 2H), 7.42 (m, 1H), 7.33 (m, 1H), 7.21 (d, 2H), 7.07 (m, 2H), 6.79 (m, 3H), 5.88 (m, 1H), 5.48 (m, 1H), 5.31 (m, 1H), 4.60 (d, 1H), 3.40-3.80 (m, 4H), 1.55-1.90 (m, 12H).

Note: For this compound or other compounds synthesized using this reaction, i) the reflux time can be longer (1-6 h), ii) petroleum ether has been used instead of isopropanol, iii) the stirring time after cooling to room temperature may be longer (2-3 days), and iv) the product may need to be purified by silica gel chromatography.

Step 2: 3-(3-Hydroxyphenyl)-2-(4-iodophenyl)-4-methyl-2H-chromen-6-ol

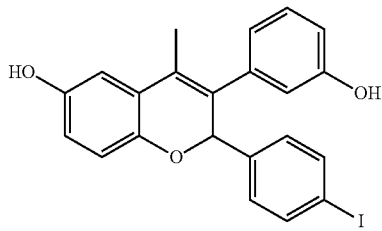 [SMILES: CC1=C(c2cccc(O)c2)C(c2ccc(I)cc2)Oc2ccc(O)cc21]

To a solution of 2-(4-iodophenyl)-6-((tetrahydro-2H-pyran-2-yl)oxy)-3-(3-((tetrahydro-2H-pyran-2-yl)oxy)phenyl)chroman-4-one (1.99 g, 3.18 mmol) in THF (40 mL) at 0° C., methyl magnesium chloride (3M in THF, 4.0 mL, 12 mmol) was added dropwise. The reaction was stirred at 0° C. for 15 min and allowed to warm to room temperature. After stirring for 2 h, the solution was cooled to 0° C., quenched with sat'd ammonium chloride, and then allowed to warm to room temperature. Ethyl acetate (100 mL) and H$_2$O (50 mL) were added, and the layers were separated. The organic layer was dried over Na$_2$SO$_4$, concentrated under reduced pressure, and purified on a silica gel column to yield a white foam (1.75 g). This purified material was heated in 80% acetic acid/H$_2$O (50 mL) overnight at 90° C. The solution was diluted with ethyl acetate (100 mL), washed (50 mL H$_2$O, 50 mL sat'd NaHCO$_3$, 50 mL brine), and dried over Na$_2$SO$_4$. The solvent was removed under reduced pressure, and the crude material was purified on a silica gel column to give 3-(3-hydroxyphenyl)-2-(4-iodophenyl)-4-methyl-2H-chromen-6-ol (0.99 g, 68%) as a beige solid. $^1$H NMR (DMSO-d$_6$): δ 9.46 (s, 1H), 9.00 (s, 1H), 7.62 (d, 2H), 7.17 (t, 1H), 7.01 (d, 2H), 6.70 (m, 4H), 6.51 (s, 2H), 5.90 (s, 1H), 2.03 (s, 3H).

Step 3: 2-(4-Iodophenyl)-4-methyl-6-((tetrahydro-2H-pyran-2-yl)oxy)-3-(3-((tetrahydro-2H-pyran-2-yl)oxy)phenyl)-2H-chromene

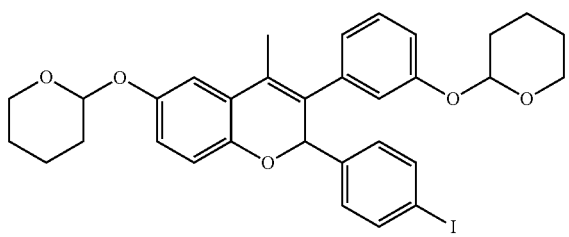 [SMILES: CC1=C(c2cccc(OC3CCCCO3)c2)C(c2ccc(I)cc2)Oc2ccc(OC3CCCCO3)cc21]

To a solution of 3-(3-hydroxyphenyl)-2-(4-iodophenyl)-4-methyl-2H-chromen-6-ol (990 mg, 2.19 mmol) and pyridinium p-toluene sulfonate (115 mg, 0.458 mmol) in DCM (30 mL) was added 3,4-dihydro-2H-pyran (1.1 mL, 12 mmol). The reaction was stirred at room temperature for 3 h, diluted with DCM (100 mL), washed (100 mL sat'd NaHCO$_3$, 2×50 mL H$_2$O, 50 mL brine), and dried over Na$_2$SO$_4$. The solvent was removed under reduced pressure and the crude material was purified on a silica gel column to give 2-(4-iodophenyl)-4-methyl-6-((tetrahydro-2H-pyran-2-yl)oxy)-3-(3-((tetrahydro-2H-pyran-2-yl)oxy)phenyl)-2H-chromene (1.30 g, 95%) as a white foam. $^1$H NMR (DMSO-d$_6$): δ 7.62 (d, 2H), 7.27 (t, 1H), 7.10 (d, 2H), 6.92 (m, 4H), 6.81 (d, 1H), 6.63 (d, 1H), 6.04 (d, 1H), 5.43 (m, 1H), 5.36 (s, 1H), 3.75 (m, 2H), 3.55 (m, 2H), 2.05 (s, 3H), 1.50-1.99 (m, 12H).

Intermediate 4

1-(2,4-Dihydroxyphenyl)-2-(3-hydroxyphenyl)ethanone

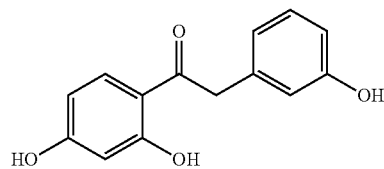 [SMILES: O=C(Cc1cccc(O)c1)c1ccc(O)cc1O]

A solution of resorcinol (3.56 g, 32.3 mmol), 2-(3-hydroxyphenyl)acetic acid (5.39 g, 35.4 mmol), and boron trifluoride etherate (12 mL) in toluene (10 mL) was heated at 90° C. for 2 h. The reaction mixture was allowed to cool to room temperature, and a solution of 12% sodium acetate in H$_2$O (17 mL) was added. After stirring for 3 h, the resulting precipitate was collected by filtration to give 1-(2,4-dihydroxyphenyl)-2-(3-hydroxyphenyl)ethanone (4.47 g, 57%) as a yellow solid. $^1$H NMR (DMSO-d$_6$): δ 12.57 (s, 1H), 10.67 (s, 1H), 9.34 (s, 1H), 7.92 (d, 1H), 7.09 (m, 2H), 6.65 (m, 2H), 6.40 (m, 1H), 6.25 (s, 1H), 4.14 (s, 2H).

Intermediate 5

1-(2,5-Dimethoxyphenyl)-2-(3-fluorophenyl)ethanone

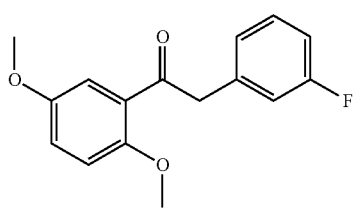 [SMILES: COc1ccc(OC)c(C(=O)Cc2cccc(F)c2)c1]

To a mixture of magnesium (1.75 g, 72.0 mmol) in diethylether (7.8 mL) at 0° C. was added a portion (0.5 mL) of a solution of 3-fluorobenzyl chloride (3.25 g, 22.5 mmol) in diethyl ether (30 mL). The mixture was allowed to warm to room temperature to ensure that the reaction initiated, recooled to 0° C., and the remainder of 3-flurobenzyl chloride solution was added dropwise over 2 h. The reaction mixture was stirred at 0° C. for 2 h and then added to a solution of Intermediate 1 (2.15 g, 9.56 mmol) in THF (20 mL) and diethyl ether (40 mL) at 0° C. The solution was stirred for 1 h at 0° C., quenched with sat'd ammonium chloride (5 mL) and allowed to warm to room temperature. The mixture was diluted with ethyl acetate (150 mL), washed (100 mL brine), dried over $Na_2SO_4$, and concentrated under reduced pressure. The crude material was purified on a silica gel column to give 1-(2,5-dimethoxyphenyl)-2-(3-fluorophenyl)ethanone (2.43 g, 93%) as a white solid. $^1$H NMR (CDCl$_3$): δ 7.35 (m, 1H), 7.11 (m, 6H), 4.31 (s, 2H), 3.86 (s, 3H), 3.73 (s, 3H).

Intermediate 6

2-(2-Fluoro-4-iodophenyl)-4-methyl-6-((tetrahydro-2H-pyran-2-yl)oxy)-3-(3-((tetrahydro-2H-pyran-2-yl)oxy)phenyl)-2H-chromene

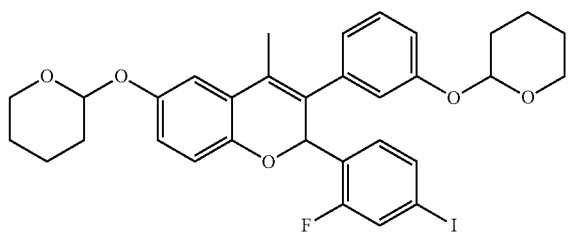 [SMILES: CC1=C(c2cccc(OC3CCCCO3)c2)C(c2ccc(I)cc2F)Oc2ccc(OC3CCCCO3)cc21]

The title compound was synthesized as described in Intermediate 3 using Intermediate 2 and 2-fluoro-4-iodobenzaldehyde as starting materials. $^1$H NMR (DMSO-d$_6$): δ 7.61 (d, 1H), 7.45 (d, 1H), 7.26 (t, 1H), 7.08 (m, 1H), 7.02 (s, 1H), 6.95 (m, 3H), 6.85 (m, 1H), 6.65 (d, 1H), 6.29 (s, 1H), 5.45 (m, 1H), 5.37 (m, 1H), 3.75 (m, 2H), 3.50 (m, 2H), 2.08 (s, 3H), 1.40-1.90 (m, 12H).

Intermediate 7

2-(4-Iodophenyl)-4-methyl-7-((tetrahydro-2H-pyran-2-yl)oxy)-3-(3-((tetrahydro-2H-pyran-2-yl)oxy)phenyl)-2H-chromene

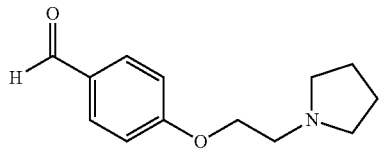 [SMILES: O=Cc1ccc(OCCN2CCCC2)cc1]

The title compound was prepared from Intermediate 4 following the synthetic sequence outlined for Intermediate 2 (Step 3) and Intermediate 3. $^1$H NMR (DMSO-d$_6$): δ 7.65 (d, 2H), 7.25 (m, 2H), 7.12 (d, 2H), 6.90 (m, 3H), 6.63 (m, 1H), 6.38 (d, 1H), 6.08 (d, 1H), 5.42 (m, 1H), 5.35 (s, 1H), 3.72 (m, 2H), 3.50 (m, 2H), 2.06 (s, 3H), 1.40-1.90 (m, 12H).

Intermediate 8

4-(2-(Pyrrolidin-1-yl)ethoxy)benzaldehyde

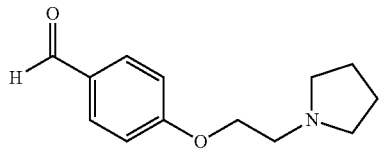 [SMILES: O=Cc1ccc(OCCN2CCCC2)cc1]

A mixture of 1-(2-chloroethyl)pyrrolidine (1.19 g, 8.83 mmol), 4-hydroxybenzaldehyde (1.02 g, 8.33 mmol), and potassium carbonate (2.30 g, 16.7 mmol) in DMF (5 mL) was heated at 60° C. overnight. The reaction mixture was diluted with H$_2$O and extracted with ethyl acetate (2×50 mL). The combined organic extracts were washed (50 mL brine), dried over Na$_2$SO$_4$, and concentrated. The crude material was purified on a silica gel column to yield 4-(2-(pyrrolidin-1-yl)ethoxy)benzaldehyde (996 mg, 53%). $^1$H NMR (CDCl$_3$): δ 9.90 (s, 1H), 7.85 (d, 2H), 7.03 (d, 2H), 4.22 (t, 2H), 2.96 (t, 2H), 2.69 (m, 4H), 1.82 (m, 4H).

Intermediate 9

(S)-2-(Pyrrolidin-1-yl)propan-1-ol

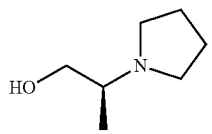

A mixture of (S)-2-aminopropan-1-ol (566 mg, 7.54 mmol), 1,4-dibromobutane, and potassium carbonate (2.09 g, 15.1 mmol) in acetonitrile (70 mL) was heated at reflux overnight and allowed to cool to room temperature. The insoluble solid was filtered off, and the filtrate was concentrated under reduced pressure. The residue was diluted with DCM (75 mL) and washed (25 mL sat'd K₂CO₃). The aqueous phase was extracted with DCM (2×25 mL) and the combined organic extracts were dried over Na₂SO₄. The solvent was removed under reduced pressure and purified on a silica gel column to yield (S)-2-(pyrrolidin-1-yl)propan-1-ol (630 mg, 65%) as a clear oil. $^1$H NMR (CDCl₃): δ 3.63 (m, 1H), 3.38 (m, 1H), 2.97 (br s, 1H), 2.69 (m, 1H), 2.60 (br s, 4H), 1.72 (br s, 4H), 1.06 (d, 3H).

Intermediate 10

(R)-2-(Pyrrolidin-1-yl)propan-1-ol

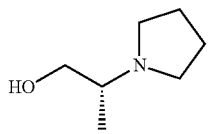

The title compound was synthesized as described in Intermediate 9 using 1,4-dibromobutane and (R)-2-aminopropan-1-ol as starting materials. $^1$H NMR (CDCl₃): δ 3.61 (m, 1H), 3.38 (m, 1H), 2.97 (br s, 1H), 2.72 (m, 1H), 2.60 (br s, 4H), 1.78 (br s, 4H), 1.06 (d, 3H).

Intermediate 11

(R)-2-(3-Methylpyrrolidin-1-yl)ethanol

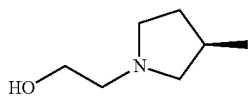

Step 1: (R)-2-Methylbutane-1,4-diol

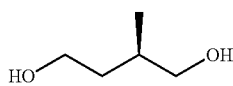

A solution of (R)-dimethyl 2-methylsuccinate (25 g, 0.16 mol) in THF (200 mL) was added dropwise to a stirred suspension of LAH (11.8 g, 0.31 mol) in THF (500 mL) at 0° C. under nitrogen atmosphere. The resulting mixture was stirred for 17 h at room temperature. After the reaction was complete, the mixture was cooled to 0° C. and the excess LAH was decomposed by successive addition of water (11.8 mL), 10% aqueous NaOH solution (24 mL) and water (36 mL). The mixture was then stirred for 3 h at room temperature. After filtration of the mixture and washing of the solid with diethyl ether, the combined filtrate and washings were dried over MgSO₄ and concentrated in vacuo. The resulting product (16.7 g, quant) was used directly for the next step. $^1$H NMR (400 MHz, CDCl₃): δ 3.82-3.73 (m, 1H), 3.66 (m, 1H), 3.57 (dd, 1H), 3.43 (dd, 1H), 3.10 (br, 2H), 1.81 (m, 1H), 1.64-1.56 (m, 2H), 0.93 (d, 3H).

Step 2: (R)-2-Methylbutane-1,4-diyl dimethanesulfonate

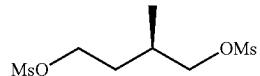

To a solution of (R)-2-methylbutane-1,4-diol (30 g, 0.29 mol) in DCM (600 mL) was added triethylamine (100 mL, 0.72 mol). The solution was cooled to −20° C., and methanesulfonyl chloride (49 mL, 0.63 mol) was added dropwise over 30 min with vigorous stirring. The resulting mixture was stirred for additional 1 h while the temperature was maintained between −20 and −15° C. The mixture was allowed to warm to 0° C. and then poured into cold 1N HCl solution (100 mL). The organic layer was separated, and aqueous phase was extracted with DCM (100 mL). The combined organic extracts were washed with sat'd NaHCO₃ solution, brine, dried over MgSO₄, filtered and concentrated in vacuo. The resulting product (75.9 g, quant) was used directly for the next step. $^1$H NMR (400 MHz, CDCl₃): δ 4.41-4.24 (m, 2H), 4.12 (dq, 2H), 3.02 (d, 6H), 2.13 (td, 1H), 1.95 (td, 1H), 1.80-1.65 (m, 1H), 1.07 (d, 3H).

Step 3: (R)-2-(3-Methylpyrrolidin-1-yl)ethanol

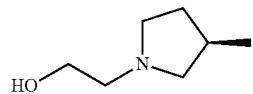

A mixture of (R)-2-methylbutane-1,4-diyl dimethanesulfonate (30 g, 0.115 mol), 2-aminoethanol (7.0 g, 0.115 mol), and K₂CO₃ (31.7 g, 0.23 mol) in acetonitrile (0.9 L) was refluxed for 20 h. The mixture was cooled to room temperature and concentrated under vacuum to afford a residue (a mixture of oil and solid). DCM (300 mL) and sat'd K₂CO₃ solution (300 mL) were added and just enough water was added to dissolve all solid. The organic layer was separated, and aqueous phase was further extracted with DCM (2×300 mL). The combined organic layers were dried over MgSO₄, filtered, and concentrated in vacuo. Purification by flash column chromatography [EA/Hex/MeOH/TEA=10:7:2:1] gave (R)-2-(3-methylpyrrolidin-1-yl)ethanol (4.19 g, 28%). $^1$H NMR (CDCl₃): δ 3.61 (t, 2H), 2.84 (dd, 1H), 2.70 (m, 1H), 2.65 (m, 1H), 2.62 (m, 1H), 2.54 (m, 1H), 2.25 (m, 1H), 2.11 (dd, 1H), 2.03 (m, 1H), 1.36 (m, 1H), 1.03 (d, 3H); MS: 130.2 (M+H)⁺.

Intermediate 12

(S)-2-(3-Methylpyrrolidin-1-yl)ethanol

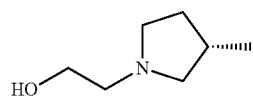

The title compound was synthesized as described in Intermediate 11 using (S)-dimethyl 2-methylsuccinate and 2-aminoethanol as starting materials. ¹H NMR (CDCl₃): δ 3.66 (t, 1H), 2.93 (dd, 1H), 2.81 (m, 1H), 2.73 (m, 1H), 2.66 (m, 1H), 2.63 (m, 1H), 2.29 (m, 1H), 2.18 (dd, 2H), 2.05 (m, 1H), 1.40 (m, 1H), 1.04 (d, 3H); MS: 130.2 (M+H)⁺.

Intermediate 13

(R)-2-((S)-3-Methylpyrrolidin-1-yl)propan-1-ol

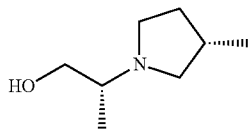

The title compound was synthesized as described in Intermediate 11 using (S)-dimethyl 2-methylsuccinate and (R)-2-aminopropan-1-ol as starting materials. ¹H NMR (CDCl₃): δ 3.60 (dd, 1H), 3.58 (br s, 1H), 3.40 (dd, 1H), 2.89 (dd, 1H), 2.72 (m, 2H), 2.63 (m, 1H), 2.24 (m, 1H), 2.17 (dd, 1H), 2.00 (m, 1H), 1.35 (m, 1H), 1.04 (m, 6H); MS: 144.3 (M+H)⁺.

Intermediate 14

(R)-2-((R)-3-Methylpyrrolidin-1-yl)propan-1-ol

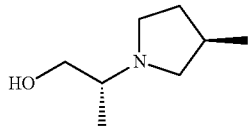

The title compound was synthesized as described in Intermediate 11 using (R)-dimethyl 2-methylsuccinate and (R)-2-aminopropan-1-ol as starting materials. ¹H NMR (CDCl₃): δ 3.57 (dd, 1H), 3.32 (dd, 1H), 3.02 (br s, 1H), 2.81 (dd, 1H), 2.69 (m, 2H), 2.60 (m, 1H), 2.20 (m, 1H), 2.12 (dd, 1H), 1.98 (m, 1H), 1.32 (m, 1H), 1.04 (m, 6H); MS: 144.3 (M+H)⁺.

Intermediate 15

(S)-2-((S)-3-Methylpyrrolidin-1-yl)propan-1-ol

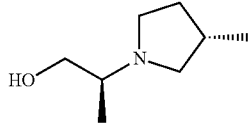

The title compound was synthesized as described in Intermediate 11 using (S)-dimethyl 2-methylsuccinate and (S)-2-aminopropan-1-ol as starting materials. ¹H NMR (CDCl₃): δ 3.57 (dd, 1H), 3.32 (dd, 1H), 3.02 (br s, 1H), 2.81 (dd, 1H), 2.69 (m, 2H), 2.60 (m, 1H), 2.21 (m, 1H), 2.12 (dd, 1H), 1.98 (m, 1H), 1.32 (m, 1H), 1.04 (m, 6H); MS: 144.3 (M+H)⁺.

Intermediate 16

(S)-2-((R)-3-Methylpyrrolidin-1-yl)propan-1-ol

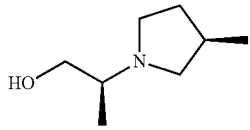

(R)-2-Methylbutane-1,4-diyl dimethanesulfonate (37.5 g, 0.144 mol, from step 2 of Intermediate 11) was added to neat (S)-2-aminopropan-1-ol (54.8 g, 0.730 mol). The mixture was stirred in a room temperature water bath to minimize the exotherm. After 24 h, the reaction was diluted with DCM (150 mL), sat'd K₂CO₃ solution (150 mL), and just enough water (60 mL) to dissolve the resulting ppt. The organic layer was separated, and the aqueous layer was extracted with DCM (150 mL). The organic layers were combined, dried (Na₂SO₄), filtered, concentrated, and purified by silica gel chromatography (10:7; ethyl acetate:hexanes→10:7:2:1; ethyl acetate:hexanes:methanol:triethylamine) to give (S)-2-((R)-3-methylpyrrolidin-1-yl)propan-1-ol (17.9 g) as a pale yellow oil. ¹H NMR (400 MHz, DMSO-d₆): δ 4.33 (t, 1H), 3.48 (m, 1H), 3.18 (m, 1H), 2.79 (dd, 1H), 2.58 (m, 1H), 2.48 (m, 1H), 2.26 (m, 1H), 2.08 (m, 1H), 2.01 (dd, 1H), 1.88 (m, 1H), 1.20 (m, 1H), 0.98 (d, 3H), 0.96 (d, 3H); LCMS: 144.3 (M+H)⁺.

Intermediate 17

(S)-2-(Piperidin-1-yl)propan-1-ol

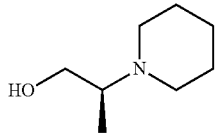

A mixture of (S)-2-aminopropan-1-ol (2.0 mL, 26 mmol), 1,5-diiodopentane (4.7 mL), and sodium carbonate (7.13 g, 67.3 mmol) in i-propanol (200 mL) was heated at reflux overnight. The reaction mixture was concentrated, diluted with ethyl acetate (100 mL) and the insoluble solid was filtered off. The solvent was removed under reduced pressure and the residue was purified on a silica gel column to yield ((S)-2-(piperidin-1-yl)propan-1-ol (2.0 g, 54%) as a clear oil. ¹H NMR (CDCl₃): δ 3.37 (dd, 1H), 3.30 (t, 1H), 2.78 (m, 1H), 2.62 (m, 2H), 2.33 (m, 2H), 1.40-1.70 (m, 6H), 0.86 (d, 3H).

Intermediate 18

(S)-2-(Azepan-1-yl)propan-1-ol

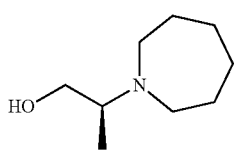

The title compound was synthesized as described in Intermediate 17 using 1,6-iodohexane and (S)-2-aminopropan-1-ol as starting materials. $^1$H NMR (CDCl$_3$): δ 3.63 (br s, 1H), 3.34 (dd, 1H), 3.23 (t, 1H), 2.88 (m, 1H), 2.75 (m, 2H), 2.47 (m, 2H), 1.50-1.80 (m, 8H), 0.86 (d, 3H).

Intermediate 19

(R)-2-(2-Methylpyrrolidin-1-yl)ethanol

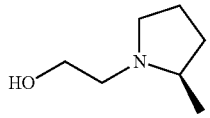

A mixture of (R)-2-methylpyrrolidine hydrochloride (4 g, 0.03 mol), 2-bromoethanol (3.7 g, 0.029 mmol) and K$_2$CO$_3$ (8.28 g, 0.0618 mol) in acetonitrile (50 mL) was stirred at room temperature overnight. The mixture was filtered, and the filter cake was washed with ethyl acetate (100 mL). The combined filtrate was concentrated and the residue was purified on a silica gel column (MeOH/DCM=1/50) to give (R)-2-(2-methylpyrrolidin-1-yl)ethanol (0.9 g) as a colorless oil. $^1$H NMR (CDCl$_3$): δ 3.63 (m, 2H), 3.14 (m, 1H), 2.95 (m, 1H), 2.44 (m, 1H), 2.24 (dt, 1H), 2.14 (m, 1H), 1.95 (m, 1H), 1.68 (m, 2H), 1.38 (m, 1H), 1.07 (d, 3H); LCMS: 130 (M+H)$^+$.

Intermediate 20

2-(4-Methylpiperidin-1-yl)ethanol

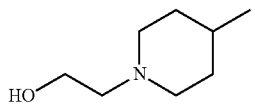

A mixture of 4-methylpiperidine (10 g, 0.10 mol), 2-bromoethanol (12.5 g, 0.10 mol), and triethylamine (15 g, 0.15 mol) in CHCl$_3$ (100 mL) was stirred at room temperature for two days. The mixture was concentrated, and the residue was purified on a silica gel column (eluting with NH$_3$—H$_2$O/MeOH/DCM=1/6/300) to give 2-(4-methylpiperidin-1-yl)ethanol (3 g) as a colorless oil. $^1$H NMR (CDCl$_3$): δ 3.57 (m, 2H), 3.24 (br s, 1H), 2.84 (m, 2H), 2.47 (m, 2H), 2.00 (dt, 2H), 1.58 (m, 2H), 1.35 (m, 1H), 1.21 (dt, 2H), 0.89 (d, 3H); LCMS: 144 (M+H)$^+$.

Intermediate 21

(S)-2-(3,3-Dimethylpyrrolidin-1-yl)propan-1-ol

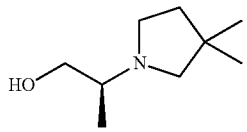

Step 1: (S)-2-(3,3-Dimethyl-2,5-dioxopyrrolidin-1-yl)propyl acetate

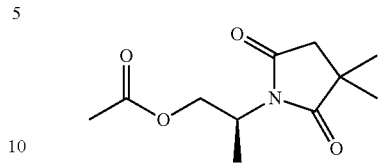

A suspension of 2,2-dimethylsuccinic acid (10.5 g, 71.7 mmol) in acetic anhydride (50 mL) was heated at 85° C. for 30 minutes and then concentrated under reduced pressure. The residue was dissolved in toluene (150 mL) and (S)-2-aminopropan-1-ol (6.0 g, 80 mmol) was added. The mixture was heated at reflux for 1 h under nitrogen atmosphere and cooled to room temperature. The solvent was removed under reduced pressure, and the residue was heated in acetic anhydride (50 mL) at 80° C. under nitrogen overnight. The reaction mixture was cooled to room temperature, and the solvent was removed under reduced pressure. The residue was purified on a silica gel column (eluting with PE/EA=3/1) to afford (S)-2-(3,3-dimethyl-2,5-dioxopyrrolidin-1-yl)propyl acetate (10.1 g, 62.3%). $^1$H-NMR (CDCl$_3$) δ 4.41 (m, 2H), 4.25 (m, 1H), 2.50 (s, 2H), 1.97 (s, 3H), 0.137 (d, 3H), 1.29 (s, 3H), 1.28 (s, 3H).

Step 2: (S)-2-(3,3-Dimethylpyrrolidin-1-yl)propan-1-ol

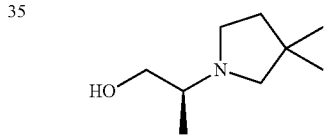

A solution of (S)-2-(3,3-dimethyl-2,5-dioxopyrrolidin-1-yl)propyl acetate (6.15 g, 27.1 mmol) in anhydrous diethyl ether (20 mL) was added to a suspension of LiAlH$_4$ (3.0 g, 79 mmol) in anhydrous diethyl ether (250 mL) at room temperature under nitrogen atmosphere. After stirring at room temperature overnight, the reaction mixture was quenched with H$_2$O (3 mL). The resulting suspension was filtered, and the filter cake was washed with ethyl acetate (50 mL). The combined filtrate was concentrated under reduced pressure, and the residue was purified on a silica gel column (eluting with DCM/MeOH=20/1) to give (S)-2-(3,3-dimethylpyrrolidin-1-yl)propan-1-ol (2.37 g, 59%). $^1$H NMR (CDCl$_3$): δ 3.53 (dd, 1H), 3.27 (dd, 1H), 2.70 (m, 3H), 2.37 (s, 2H), 1.55 (m, 2H), 1.07 (s, 3H), 1.06 (s, 3H), 0.94 (d, 3H); LCMS: 158 (M+H)$^+$.

Intermediate 22

2-(3,3-Dimethylpyrrolidin-1-yl)ethanol

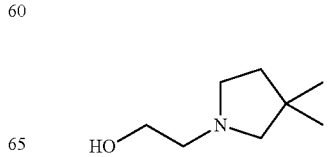

The title compound was synthesized as described in Intermediate 21 using 2,2-dimethylsuccinic acid and 2-aminoethanol as starting materials. ¹H NMR (CDCl₃): δ 3.55 (t, 2H), 3.35 (br s, 1H), 2.60 (m, 4H), 2.33 (s, 2H), 1.55 (t, 2H), 1.43 (s, 6H).

Intermediate 23

(S)-2-((S)-2-Methylpyrrolidin-1-yl)propan-1-ol

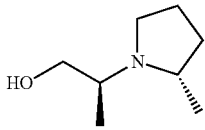

A mixture of (S)-2-aminopropan-1-ol (12.5 g, 0.166 mol), 1,4-dibromopentane (42 g, 0.18 mol) and Na₂CO₃ (53 g, 0.51 mol) in EtOH (800 mL) was heated at 100° C. for 24 h. The mixture was filtered, and the filter cake was washed with EtOH (50 mL). The combined filtrate was concentrated under reduced pressure, and the crude product was purified on a silica gel column (NH₄OH/MeOH/DCM=1/6/300) to give (S)-2-((S)-2-methylpyrrolidin-1-yl)propan-1-ol (2.1 g) as a colorless oil and a crude mixture containing (S)-2-((R)-2-methylpyrrolidin-1-yl)propan-1-ol. ¹H NMR (DMSO-d₆): δ 4.22 (br s, 1H), 3.36 (dd, 1H), 3.22 (dd, 1H), 2.82 (m, 1H), 2.65 (m, 2H), 2.42 (q, 1H), 1.78 (m, 1H), 1.60 (m, 2H), 1.25 (m, 1H), 0.95 (d, 3H), 0.84 (d, 3H); LCMS: 144 (M+H)⁺.

Intermediate 24

(S)-2-((R)-2-Methylpyrrolidin-1-yl)propan-1-ol

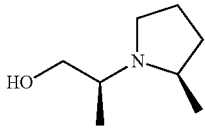

The crude mixture containing (S)-2-((R)-2-methylpyrrolidin-1-yl)propan-1-ol from the purification of Intermediate 23 was further purified (three times) on a silica gel column (NH₄OH/MeOH/DCM=1/6/300) to give (S)-2-((R)-2-methylpyrrolidin-1-yl)propan-1-ol (2.0 g) as a colorless oil. ¹H NMR (DMSO-d₆): δ 4.30 (br s, 1H), 3.50 (dd, 1H), 3.24 (m, 1H), 2.95 (m, 1H), 2.81 (m, 1H), 2.77 (m, 1H), 2.53 (m, 1H), 1.88 (m, 1H), 1.60 (m, 2H), 1.27 (m, 1H), 1.00 (d, 3H), 0.94 (d, 3H); LCMS: 144 (M+H)⁺.

Intermediate 25

2-(Azocan-1-yl)ethanol

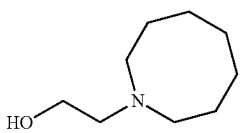

Step 1: 1-(2-((tert-Butyldimethylsilyl)oxy)ethyl)azocane

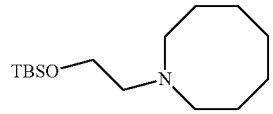 [SMILES: CC(C)(C)[Si](C)(C)OCCN1CCCCCCC1]

To a solution of azocane (5.59 g, 49.4 mmol) and triethylamine (6.53 g, 64.7 mmol) in DCM (50 mL) at room temperature was added (2-bromoethoxy)(tert-butyl)dimethylsilane (13.0 g, 54.4 mmol). The mixture was stirred overnight, and the solvent was removed under reduced pressure. The residue was dissolved in ethyl acetate, washed (brine (2×)), dried over Na₂SO₄ and filtered. The solvent was removed under reduced pressure, and the residue was purified on a silica gel column (eluting with PE/EA=10/1) to afford 1-(2-((tert-butyldimethylsilyl)oxy)ethyl)azocane (11.8 g, 88%). LCMS: 272 (M+H)⁺.

Step 2: 2-(Azocan-1-yl)ethanol

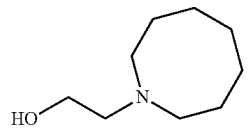 [SMILES: OCCN1CCCCCCC1]

A solution of 1-(2-((tert-butyldimethylsilyl)oxy)ethyl)azocane (9.13 g, 33.7 mmol) and TBAF (1M in THF, 36 mmol) was stirred at room temperature overnight. The mixture was concentrated and purified on a silica gel column (eluting with DCM/MeOH=30/1-50/1) to afford 2-(azocan-1-yl)ethanol (1.96 g, 37%). ¹H NMR (DMSO-d₆): δ 4.33 (br s, 1H), 3.45 (t, 2H), 2.53 (m, 6H), 1.54 (m, 10H); LCMS: 158 (M+H)⁺.

Intermediate 26

(S)-2-(Azetidin-1-yl)propan-1-ol

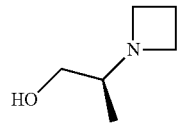

Step 1: (S)-2-(Azetidin-1-yl)propan-1-ol

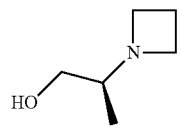

A mixture of 1,3-dibromopropane (21.1 g, 104.5 mmol), (S)-2-aminopropan-1-ol (7.48 g, 99.7 mmol), and NaHCO₃

(18.98 g, 226.0 mmol) in anhydrous toluene (150 mL) was degassed and bubbled with nitrogen for 10 min. The mixture was heated to 130° C. and stirred for 22 h. The mixture cooled to room temperature and filtered. The filtrate was used directly in the following step. LCMS: 116 (M+H)$^+$.

Step 2: (S)-1-(1-((tert-Butyldimethylsilyl)oxy)propan-2-yl)azetidine

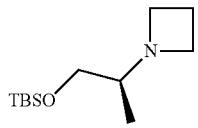

A mixture of (S)-2-(azetidin-1-yl)propan-1-ol (99.7 mmol), TBSCl (15.8 g, 105 mmol), DMAP (1.22 g, 10 mmol), and TEA (30.3 g, 0.30 mol) in toluene (150 mL) was stirred at room temperature overnight. The solvent was removed under reduced pressure. The residue was purified on a silica gel column eluted with a 1:5 ethyl acetate/petroleum ether then a 1:10 MeOH/DCM, to afford the title compound (2.92 g). $^1$H NMR (CDCl$_3$): δ 3.54-3.49 (m, 1H), 3.29-3.16 (m, 5H), 2.33-2.27 (m, 1H), 2.07-1.98 (m, 2H), 0.88 (s, 9H), 0.87 (d, 3H), 0.03 (s, 6H); LCMS: 230 (M+H)$^+$.

Step 3: (S)-2-(Azetidin-1-yl)propan-1-ol

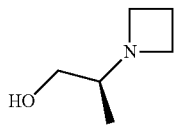

In a 100-mL round-bottom flask, (S)-1-(1-((tert-butyldimethylsilyl)oxy)propan-2-yl)azetidine (10.8 g, 47.2 mmol) was dissolved in CHCl$_3$ (50 mL) and CH$_3$CN (50 mL) at room temperature. To this solution, BF$_3$-Et$_2$O (45 mL) was added. The resulting mixture was stirred at room temperature overnight, quenched with MeOH (50 mL), and filtered through a pad of silica gel. The filtrate was concentrated to give the crude product which was purified on a silica gel column eluted with a 1:10 MeOH/DCM (containing NH$_3$), to afford the title compound (3.75 g). $^1$H NMR (DMSO-d$_6$): δ 4.36 (br s, 1H), 3.28-3.24 (m, 1H), 3.10-3.01 (m, 5H), 2.18-2.11 (m, 1H), 1.92-1.83 (m, 2H), 0.78 (d, 3H); LCMS: 116 (M+H)$^+$.

Intermediate 27

2-(Azetidin-1-yl)ethanol

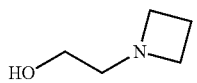

Step 1: Azetidine

A mixture of azetidine hydrochloride (40 g, 0.43 mol) and NaOH (20 g, 0.50 mol) in H$_2$O (40 mL) was stirred at room temperature for 1 h. The organic phase slowly formed and was separated from the aqueous phase. The organic layer was distilled to afford the title compound (18 g). bp: 60° C. (lit: 61-62° C.).

Step 2: 2-(Azetidin-1-yl)ethanol

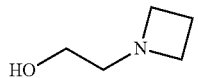

In a 500-mL round-bottom flask, azetidine (8.22 g, 144.4 mmol) was dissolved in CH$_3$CN (200 mL) at room temperature. To this solution, Cs$_2$CO$_3$ (47.1 g, 144.5 mmol) and 2-bromoethanol (18.3 g, 146 mmol) were slowly added. The resulting mixture was stirred at room temperature over the weekend. The mixture was filtered, and the solid was washed with CH$_3$CN. The combined filtrate was concentrated, and the residue was distilled under vacuum by an oil pump. The fraction with boiling point 84° C. was collected and further purified by a silica gel column eluted with a 1:10 MeOH/DCM (containing NH$_3$), to afford the title compound (1.5 g). $^1$H NMR (DMSO-d$_6$): δ 4.30 (brs, 1H), 3.30-3.25 (m, 2H), 3.06 (t, 4H), 2.36 (t, 2H), 1.90 (pent, 2H); LCMS: 102 (M+H)$^+$.

Intermediate 28

4-(Chloromethyl)-2-methoxy-1-methylbenzene

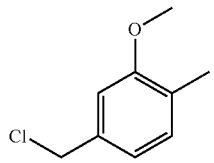

Step 1: (3-Methoxy-4-methylphenyl)methanol

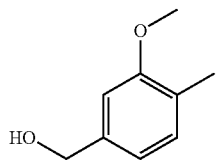

To a solution of 3-methoxy-4-methyl-benzoic acid (20.0 g, 0.12 mol) in dry THF (200 mL) at 0° C., LiAlH$_4$ (6.9 g) was slowly added. The reaction was warmed to room temperature and stirred overnight. Water (20 mL) was slowly added at 0° C., and then 15% aqueous NaOH solution (50 mL) was added. The mixture was filtered, and the filtrate was extracted with ethyl acetate (3×100 mL). The combined extracts were dried over MgSO$_4$, filtered and evaporated to give the title compound as pale yellow oil (16.0 g). $^1$H NMR (CDCl$_3$): δ 7.13 (d, 1H), 6.85-6.79 (m, 2H), 4.64 (s, 2H), 3.84 (s, 3H), 2.21 (s, 3H).

Step 2:
4-(Chloromethyl)-2-methoxy-1-methylbenzene

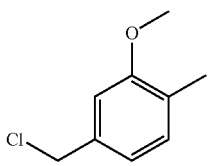

To a solution of (3-methoxy-4-methylphenyl)methanol (2.0 g, 13.0 mmol) in dry DCM (20 mL) at 0° C., SOCl$_2$ (3.1 g, 26.0 mmol) was added slowly. The resulting solution was stirred at room temperature for 0.5 h. The mixture was evaporated, and the residue was dissolved in DCM (20 mL). The mixture was washed with saturated NaHCO$_3$ (3×10 mL), dried over Na$_2$SO$_4$ and evaporated to give the title compound as brown oil (2.1 g).

Intermediate 29

1-(Chloromethyl)-4-methoxy-2-methylbenzene

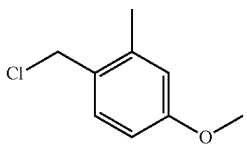

Step 1: Methyl 4-methoxy-2-methylbenzoate

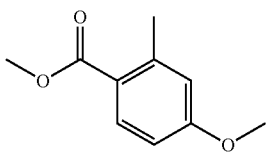

To a suspension of 4-hydroxy-2-methyl benzoic acid (10.0 g, 65.7 mmol) and cesium carbonate (53.5 g, 164.3 mmol) in DMF (70 mL) at 0° C., iodomethane (10.3 mL, 164.3 mmol) in DMF (10 mL) was added over 20 min. The reaction warmed from 0° C. to room temperature overnight. The mixture filtered and washed with ether. The filtrate was washed with water and the layers separated. The aqueous was washed with ether (3×100 mL). The organics were combined and washed with H$_2$O then brine, dried over Na$_2$SO$_4$, and concentrated under reduced pressure to give methyl 4-methoxy-2-methylbenzoate (11.4 g) as a yellow oil. $^1$H NMR (300 MHz, CDCl$_3$): δ 7.95 (m, 1H), 6.76 (m, 2H), 3.87 (s, 3H), 3.85 (s, 3H), 2.62 (s, 3H).

Step 2: (4-Methoxy-2-methylphenyl)methanol

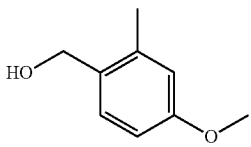

To a solution of methyl 4-methoxy-2-methylbenzoate (11.4 g, 63.3 mmol) in THF (65 mL) at 0° C., LiAlH$_4$ (1M in ether, 76.0 mL, 75.9 mmol) was added via addition funnel over 50 min. The ice water bath was removed, and the reaction was allowed to stir at room temperature for 30 min. Upon completion, the reaction was cooled to 0° C. and sodium sulfate decahydrate was added portionwise until the bubbling ceased. The reaction was then diluted with ether and filtered. The filtrate was concentrated under reduced pressure to give (4-methoxy-2-methylphenyl)methanol (8.2 g) as a clear oil. $^1$H NMR (300 MHz, CDCl$_3$): δ 7.23 (d, 1H), 6.72 (m, 2H), 4.63 (d, 2H), 3.79 (s, 3H), 2.36 (s, 3H), 1.42 (t, 1H).

Step 3:
1-(Chloromethyl)-4-methoxy-2-methylbenzene

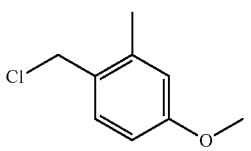

To a solution of (4-methoxy-2-methylphenyl)methanol (8.2 g, 54.0 mmol) and triethylamine (9.1 mL, 65.0 mmol) in toluene (100 mL) at 0° C., methanesulfonyl chloride (5.1 mL, 65.0 mmol) was added via syringe over 20 min. The ice water bath was removed, and the reaction was allowed to stir at room temperature for 30 min, heated at 80° C. for 3 days, and then concentrated. The reaction was diluted with DCM, washed with H$_2$O (3×100 mL) and brine, dried over Na$_2$SO$_4$, and concentrated under reduced pressure to 1-(chloromethyl)-4-methoxy-2-methylbenzene (8.1 g) as a dark brown oil. $^1$H NMR (300 MHz, CDCl$_3$): δ 7.25 (d, 1H), 6.75 (m, 2H), 4.62 (s, 2H), 3.82 (s, 3H), 2.43 (s, 3H).

Intermediate 30

1-(2,5-Dimethoxyphenyl)-2-(3-fluoro-5-methoxyphenyl)ethanone

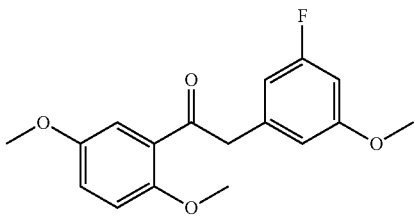

Step 1: 3-Fluoro-5-methoxybenzoic acid

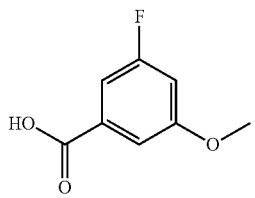

To a solution of 3,5-difluoro-benzoic acid (6.38 g, 40.3 mmol) in DMF (10 mL), NaOMe (6.48 g, 121 mmol) was added at room temperature. The mixture was stirred at 120° C. for 12 h, cooled to room temperature and filtered. The solid obtained was dissolved in $H_2O$ and pH was adjusted to 3~4 with 4M aqueous HCl solution. The mixture was filtered again and the white solid was washed with water (3×10 mL) to give 5.1 g of 3-fluoro-5-methoxybenzoic acid. $^1H$ NMR (CDCl$_3$): δ 7.37-7.43 (m, 2H), 6.83-6.88 (m, 1H), 3.86 (s, 3H).

Step 2: (3-Fluoro-5-methoxyphenyl)methanol

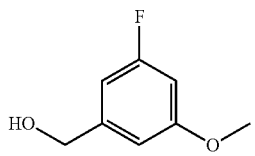

To a solution of 3-fluoro-5-methoxybenzoic acid (5.1 g, 30 mmol) in dry ether at 0° C., LiAlH$_4$ (3.44 g, 90 mmol) was added slowly. The reaction mixture was stirred at room temperature for 3 h, and quenched by slow addition of 1 M aqueous HCl solution (30 mL). The mixture was extracted with ethyl acetate (3×15 mL). The organic phase was dried over Na$_2$SO$_4$ and concentrated to give 4.9 g of (3-fluoro-5-methoxyphenyl)methanol. $^1H$ NMR (CDCl$_3$): δ 6.67-6.70 (m, 2H), 6.50-6.55 (m, 1H), 4.64 (d, 2H), 3.79 (s, 3H).

Step 3: 1-(Chloromethyl)-3-fluoro-5-methoxybenzene

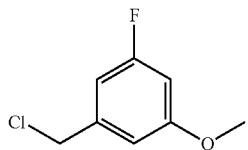

To a solution of (3-fluoro-5-methoxyphenyl)methanol (4.9 g, 30 mmol) in CCl$_4$ (50 mL), PCl$_5$ (13 g, 60 mmol) was added. The mixture was stirred at room temperature for 1 h. To this mixture, saturated Na$_2$CO$_3$ solution was slowly added until pH was adjusted to 7~8. The mixture was extracted with DCM (3×15 mL), and the organic phase was concentrated to give a colorless oil, which was purified by silica-gel column chromatography (100% petroleum ether) to give 2.9 g of 1-(chloromethyl)-3-fluoro-5-methoxybenzene. $^1H$ NMR (CDCl$_3$): δ 6.68-6.72 (m, 2H), 6.54-6.59 (m, 1H), 4.51 (s, 2H), 3.81 (s, 3H).

Step 4: 2-(3-Fluoro-5-methoxyphenyl)acetonitrile

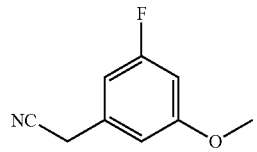

To a solution of 1-(chloromethyl)-3-fluoro-5-methoxybenzene (2.9 g, 17 mmol) in DMSO (20 mL), a solution of KCN (2.2 g, 34 mmol) and KI (5.6 g, 34 mmol) in H$_2$O (10 mL) was added. The mixture was stirred at 45° C. for 6 h, poured into H$_2$O (20 mL), and extracted with DCM (3×30 mL). The organic phase was washed with brine (2×10 mL), dried over Na$_2$SO$_4$, and concentrated to give 2.62 g of 2-(3-fluoro-5-methoxyphenyl)acetonitrile. $^1H$ NMR (CDCl$_3$): δ 6.62-6.68 (m, 2H), 6.56-6.60 (m, 1H), 3.80 (s, 3H), 3.70 (s, 2H).

Step 5: 2-(3-Fluoro-5-methoxyphenyl)acetic acid

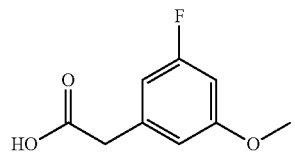

To a solution of 2-(3-fluoro-5-methoxyphenyl)acetonitrile (2.62 g, 16 mmol) in MeOH:H$_2$O (1:1; 15 mL), NaOH (1.28 g, 32 mmol) was added. Then the mixture was stirred at 65° C. for 4 h. The mixture was cooled to room temperature, and 4M aqueous HCl solution was added until the pH was adjusted to 4~5. The mixture was filtered and the solid obtained was washed with H$_2$O (2×5 mL) to give 2.33 g of 2-(3-fluoro-5-methoxyphenyl)acetic acid. $^1H$ NMR (CDCl$_3$): δ 6.52-6.62 (m, 3H), 3.78 (s, 3H), 3.59 (s, 2H).

Step 6: 1-(2,5-Dimethoxyphenyl)-2-(3-fluoro-5-methoxyphenyl)ethanone

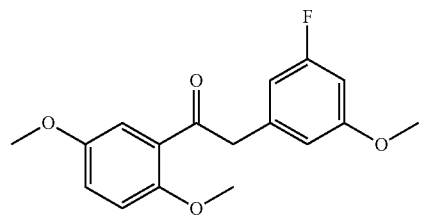

To a solution of 1,4-dimethoxybenzene (2.62 g, 19 mmol) in PPA (10 mL) at room temperature, 2-(3-fluoro-5-methoxyphenyl)acetic acid (2.33 g, 12.6 mmol) was added. The mixture was stirred at 80° C. for 3 h, cooled to room temperature, and then H$_2$O (100 mL) was added. After extraction with ethyl acetate (3×50 mL), the organic phase was dried over Na$_2$SO$_4$, concentrated, and the crude was purified by silica-gel column chromatography (ethyl acetate/petroleum ether=1/4) to give 1.0 g of 1-(2,5-dimethoxyphenyl)-2-(3-fluoro-5-methoxyphenyl)ethanone. LCMS: 305.1 [M+H]$^+$.

Intermediate 31

2-(4-Chlorophenyl)-1-(2,5-dimethoxyphenyl)ethanone

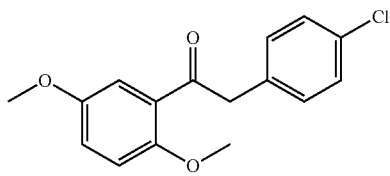 [SMILES: COc1ccc(OC)c(C(=O)Cc2ccc(Cl)cc2)c1]

To a solution of Intermediate 1 (3.0 g, 13.3 mmol) in THF (24 mL) at 0° C., 4-chlorobenzylmegnesium chloride (0.25M in ether, 100 mL, 24.9 mmol) was added via syringe over 30 min. The reaction was stirred at 0° C. for 30 min and then warmed to room temperature over 1 h. The mixture was cooled to 0° C. and neutralized with 1.0 M aqueous HCl solution. The layers were separated, and the aqueous was washed with ether (100 mL). The organic layers were combined, washed with H$_2$O (200 mL) and then brine, dried over Na$_2$SO$_4$, and concentrated under reduced pressure. The crude material was purified on a silica gel column to give 2-(4-chlorophenyl)-1-(2,5-dimethoxyphenyl)ethanone (3.1 g) as a light yellow oil. $^1$H NMR (300 MHz, DMSO-d$_6$): δ 7.38-7.33 (m, 2H), 7.22 (m, 2H), 7.13 (m, 2H), 7.10 (m, 1H), 4.30 (s, 2H), 3.90 (s, 3H), 3.73 (s, 3H).

Intermediate 32

2-(3,4-Difluorophenyl)-1-(2,5-dimethoxyphenyl) ethanone

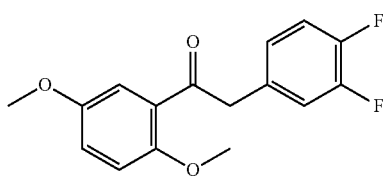 [SMILES: COc1ccc(OC)c(C(=O)Cc2ccc(F)c(F)c2)c1]

3,4-Difluorophenylacetic acid (3.0 g, 17.4 mmol) and 1,4-dimethoxybenzene (3.6 g, 26.1 mmol) in polyphosphoric acid (50 g) was heated at 72° C. for 3 h. The reaction was cooled to 50° C., and H$_2$O (70 mL) was added. The resulting mixture was extracted with ethyl acetate (2×100 mL). The organic layers were combined, washed with brine, dried over Na$_2$SO$_4$, and concentrated under reduced pressure. The crude material was purified on a silica gel column to give 2-(3,4-difluorophenyl)-1-(2,5-dimethoxyphenyl)ethanone (1.3 g) as a pale yellow solid. $^1$H NMR (300 MHz, DMSO-d$_6$): δ 7.40-7.25 (m, 2H), 7.14-7.10 (m, 3H), 7.08-7.7.03 (m, 1H), 4.29 (s, 2H), 3.86 (s, 3H), 3.73 (s, 3H).

Intermediate 33

2-(3,4-Difluoro-5-methoxyphenyl)-1-(2,5-dimethoxyphenyl)ethanone

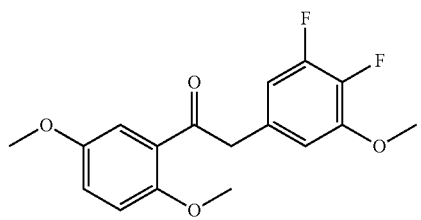

Step 1: 5-Bromo-1,2-difluoro-3-methoxybenzene

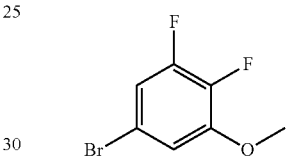

To a solution of 5-bromo-2,3-difluorophenol (19 g, 90 mmol) in acetone (180 mL), K$_2$CO$_3$ (18 g, 0.13 mol) and iodomethane (25.8 g, 0.18 mol) were added. The resulting mixture was refluxed for 4 h. Upon completion, the mixture was cooled to room temperature and filtered, and the filtrate was evaporated to give the crude product, which was further purified by column chromatography on silica gel (eluting with petroleum ether/ethyl acetate=80/1-40/1) to give a light yellow liquid 5-bromo-1,2-difluoro-3-methoxybenzene (19 g). $^1$H NMR (CDCl$_3$): δ 7.00-6.88 (m, 2H), 3.89 (s, 3H).

Step 2: 2-(3,4-Difluoro-5-methoxyphenyl)-1-(2,5-dimethoxyphenyl)ethanone

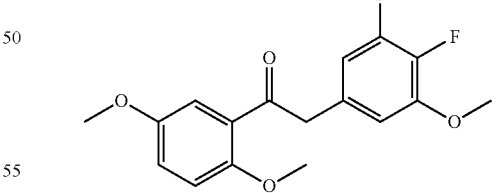

A 100-mL round-bottom flask charged with Pd$_2$dba$_3$ (69 mg, 0.075 mmol), BINAP (112 mg, 0.18 mmol), and NaO$^t$-Bu (650 mg, 6.5 mmol) was degassed and filled with N$_2$. THF (20 mL) was added, followed by a solution 5-bromo-1,2-difluoro-3-methoxybenzene (1.1 g, 5 mmol) and 1-(2,5-dimethoxyphenyl)ethanone (1.08 g, 6 mmol) in THF (10 mL). The resulting mixture was heated at 70° C. for 16 h. Water (30 mL) was added, and the mixture was extracted with ether (3×50 mL). The combined organics were dried over anhydrous Na$_2$SO$_4$, filtered, and concentrated to give the crude product, which was purified by column chromatography on silica gel (eluting with petroleum ether/ethyl acetate=80/1-40/1) to give 2-(3,4-difluoro-5-methoxyphenyl)-1-(2,5-dimethoxyphenyl)ethanone (0.4 g) as a light yellow solid. $^1$H NMR (CDCl$_3$): δ 7.24 (d, 1H), 7.04 (dd, 1H), 6.92 (d, 1H), 6.68-6.61 (m, 2H), 4.23 (s, 2H), 3.90 (s, 3H), 3.87 (s, 3H), 3.78 (s, 3H); LCMS: 323 (M+H)$^+$.

Intermediate 34

(S)-2-(4-Methyl-1H-imidazol-1-yl)propan-1-ol

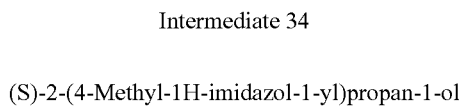

Step 1: (S)-1-((1-Hydroxypropan-2-yl)amino)propan-2-one

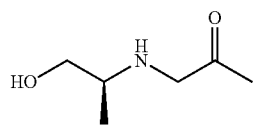

A solution of 1-bromopropan-2-one (7.8 mL, 102 mmol) in DCM (15 mL) was added dropwise to a solution of (S)-2-aminopropan-1-ol (18.2 g, 0.243 mol) and anhydrous DCM (150 mL) at 0° C. The reaction stirred at 0° C. for 2 h. Water (150 mL) was added, and the organic phase was separated. The aqueous was extracted with DCM (3×40 mL), and the combined organic layers were washed with brine (50 mL), dried over Na$_2$SO$_4$, filtered, and concentrated to give the crude product 19.5 g, which was used directly in the following step. LCMS: 132 (M+H)$^+$.

Step 2: (S)-2-(4-Methyl-1H-imidazol-1-yl)propan-1-ol

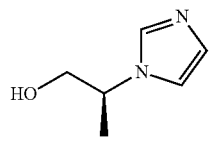

To a 100-mL round-bottom flask equipped with an air-cooled condenser, (S)-1-((1-hydroxypropan-2-yl)amino)propan-2-one (16 g) was added dropwise to formamide (30 mL) that was heated at 180° C. The resulting mixture was heated at 200° C. for 3.5 h and then cooled to room temperature. Most of formamide was removed under vacuum. The residue was purified twice on a silica gel column eluted with 1/20-1/12 MeOH/DCM (containing some NH$_3$). The crude product obtained (12.0 g) was contaminated with formamide and another unknown impurity. LCMS: 141 (M+H)$^+$.

Step 3: (S)-1-(1-((tert-Butyldimethylsilyl)oxy)propan-2-yl)-4-methyl-1H-imidazole

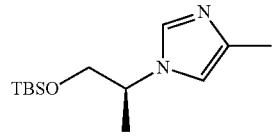 [SMILES: Cc1cn([C@@H](C)CO[Si](C)(C)C(C)(C)C)cn1]

In a 500-mL round-bottom flask, (S)-2-(4-methyl-1H-imidazol-1-yl)propan-1-ol (12.0 g) and TEA (12 mL) were dissolved in DCM at room temperature. To this solution, TBSCl (21.3 g, 0.141 mol) was added, and the resulting mixture was stirred at room temperature overnight. The mixture was washed with H$_2$O, the organic phase was separated, and the aqueous was extracted with DCM. The combined organic layers were washed with brine (50 mL), dried over Na$_2$SO$_4$, filtered, and concentrated in vacuo. The residue was purified on a silica gel column eluted with 1/30-1/9 MeOH/DCM, affording a sample (1.20 g), which was further purified by prep-HPLC, to afford the title compound (0.557 g). $^1$H NMR (CDCl$_3$): δ 7.41 (d, 1H), 6.67-6.65 (m, 1H), 4.16-4.10 (m, 1H), 3.73-3.62 (m, 2H), 2.20 (d, 3H), 1.44 (d, 3H), 0.86 (s, 9H), −0.04 (s, 6H); LCMS: 255 (M+H)$^+$.

Step 4: (S)-2-(4-Methyl-1H-imidazol-1-yl)propan-1-ol

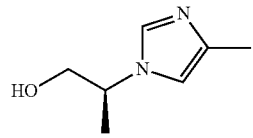

To a solution (S)-1-(1-((tert-butyldimethylsilyl)oxy)propan-2-yl)-4-methyl-1H-imidazole (0.425 g, 1.67 mmol) in DCM (5 mL) was added 3M HCl in ether (10 mL) at room temperature. The resulting mixture was stirred at room temperature overnight. The mixture was concentrated under vacuum. The residue was dissolved in MeOH, and solid NaHCO$_3$ was added. The mixture was stirred at room temperature for 1 h. The solid was filtered and washed with MeOH. The combined organic layers were concentrated to afford the title compound (0.212 g). $^1$H NMR (CDCl$_3$): δ 7.33 (s, 1H), 6.63 (s, 1H), 4.18-4.12 (m, 1H), 3.78-3.47 (m, 2H), 2.10 (s, 3H), 1.42 (d, 3H); LCMS: 141 (M+H)$^+$.

Intermediate 35

(R)-2-(3-Methylpiperidin-1-yl)ethanol

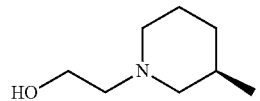

Step 1: (R)-3-Methylpiperidinium L-(+)-tartrate

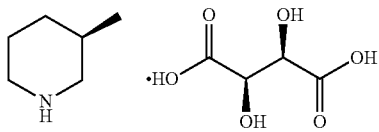

To a solution of L-(+)-tartaric acid (37.9 g, 0.253 mol) in H$_2$O (40 mL), racemic 3-methyl-piperidine (25 g, 0.252 mol) was added slowly. The mixture was kept at room temperature for 2 h. The desired isomer was crystallized from water and collected by filtration. The solid obtained was recrystallized three times from MeOH/EtOH/H$_2$O=50/25/2 (154 mL) to give the desired product (13.5 g) as a white solid (99.6% ee). [Enantiomeric excess (% ee) was determined by HPLC after derivatization with Cbz-Val].

Step 2: (2-Bromo-ethoxy)-tert-butyl-dimethyl-silane

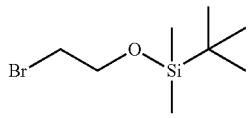

To a mixture of 2-bromo-ethanol (12.5 g, 0.1 mol) and TEA (11.2 g, 0.11 mol) in CH$_2$Cl$_2$ (40 mL), TBSCl (15.8 g, 0.105 mol) and DMAP (0.122 g, 1 mmol) were added. The reaction mixture was stirred at room temperature for 12 h, washed (10 mL 2M HCl, 10 mL H$_2$O), dried (Na$_2$SO$_4$) and concentrated to give the desired product as colorless oil. $^1$H NMR (CDCl$_3$): δ 3.88 (m, 2H), 3.39 (m, 2H), 0.89 (s, 9H), 0.08 (s, 6H).

Step 3: (R)-1-[2-(tert-Butyl-dimethyl-silanyloxy)-ethyl]-3-methyl-piperidine

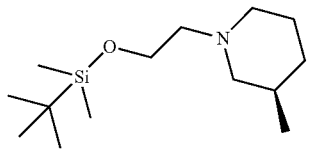 [SMILES: C[C@@H]1CCCN(CCO[Si](C)(C)C(C)(C)C)C1]

To a solution of (2-bromo-ethoxy)-tert-butyl-dimethyl-silane (6.2 g, 26 mmol) and TEA (10.4 g, 104 mmol) in CH$_2$Cl$_2$ (100 mL), (R)-3-methylpiperidinium L-(+)-tartrate (6.5 g, 26 mmol) was added. The reaction mixture was heated at 40° C. for 48 h. The solution was washed (3×20 mL H$_2$O), dried (Na$_2$SO$_4$), and concentrated. The residue was purified by silica gel column chromatography (MeOH/CH$_2$Cl$_2$=1/50) to give (R)-1-[2-(tert-butyl-dimethyl-silanyloxy)-ethyl]-3-methyl-piperidine (4.9 g) as yellow oil. $^1$H NMR (CDCl$_3$): δ 3.83 (t, 2H), 3.02-2.94 (m, 2H), 2.61 (t, 2H), 2.11-2.03 (m, 1H), 1.82-1.64 (m, 5H), 0.90-0.80 (m, 13H), 0.05 (s, 6H); LCMS: 258.2 (M+H)$^+$.

Step 4: (R)-2-(3-Methyl-piperidin-1-yl)-ethanol

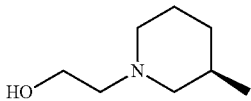

To a solution of (R)-1-[2-(tert-butyl-dimethyl-silanyloxy)-ethyl]-3-methyl-piperidine (500 mg, 1.9 mmol) in THF (5 mL) at 0° C., TBAF (1M in THF, 2.8 mL) was slowly added.
The reaction mixture was stirred at room temperature for 2 h and concentrated. The residue was purified by silica gel column chromatography (MeOH/CH$_2$Cl$_2$=1/50) to give (R)-2-(3-methyl-piperidin-1-yl)-ethanol (0.23 g) as colorless oil. $^1$H NMR (DMSO-d$_6$): δ 4.39 (br s, 1H), 3.48 (t, 2H), 2.80-2.77 (m, 2H), 2.38 (t, 2H), 1.88-1.86 (m, 1H), 1.65-1.47 (m, 5H), 0.81 (d, 3H), 0.82-0.78 (m, 1H); LCMS: 144.1 [M+H]$^+$.

Intermediate 36

2-(2-Fluoro-3-methoxyphenyl)acetic acid

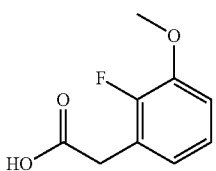

Step 1: (2-Fluoro-3-methoxyphenyl)methanol

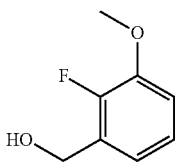

To a mixture of 2-fluoro-3-methoxybenzoic acid (14.5 g, 85.2 mmol) in dry ethyl ether (300 mL) at 0° C., LiAlH$_4$ (9.3 g, 245 mmol) was added over a 20 min period. The resulting mixture was heated at 80° C. for 20 min and then stirred at room temperature for 1 h. The mixture was carefully quenched with 15% NaOH (10 mL) at 0° C., and water (100 mL) was added. The mixture was extracted with ethyl acetate (3×100 mL), and the combined organic layers were dried (Na$_2$SO$_4$) and concentrated in vacuo to give the title compound (13.5 g).

Step 2: 1-(Chloromethyl)-2-fluoro-3-methoxybenzene

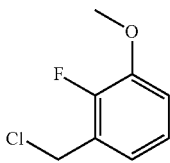

To a solution of (2-fluoro-3-methoxyphenyl)methanol (13 g, 83.2 mmol) in CCl$_4$ (75 mL), PCl$_5$ (26 g, 128.7 mmol) was added. The resulting mixture was heated at 90° C. for 30 min and then stirred at room temperature for 1 h. The mixture was poured into water (160 mL) and extracted with dichloromethane (2×150 mL). The combined organic layers were washed with brine (200 mL), dried (Na$_2$SO$_4$), and concentrated in vacuo. The residue was purified by silica gel column chromatography (1:15 EtOAc/petroleum ether) to give the title compound (11.5 g). $^1$H NMR (CDCl$_3$): δ 7.10-6.91 (m, 3H), 4.63 (s, 2H), 3.89 (s, 3H).

Step 3: 2-(2-Fluoro-3-methoxyphenyl)acetonitrile

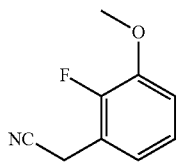

To a solution of 1-(chloromethyl)-2-fluoro-3-methoxybenzene (8.6 g, 49.3 mmol) in ethanol (60 mL) and water (10 mL), sodium cyanide (4.8 g, 98.5 mmol) was added. The resulting solution was heated at 70° C. for 16 h. After cooling to room temperature, the solution was poured into water (200 mL) and extracted with ethyl acetate (2×200 mL). The combined organic layers were washed (brine), dried (Na$_2$SO$_4$), and concentrated in vacuo to give the title compound (6.7 g). $^1$H NMR (CDCl$_3$): δ 7.13-7.07 (m, 1H), 7.02-6.92 (m, 2H), 3.89 (s, 3H), 3.81 (s, 2H).

Step 4: 2-(2-Fluoro-3-methoxyphenyl)acetic acid

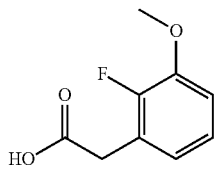

To a mixture of 2-(2-fluoro-3-methoxyphenyl)acetonitrile (6.7 g, 40.6 mmol) in water (40 mL) and methanol (40 mL), sodium hydroxide (3.2 g, 81.1 mmol) was added. The resulting mixture was stirred at 60° C. for 5 h. After cooling to room temperature, methanol was evaporated under reduced pressure. The residue was acidified with 10% HCl until pH 5. The resulting precipitate was collected by filtration and dried to afford the title compound (6.3 g).

Intermediate 37

1-(2-Fluoro-3,6-dimethoxyphenyl)-2-(3-methoxyphenyl)ethanone

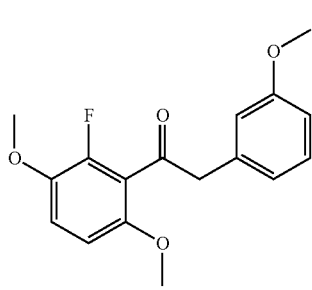 [SMILES: COc1cccc(CC(=O)c2c(OC)ccc(OC)c2F)c1]

Step 1: Ethyl 2-fluoro-3,6-dimethoxybenzoate

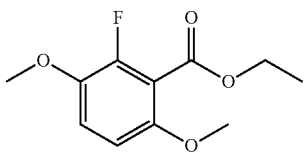 [SMILES: CCOC(=O)c1c(OC)ccc(OC)c1F]

To a solution of 2-fluoro-1,4-dimethoxybenzene (8.1 g, 52.0 mmol) in anhydrous THF at −78° C., n-BuLi (2.5 M in hexane, 22 mL, 55 mmol) was added dropwise. The resulting mixture was stirred at −78° C. for 1 h, and then ethyl chloroformate (5 mL, 52.1 mmol) was added dropwise. The reaction mixture was stirred at −78° C. for additional 2 h and quenched with water (200 mL). The mixture was extracted with ethyl acetate (2×180 mL). The combined organic layers were washed with brine (200 mL), dried (Na$_2$SO$_4$), and concentrated in vacuo. The residue was purified by silica gel column chromatography (1:5 EtOAc/petroleum ether) to give ethyl 2-fluoro-3,6-dimethoxybenzoate (8.1 g).

Step 2: 2-Fluoro-3,6-dimethoxybenzoic acid

To a mixture of ethyl 2-fluoro-3,6-dimethoxybenzoate (8.1 g, 35.5 mmol) in methanol (150 mL) and water (50 mL), lithium hydroxide (7.5 g, 178 mmol) was added. The resulting mixture was heated at 80° C. for 5 h. The reaction mixture was concentrated to remove methanol, acidified with 2 M HCl until pH 4, and extracted with dichloromethane (4×200 mL). The combined organic layers were dried (Na$_2$SO$_4$) and concentrated under reduced pressure to give the title compound (6.98 g). $^1$H NMR (DMSO-d$_6$): δ 13.39 (br s, 1H), 7.19 (t, 1H), 6.82 (dd, 1H), 3.79 (s, 3H), 3.75 (s, 3H).

Step 3: Ethyl 3-(2-fluoro-3,6-dimethoxyphenyl)-2-(3-methoxyphenyl)-3-oxopropanoate

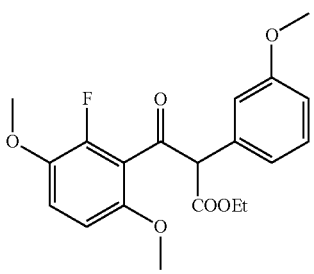 [SMILES: CCOC(=O)C(C(=O)c1c(OC)ccc(OC)c1F)c1cccc(OC)c1]

To a mixture of 2-fluoro-3,6-dimethoxybenzoic acid (4.8 g, 24 mmol) in anhydrous dichloromethane (75 mL) at 0° C., SOCl$_2$ (14.2 g, 120 mmol) was slowly added followed by DMF (0.1 mL). The resulting mixture was stirred at room temperature for 2 h and concentrated in vacuo to give 2-fluoro-3,6-dimethoxybenzoyl chloride (5.2 g). To a solution of ethyl 2-(3-methoxyphenyl)acetate (4.7 g, 24 mmol) in anhydrous THF (40 mL) at −78° C., LiHMDS (1.0 M in THF, 36 mL) was added dropwise. The resulting solution was stirred at −78° C. for 30 min and a solution of 2-fluoro-3,6-dimethoxybenzoyl chloride (5.2 g, 24 mmol) in anhydrous THF (60 ml) was added dropwise. The reaction mixture was stirred for additional 2 h at −78° C. and quenched with saturated NH$_4$Cl. The mixture was extracted with ethyl acetate (3×200 mL). The combined organic layers were dried (Na$_2$SO$_4$) and concentrated under reduced pressure to afford the title compound (7.8 g).

Step 4: 1-(2-Fluoro-3,6-dimethoxyphenyl)-2-(3-methoxyphenyl)ethanone

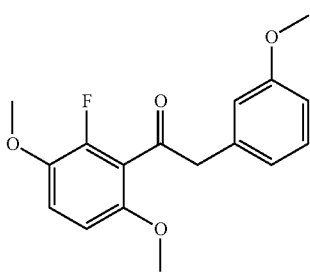 [SMILES: COc1cccc(CC(=O)c2c(OC)ccc(OC)c2F)c1]

A mixture of ethyl 3-(2-fluoro-3,6-dimethoxyphenyl)-2-(3-methoxyphenyl)-3-oxopropanoate (7.8 g, 20.7 mmol) in DMSO (75 mL) and brine (7.5 mL) was stirred at 150° C. for 5 h. The reaction mixture was concentrated in vacuo and the residue was purified by silica gel column chromatography (1:10 EtOAc/petroleum ether) to give the title compound (3.6 g). $^1$H NMR (CDCl$_3$): δ 7.24-7.15 (m, 1H), 6.90 (t, 1H), 6.84-6.75 (m, 3H), 6.56 (dd, 1H), 4.08 (s, 2H), 3.82 (s, 3H), 3.77 (s, 3H), 3.76 (s, 3H).

Intermediate 38

2-(Bromomethyl)-1-fluoro-4-methoxybenzene

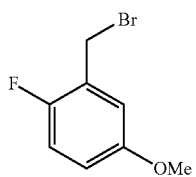 [SMILES: COc1ccc(F)c(CBr)c1]

To a solution of 1-fluoro-4-methoxy-2-methylbenzene (2.0 g, 14.29 mmol) in CCl$_4$, NBS (2.55 g, 14.29 mmol) and PhCO$_3$H (80 mg) were added. The reaction mixture was heated at reflux for 2 h, cooled to room temperature, and the solid was filtered off. The filtrate was concentrated, and the residue was purified by silica gel column chromatography (eluting with PE/EA=20/1) to give the target compound (3.0 g) as an oil. $^1$H NMR (CDCl$_3$): δ 6.97-6.83 (m, 3H), 4.48 (s, 2H), 3.78 (s, 3H).

Intermediate 39

(S)-2-((R)-3-Fluoropyrrolidin-1-yl)propan-1-ol

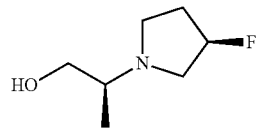

Step 1: (R)-1-(Trityloxy)propan-2-yl methanesulfonate

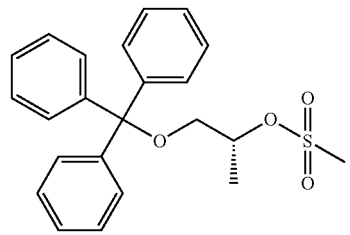 [SMILES: C[C@H](COC(c1ccccc1)(c1ccccc1)c1ccccc1)OS(C)(=O)=O]

To a solution of (R)-propane-1,2-diol (2.82 g, 37.1 mmol) and trityl chloride (10.5 g, 37.7 mmol) in DCM (100 mL) at 0° C., dimethylaminopyridine (53 mg, 0.43 mmol) was added followed by dropwise addition of triethylamine (13.0 mL, 93.3 mmol). The solution was allowed to warm to room temperature, stirred overnight, and re-cooled to 0° C. Methanesulfonyl chloride (3.2 mL, 41.2 mmol) was added to the reaction, and the mixture was stirred for 4 h at 0° C. The reaction was quenched (50 mL 1N HCl), and the layers were separated. The organic phase was washed (50 mL 1N HCl and 50 mL brine), dried (Na$_2$SO$_4$) and concentrated under reduced pressure. The crude material was purified on a silica gel column to give (R)-1-(trityloxy)propan-2-yl methanesulfonate (13.1 g) as a thick oil which solidified over time. $^1$H NMR (DMSO-d$_6$): δ 7.50-7.20 (m, 15H), 4.85 (m, 1H), 3.34 (s, 3H), 3.12 (m, 2H), 1.28 (d, 3H).

Step 2: (R)-3-Fluoro-1-((S)-1-(trityloxy)propan-2-yl)pyrrolidine

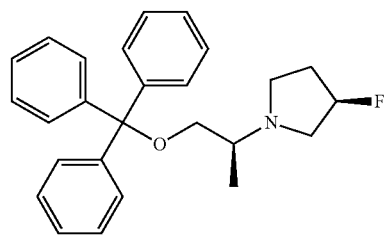 [SMILES: C[C@@H](COC(c1ccccc1)(c1ccccc1)c1ccccc1)N1CC[C@@H](F)C1]

A mixture of (R)-1-(trityloxy)propan-2-yl methanesulfonate (1.25 g, 3.15 mmol), (R)-3-fluoropyrrolidine hydrochloride (480 mg, 3.52 mmol), and K$_2$CO$_3$ (1.31 g, 9.48 mmol) in acetonitrile (40 mL) was heated at reflux for 4 days. The reaction was cooled to room temperature, concentrated under reduced pressure, and diluted with DCM (100 mL). The solution was washed (50 mL sat'd NaHCO₃), dried (Na₂SO₄), and concentrated under reduced pressure. The crude material was purified on a silica gel column to yield (R)-3-fluoro-1-((S)-1-(trityloxy)propan-2-yl)pyrrolidine (725 mg) as a pale brown oil. ¹H NMR (CDCl₃): δ 7.60-7.20 (m, 15H), 5.40-4.95 (m, 1H), 3.30 (m, 1H), 3.05-2.50 (m, 5H), 2.29 (m, 1H), 2.06-1.70 (m, 2H), 1.07 (d, 3H).

Step 3: (S)-2-((R)-3-Fluoropyrrolidin-1-yl)propan-1-ol

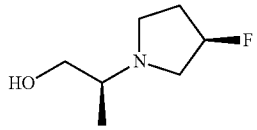

(R)-3-Fluoro-1-((S)-1-(trityloxy)propan-2-yl)pyrrolidine (732 mg, 1.87 mmol) and HCl (2N in Et₂O, 1.4 mL, 2.8 mmol) were stirred at room temperature for 5 h. The solvent was decanted off, and the solid was dissolved in DCM (30 mL). The solution was washed (sat'd K₂CO₃), dried (Na₂SO₄), and concentrated under reduced pressure. The crude material was purified on a silica gel column to yield (S)-2-((R)-3-fluoropyrrolidin-1-yl)propan-1-ol (115 mg) as a clear oil. ¹H NMR (DMSO-d₆): δ 5.26-5.00 (m, 1H), 4.42 (t, 1H), 3.50 (m, 1H), 3.22 (m, 1H), 2.90-2.65 (m, 3H), 2.45-2.20 (m, 2H), 2.15-1.75 (m, 2H), 1.00 (d, 3H).

Intermediate 40

(S)-2-(7-Azabicyclo[2.2.1]heptan-7-yl)propan-1-ol

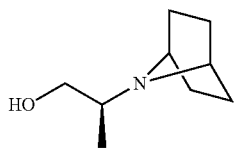

The title compound was synthesized as described in Intermediate 39 (steps 2-3) using (R)-1-(trityloxy)propan-2-yl methanesulfonate and 7-azabicyclo[2.2.1]heptane hydrochloride as starting materials. ¹H NMR (DMSO-d₆): δ 4.36 (t, 1H), 3.42 (m, 3H), 3.07 (m, 1H), 2.26 (m, 1H), 1.54 (m, 4H), 1.18 (m, 4H), 0.96 (d, 3H).

Intermediate 41

2-(4-Iodophenyl)-6-((tetrahydro-2H-pyran-2-yl)oxy)-3-(4-((tetrahydro-2H-pyran-2-yl)oxy)phenyl)-4-(trifluoromethyl)-2H-chromene

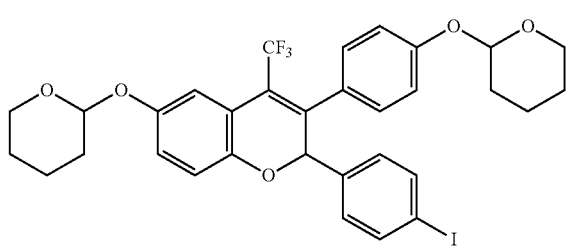 [SMILES: FC(F)(F)C1=C(c2ccc(OC3CCCCO3)cc2)C(c2ccc(I)cc2)Oc2ccc(OC3CCCCO3)cc21]

Step 1: {2-(4-Iodo-phenyl)-6-(tetrahydro-pyran-2-yloxy)-3-[4-(tetrahydro-pyran-2-yloxy)-phenyl]-4-trifluoromethyl-chroman-4-yloxy}-trimethyl-silane

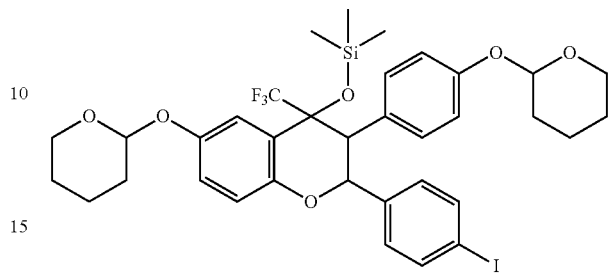

To a solution of 2-(4-iodo-phenyl)-6-(tetrahydro-pyran-2-yloxy)-3-[4-(tetrahydro-pyran-2-yloxy)-phenyl]-chroman-4-one (16.5 g, 26.36 mmol) in DME (160 mL), CsF (450 mg, 2.96 mmol) and CF₃TMS (16 mL, 0.11 mol) were added at room temperature. The resulting mixture was stirred at room temperature for 24 h and diluted with H₂O (200 mL). The reaction mixture was extracted with ethyl acetate (4×150 mL), and the combined organic extracts were dried (Na₂SO₄), and concentrated in vacuo. The residue was purified by silica gel column chromatography to afford the desired product (15 g). ¹H NMR (DMSO-d₆): δ 7.64-7.54 (m, 1H), 7.51 (d, 2H), 7.35 (dd, 1H), 6.99-6.97 (m, 1H), 6.90-6.88 (m, 6H), 5.43-5.13 (m, 3H), 4.04 (dd, 1H), 3.91-3.55 (m, 4H), 1.97-1.57 (m, 12H), 0.04 (s, 9H).

Step 2: 3-(4-Hydroxyphenyl)-2-(4-iodophenyl)-4-(trifluoromethyl)chroman-4,6-diol

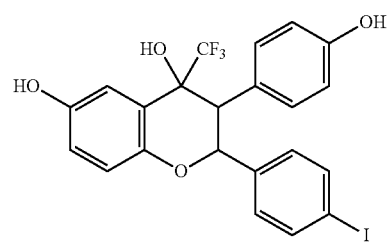 [SMILES: Oc1ccc(C2C(c3ccc(I)cc3)Oc3ccc(O)cc3C2(O)C(F)(F)F)cc1]

To a solution of {2-(4-iodo-phenyl)-6-(tetrahydro-pyran-2-yloxy)-3-[4-(tetrahydro-pyran-2-yloxy)-phenyl]-4-trifluoromethyl-chroman-4-yloxy}-trimethyl-silane (15 g, 73 mmol) in MeOH (400 mL), concentrated HCl (100 mL) was added. The reaction mixture was stirred at room temperature for 4 h, concentrated, and re-dissolved in DCM (150 mL). The solution was washed (3×100 mL brine), dried (Na₂SO₄), filtered, and concentrated. The residue was purified by silica gel column chromatography (PE/EA=10/1) to afford the desired product (10 g). ¹H NMR (DMSO-d₆): δ 9.17 (s, 1H), 9.08 (s, 1H), 7.55 (d, 2H), 7.10 (d, 2H), 7.06-6.99 (m, 3H), 6.76-6.65 (m, 2H), 6.55-6.48 (m, 3H), 5.77 (d, 1H), 3.55 (d, 1H); LCMS: 527 (M−H)⁻.

Step 3: 3-(4-Hydroxy-phenyl)-2-(4-iodo-phenyl)-4-trifluoromethyl-2H-chromen-6-ol

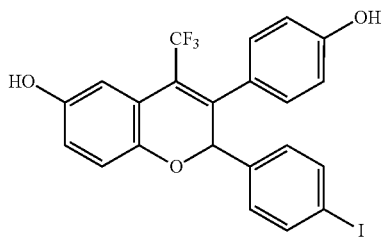 [SMILES: Oc1ccc(C2=C(C(F)(F)F)c3cc(O)ccc3OC2c2ccc(I)cc2)cc1]

A mixture of 2-(4-iodo-phenyl)-6-(tetrahydro-pyran-2-yloxy)-3-[4-(tetrahydro-pyran-2-yloxy)-phenyl]-4-trifluoromethyl-chroman-4-ol (3.0 g, 5.7 mmol) and TsOH (0.6 g, 3.18 mmol) in toluene (60 mL) was refluxed for 18 h, removing water with a Dean Stark trap. The mixture was cooled to room temperature and concentrated. The residue was purified by silica gel column chromatography (PE/EA=10/1-4/1) to afford a white solid (1.5 g). $^1$H NMR (DMSO-$d_6$): δ 9.17 (s, 1H), 9.07 (s, 1H), 7.56-7.54 (m, 2H), 7.35-6.95 (m, 5H), 6.67-6.50 (m, 4H), 5.73 (s, 1H). LCMS: 509 (M−H)⁻.

Step 4: 2-(4-Iodo-phenyl)-6-(tetrahydro-pyran-2-yloxy)-3-[4-(tetrahydro-pyran-2-yloxy)-phenyl]-4-trifluoromethyl-2H-chromene

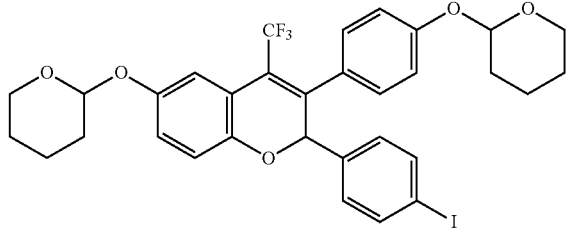 [SMILES: FC(F)(F)C1=C(c2ccc(OC3CCCCO3)cc2)C(c2ccc(I)cc2)Oc2ccc(OC3CCCCO3)cc21]

To a solution of 3-(4-hydroxy-phenyl)-2-(4-iodo-phenyl)-4-trifluoromethyl-2H-chromen-6-ol (1.5 g, 2.94 mmol) in DCM (50 mL), DHP (1.45 g, 17.65 mmol) and PPTS (370 mg, 1.47 mmol) were added. The mixture was stirred at 30° C. for 16 h, washed (2×100 mL H$_2$O, brine 100 ml), dried (Na$_2$SO$_4$), filtered, and concentrated. The residue was purified by silica gel column chromatography to afford the title compound (1.5 g). $^1$H NMR (DMSO-$d_6$): δ 7.62 (d, 2H), 7.33 (dt, 2H), 7.04-6.99 (m, 5H), 6.90 (dt, 1H), 6.74 (d, 1H), 6.20 (br s, 1H), 5.45 (br s, 1H), 5.32-5.29 (m, 1H), 3.83-3.31 (m, 4H), 1.86-1.42 (m, 12H).

Intermediate 42

1-(2,5-Dimethoxyphenyl)-2-(3-methoxy-4-(trifluoromethyl)phenyl)ethanone

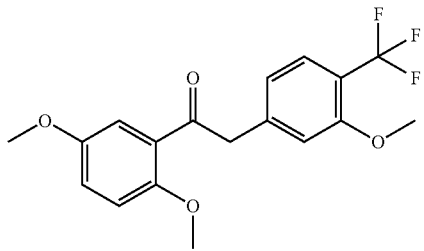 [SMILES: COc1ccc(OC)c(C(=O)Cc2ccc(C(F)(F)F)c(OC)c2)c1]

Step 1: Methyl 2-(3-methoxy-4-(trifluoromethyl)phenyl)acetate

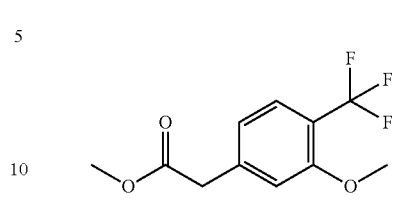

To a solution of 2-(3-methoxy-4-(trifluoromethyl)phenyl)acetic acid (17.0 g, 72.6 mmol) in MeOH (200 mL), thionyl chloride (10 mL, 141 mmol) was added dropwise. The resulting mixture was stirred at room temperature for 16 h and concentrated under vacuum to afford the title compound (18.8 g). $^1$H NMR (DMSO-$d_6$): δ 7.49 (s, 1H), 7.40 (d, 1H), 6.96 (d, 1H), 3.87 (s, 3H), 3.68 (s, 3H), 3.64-3.58 (m, 2H).

Step 2: Methyl 3-(2,5-dimethoxyphenyl)-2-(3-methoxy-4-(trifluoromethyl)phenyl)-3-oxopropanoate

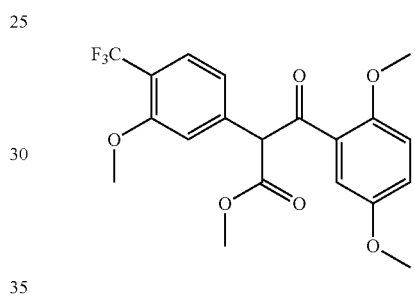

To a solution of methyl 2-(3-methoxy-4-(trifluoromethyl)phenyl)acetate (18.6 g, 75 mmol) in anhydrous THF (250 mL) at −78° C., LiHMDS (1.0 M in THF, 79 mL, 79 mmol) was added dropwise under N$_2$. The resulting mixture was stirred at −78° C. for 30 minutes, and a solution of 2,5-dimethoxybenzoyl chloride (15.9 g, 78 mmol; intermediate in Intermediate 1) in anhydrous THF (50 mL) was added dropwise. The reaction mixture was stirred for another 1 h at −78° C., quenched with saturated aqueous NH$_4$Cl (100 mL), and extracted with ethyl acetate (2×100 mL). The combined organic layers were dried over anhydrous sodium sulfate and concentrated under vacuum to give the title compound (30.1 g). $^1$H NMR (DMSO-$d_6$): δ 7.50 (d, 1H), 7.34 (d, 1H), 7.09-7.07 (m, 1H), 6.94-6.87 (m, 3H), 5.71 (s, 1H), 3.92 (s, 3H), 3.85 (s, 3H), 3.77 (s, 3H), 3.65 (s, 3H).

Step 3: 1-(2,5-Dimethoxyphenyl)-2-(3-methoxy-4-(trifluoromethyl)phenyl)ethanone

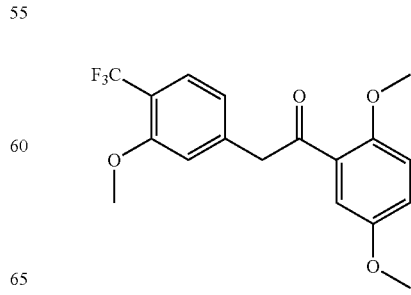

To a solution of methyl 3-(2,5-dimethoxyphenyl)-2-(3-methoxy-4-(trifluoromethyl)phenyl)-3-oxopropanoate (30.1 g, 73 mmol) in EtOH (400 mL), concentrated HCl (100 mL) was added. The reaction mixture was heated at 130° C. for 3 h, cooled to room temperature, and concentrated. The residue was dissolved in dichloromethane (150 mL) and washed with brine (3×100 mL). The organic layer was dried ($Na_2SO_4$), concentrated and purified by silica gel column chromatography (1:10 EtOAc/petroleum ether) to afford the title compound (27.7 g). $^1$H NMR (DMSO-$d_6$): δ 7.48 (d, 1H), 7.26-7.25 (m, 1H), 7.07-7.03 (m, 1H), 6.93-6.84 (m, 3H), 4.33 (s, 2H), 3.90 (s, 3H), 3.87 (s, 3H), 3.77 (s, 3H).

Intermediate 43

(S)-2-Morpholinopropan-1-ol

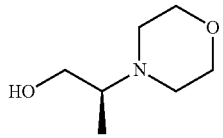

Bis(2-bromoethyl) ether (2.3 g, 10 mmol) was added to (S)-2-aminopropan-1-ol (3.8 g, 50 mmol) at rt with vigorous stirring. The reaction slowly exothermed, and the internal temperature peaked at 42° C. after 19 min. After 24 h, the reaction was diluted with dichloromethane (10 mL) and quenched with sat'd potassium carbonate solution (10 mL). Water (~2.5 mL) was added to the heterogeneous mixture until the solids dissolved. The layers were separated, and the aqueous layer was extracted with dichloromethane (10 mL×2). The organic layers were combined, dried ($MgSO_4$), filtered, concentrated, and purified by silica gel chromatography (10:7; ethyl acetate:hexanes→10:7:2:1; ethyl acetate:hexanes:methanol:triethylamine) to give 1.27 g of (S)-2-morpholinopropan-1-ol. $^1$H NMR (DMSO-$d_6$): δ 4.29 (dd, 1H), 3.54 (t, 4H), 3.45 (ddd, 1H), 3.25 (ddd, 1H), 2.54-2.40 (m, 5H), 0.92 (d, 3H); MS: 146.1 (M+H)$^+$.

Intermediate 44

(2S)-2-(3-Azabicyclo[3.1.0]hexan-3-yl)propan-1-ol

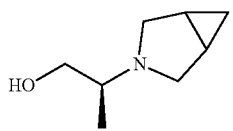

Step 1: (2S)-2-(2,4-Dioxo-3-azabicyclo[3.1.0]hexan-3-yl)propyl acetate

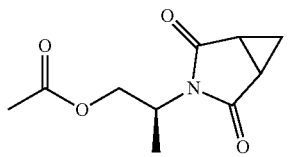

A solution of 3-oxabicyclo[3.1.0]hexane-2,4-dione (1.0 g, 8.9 mmol), (S)-2-aminopropan-1-ol (1.5 g, 20 mmol), and toluene (20 mL) was refluxed under $N_2$ for 1.75 h, allowed to cool to rt, and concentrated. Acetic anhydride (10 mL) was added to the residue, and the reaction was heated at 80° C. for 18.5 h, allowed to cool to rt, and concentrated. The residue was purified by silica gel chromatography (9:1→0:1; hexanes:ethyl acetate) to give 0.97 g of (2S)-2-(2,4-dioxo-3-azabicyclo[3.1.0]hexan-3-yl)propyl acetate. $^1$H NMR (DMSO-$d_6$): δ 4.25-4.16 (m, 1H), 4.14-4.05 (m, 2H), 2.56 (dd, 2H), 1.96 (s, 3H), 1.52 (m, 1H), 1.34 (m, 1H), 1.21 (d, 3H).

Step 2: (2S)-2-(3-azabicyclo[3.1.0]hexan-3-yl)propan-1-ol

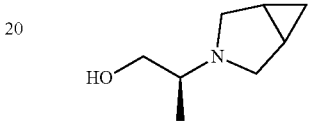

A solution of (2S)-2-(2,4-dioxo-3-azabicyclo[3.1.0]hexan-3-yl)propyl acetate (485 mg, 2.3 mmol) and anhydrous diethyl ether (3 mL) was added over 5 min to a suspension of $LiAlH_4$ (262 mg, 6.9 mmol) and anhydrous diethyl ether (20 mL) at rt under $N_2$ (water bath used to control exotherm). After ~9 h, anhydrous diethyl ether (10 mL) was added. After 24 h, $Na_2SO_4$*$10H_2O$ was added one crystal at a time until the bubbling ceased. The mixture was diluted with diethyl ether (50 mL) and filtered through Celite with additional diethyl ether (100 mL). The filtrate was concentrated and purified by silica gel chromatography (10:7; ethyl acetate:hexanes→10:7:2:1; ethyl acetate:hexanes:methanol:triethylamine) to give 220 mg of (2S)-2-(3-azabicyclo[3.1.0]hexan-3-yl)propan-1-ol. $^1$H NMR (DMSO-$d_6$): δ 4.26 (t, 1H), 3.42 (m, 1H), 3.13 (ddd, 1H), 2.91 (d, 1H), 2.85 (d, 1H), 2.39-2.28 (m, 3H), 1.31 (m, 2H), 0.93 (d, 3H), 0.54 (m, 1H), 0.25 (m, 1H); MS: 142.2 (M+H)$^+$.

Example 1

3-(3-Hydroxyphenyl)-4-methyl-2-(4-((S)-2-(piperidin-1-yl)propoxy)phenyl)-2H-chromen-6-ol

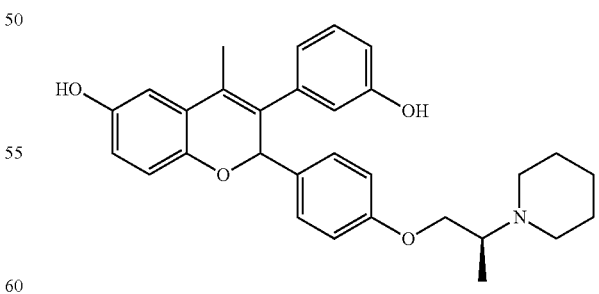

A mixture of Intermediate 3 (180 mg, 0.288 mmol), Intermediate 17 (0.3 mL), copper iodide (55 mg, 0.29 mmol), 2,2'-bipyridine (54 mg, 0.35 mmol) and potassium carbonate (130 mg, 0.942 mmol) was degassed by bubbling nitrogen for 15 min. The reaction mixture was heated at 140° C. overnight, allowed to cool to room temperature, and diluted with ethyl acetate (75 mL). Insoluble material was filtered off by passing the solution through Celite, and the Celite was washed with ethyl acetate (50 mL). The filtrate was washed (50 mL H$_2$O, 2×50 mL 0.1 M copper sulfate, and 50 mL brine), dried over Na$_2$SO$_4$, and concentrated under reduced pressure. The crude material was purified on a silica gel column to yield 1-((2S)-1-(4-(4-methyl-6-((tetrahydro-2H-pyran-2-yl)oxy)-3-(3-((tetrahydro-2H-pyran-2-yl)oxy)phenyl)-2H-chromen-2-yl)phenoxy)propan-2-yl)piperidine as a white foam (130 mg). The white foam was dissolved in 80% acetic acid/H$_2$O (2 mL) and heated at 90° C. for 15 min. The solvent was removed under reduced pressure and the residue was purified by reverse phase HPLC (acetonitrile, H$_2$O, TFA) to yield 3-(3-hydroxyphenyl)-4-methyl-2-(4-((S)-2-(piperidin-1-yl)propoxy)phenyl)-2H-chromen-6-ol as a TFA salt (79 mg). $^1$H NMR (DMSO-d$_6$): δ 9.46 (s, 1H), 9.03 (br s, 1H), 8.97 (s, 1H), 7.25 (d, 2H), 7.14 (t, 1H), 6.88 (m, 2H), 6.69 (m, 4H), 6.48 (m, 2H), 5.88 (s, 1H), 4.16 (m, 2H), 3.69 (m, 2H), 3.01 (m, 3H), 2.04 (s, 3H), 1.83 (m, 5H), 1.40 (m, 1H), 1.33 (d, 3H); LCMS: 472.7 (M+H)$^+$.

Example 2

3-(3-Hydroxyphenyl)-4-methyl-2-(4-((S)-2-((R)-3-methylpyrrolidin-1-yl)propoxy)phenyl)-2H-chromen-6-ol

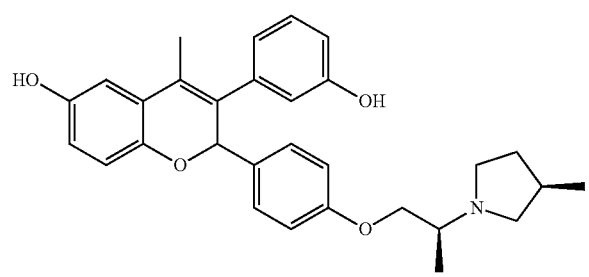

Step 1: (3R)-3-Methyl-1-((2S)-1-(4-(4-methyl-6-((tetrahydro-2H-pyran-2-yl)oxy)-3-(3-((tetrahydro-2H-pyran-2-yl)oxy)phenyl)-2H-chromen-2-yl)phenoxy)propan-2-yl)pyrrolidine

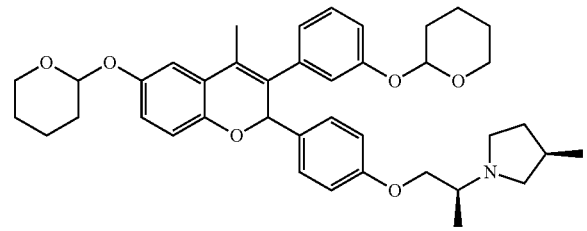 [SMILES: CC1=C(c2cccc(OC3CCCCO3)c2)C(c2ccc(OC[C@H](C)N3CC[C@@H](C)C3)cc2)Oc2ccc(OC3CCCCO3)cc21]

A mixture of Intermediate 3 (242 mg, 0.388 mmol), Intermediate 16 (115 mg, 0.804 mmol), copper iodide (8 mg, 0.04 mmol), and cesium carbonate (255 mg, 0.785 mmol) in butyronitrile (0.4 mL) was degassed by bubbling nitrogen for 15 min. The reaction mixture was heated at 125° C. overnight, allowed to cool to room temperature, and diluted with ethyl acetate (50 mL). Insoluble material was filtered off by passing the solution through Celite, and the Celite was washed with ethyl acetate (25 mL). The filtrate was washed (50 mL H$_2$O, 50 mL brine), dried over Na$_2$SO$_4$, and concentrated under reduced pressure. The crude material was purified on a silica gel column to yield (3R)-3-methyl-1-((2S)-1-(4-(4-methyl-6-((tetrahydro-2H-pyran-2-yl)oxy)-3-(3-((tetrahydro-2H-pyran-2-yl)oxy)phenyl)-2H-chromen-2-yl)phenoxy)propan-2-yl)pyrrolidine (155 mg, 63%) as a white foam. $^1$H NMR (DMSO-d$_6$): δ 7.25 (m, 3H), 7.00 (s, 1H), 6.92 (m, 3H), 6.78 (m, 3H), 6.60 (d, 1H), 5.98 (d, 1H), 5.40 (m, 1H), 5.35 (s, 1H), 3.95 (m, 1H), 3.75 (m, 3H), 3.55 (m, 2H), 2.85 (m, 1H), 2.60 (m, 3H), 2.07 (m, 4H), 1.50-1.99 (m, 13H), 1.25 (m, 2H), 1.19 (d, 3H), 0.95 (d, 3H).

Note: For this compound or other compounds synthesized using this reaction, i) the reaction time varied depending on the amino alcohol (overnight to 3 days; progress was monitored by LCMS), and ii) potassium carbonate may be used with longer reaction times (5-7 days).

Step 2: 3-(3-Hydroxyphenyl)-4-methyl-2-(4-((S)-2-((R)-3-methylpyrrolidin-1-yl)propoxy)phenyl)-2H-chromen-6-ol

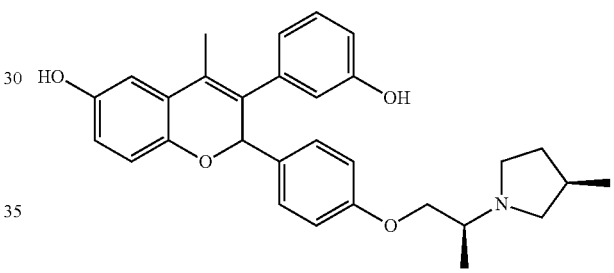

A solution of (3R)-3-methyl-1-((2S)-1-(4-(4-methyl-6-((tetrahydro-2H-pyran-2-yl)oxy)-3-(3-((tetrahydro-2H-pyran-2-yl)oxy)phenyl)-2H-chromen-2-yl)phenoxy)propan-2-yl)pyrrolidine (360 mg, 0.560 mmol) in 80% acetic acid/H$_2$O (6 mL) was heated at 90° C. for 15 min. The reaction was concentrated under reduced pressure, and purified by reverse phase HPLC (acetonitrile, H$_2$O, TFA) to give the desired compound as a TFA salt. The compound was freebased with sodium bicarbonate by extracting with ethyl acetate to yield 3-(3-hydroxyphenyl)-4-methyl-2-(4-((S)-2-((R)-3-methylpyrrolidin-1-yl)propoxy)phenyl)-2H-chromen-6-ol (210 mg, 74%) as a white foam. $^1$H NMR (DMSO-d$_6$): δ 9.44 (s, 1H), 8.95 (s, 1H), 7.19 (d, 2H), 7.15 (t, 1H), 6.78 (d, 2H), 6.70 (m, 4H), 6.48 (m, 2H), 5.84 (s, 1H), 3.98 (m, 1H), 3.71 (m, 1H), 2.82 (m, 1H), 2.62 (m, 2H), 2.10 (m, 1H), 2.07 (s, 3H), 1.90 (m, 1H), 1.55 (m, 1H), 1.35 (m, 1H), 1.25 (m, 1H), 1.19 (d, 3H), 0.94 (d, 3H); LCMS: 472.7 (M+H)$^+$.

Note: For this compound and other compounds synthesized using this reaction, i) the reaction can be performed at room temperature over an extended time (2 h-overnight), and ii) the compound can be converted into hydrochloride salt by the following the general method: The compound was suspended in diethyl ether, and methanol was added until the solution became clear. Hydrogen chloride in diethyl ether (2N) was added, and the solvent was removed under reduced pressure.

Example 2a (S)-3-(3-Hydroxyphenyl)-4-methyl-2-(4-((S)-2-((R)-3-methylpyrrolidin-1-yl)propoxy)phenyl)-2H-chromen-6-ol

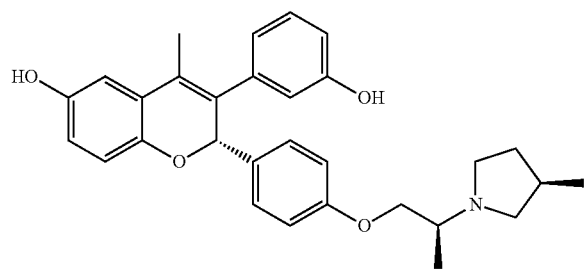 [SMILES: CC1=C(c2cccc(O)c2)[C@H](c2ccc(OC[C@H](C)N3CC[C@@H](C)C3)cc2)Oc2ccc(O)cc21]

The title compound is the 1$^{st}$ eluting diastereomer when Example 2 is separated on a CHIRALPAK® IA column [hexanes/ethanol/tetrahydrofuran/diethylamine (22:2:1:0.009)]. LCMS: 472.7 (M+H)$^+$; Diastereomeric ratio: >99:1.

Example 2b (R)-3-(3-Hydroxyphenyl)-4-methyl-2-(4-((S)-2-((R)-3-methylpyrrolidin-1-yl)propoxy)phenyl)-2H-chromen-6-ol

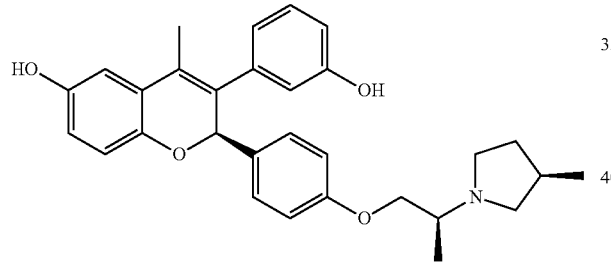

The title compound is the 2$^{nd}$ eluting diastereomer when Example 2 is separated on a CHIRALPAK® IA column [hexanes/ethanol/tetrahydrofuran/diethylamine (22:2:1:0.009)]. LCMS: 472.7 (M+H)$^+$; Diastereomeric ratio: 99:1.

Example 3

3-(3-Hydroxyphenyl)-4-methyl-2-(4-(2-(methylamino)ethoxy)phenyl)-2H-chromen-6-ol

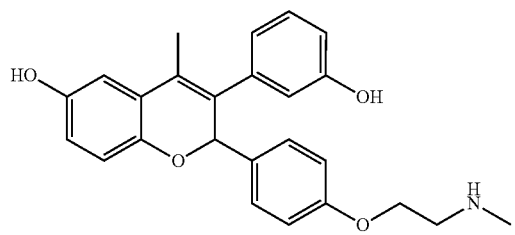 [SMILES: CNCCOc1ccc(C2Oc3ccc(O)cc3C(C)=C2c2cccc(O)c2)cc1]

A mixture of Intermediate 3 (115 mg, 0.184 mmol), 2-(methylamino)ethanol (71 mg, 0.95 mmol), copper iodide (19 mg, 0.099 mmol), and cesium carbonate (122 mg, 0.375 mmol) in butyronitrile (0.4 mL) was degassed by bubbling nitrogen for 15 min. The reaction mixture was heated at 125° C. for 4 h, allowed to cool to room temperature, and diluted with ethyl acetate (15 mL). Insoluble material was filtered off by passing the solution through Celite, and the Celite was washed with ethyl acetate (10 mL). The filtrate was washed (2×5 mL H$_2$O, 5 mL brine), dried over Na$_2$SO$_4$, and concentrated under reduced pressure. The crude material was purified on a silica gel column to give N-methyl-2-(4-(4-methyl-6-((tetrahydro-2H-pyran-2-yl)oxy)-3-(3-((tetrahydro-2H-pyran-2-yl)oxy)phenyl)-2H-chromen-2-yl)phenoxy)ethanamine. The isolated intermediate was dissolved in 80% acetic acid/H$_2$O (1 mL) and heated at 90° C. for 15 min. The solvent was removed under reduced pressure and the residue was purified by reverse phase HPLC (acetonitrile, H$_2$O, TFA) to yield 3-(3-hydroxyphenyl)-4-methyl-2-(4-(2-(methylamino)ethoxy)phenyl)-2H-chromen-6-ol as a TFA salt (79 mg). $^1$H NMR (DMSO-d$_6$): δ 9.45 (s, 1H), 8.96 (s, 1H), 8.53 (br s, 2H), 7.24 (d, 2H), 7.16 (t, 1H), 6.86 (d, 2H), 6.75 (s, 1H), 6.70 (m, 3H), 6.48 (m, 2H), 5.87 (s, 1H), 4.14 (t, 2H), 3.37 (br s, 2H), 2.60 (m, 3H), 2.04 (s, 3H); LCMS: 404.6 (M+H)$^+$.

Example 4

2-(4-((2-Hydroxyethyl)(methyl)amino)phenyl)-3-(3-hydroxyphenyl)-4-methyl-2H-chromen-6-ol

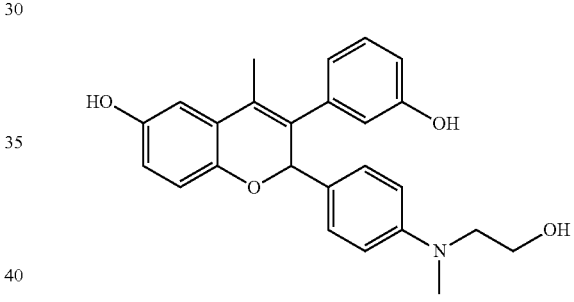

During the silica gel purification described in Example 3, the bis-THP precursor to Example 4 was isolated. This precursor was deprotected following the procedure described in Example 3 to give Example 4. $^1$H NMR (DMSO-d$_6$): δ 8.34 (s, 1H), 7.81 (s, 1H), 7.17 (m, 3H), 6.87 (d, 2H), 6.48 (m, 4H), 5.63 (s, 1H), 3.66 (m, 3H), 3.43 (t, 2H), 2.92 (br s, 5H), 2.10 (s, 3H); LCMS: 404.6 (M+H)$^+$.

Example 5

2-(4-(2-(Diethylamino)ethoxy)phenyl)-3-(3-hydroxyphenyl)-4-methyl-2H-chromen-6-ol

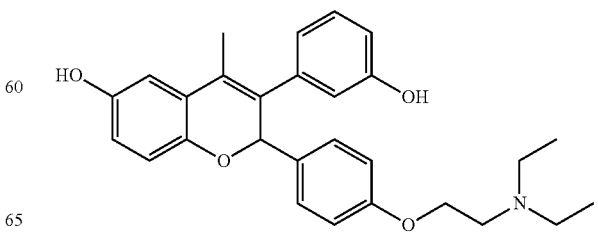

The title compound was synthesized as described in Example 1 using Intermediate 3 and 2-(diethylamino)ethanol as starting materials. $^1$H NMR (DMSO-$d_6$; TFA salt): δ 9.44 (br s, 1H), 9.25 (br s, 1H), 8.95 (br s, 1H), 7.25 (d, 2H), 7.13 (t, 1H), 6.87 (d, 2H), 6.75 (s, 1H), 6.71 (m, 3H), 6.49 (m, 2H), 5.88 (s, 1H), 4.23 (t, 2H), 3.46 (m, 2H), 3.20 (m, 4H), 2.04 (s, 3H), 1.19 (t, 6H); LCMS: 446.7 (M+H)$^+$.

Example 6

3-(3-Hydroxyphenyl)-4-methyl-2-(4-((S)-2-(pyrrolidin-1-yl)propoxy)phenyl)-2H-chromen-6-ol

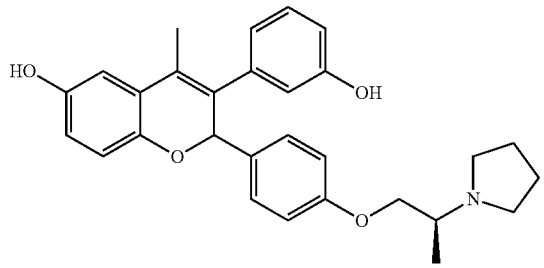 [SMILES: CC1=C(c2cccc(O)c2)C(c2ccc(OC[C@H](C)N3CCCC3)cc2)Oc2ccc(O)cc21]

The title compound was synthesized as described in Example 1 using Intermediate 3 and Intermediate 9 as starting materials. $^1$H NMR (DMSO-$d_6$; TFA salt): δ 9.58 (br s, 1H), 9.45 (br s, 1H), 8.96 (br s, 1H), 7.25 (d, 2H), 7.14 (t, 1H), 6.87 (d, 2H), 6.75 (s, 1H), 6.71 (m, 3H), 6.49 (m, 2H), 5.88 (s, 1H), 4.10 (m, 2H), 3.70 (m, 3H), 3.17 (m, 2H), 2.04 (s, 3H), 1.98 (m, 2H), 1.84 (m, 2H), 1.34 (d, 3H); LCMS: 458.7 (M+H)$^+$.

Example 7

3-(3-Hydroxyphenyl)-4-methyl-2-(4-((R)-2-(pyrrolidin-1-yl)propoxy)phenyl)-2H-chromen-6-ol

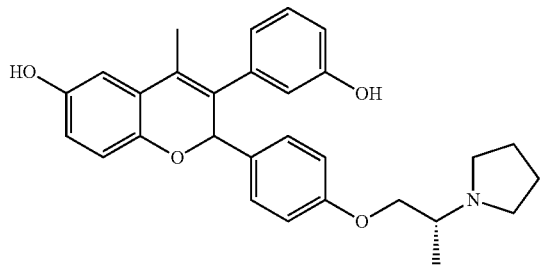 [SMILES: CC1=C(c2cccc(O)c2)C(c2ccc(OC[C@@H](C)N3CCCC3)cc2)Oc2ccc(O)cc21]

The title compound was synthesized as described in Example 1 using Intermediate 3 and Intermediate 10 as starting materials. $^1$H NMR (DMSO-$d_6$; TFA salt): δ 9.56 (br s, 1H), 9.45 (s, 1H), 8.95 (s, 1H), 7.25 (d, 2H), 7.14 (t, 1H), 6.89 (d, 2H), 6.75 (s, 1H), 6.68 (m, 3H), 6.49 (m, 2H), 5.88 (s, 1H), 4.10 (m, 2H), 3.70 (m, 2H), 3.45 (m, 1H), 3.16 (m, 2H), 2.04 (s, 3H), 1.98 (m, 2H), 1.84 (m, 2H), 1.34 (d, 3H); LCMS: 458.7 (M+H)$^+$.

Example 8

3-(3-Hydroxyphenyl)-4-methyl-2-(4-(2-((R)-3-methylpyrrolidin-1-yl)ethoxy)phenyl)-2H-chromen-6-ol

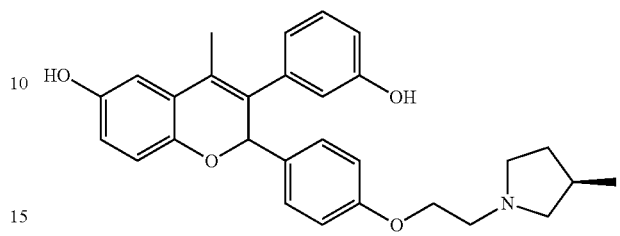

The title compound was synthesized as described in Example 1 using Intermediate 3 and Intermediate 11 as starting materials. $^1$H NMR (DMSO-$d_6$; TFA salt): δ 9.72 (br s, 1H), 9.45 (s, 1H), 8.96 (s, 1H), 7.25 (d, 2H), 7.14 (t, 1H), 6.87 (d, 2H), 6.73 (s, 1H), 6.68 (m, 3H), 6.48 (m, 2H), 5.88 (s, 1H), 4.20 (m, 2H), 3.65 (m, 1H), 3.54 (m, 3H), 3.20 (m, 1H), 3.07 (m, 1H), 2.73 (m, 1H), 2.28 (m, 1H), 2.04 (s, 3H), 1.60 (m, 1H), 1.03 (t, 3H); LCMS: 458.7 (M+H)$^+$.

Example 9

3-(3-Hydroxyphenyl)-4-methyl-2-(4-(2-piperidylethoxy)phenyl)-2H-chromen-6-ol

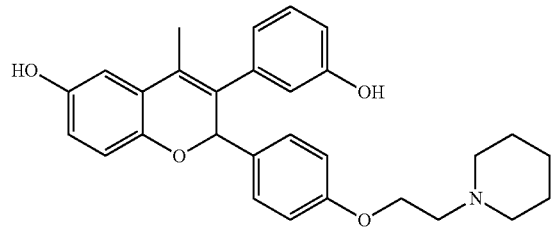 [SMILES: CC1=C(c2cccc(O)c2)C(c2ccc(OCCN3CCCCC3)cc2)Oc2ccc(O)cc21]

The title compound was synthesized as described in Example 1 using Intermediate 3 and 2-(piperidin-1-yl)ethanol as starting materials. $^1$H NMR (DMSO-$d_6$; TFA salt): δ 9.45 (s, 1H), 9.25 (br s, 1H), 8.96 (s, 1H), 7.25 (d, 2H), 7.14 (t, 1H), 6.87 (d, 2H), 6.75 (s, 1H), 6.71 (m, 3H), 6.49 (m, 2H), 5.88 (s, 1H), 4.26 (t, 2H), 3.45 (m, 4H), 2.90 (m, 2H), 2.04 (s, 3H), 1.80 (m, 2H), 1.66 (m, 3H), 1.38 (m, 1H); LCMS: 458.7 (M+H)$^+$.

Example 10

3-(3-Hydroxyphenyl)-4-methyl-2-(4-((R)-2-((R)-3-methylpyrrolidin-1-yl)propoxy)phenyl)-2H-chromen-6-ol

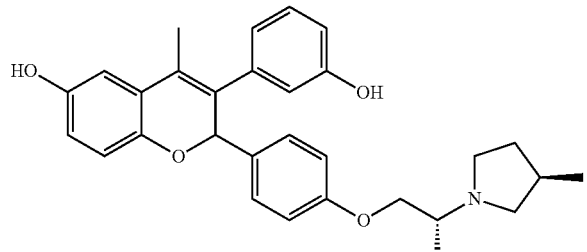

The title compound was synthesized as described in Example 1 using Intermediate 3 and Intermediate 14 as starting materials. ¹H NMR (DMSO-d₆; TFA salt): δ 9.65 (br s, 1H), 9.45 (s, 1H), 8.96 (s, 1H), 7.26 (d, 2H), 7.14 (t, 1H), 6.88 (d, 2H), 6.72 (s, 1H), 6.65 (m, 3H), 6.48 (m, 2H), 5.88 (s, 1H), 4.17 (m, 2H), 3.71 (m, 1H), 3.56 (m, 1H), 3.17 (m, 1H), 3.00 (m, 1H), 2.72 (m, 1H), 2.28 (m, 2H), 2.04 (s, 3H), 1.55 (m, 1H), 1.33 (d, 3H), 1.02 (t, 3H); LCMS: 472.7 (M+H)⁺.

Example 11

3-(3-Hydroxyphenyl)-4-methyl-2-(4-(2-((S)-3-methylpyrrolidin-1-yl)ethoxy)phenyl)-2H-chromen-6-ol

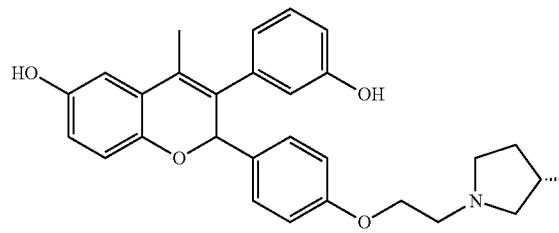

The title compound was synthesized as described in Example 1 using Intermediate 3 and Intermediate 12 as starting materials. ¹H NMR (DMSO-d₆; TFA salt): δ 9.71 (br s, 1H), 9.45 (br s, 1H), 8.96 (br s, 1H), 7.25 (d, 2H), 7.14 (t, 1H), 6.87 (d, 2H), 6.73 (s, 1H), 6.68 (m, 3H), 6.48 (m, 2H), 5.88 (s, 1H), 4.20 (m, 2H), 3.65 (m, 4H), 3.30 (m, 1H), 3.11 (m, 1H), 2.73 (m, 1H), 2.28 (m, 1H), 2.04 (s, 3H), 1.60 (m, 1H), 1.03 (t, 3H); LCMS: 458.7 (M+H)⁺.

Example 12

3-(3-Hydroxyphenyl)-4-methyl-2-(4-((S)-2-((S)-3-methylpyrrolidin-1-yl)propoxy)phenyl)-2H-chromen-6-ol

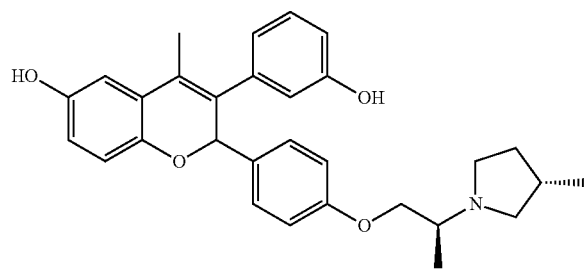 [SMILES: CC1=C(c2cccc(O)c2)C(c2ccc(OC[C@H](C)N3CC[C@H](C)C3)cc2)Oc2ccc(O)cc21]

The title compound was synthesized as described in Example 1 using Intermediate 3 and Intermediate 15 as starting materials. ¹H NMR (DMSO-d₆; TFA salt): δ 9.68 (br s, 1H), 9.45 (s, 1H), 8.96 (s, 1H), 7.26 (d, 2H), 7.14 (t, 1H), 6.88 (d, 2H), 6.71 (s, 1H), 6.65 (m, 3H), 6.48 (m, 2H), 5.88 (s, 1H), 4.17 (m, 2H), 3.71 (m, 1H), 3.56 (m, 1H), 3.17 (m, 1H), 3.00 (m, 1H), 2.72 (m, 1H), 2.28 (m, 2H), 2.04 (s, 3H), 1.55 (m, 1H), 1.33 (d, 3H), 1.02 (m, 3H); LCMS: 472.6 (M+H)⁺.

Example 13

3-(3-Hydroxyphenyl)-4-methyl-2-(4-((R)-2-((S)-3-methylpyrrolidin-1-yl)propoxy)phenyl)-2H-chromen-6-ol

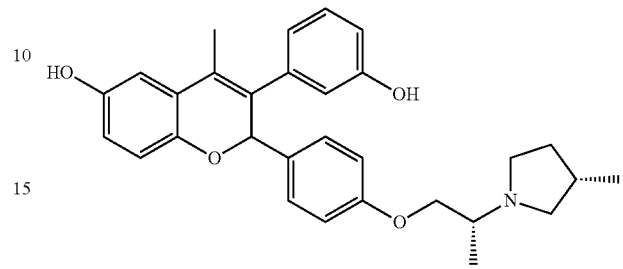

The title compound was synthesized as described in Example 1 using Intermediate 3 and Intermediate 13 as starting materials. ¹H NMR (DMSO-d₆; TFA salt): δ 9.68 (br s, 1H), 9.45 (s, 1H), 8.96 (s, 1H), 7.26 (d, 2H), 7.14 (t, 1H), 6.88 (d, 2H), 6.71 (s, 1H), 6.65 (m, 3H), 6.48 (m, 2H), 5.88 (s, 1H), 4.17 (m, 2H), 3.71 (m, 2H), 3.35 (m, 1H), 3.00 (m, 1H), 2.72 (m, 1H), 2.47 (m, 1H), 2.28 (m, 1H), 2.04 (s, 3H), 1.55 (m, 1H), 1.33 (m, 3H), 1.03 (d, 3H); LCMS: 472.6 (M+H)⁺.

Example 14

3-(3-Hydroxyphenyl)-4-methyl-2-(4-(2-pyrrolylethoxy)phenyl)-2H-chromen-6-ol

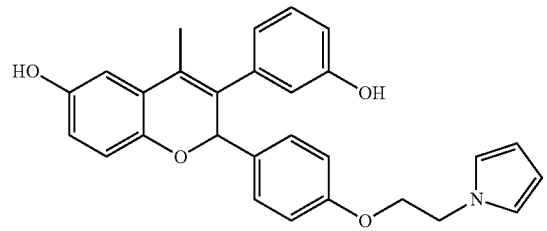 [SMILES: CC1=C(c2cccc(O)c2)C(c2ccc(OCCn3cccc3)cc2)Oc2ccc(O)cc21]

The title compound was synthesized as described in Example 1 using Intermediate 3 and 2-(1H-pyrrol-1-yl)ethanol as starting materials. ¹H NMR (acetone-d₆): δ 8.34 (s, 1H), 7.85 (s, 1H), 7.27 (d, 2H), 7.17 (t, 1H), 6.77 (m, 8H), 6.60 (m, 2H), 6.00 (m, 2H), 5.83 (s, 1H), 4.26 (m, 4H), 2.81 (s, 3H); LCMS: 440.7 (M+H)⁺.

Example 15

2-(4-((S)-2-(Azepan-1-yl)propoxy)phenyl)-3-(3-hydroxyphenyl)-4-methyl-2H-chromen-6-ol

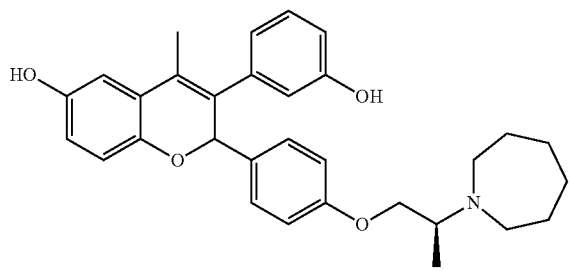 [SMILES: CC1=C(c2cccc(O)c2)C(c2ccc(OC[C@H](C)N3CCCCCC3)cc2)Oc2ccc(O)cc21]

The title compound was synthesized as described in Example 1 using Intermediate 3 and Intermediate 18 as starting materials. $^1$H NMR (DMSO-$d_6$; TFA salt): δ 9.47 (s, 1H), 9.07 (br s, 1H), 8.97 (s, 1H), 7.25 (d, 2H), 7.14 (t, 1H), 6.88 (m, 2H), 6.72 (s, 1H), 6.69 (m, 3H), 6.48 (m, 2H), 5.88 (s, 1H), 4.18 (m, 2H), 3.80 (m, 1H), 3.36 (m, 4H), 2.04 (s, 3H), 1.80 (m, 4H), 1.59 (m, 4H), 1.33 (d, 3H); LCMS: 486.8 (M+H)$^+$.

Example 16

3-(3-Hydroxyphenyl)-2-(4-(2-imidazolylethoxy)phenyl)-4-methyl-2H-chromen-6-ol

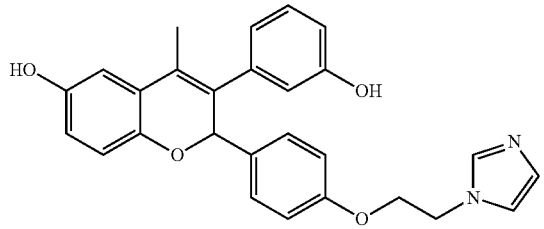 [SMILES: CC1=C(c2cccc(O)c2)C(c2ccc(OCCn3ccnc3)cc2)Oc2ccc(O)cc21]

The title compound was synthesized as described in Example 1 using Intermediate 3 and 2-(1H-imidazol-1-yl)ethanol as starting materials. $^1$H NMR (MeOD-$d_3$; TFA salt): δ 9.00 (s, 1H), 7.70 (d, 1H), 7.55 (d, 1H), 7.23 (d, 2H), 7.13 (t, 1H), 6.80 (m, 3H), 6.67 (d, 2H), 6.62 (d, 1H), 6.52 (m, 2H), 5.78 (s, 1H), 4.63 (t, 2H), 4.33 (t, 2H), 2.07 (s, 3H); LCMS: 441.6 (M+H)$^+$.

Example 17

2-(4-(2-(Azepan-1-yl)ethoxy)phenyl)-3-(3-hydroxyphenyl)-4-methyl-2H-chromen-6-ol

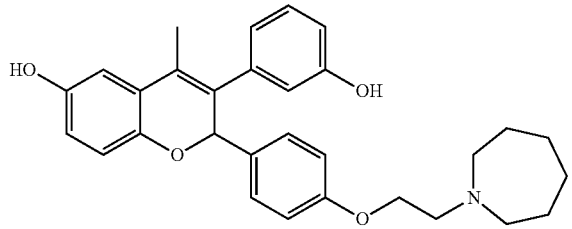 [SMILES: CC1=C(c2cccc(O)c2)C(c2ccc(OCCN3CCCCCC3)cc2)Oc2ccc(O)cc21]

The title compound was synthesized as described in Example 2 using Intermediate 3 and 2-(azepan-1-yl)ethanol as starting materials. $^1$H NMR (DMSO-$d_6$; TFA salt): δ 9.46 (s, 1H), 9.37 (br s, 1H), 8.97 (s, 1H), 7.26 (d, 2H), 7.14 (t, 1H), 6.87 (m, 2H), 6.72 (s, 1H), 6.69 (m, 3H), 6.48 (m, 2H), 5.88 (s, 1H), 4.25 (t, 2H), 3.50 (m, 2H), 3.36 (m, 2H), 3.22 (m, 2H), 2.04 (s, 3H), 1.80 (m, 4H), 1.59 (m, 4H); LCMS: 472.7 (M+H)$^+$.

Example 18

2-(4-((S)-2-(3,3-Dimethylpyrrolidin-1-yl)propoxy)phenyl)-3-(3-hydroxyphenyl)-4-methyl-2H-chromen-6-ol

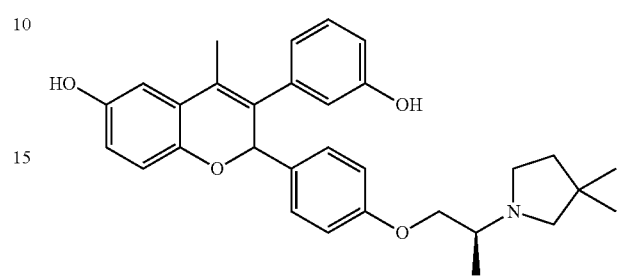

The title compound was synthesized as described in Example 2 using Intermediate 3 and Intermediate 21 as starting materials. $^1$H NMR (DMSO-$d_6$; TFA salt): δ 9.68 (br s, 1H), 9.46 (s, 1H), 8.97 (s, 1H), 7.26 (d, 2H), 7.14 (t, 1H), 6.88 (d, 2H), 6.72 (s, 1H), 6.69 (m, 3H), 6.48 (m, 2H), 5.88 (s, 1H), 4.13 (m, 2H), 3.69 (m, 1H), 3.52 (m, 1H), 3.24 (m, 2H), 3.01 (m, 1H), 2.04 (s, 3H), 1.78 (m, 2H), 1.33 (dd, 3H), 1.13 (m, 6H); LCMS: 486.7 (M+H)$^+$.

Example 19

2-(4-(2-(3,3-Dimethylpyrrolidin-1-yl)ethoxy)phenyl)-3-(3-hydroxyphenyl)-4-methyl-2H-chromen-6-ol

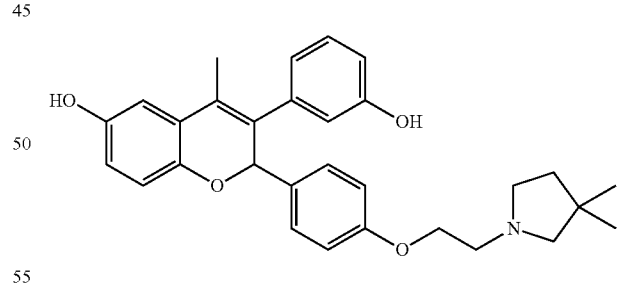

The title compound was synthesized as described in Example 2 using Intermediate 3 and Intermediate 22 as starting materials. $^1$H NMR (DMSO-$d_6$; TFA salt): δ 9.77 (br s, 1H), 9.46 (s, 1H), 8.97 (s, 1H), 7.26 (d, 2H), 7.14 (t, 1H), 6.88 (d, 2H), 6.72 (s, 1H), 6.69 (m, 3H), 6.48 (m, 2H), 5.88 (s, 1H), 4.21 (t, 2H), 3.63 (m, 2H), 3.54 (m, 2H), 2.92 (m, 2H), 2.04 (s, 3H), 1.85 (m, 2H), 1.13 (s, 3H), 1.08 (s, 3H); LCMS: 472.7 (M+H)$^+$.

Example 20

3-(3-Hydroxyphenyl)-4-methyl-2-(4-(2-((R)-2-methylpyrrolidin-1-yl)ethoxy)phenyl)-2H-chromen-6-ol

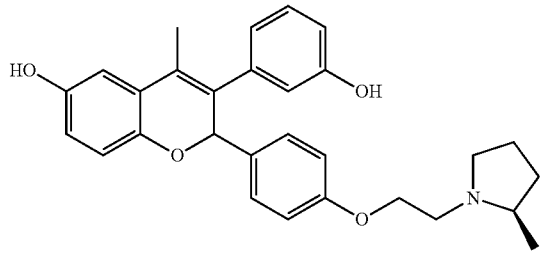

The title compound was synthesized as described in Example 2 using Intermediate 3 and Intermediate 19 as starting materials. $^1$H NMR (DMSO-$d_6$; TFA salt): δ 9.46 (s, 1H), 9.22 (br s, 1H), 8.97 (s, 1H), 7.26 (d, 2H), 7.14 (t, 1H), 6.88 (d, 2H), 6.72 (s, 1H), 6.69 (m, 3H), 6.48 (m, 2H), 5.88 (s, 1H), 4.22 (m, 2H), 3.65 (m, 2H), 3.47 (m, 1H), 3.20 (m, 2H), 2.20 (m, 1H), 2.04 (s, 3H), 1.90 (m, 2H), 1.57 (m, 1H), 1.32 (d, 3H); LCMS: 458.7 (M+H)$^+$.

Example 21

3-(3-Hydroxyphenyl)-4-methyl-2-(4-(2-(4-methylpiperidin-1-yl)ethoxy)phenyl)-2H-chromen-6-ol

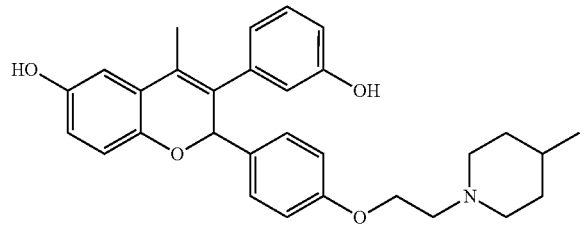 [SMILES: CC1=C(c2cccc(O)c2)C(c2ccc(OCCN3CCC(C)CC3)cc2)Oc2ccc(O)cc21]

The title compound was synthesized as described in Example 2 using Intermediate 3 and Intermediate 20 as starting materials. $^1$H NMR (DMSO-$d_6$; TFA salt): δ 9.46 (s, 1H), 9.15 (br s, 1H), 8.97 (s, 1H), 7.25 (d, 2H), 7.14 (t, 1H), 6.87 (d, 2H), 6.75 (s, 1H), 6.71 (m, 3H), 6.49 (m, 2H), 5.88 (s, 1H), 4.26 (t, 2H), 3.45 (m, 4H), 2.90 (m, 2H), 2.04 (s, 3H), 1.80 (m, 2H), 1.66 (m, 2H), 1.38 (m, 1H), 0.89 (d, 3H); LCMS: 472.7 (M+H)$^+$.

Example 22

3-(3-Hydroxyphenyl)-4-methyl-2-(4-((2-(pyrrolidin-1-yl)ethyl)amino)phenyl)-2H-chromen-6-ol

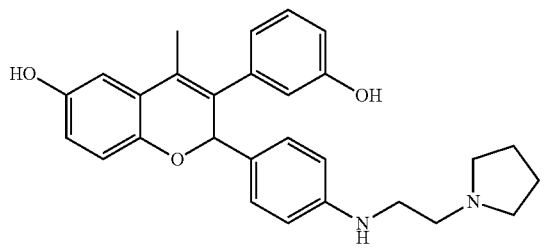 [SMILES: CC1=C(c2cccc(O)c2)C(c2ccc(NCCN3CCCC3)cc2)Oc2ccc(O)cc21]

The title compound was synthesized as described in Example 2 using Intermediate 3 and 2-(pyrrolidin-1-yl)ethanamine as starting materials. $^1$H NMR (DMSO-$d_6$; TFA salt): δ 9.44 (s, 1H), 9.35 (br s, 1H), 8.92 (s, 1H), 7.13 (t, 1H), 7.05 (d, 2H), 6.70 (m, 4H), 6.46 (m, 4H), 5.88 (br s 1H), 5.75 (s, 1H), 3.52 (m, 2H), 3.24 (m, 2H), 3.01 (m, 2H), 2.55 (m, 2H), 2.03 (s, 3H), 1.98 (m, 2H), 1.83 (m, 2H); LCMS: 443.7 (M+H)$^+$.

Example 23

3-(3-Hydroxyphenyl)-4-methyl-2-(4-((S)-2-((R)-2-methylpyrrolidin-1-yl)propoxy)phenyl)-2H-chromen-6-ol

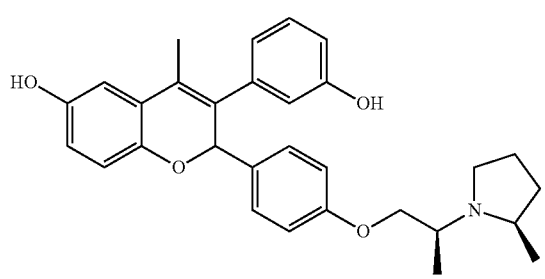 [SMILES: CC1=C(c2cccc(O)c2)C(c2ccc(OC[C@H](C)N3CCC[C@H]3C)cc2)Oc2ccc(O)cc21]

The title compound was synthesized as described in Example 2 using Intermediate 3 and Intermediate 24 as starting materials. $^1$H NMR (DMSO-$d_6$; HCl salt): δ 10.05 (br s, 1H), 9.49 (br s, 1H), 8.96 (br s, 1H), 7.25 (d, 2H), 7.13 (t, 1H), 6.88 (d, 2H), 6.75 (d, 1H), 6.68 (m, 3H), 6.45 (m, 2H), 5.87 (s, 1H), 4.19 (m, 2H), 3.86 (m, 1H), 3.70 (m, 1H), 3.40 (m, 2H), 2.13 (m, 1H), 2.04 (s, 3H), 1.88 (m, 2H), 1.60 (m, 1H), 1.36 (m, 6H); LCMS: 472.7 (M+H)$^+$.

Example 24

3-(3-Hydroxyphenyl)-4-methyl-2-(4-((S)-2-((S)-2-methylpyrrolidin-1-yl)propoxy)phenyl)-2H-chromen-6-ol

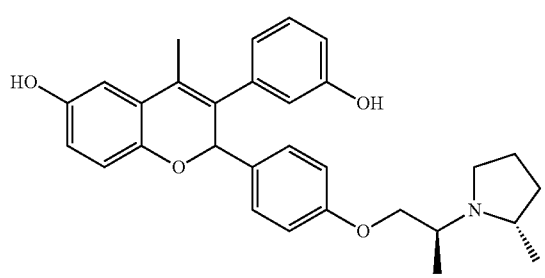 [SMILES: CC1=C(c2cccc(O)c2)C(c2ccc(OC[C@H](C)N3CCC[C@@H]3C)cc2)Oc2ccc(O)cc21]

The title compound was synthesized as described in Example 2 using Intermediate 3 and Intermediate 23 as starting materials. $^1$H NMR (DMSO-$d_6$; HCl salt): δ 9.78 (br s, 1H), 9.48 (br s, 1H), 8.99 (br s, 1H), 7.25 (d, 2H), 7.14 (t, 1H), 6.88 (d, 2H), 6.75 (m, 1H), 6.68 (m, 3H), 6.45 (m, 2H), 5.87 (s, 1H), 4.19 (m, 2H), 3.83 (m, 1H), 3.61 (m, 1H), 3.40 (m, 2H), 2.13 (m, 1H), 2.04 (s, 3H), 1.88 (m, 2H), 1.60 (m, 1H), 1.36 (m, 6H); LCMS: 472.7 (M+H)$^+$.

Example 25

2-(4-(2-(Azocan-1-yl)ethoxy)phenyl)-3-(3-hydroxyphenyl)-4-methyl-2H-chromen-6-ol

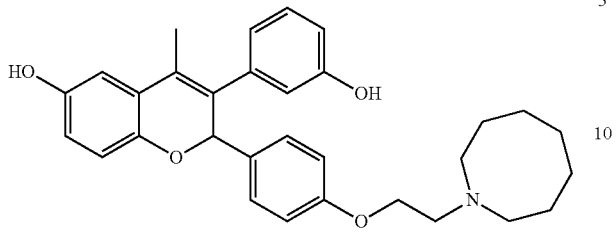

The title compound was synthesized as described in Example 2 using Intermediate 3 and Intermediate 25 as starting materials. $^1$H NMR (DMSO-d$_6$; TFA salt): δ 9.46 (s, 1H), 9.22 (br s, 1H), 8.97 (s, 1H), 7.26 (d, 2H), 7.14 (t, 1H), 6.87 (d, 2H), 6.75 (s, 1H), 6.69 (m, 3H), 6.48 (m, 2H), 5.88 (s, 1H), 4.25 (t, 2H), 3.50 (m, 2H), 3.36 (m, 2H), 3.19 (m, 2H), 2.04 (s, 3H), 1.89 (m, 2H), 1.63 (m, 8H); LCMS: 486.8 (M+H)$^+$.

Example 26

3-(3-Hydroxyphenyl)-4-methyl-2-(4-(2-(pyrrolidin-1-yl)ethoxy)phenyl)-2H-chromen-7-ol

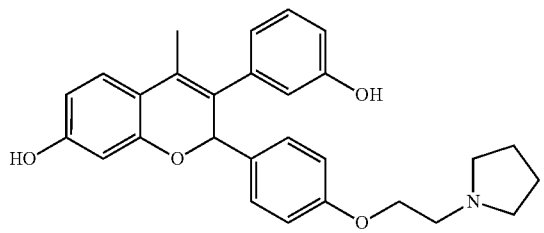 [SMILES: CC1=C(c2cccc(O)c2)C(c2ccc(OCCN3CCCC3)cc2)Oc2cc(O)ccc21]

The title compound was synthesized as described in Example 1 using Intermediate 7 and 2-(pyrrolidin-1-yl)ethanol as starting materials. $^1$H NMR (DMSO-d$_6$; TFA salt): δ 9.63 (br s, 1H), 9.50 (s, 1H), 9.42 (s, 1H), 7.27 (d, 2H), 7.16 (m, 2H), 6.88 (d, 2H), 6.65 (m, 3H), 6.34 (dd, 1H), 6.07 (d, 1H), 5.91 (s, 1H), 4.22 (t, 2H), 3.54 (m, 4H), 3.08 (m, 2H), 2.04 (s, 3H), 2.00 (m, 2H), 1.87 (m, 2H); LCMS: 444.7 (M+H)$^+$.

Example 27

3-(3-Hydroxyphenyl)-4-methyl-2-(4-((S)-2-((R)-3-methylpyrrolidin-1-yl)propoxy)phenyl)-2H-chromen-7-ol

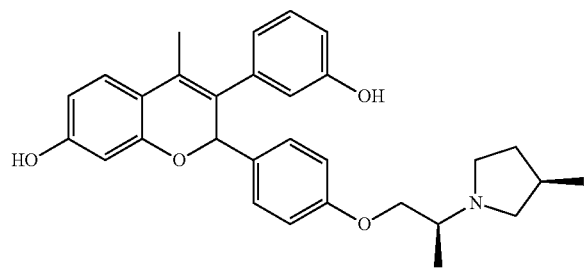 [SMILES: CC1=C(c2cccc(O)c2)C(c2ccc(OC[C@H](C)N3CC[C@@H](C)C3)cc2)Oc2cc(O)ccc21]

The title compound was synthesized as described in Example 1 using Intermediate 7 and Intermediate 16 as starting materials. $^1$H NMR (DMSO-d$_6$; TFA salt): δ 9.67 (br s, 1H), 9.50 (br s, 1H), 9.40 (br s, 1H), 7.27 (d, 2H), 7.16 (m, 2H), 6.90 (d, 2H), 6.61 (m, 3H), 6.34 (dd, 1H), 6.07 (d, 1H), 5.91 (s, 1H), 4.13 (m, 2H), 3.71 (m, 1H), 3.53 (m, 2H), 3.32 (m, 1H), 3.00 (m, 1H), 2.72 (m, 1H), 2.27 (m, 1H), 2.04 (s, 3H), 1.62 (m, 1H), 1.34 (m, 3H), 1.03 (d, 3H); LCMS: 472.7 (M+H)$^+$.

Example 28

3-(4-Hydroxyphenyl)-4-methyl-2-(4-((S)-2-((R)-3-methylpyrrolidin-1-yl)propoxy)phenyl)-2H-chromen-7-ol

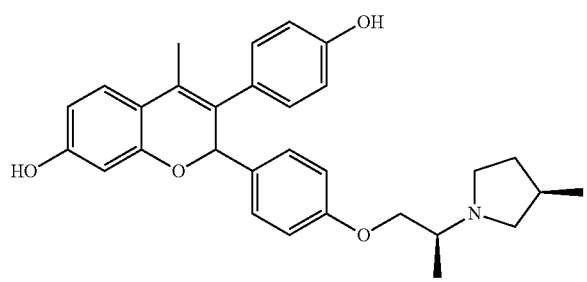 [SMILES: CC1=C(c2ccc(O)cc2)C(c2ccc(OC[C@H](C)N3CC[C@@H](C)C3)cc2)Oc2cc(O)ccc21]

The title compound was prepared from resorcinol and 4-hydroxyphenylacetic following the synthetic sequence outlined for Intermediate 4, Intermediate 7, and Example 27. $^1$H NMR (DMSO-d$_6$; TFA salt): δ 9.66 (br s, 1H), 9.46 (s, 1H), 9.45 (s, 1H), 7.25 (d, 2H), 7.10 (m, 3H), 6.88 (d, 2H), 6.71 (d, 2H), 6.34 (dd, 1H), 6.07 (d, 1H), 5.93 (s, 1H), 4.12 (m, 2H), 3.68 (m, 1H), 3.50 (m, 2H), 3.00 (m, 1H), 2.73 (m, 1H), 2.28 (m, 1H), 2.10 (m, 1H), 2.03 (s, 3H), 1.55 (m, 1H), 1.33 (m, 3H), 1.03 (d, 3H); LCMS: 472.7 (M+H)$^+$.

Example 29

4-Methyl-2-(4-((S)-2-((R)-3-methylpyrrolidin-1-yl)propoxy)phenyl)-3-phenyl-2H-chromen-6-ol

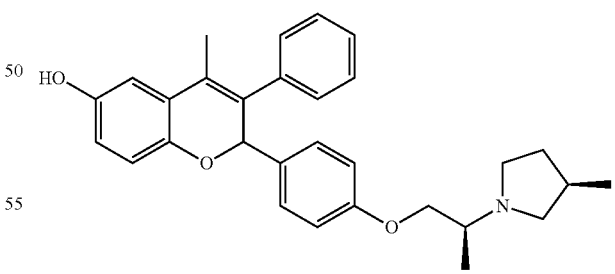

The title compound was prepared from benzyl chloride and Intermediate 1 following the synthetic sequence outlined for Intermediate 2, Intermediate 3, and Example 2. $^1$H NMR (DMSO-d$_6$; HCl salt): δ 10.00 (br s, 1H), 8.99 (s, 1H), 7.30 (m, 7H), 6.86 (d, 2H), 6.77 (m, 1H), 6.50 (m, 2H), 5.97 (s, 1H), 4.16 (m, 2H), 3.67 (m, 1H), 3.42 (m, 2H), 3.15 (m, 1H), 2.98 (m, 1H), 2.71 (m, 1H), 2.48 (m, 1H), 2.03 (s, 3H), 1.55 (m, 1H), 1.37 (m, 3H), 1.03 (m, 3H); LCMS: 456.7 (M+H)$^+$.

Example 30

3-(4-Fluorophenyl)-4-methyl-2-(4-((S)-2-((R)-3-methylpyrrolidin-1-yl)propoxy)phenyl)-2H-chromen-6-ol

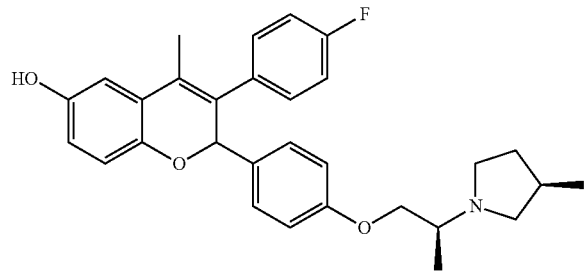 [SMILES: CC1=C(c2ccc(F)cc2)C(c2ccc(OC[C@H](C)N3CC[C@@H](C)C3)cc2)Oc2ccc(O)cc21]

The title compound was prepared from 4-fluorobenzyl chloride and Intermediate 1 following the synthetic sequence outlined for Intermediate 2, Intermediate 3, and Example 2. $^1$H NMR (DMSO-$d_6$; HCl salt): δ 10.30 (br, 1H), 9.00 (s, 1H), 7.35 (m, 2H), 7.19 (m, 4H), 6.86 (d, 2H), 6.77 (d, 1H), 6.50 (m, 2H), 5.95 (s, 1H), 4.16 (m, 2H), 3.67 (m, 1H), 3.42 (m, 2H), 3.15 (m, 1H), 2.98 (m, 1H), 2.74 (m, 1H), 2.25 (m, 1H), 2.03 (s, 3H), 1.55 (m, 1H), 1.35 (m, 3H), 1.03 (m, 3H); LCMS: 474.7 (M+H)$^+$.

Example 30a (S)-3-(4-Fluorophenyl)-4-methyl-2-(4-((S)-2-((R)-3-methylpyrrolidin-1-yl)propoxy)phenyl)-2H-chromen-6-ol The title compound is the 1$^{st}$ eluting diastereomer when Example 30 is separated on a CHIRALPAK® IA column [hexanes/ethanol/tetrahydrofuran/diethylamine (47:2:1:0.009)]. LCMS: 474.1 (M+H)$^+$; Diastereomeric ratio: >99:1.

Example 30b (R)-3-(4-Fluorophenyl)-4-methyl-2-(4-((S)-2-((R)-3-methylpyrrolidin-1-yl)propoxy)phenyl)-2H-chromen-6-ol The title compound is the 2$^{nd}$ eluting diastereomer when Example 30 is separated on a CHIRALPAK® IA column [hexanes/ethanol/tetrahydrofuran/diethylamine (47:2:1:0.009)]. LCMS: 474.1 (M+H)$^+$; Diastereomeric ratio: 98:2.

Example 31

3-(4-Hydroxyphenyl)-4-methyl-2-(4-((S)-2-((R)-3-methylpyrrolidin-1-yl)propoxy)phenyl)-2H-chromen-6-ol The title compound was prepared from 4-methoxybenzyl chloride and Intermediate 1 following the synthetic sequence outlined for Intermediate 2, Intermediate 3, and Example 2. $^1$H NMR (DMSO-$d_6$; HCl salt): δ 10.30 (br, 1H), 9.55 (s, 1H), 8.95 (s, 1H), 7.23 (d, 2H), 7.11 (d, 2H), 6.86 (d, 2H), 6.73 (m, 3H), 6.47 (d, 2H), 5.91 (s, 1H), 4.14 (m, 2H), 3.67 (m, 1H), 3.46 (m, 2H), 3.35 (m, 1H), 2.98 (m, 1H), 2.74 (m, 1H), 2.25 (m, 1H), 2.04 (s, 3H), 1.55 (m, 1H), 1.33 (m, 3H), 1.03 (m, 3H); LCMS: 472.7 (M+H)$^+$.

Example 32

3-(3-Fluorophenyl)-4-methyl-2-(4-((S)-2-((R)-3-methylpyrrolidin-1-yl)propoxy)phenyl)-2H-chromen-6-ol The title compound was prepared from Intermediate 5 following the synthetic sequence outlined for Intermediate 2, Intermediate 3, and Example 2. $^1$H NMR (DMSO-$d_6$; HCl salt): δ 10.30 (br, 1H), 9.02 (s, 1H), 7.41 (m, 1H), 7.25 (d, 2H), 7.18 (m, 3H), 6.88 (d, 2H), 6.77 (d, 1H), 6.50 (m, 2H), 5.94 (s, 1H), 4.16 (m, 2H), 3.68 (m, 1H), 3.48 (m, 2H), 3.37 (m, 1H), 2.98 (m, 1H), 2.73 (m, 1H), 2.25 (m, 1H), 2.06 (s, 3H), 1.55 (m, 1H), 1.34 (m, 3H), 1.02 (m, 3H); LCMS: 474.7 (M+H)+.

Example 33

3-(3-Fluoro-4-hydroxyphenyl)-4-methyl-2-(4-((S)-2-((R)-3-methylpyrrolidin-1-yl)propoxy)phenyl)-2H-chromen-6-ol

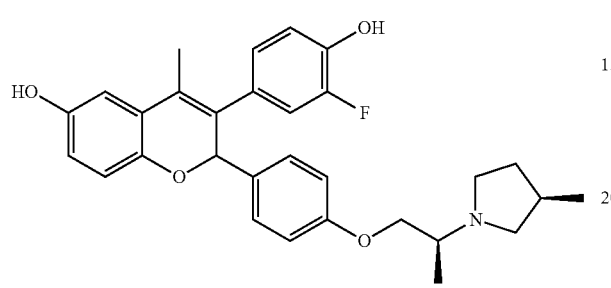

The title compound was prepared from 3-fluoro-4-methoxybenzyl chloride and Intermediate 1 following the synthetic sequence outlined for Intermediate 2, Intermediate 3, and Example 2. $^1$H NMR (DMSO-d$_6$; HCl salt): δ 10.30 (br, 1H), 9.99 (s, 1H), 8.98 (s, 1H), 7.23 (d, 2H), 7.10 (dd, 1H), 6.92 (m, 2H), 6.86 (d, 2H), 6.73 (m, 1H), 6.47 (m, 2H), 5.94 (s, 1H), 4.15 (m, 2H), 3.67 (m, 1H), 3.46 (m, 2H), 3.37 (m, 1H), 2.98 (m, 1H), 2.74 (m, 1H), 2.25 (m, 1H), 2.05 (s, 3H), 1.55 (m, 1H), 1.33 (m, 3H), 1.03 (m, 3H); LCMS: 490.7 (M+H)+.

Example 34

2-(2-Fluoro-4-(2-(pyrrolidin-1-yl)ethoxy)phenyl)-3-(3-hydroxyphenyl)-4-methyl-2H-chromen-6-ol

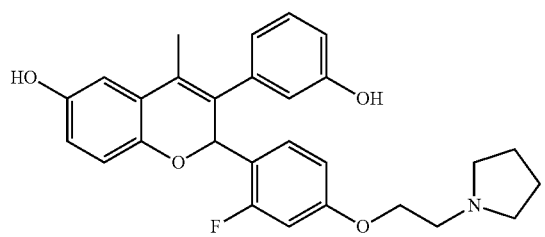 [SMILES: CC1=C(c2cccc(O)c2)C(c2ccc(OCCN3CCCC3)cc2F)Oc2ccc(O)cc21]

The title compound was synthesized as described in Example 1 using Intermediate 6 and 2-(pyrrolidin-1-yl)ethanol as starting materials. H NMR (DMSO-d$_6$): δ 9.90 (s, 1H), 9.49 (s, 1H), 9.02 (s, 1H), 7.14 (m, 2H), 6.85 (dd, 1H), 6.77 (d, 1H), 6.60 (m, 4H), 6.52 (m, 2H), 6.13 (s, 1H), 4.26 (t, 2H), 3.53 (m, 4H), 3.17 (m, 2H), 2.06 (s, 3H), 1.99 (m, 2H), 1.86 (m, 2H); LCMS: 462.6 (M+H)+.

Example 35

2-(2-Fluoro-4-((S)-2-((R)-3-methylpyrrolidin-1-yl)propoxy)phenyl)-3-(3-hydroxyphenyl)-4-methyl-2H-chromen-6-ol

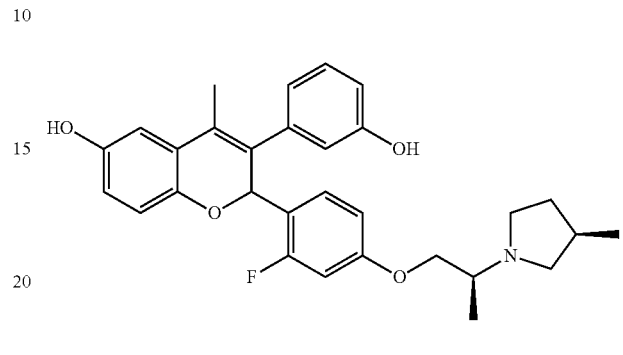

The title compound was synthesized as described in Example 1 using Intermediate 6 and Intermediate 16 as starting materials. $^1$H NMR (DMSO-d$_6$; HCl salt): δ 10.30 (br, 1H), 9.50 (s, 1H), 9.03 (s, 1H), 7.20 (m, 2H), 6.86 (d, 1H), 6.78 (d, 1H), 6.68 (m, 4H), 6.50 (m, 2H), 6.13 (s, 1H), 4.18 (m, 2H), 3.67 (m, 1H), 3.46 (m, 1H), 3.30 (m, 1H), 3.15 (m, 1H), 2.98 (m, 1H), 2.74 (m, 1H), 2.25 (m, 1H), 2.06 (s, 3H), 1.53 (m, 1H), 1.32 (m, 3H), 1.06 (m, 3H); LCMS: 490.7 (M+H)+.

Example 36

3-(3-Hydroxyphenyl)-4-methyl-2-(4-(2-(pyrrolidin-1-yl)ethoxy)phenyl)-2H-chromen-6-ol

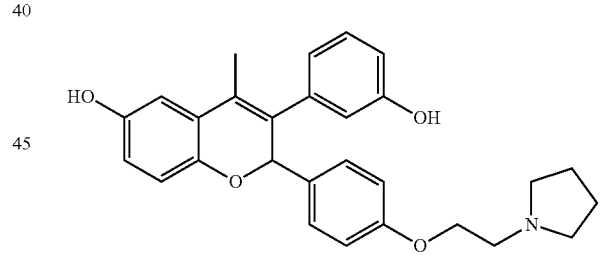

Step 1: 2-(4-(2-(Pyrrolidin-1-yl)ethoxy)phenyl)-6-((tetrahydro-2H-pyran-2-yl)oxy)-3-(3-((tetrahydro-2H-pyran-2-yl)oxy)phenyl)chroman-4-one

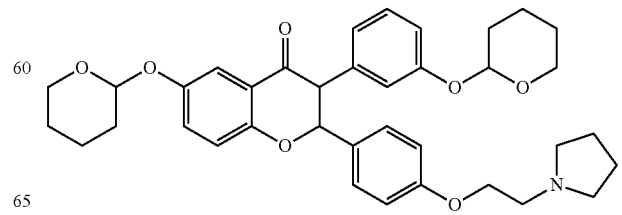

A solution of Intermediate 2 (475 mg, 1.15 mmol), Intermediate 8 (262 mg, 1.19 mmol), piperidine (30 mg, 0.35 mmol), and DBU (54 mg, 0.36 mmol) in s-butanol (6 mL) was heated at reflux for 3 h. The solution was cooled to 90° C., i-propanol (10 mL) was added, and the reaction mixture was allowed to cool to room temperature and stirred for 3 days. The solvent was removed under reduced pressure and the crude material was purified on a silica gel column to yield 2-(4-(2-(pyrrolidin-1-yl)ethoxy)phenyl)-6-((tetrahydro-2H-pyran-2-yl)oxy)-3-(3-((tetrahydro-2H-pyran-2-yl)oxy)phenyl)chroman-4-one (312 mg, 44%) as a yellow foam. $^1$H NMR (DMSO-d$_6$): δ 7.41 (m, 1H), 7.31 (d, 2H), 7.05 (m, 2H), 6.80 (m, 5H), 6.52 (m, 1H), 5.80 (m, 1H), 5.46 (m, 1H), 5.31 (m, 1H), 4.60 (d, 1H), 3.97 (t, 2H), 3.76 (m, 2H), 3.57 (m, 2H), 2.72 (t, 2H), 2.50 (m, 4H), 1.50-1.90 (m, 16H).

Step 2: 3-(3-Hydroxyphenyl)-4-methyl-2-(4-(2-(pyrrolidin-1-yl)ethoxy)phenyl)-2H-chromen-6-ol

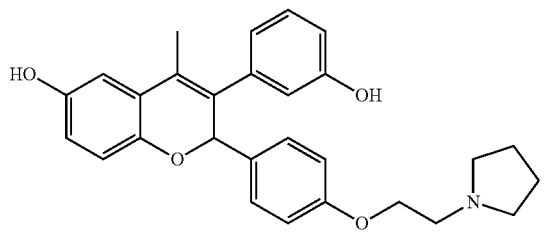 [SMILES: CC1=C(c2cccc(O)c2)C(c2ccc(OCCN3CCCC3)cc2)Oc2ccc(O)cc21]

To a solution of 2-(4-(2-(pyrrolidin-1-yl)ethoxy)phenyl)-6-((tetrahydro-2H-pyran-2-yl)oxy)-3-(3-((tetrahydro-2H-pyran-2-yl)oxy)phenyl)chroman-4-one (30 mg, 0.049 mmol) in THF (40 mL) at −78° C. was added methyl lithium (1.6 M in diethyl ether, 0.09 mL, 0.14 mmol). The solution was stirred at −78° C. for 30 min and allowed to warm to room temperature. After stirring for 1 h, the reaction was cooled to −78° C., quenched with sat'd. ammonium chloride (0.5 mL), and then warmed to room temperature. The reaction was diluted with ethyl acetate (20 mL), washed (2×5 mL sat'd. NaHCO$_3$), and dried over Na$_2$SO$_4$. The solvent was removed under reduced pressure and the crude material was heated in 80% acetic acid/H$_2$O (1 mL) at 90° C. overnight. The solvent was concentrated under reduced pressure by purified on reverse phase HPLC (acetonitrile, H$_2$O, TFA) to yield 3-(3-hydroxyphenyl)-4-methyl-2-(4-(2-(pyrrolidin-1-yl)ethoxy)phenyl)-2H-chromen-6-ol (7.8 mg) as a TFA salt. $^1$H NMR (MeOD-d$_3$): δ 7.28 (d, 2H), 7.14 (t, 1H), 6.88 (d, 2H), 6.81 (d, 1H), 6.67 (m, 3H), 6.53 (m, 2H), 5.81 (s, 1H), 4.27 (t, 2H), 3.67 (m, 2H), 3.62 (t, 2H), 3.31 (m, 2H), 2.08 (m, 7H).

Example 37

2-(4-((S)-2-(Azetidin-1-yl)propoxy)phenyl)-3-(3-hydroxyphenyl)-4-methyl-2H-chromen-6-ol

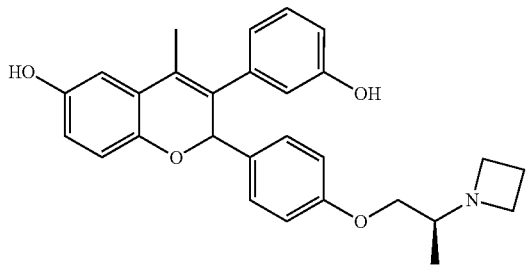 [SMILES: CC1=C(c2cccc(O)c2)C(c2ccc(OC[C@H](C)N3CCC3)cc2)Oc2ccc(O)cc21]

The title compound was synthesized as described in Example 2 using Intermediate 3 and Intermediate 26 as starting materials. $^1$H NMR (300 MHz, DMSO-d$_6$): δ 9.44 (br s, 1H), 8.99 (br s, 1H), 7.20-7.10 (m, 3H), 6.87-6.74 (m, 3H), 6.70-6.62 (m, 3H), 6.44 (m, 2H), 5.84 (s, 1H), 3.70 (m, 1H), 3.60 (m, 1H), 3.11 (m, 4H), 2.03 (s, 2H), 1.88 (m, 2H), 1.21 (m, 2H), 0.87 (d, 3H); LCMS: 444.7 (M+H)$^+$.

Example 38

2-(4-(2-(Azetidin-1-yl)ethoxy)phenyl)-3-(3-hydroxyphenyl)-4-methyl-2H-chromen-6-ol

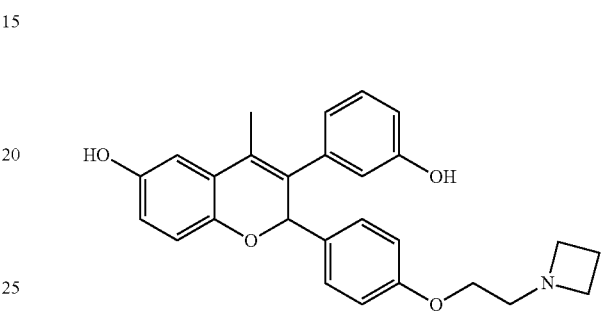

The title compound was synthesized as described in Example 2 using Intermediate 3 and Intermediate 27 as starting materials. $^1$H NMR (300 MHz, DMSO-d$_6$): δ 9.44 (br s, 1H), 8.94 (br s, 1H), 7.20-7.10 (m, 3H), 6.78-6.74 (m, 3H), 6.70-6.62 (m, 3H), 6.48 (m, 2H), 5.83 (s, 1H), 3.81 (t, 2H), 3.71 (m, 1H), 3.15 (t, 3H), 2.65 (m, 2H), 2.03 (s, 3H), 1.93 (m, 2H); LCMS: 430 (M+H)$^+$.

Example 39

3-(3-Hydroxy-4-methylphenyl)-4-methyl-2-(4-((S)-2-((R)-3-methylpyrrolidin-1-yl)propoxy)phenyl)-2H-chromen-6-ol

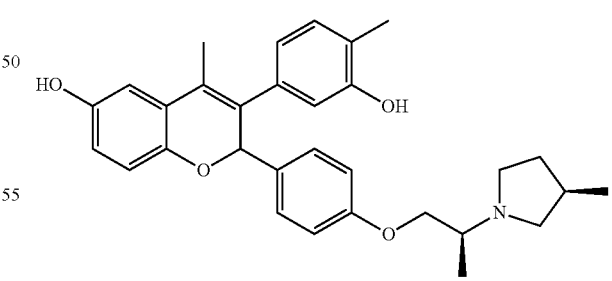

The title compound was prepared from Intermediate 28 and Intermediate 1 following the synthetic sequence outlined for Intermediate 2, Intermediate 3, and Example 2. $^1$H NMR (300 MHz, DMSO-d$_6$; HCl salt): δ 10.10 (br s, 1H), 9.31 (s, 1H), 8.97 (s, 1H), 7.24 (d, 2H), 7.01 (d, 1H), 6.87 (d, 2H), 6.74 (s, 1H), 6.68 (s, 1H), 6.62 (d, 1H), 6.48 (m, 2H), 5.84 (s, 1H), 4.16 (m, 2H), 3.67 (m, 1H), 3.50 (m, 2H), 3.22-2.94 (m, 2H), 2.74 (m, 1H), 2.28 (m, 1H), 2.07 (s, 3H), 2.04 (s, 3H), 1.44 (m, 1H), 1.33 (m, 3H), 1.03 (m, 3H); LCMS: 486.9 (M+H)+.

Example 40

3-(3-Hydroxy-2-methylphenyl)-4-methyl-2-(4-((S)-2-((R)-3-methylpyrrolidin-1-yl)propoxy)phenyl)-2H-chromen-6-ol

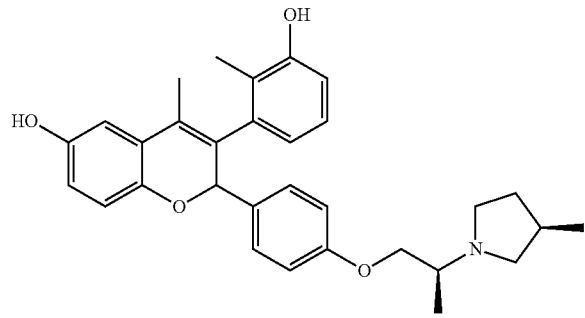 [SMILES: CC1=C(c2cccc(O)c2C)C(c2ccc(OC[C@H](C)N3CC[C@@H](C)C3)cc2)Oc2ccc(O)cc21]

The title compound was prepared from 3-methoxy-2-methylbenzoic acid following the synthetic sequence outlined for Intermediate 28, Intermediate 2, Intermediate 3, and Example 2. ¹H NMR (300 MHz, DMSO-d₆; HCl salt): δ 10.26 (br d), 9.40 (s), 9.33 (s), 8.99 (d), 7.28 (d), 7.10-7.00 (m), 6.90-6.78 (m), 6.75-6.68 (m), 6.55-6.44 (m), 6.17 (d), 5.85 (s), 5.56 (s), 4.16 (m), 3.67 (m), 3.50-3.27 (m), 3.15 (m), 3.08-2.95 (m), 2.73 (m), 2.27 (m), 2.14 (m), 1.82 (s), 1.73 (s), 1.64 (s), 1.56 (m), 1.36 (m), 1.04 (m). LCMS: 486.9 (M+H)+.

Example 41

3-(4-Hydroxy-2-methylphenyl)-4-methyl-2-(4-((S)-2-((R)-3-methylpyrrolidin-1-yl)propoxy)phenyl)-2H-chromen-6-ol

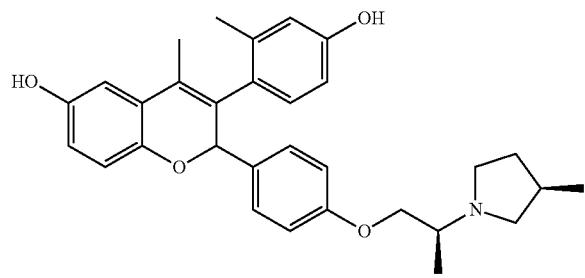

The title compound was prepared from Intermediate 29 and Intermediate 1 following the synthetic sequence outlined for Intermediate 2, Intermediate 3, and Example 2. ¹H NMR (300 MHz, DMSO-d₆; HCl salt): δ 10.32 (br d), 9.35 (s), 9.31 (s), 8.96 (d), 7.27 (d), 7.15-7.06 (m), 6.90-6.81 (m), 6.73-6.62 (m), 6.53-6.36 (m), 5.78 (s), 5.54 (s), 4.18 (m), 3.68 (m), 3.47 (m), 3.16 (m), 3.00 (m), 2.72 (m), 2.25 (s), 2.07 (m), 1.74 (m), 1.50 (m), 1.35 (m), 1.04 (m). LCMS: 486.9 (M+H)+.

Example 42

3-(4-Hydroxy-3-methylphenyl)-4-methyl-2-(4-((S)-2-((R)-3-methylpyrrolidin-1-yl)propoxy)phenyl)-2H-chromen-6-ol

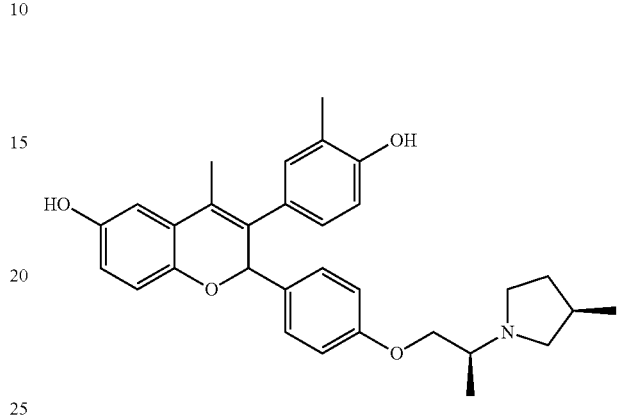

The title compound was prepared from 3-methoxy-3-methylbenzoic acid following the synthetic sequence outlined for Intermediate 28, Intermediate 2, Intermediate 3, and Example 2. ¹H NMR (300 MHz, DMSO-d₆; HCl salt): δ 10.31 (br s, 1H), 9.43 (s, 1H), 8.94 (s, 1H), 7.23 (d, 2H), 7.03 (s, 1H), 6.94 (d, 1H), 6.86 (d, 2H), 6.74 (m, 2H), 6.46 (s, 2H), 5.91 (s, 1H), 4.17 (m, 2H), 3.67 (m, 1H), 3.55-3.26 (m, 2H), 3.22-2.94 (m, 2H), 2.73 (m, 1H), 2.28 (m, 1H), 2.08 (s, 3H), 2.04 (s, 3H), 1.50 (m, 1H), 1.33 (m, 3H), 1.03 (m, 3H); LCMS: 486.9 (M+H)+.

Example 43

3-(3-Fluoro-5-hydroxyphenyl)-4-methyl-2-(4-((S)-2-((R)-3-methylpyrrolidin-1-yl)propoxy)phenyl)-2H-chromen-6-ol

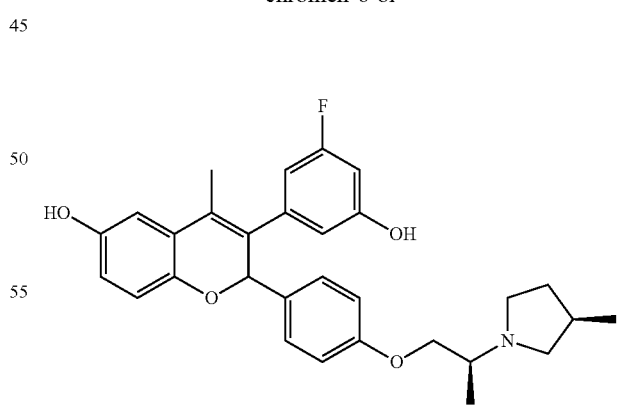

The title compound was prepared from Intermediate 30 following the synthetic sequence outlined for Intermediate 2 (steps 2-3), Intermediate 3, and Example 2. ¹H NMR (300 MHz, DMSO-d₆; HCl salt): δ 10.35 (br d, 1H), 10.02 (s, 1H), 9.01 (s, 1H), 7.25 (d, 2H), 6.89 (d, 2H), 6.76 (d, 1H), 6.57-6.45 (m, 5H), 5.89 (s, 1H), 4.17 (m, 2H), 3.67 (m, 1H), 3.58-3.27 (m, 2H), 3.22-2.94 (m, 1H), 2.74 (m, 1H), 2.28 (m, 1H), 2.05 (s, 4H), 1.50 (m, 1H), 1.35 (m, 3H), 1.03 (m, 3H); LCMS: 490.1 (M+H)$^+$.

Example 44

3-(4-Chlorophenyl)-4-methyl-2-(4-((S)-2-((R)-3-methylpyrrolidin-1-yl)propoxy)phenyl)-2H-chromen-6-ol

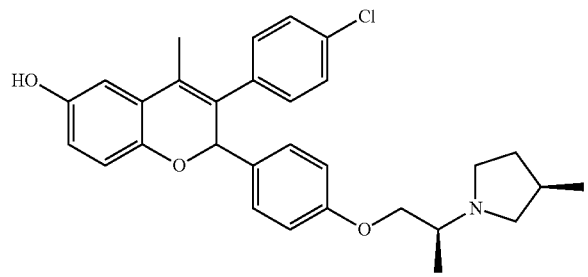

The title compound was prepared from Intermediate 31 following the synthetic sequence outlined for Intermediate 2 (steps 2-3), Intermediate 3, and Example 2. $^1$H NMR (300 MHz, DMSO-d$_6$; HCl salt): δ 10.40 (br d, 1H), 9.02 (s, 1H), 7.42 (d, 2H), 7.33 (d, 2H), 7.25 (d, 2H), 6.87 (d, 2H), 6.77 (d, 1H), 6.51 (m, 2H), 5.96 (s, 1H), 4.16 (m, 2H), 3.67 (m, 1H), 3.54-3.27 (m, 2H), 3.22-2.94 (m, 1H), 2.73 (m, 1H), 2.28 (m, 1H), 2.04 (m, 4H), 1.50 (m, 1H), 1.35 (m, 3H), 1.03 (m, 3H); LCMS: 490.1 (M+H)$^+$.

Example 45

3-(2-Fluoro-4-hydroxyphenyl)-4-methyl-2-(4-((S)-2-((R)-3-methylpyrrolidin-1-yl)propoxy)phenyl)-2H-chromen-6-ol

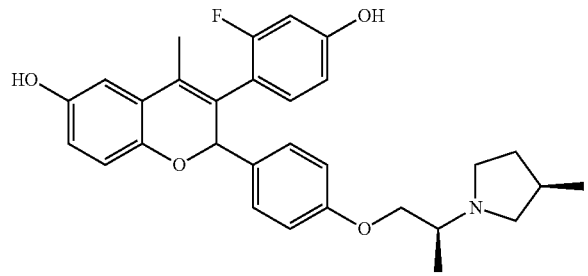 [SMILES: CC1=C(c2ccc(O)cc2F)C(c2ccc(OC[C@H](C)N3CC[C@@H](C)C3)cc2)Oc2ccc(O)cc21]

The title compound was prepared from 2-fluoro-4-methoxybenzoic acid following the synthetic sequence outlined for Intermediate 30 (steps 2-6), Intermediate 2 (steps 2-3), Intermediate 3, and Example 2. $^1$H NMR (300 MHz, DMSO-d$_6$; HCl salt): δ 10.35 (br s, 1H), 10.03 (s, 1H), 8.99 (s, 1H), 7.23 (d, 2H), 7.10 (t, 1H), 6.87 (d, 2H), 6.74 (d, 1H), 6.61-6.46 (m, 4H), 5.83 (s, 1H), 4.20 (m, 2H), 3.67 (m, 1H), 3.55-3.22 (m, 2H), 3.21-2.92 (m, 1H), 2.73 (m, 1H), 2.28 (m, 1H), 2.09 (m, 1H), 1.92 (s, 3H), 1.50 (m, 1H), 1.35 (m, 3H), 1.05 (m, 3H); LCMS: 490.1 (M+H)$^+$.

Example 46

3-(3,4-Difluorophenyl)-4-methyl-2-(4-((S)-2-((R)-3-methylpyrrolidin-1-yl)propoxy)phenyl)-2H-chromen-6-ol

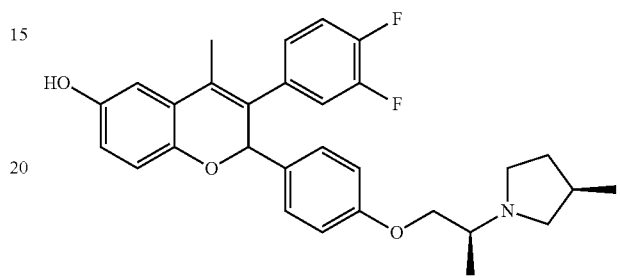

The title compound was prepared from Intermediate 32 following the synthetic sequence outlined for Intermediate 2 (steps 2-3), Intermediate 3, and Example 2. $^1$H NMR (300 MHz, DMSO-d$_6$; HCl salt): δ 10.40 (br d, 1H), 9.03 (s, 1H), 7.49-7.37 (m, 2H), 7.25 (d, 2H), 7.17-7.14 (m, 1H), 6.87 (d, 2H), 6.77 (d, 1H), 6.55-6.48 (m, 2H), 5.99 (s, 1H), 4.16 (m, 2H), 3.67 (m, 1H), 3.55-3.27 (m, 1H), 3.16-2.96 (m, 1H), 2.73 (m, 1H), 2.47-2.21 (m, 2H), 2.11 (m, 4H), 1.55 (m, 1H), 1.33 (m, 3H), 1.03 (m, 3H); LCMS: 492.1 (M+H)$^+$.

Example 47

3-(3,5-Difluoro-4-hydroxyphenyl)-4-methyl-2-(4-((S)-2-((R)-3-methylpyrrolidin-1-yl)propoxy)phenyl)-2H-chromen-6-ol

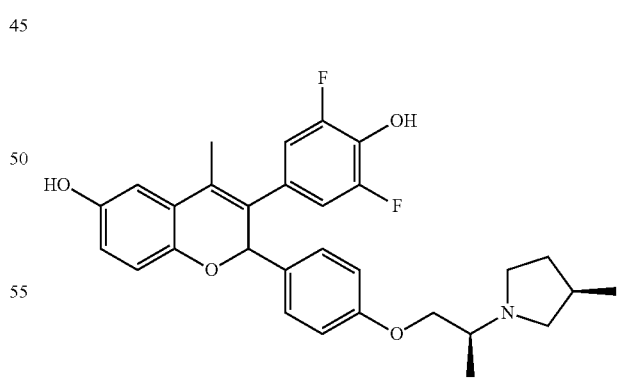

The title compound was prepared from 3,5-difluoro-4-methoxyphenylacetic acid following the synthetic sequence outlined for Intermediate 32, Intermediate 2 (steps 2-3), Intermediate 3, and Example 2. $^1$H NMR (300 MHz, DMSO-d$_6$; HCl salt): δ 10.31 (s, 1H), 10.10 (br s, 1H), 8.99 (s, 1H), 7.24 (d, 2H), 7.03 (d, 2H), 6.87 (d, 2H), 6.75 (d, 1H), 6.49 (d, 2H), 5.97 (s, 1H), 4.12 (m, 2H), 3.67 (m, 1H), 3.47 (m, 2H), 3.21-2.96 (m, 1H), 2.73 (m, 1H), 2.28 (m, 1H), 2.07 (m, 4H), 1.51 (m, 1H), 1.34 (m, 3H), 1.01 (m, 3H); LCMS: 508.1 (M+H)$^+$.

Example 48

3-(2,4-Difluoro-3-hydroxyphenyl)-4-methyl-2-(4-((S)-2-((R)-3-methylpyrrolidin-1-yl)propoxy)phenyl)-2H-chromen-6-ol

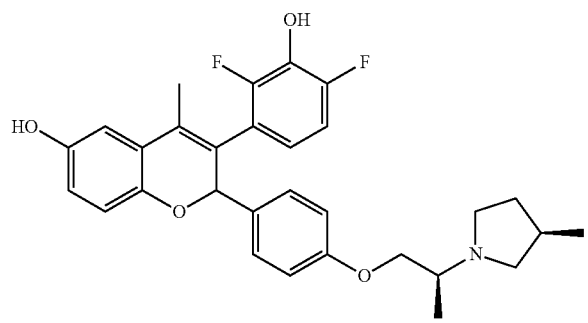 [SMILES: CC1=C(c2ccc(F)c(O)c2F)C(c2ccc(OC[C@H](C)N3CC[C@@H](C)C3)cc2)Oc2ccc(O)cc21]

The title compound was prepared from 2,4-difluoro-3-methoxyphenylacetic acid following the synthetic sequence outlined for Intermediate 32, Intermediate 2 (steps 2-3), Intermediate 3, and Example 2. $^1$H NMR (300 MHz, DMSO-d$_6$; HCl salt): δ 10.37 (br, 1H), 10.23 (s, 1H), 9.04 (s, 1H), 7.25 (d, 2H), 7.01 (dt, 1H), 6.88 (d, 2H), 6.77 (d, 1H), 6.71 (br s, 1H), 6.56-6.42 (m, 2H), 5.84 (s, 1H), 4.16 (m, 2H), 3.68 (m, 1H), 3.54-3.22 (m, 2H), 3.20-2.94 (m, 1H), 2.73 (m, 1H), 2.45-2.22 (m, 1H), 2.10 (m, 1H), 1.93 (s, 3H), 1.55 (m, 1H), 1.36 (m, 3H), 1.03 (m, 3H); LCMS: 508.1 (M+H)$^+$.

Example 49

3-(3,4-Difluoro-5-hydroxyphenyl)-4-methyl-2-(4-((S)-2-((R)-3-methylpyrrolidin-1-yl)propoxy)phenyl)-2H-chromen-6-ol

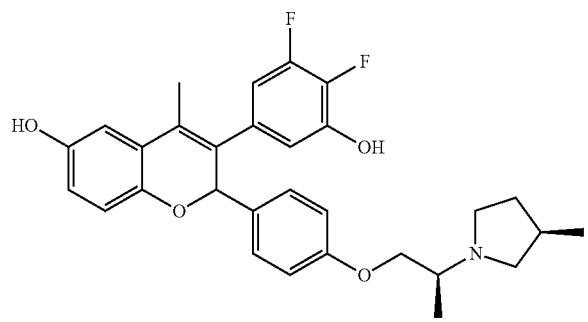 [SMILES: CC1=C(c2cc(O)c(F)c(F)c2)C(c2ccc(OC[C@H](C)N3CC[C@@H](C)C3)cc2)Oc2ccc(O)cc21]

The title compound was prepared from Intermediate 33 following the synthetic sequence outlined for Intermediate 2 (steps 2-3), Intermediate 3, and Example 2. $^1$H NMR (300 MHz, DMSO-d$_6$; HCl salt): δ 10.50 (s, 1H), 10.17 (br s, 1H), 9.02 (s, 1H), 7.24 (d, 2H), 6.89 (d, 2H), 6.82-6.76 (m, 2H), 6.67 (m, 1H), 6.54-6.47 (m, 2H), 5.88 (s, 1H), 4.17 (m, 2H), 3.77-3.41 (m, 2H), 3.00 (m, 1H), 2.73 (m, 1H), 2.27 (m, 1H), 2.04 (m, 4H), 1.50 (m, 2H), 1.34 (m, 3H), 1.03 (m, 3H); LCMS: 508.1 (M+H)$^+$.

Example 50

3-(2-Chloro-4-fluorophenyl)-4-methyl-2-(4-((S)-2-((R)-3-methylpyrrolidin-1-yl)propoxy)phenyl)-2H-chromen-6-ol

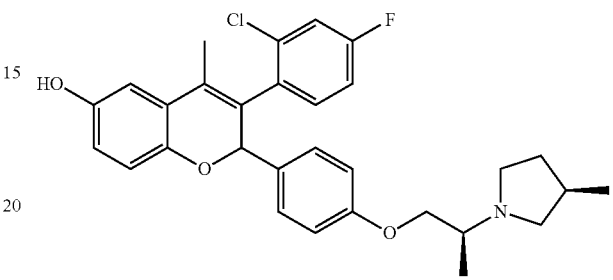

The title compound was prepared from 2-chloro-4-fluorophenylacetic acid following the synthetic sequence outlined for Intermediate 32, Intermediate 2 (steps 2-3), Intermediate 3, and Example 2. $^1$H NMR (300 MHz, DMSO-d$_6$; HCl salt): δ 10.38 (br), 9.05 (s), 7.64-7.53 (m), 7.39-7.26 (m), 7.23-7.11 (m), 6.99-6.87 (m), 6.86-6.77 (m), 6.59-6.48 (m), 5.91 (s), 5.71 (s), 4.16 (m), 3.67 (m), 3.53-3.26 (m), 3.15 (m), 3.01 (m), 2.73 (m), 2.45-2.12 (m), 2.11 (m), 1.83 (s), 1.52 (m), 1.34 (m), 1.04 (m). LCMS: 508.1 (M+H)$^+$.

Example 51

3-(3-Hydroxyphenyl)-4-methyl-2-(4-((S)-2-(4-methyl-1H-imidazol-1-yl)propoxy)phenyl)-2H-chromen-6-ol

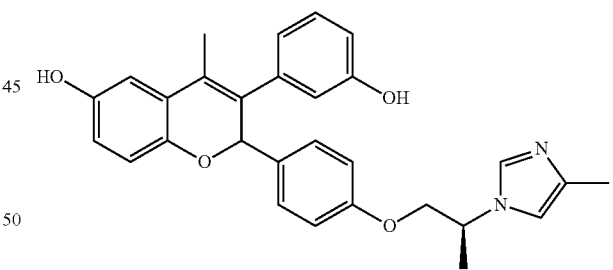

A mixture of Intermediate 3 (80 mg, 0.128 mmol), Intermediate 34, 1,10-phenanthroline (5.2 mg, 0.030 mmol), copper iodide (3.6 mg, 0.018 mmol), and cesium carbonate (84 mg, 0.256 mmol) was degassed by evacuating and backfilling with nitrogen 3 times. The reaction was heated at 110° C. for two days, allowed to cool to rt, diluted with ethyl acetate, filtered through pad of celite, and concentrated under reduced pressure. The crude material was purified on a silica gel column to yield 4-methyl-1-((2S)-1-(4-(4-methyl-6-((tetrahydro-2H-pyran-2-yl)oxy)-3-(3-((tetrahydro-2H-pyran-2-yl)oxy)phenyl)-2H-chromen-2-yl)phenoxy)propan-2-yl)-1H-imidazole as a yellow foam (44 mg). The yellow foam was dissolved in 80% acetic acid/H$_2$O (2 mL) and stirred at room temperature overnight. The mixture was diluted with ethyl acetate, neutralized with saturated NaHCO₃ solution, and the layers separated. The organic layer was washed with H₂O and brine, dried over Na₂SO₄, and concentrated under reduced pressure. The crude material was purified by reverse phase HPLC (acetonitrile, H₂O, TFA) to yield 3-(3-hydroxyphenyl)-4-methyl-2-(4-((S)-2-(4-methyl-1H-imidazol-1-yl)propoxy)phenyl)-2H-chromen-6-ol (13.8 mg). $^1$H NMR 300 MHz, (DMSO-d₆): δ 9.52 (s, 1H), 8.94 (s, 1H), 7.53 (s, 1H), 7.20-7.10 (m, 3H), 6.94 (s, 1H), 6.79-6.74 (m, 3H), 6.66 (dt, 2H), 6.58 (m, 1H), 6.47 (m, 2H), 5.82 (s, 1H), 4.07 (d, 2H), 2.03 (s, 4H), 1.41 (d, 3H), 1.24 (s, 3H); LCMS: 469.1 (M+H)⁺.

Example 52

3-(2,4-Difluorophenyl)-4-methyl-2-(4-((S)-2-((R)-3-methylpyrrolidin-1-yl)propoxy)phenyl)-2H-chromen-6-ol

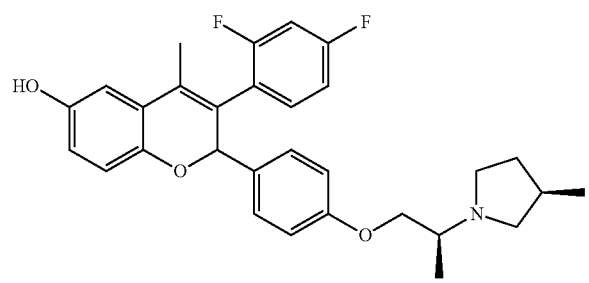 [SMILES: CC1=C(c2ccc(F)cc2F)C(c2ccc(OC[C@H](C)N3CC[C@@H](C)C3)cc2)Oc2ccc(O)cc21]

The title compound was prepared from 2,4-difluorophenylacetic acid following the synthetic sequence outlined for Intermediate 32, Intermediate 2 (steps 2-3), Intermediate 3, and Example 2. $^1$H NMR (300 MHz, DMSO-d₆; HCl salt): δ 10.22 (br d, 1H), 8.96 (s, 1H), 7.28 (br, 1H), 7.16 (m, 3H), 7.04-6.98 (m, 1H), 6.79 (d, 2H), 6.69 (d, 1H), 6.44 (m, 2H), 5.78 (s, 1H), 4.07 (m, 2H), 3.58 (m, 1H), 3.42-3.33 (m, 2H), 3.15-2.87 (m, 1H), 2.64 (m, 1H), 2.19 (m, 1H), 2.00 (m, 1H), 1.82 (s, 3H), 1.45 (m, 1H), 1.25 (m, 3H), 0.96 (m, 3H); LCMS: 492.1 (M+H)⁺.

Example 53

3-(3-Hydroxyphenyl)-4-methyl-2-(4-(2-((R)-3-methylpiperidin-1-yl)ethoxy)phenyl)-2H-chromen-6-ol

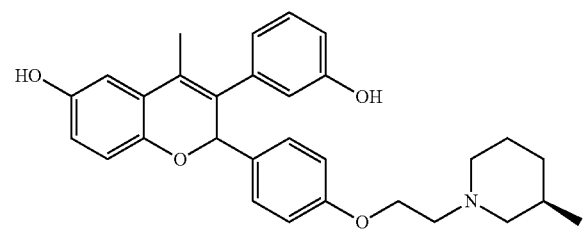 [SMILES: CC1=C(c2cccc(O)c2)C(c2ccc(OCCN3CCC[C@@H](C)C3)cc2)Oc2ccc(O)cc21]

The title compound was synthesized as described in Example 2 using Intermediate 3 and Intermediate 35 as starting materials. $^1$H NMR (DMSO-d₆; TFA salt): δ 9.47 (br s, 1H), 9.36 (br s, 1H), 8.98 (br s, 1H), 7.26 (d, 2H), 7.14 (t, 1H), 6.87 (d, 2H), 6.72 (m, 1H), 6.68 (m, 3H), 6.48 (m, 2H), 5.88 (s, 1H), 4.27 (t, 2H), 3.44 (m, 4H), 2.80 (m, 1H), 2.55 (m, 1H), 2.04 (s, 3H), 1.73 (m, 4H), 1.02 (m, 1H), 0.88 (d, 3H); LCMS: 472.7 (M+H)⁺.

Example 54

3-(4-Bromophenyl)-4-methyl-2-(4-((S)-2-((R)-3-methylpyrrolidin-1-yl)propoxy)phenyl)-2H-chromen-6-ol

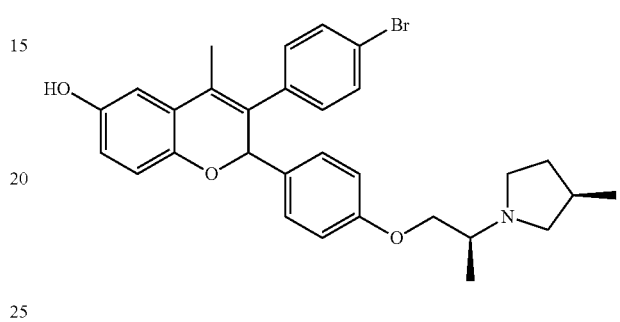

The title compound was prepared from 2-(4-bromophenyl)acetic acid and 1,4-dimethoxybenzene following the synthetic sequence outlined for Intermediate 32, Intermediate 2 (steps 2-3), Intermediate 3, and Example 2. $^1$H NMR (DMSO-d₆; HCl salt): δ 10.40 (br s, 1H), 9.02 (s, 1H), 7.55 (d, 2H), 7.26 (d, 2H), 7.23 (d, 2H), 6.86 (d, 2H), 6.77 (d, 1H), 6.51 (m, 2H), 5.96 (s, 1H), 4.16 (m, 2H), 3.67 (m, 1H), 3.42 (m, 1H), 3.29 (m, 1H), 3.00 (m, 1H), 2.70 (m, 1H), 2.35 (m, 1H), 2.10 (m, 1H), 2.03 (s, 3H), 1.50 (m, 1H), 1.34 (m, 3H), 1.03 (m, 3H); LCMS: 534.1 (M+H)⁺.

Example 55

3-(4-Fluorophenyl)-4-methyl-2-(4-(2-(pyrrolidin-1-yl)ethoxy)phenyl)-2H-chromen-6-ol

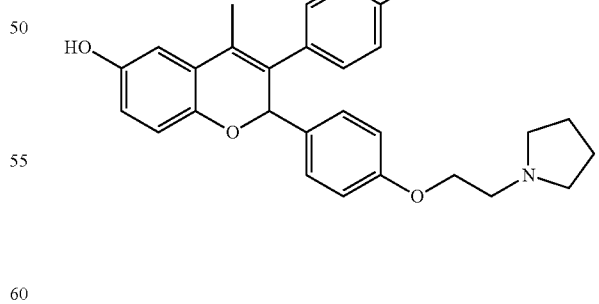

The title compound was synthesized as described in Example 30 using 3-(4-fluorophenyl)-2-(4-iodophenyl)-4-methyl-6-((tetrahydro-2H-pyran-2-yl)oxy)-2H-chromene and 2-(pyrrolidin-1-yl)ethanol as starting materials. $^1$H NMR (DMSO-d₆; TFA salt): δ 9.65 (br s, 1H), 8.99 (br s, 1H), 7.32 (m, 2H), 7.22 (m, 4H), 6.86 (d, 2H), 6.76 (m, 1H), 6.50 (m, 2H), 5.96 (s, 1H), 4.21 (t, 2H), 3.54 (m, 4H), 3.08 (m, 2H), 2.02 (s, 3H), 1.99 (m, 2H), 1.84 (m, 2H); LCMS: 446 (M+H)$^+$.

Example 56

4-Methyl-2-(4-((S)-2-((R)-3-methylpyrrolidin-1-yl)propoxy)phenyl)-3-(o-tolyl)-2H-chromen-6-ol

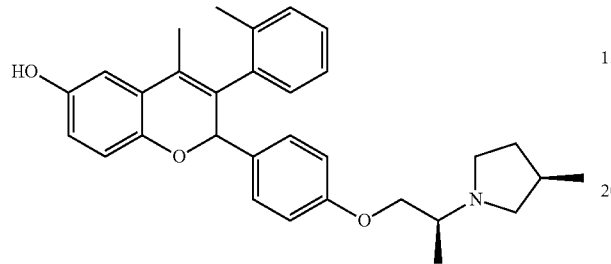

The title compound was prepared from 1-(chloromethyl)-2-methylbenzene and Intermediate 1 following the synthetic sequence outlined for Intermediate 2, Intermediate 3, and Example 2. $^1$H NMR (DMSO-d$_6$): δ 9.00 (s), 8.97 (s), 7.40-7.00 (m), 6.83 (d), 6.78-6.70 (m), 6.57 (s), 6.52 (m), 5.82 (s), 5.58 (s), 4.07-3.91 (m), 3.80-3.68 (m), 2.83 (m), 2.64 (m), 2.50 (s), 2.35 (s), 2.08 (m), 1.90 (m), 1.80 (s), 1.74 (s), 1.22 (m), 1.07 (m), 0.91 (m). The number of protons (#H) was not reported due to the complexity of the NMR resulting, presumably, from restricted rotation. LCMS: 470.1 (M+H)$^+$.

Example 57

3-(4-Fluoro-3-hydroxyphenyl)-4-methyl-2-(4-((S)-2-((R)-3-methylpyrrolidin-1-yl)propoxy)phenyl)-2H-chromen-6-ol

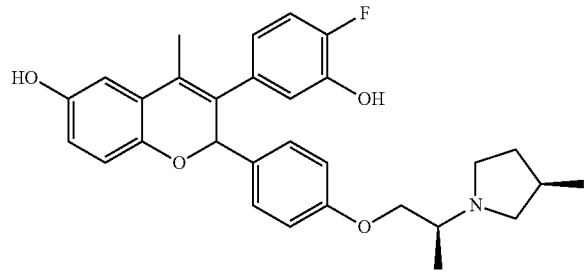 [SMILES: CC1=C(c2ccc(F)c(O)c2)C(c2ccc(OC[C@H](C)N3CC[C@@H](C)C3)cc2)Oc2ccc(O)cc21]

The title compound was prepared from 2-(4-fluoro-3-methoxyphenyl)acetic acid and 1,4-dimethoxybenzene following the synthetic sequence outlined for Intermediate 32, Intermediate 2 (steps 2-3), Intermediate 3, and Example 2. $^1$H NMR (DMSO-d$_6$; HCl salt): δ 10.20 (br, 1H), 9.91 (s, 1H), 8.99 (s, 1H), 7.24 (d, 2H), 7.10 (dd, 1H), 6.88 (d, 2H), 6.83 (dd, 1H), 6.75 (d, 1H), 6.69 (m, 1H), 6.49 (m, 2H), 5.86 (s, 1H), 4.17 (m, 2H), 3.67 (m, 1H), 3.48 (m, 2H), 3.15-2.90 (m, 1H), 2.75 (m, 1H), 2.35 (m, 1H), 2.10 (m, 1H), 2.03 (s, 3H), 1.52 (m, 1H), 1.34 (m, 3H), 1.03 (m, 3H); LCMS: 490 (M+H)$^+$.

Example 58

3-(4-Ethynylphenyl)-4-methyl-2-(4-((S)-2-((R)-3-methylpyrrolidin-1-yl)propoxy)phenyl)-2H-chromen-6-ol

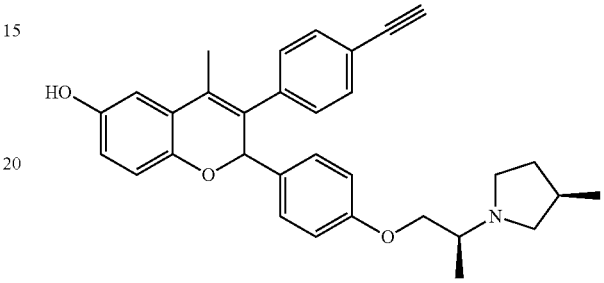

A solution of (3R)-1-((2S)-1-(4-(3-(4-bromophenyl)-4-methyl-6-((tetrahydro-2H-pyran-2-yl)oxy)-2H-chromen-2-yl)phenoxy)propan-2-yl)-3-methylpyrrolidine (150 mg, 0.243 mmol; intermediate from the synthesis of Example 54), bis(triphenylphosphine)palladium(II) dichloride (150 mg, 0.214 mmol), copper iodide (100 mg, 0.525 mmol), and triethylamine (1.0 mL, 7.17 mmol) in THF (2 mL) was degassed by bubbling nitrogen for 15 min. After addition of ethynyltrimethylsilane, the reaction mixture was heated at 70° C. overnight. The reaction was diluted with ethyl acetate (75 mL), filtered through Celite, and the Celite was washed with additional ethyl acetate (50 mL). The filtrate was washed (50 mL sat'd NaHCO$_3$, 50 mL brine), dried (Na$_2$SO$_4$), and concentrated under reduced pressure. The crude material was purified on a silica gel column to yield (3R)-3-methyl-1-((2S)-1-(4-(4-methyl-6-((tetrahydro-2H-pyran-2-yl)oxy)-3-(4-((trimethylsilyl)ethynyl)phenyl)-2H-chromen-2-yl)phenoxy)propan-2-yl)pyrrolidine as a brown foam (150 mg). The foam and potassium carbonate (150 mg, 1.09 mmol) in methanol (10 mL) were stirred at room temperature for 3.5 h. The solvent was removed under reduced pressure, and the residue was dissolved in ethyl acetate (100 mL). The mixture was washed (50 mL sat'd NaHCO$_3$, 50 mL brine), dried (Na$_2$SO$_4$), and concentrated under reduced pressure. The crude material was dissolved in 80% AcOH/water (2 mL) and stirred overnight at room temperature. The solvent was removed under reduced pressure, and the residue was purified by reverse-phase HPLC to give 3-(4-ethynylphenyl)-4-methyl-2-(4-((S)-2-((R)-3-methylpyrrolidin-1-yl)propoxy)phenyl)-2H-chromen-6-ol. $^1$H NMR (DMSO-d$_6$; TFA salt): δ 8.98 (s, 1H), 7.44 (d, 2H), 7.31 (d, 2H), 7.19 (d, 2H), 6.79 (d, 2H), 6.76 (m, 1H), 6.50 (m, 2H), 5.95 (s, 1H), 4.21 (s, 1H), 3.96 (m, 1H), 3.71 (m, 1H), 3.48-3.25 (m, 2H), 2.83 (m, 1H), 2.63 (m, 2H), 2.05 (m, 1H), 2.03 (s, 3H), 1.88 (m, 1H), 1.22 (m, 1H), 1.06 (d, 3H), 0.85 (d, 3H); LCMS: 480 (M+H)$^+$.

Example 59

4-Methyl-2-(4-((S)-2-((R)-3-methylpyrrolidin-1-yl)propoxy)phenyl)-3-(4-(methylsulfonyl)phenyl)-2H-chromen-6-ol

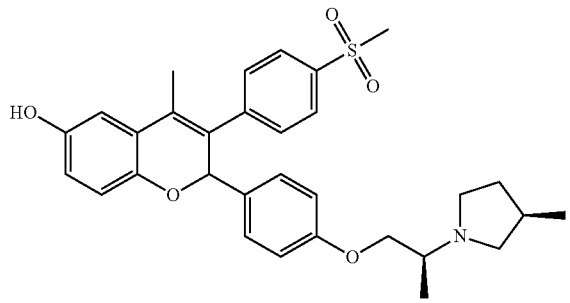 [SMILES: CC1=C(c2ccc(S(C)(=O)=O)cc2)C(c2ccc(OC[C@H](C)N3CC[C@@H](C)C3)cc2)Oc2ccc(O)cc21]

A mixture of (3R)-1-((2S)-1-(4-(3-(4-bromophenyl)-4-methyl-6-((tetrahydro-2H-pyran-2-yl)oxy)-2H-chromen-2-yl)phenoxy)propan-2-yl)-3-methylpyrrolidine (32 mg, 0.052 mmol; intermediate from the synthesis of Example 54), sodium methanesulfinate (12 mg, 0.118 mmol), copper iodide (11 mg, 0.058 mmol), DL-proline (12 mg, 0.104 mmol), and sodium hydroxide (5 mg, 0.125 mmol) in DMSO (0.5 mL) was heated at 95° C. overnight. The reaction mixture was diluted with ethyl acetate (20 mL), washed (50 mL sat'd NaHCO$_3$, 50 mL brine), and dried (Na$_2$SO$_4$). The solvent was removed under reduced pressure, and the residue was stirred in 80% AcOH/water (0.5 mL) overnight at room temperature. The solvent was removed under reduced pressure, and the residue was purified by reverse-phase HPLC to give 4-methyl-2-(4-((S)-2-((R)-3-methylpyrrolidin-1-yl)propoxy)phenyl)-3-(4-(methylsulfonyl)phenyl)-2H-chromen-6-ol. $^1$H NMR (DMSO-d$_6$; TFA salt): δ 11.60 (br, 1H), 7.93 (d, 2H), 7.62 (d, 2H), 7.34 (d, 2H), 6.92 (d, 1H), 6.83 (d, 2H), 6.64 (dd, 1H), 6.60 (br, 1H), 6.56 (d, 1H), 6.00 (s, 1H), 3.84 (m, 2H), 3.60 (m, 1H), 3.36 (m, 1H), 3.13 (s, 3H), 2.93 (m, 1H), 2.50 (m, 2H), 2.23 (m, 2H), 2.13 (s, 3H), 1.70 (m, 1H), 1.54 (m, 3H), 1.11 (m, 3H); LCMS: 534.9 (M+H)$^+$.

Example 60

3-(2-Fluoro-3-hydroxyphenyl)-4-methyl-2-(4-((S)-2-((R)-3-methylpyrrolidin-1-yl)propoxy)phenyl)-2H-chromen-6-ol

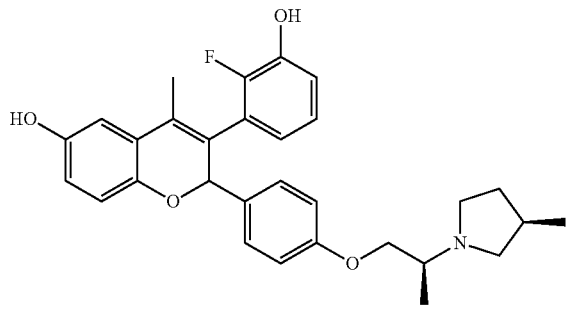

The title compound was prepared from Intermediate 36 and 1,4-dimethoxybenzene following the synthetic sequence outlined for Intermediate 32, Intermediate 2 (steps 2-3), Intermediate 3, and Example 2. $^1$H NMR (DMSO-d$_6$): δ 9.87 (s, 1H), 8.99 (s, 1H), 7.19 (d, 2H), 6.91 (m, 1H), 6.85 (m, 1H), 6.79 (d, 2H), 6.76 (d, 1H), 6.66 (m, 1H), 6.51 (m, 2H), 5.82 (s, 1H), 3.96 (m, 1H), 3.72 (m, 1H), 3.33 (m, 1H), 2.83 (m, 1H), 2.63 (m, 2H), 2.08 (m, 2H), 1.99 (s, 3H), 1.84 (m, 1H), 1.24 (m, 1H), 1.06 (d, 3H), 0.85 (d, 3H); LCMS: 490.1 (M+H)$^+$.

Example 61

5-Fluoro-3-(3-hydroxyphenyl)-4-methyl-2-(4-((S)-2-((R)-3-methylpyrrolidin-1-yl)propoxy)phenyl)-2H-chromen-6-ol

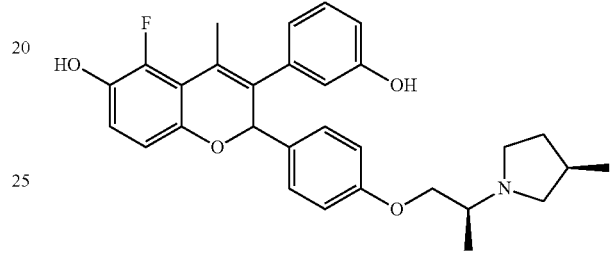

The title compound was prepared from Intermediate 37 following the synthetic sequence outlined for Intermediate 2 (steps 2-3), Intermediate 3, and Example 2. $^1$H NMR (DMSO-d$_6$): δ 9.49 (s, 1H), 9.24 (s, 1H), 7.23 (d, 2H), 7.17 (t, 1H), 6.80 (m, 3H), 6.67 (m, 3H), 6.37 (d, 1H), 5.88 (s, 1H), 3.95 (m, 1H), 3.71 (m, 1H), 3.32 (m, 1H), 2.81 (m, 1H), 2.62 (m, 2H), 2.15 (d, 3H), 2.08 (m, 2H), 1.87 (m, 1H), 1.18 (m, 1H), 1.07 (m, 3H), 0.95 (m, 3H); LCMS: 490.1 (M+H)$^+$.

Example 62

3-(2-Fluoro-5-hydroxyphenyl)-4-methyl-2-(4-((S)-2-((R)-3-methylpyrrolidin-1-yl)propoxy)phenyl)-2H-chromen-6-ol

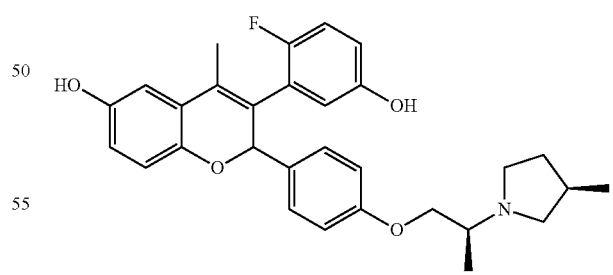

The title compound was prepared from Intermediate 38 following the synthetic sequence outlined for Intermediate 36 (steps 3-4), Intermediate 32, Intermediate 2 (steps 2-3), Intermediate 3, and Example 2. $^1$H NMR (DMSO-d$_6$; HCl salt): δ 10.52 (br, 1H), 9.48 (s, 1H), 9.03 (s, 1H), 7.26 (d, 2H), 7.00 (t, 1H), 6.88 (d, 2H), 6.77 (d, 1H), 6.69 (m, 1H), 6.58 (m, 1H), 6.52 (m, 2H), 5.81 (s, 1H), 3.17 (m, 2H), 3.66 (m, 1H), 3.49 (m, 1H), 3.27 (m, 1H), 3.20-2.93 (m, 1H), 2.72 (m, 1H), 2.48-2.20 (m, 1H), 2.09 (m, 1H), 1.94 (s, 3H), 1.53 (m, 1H), 1.35 (m, 3H), 1.06 (m, 3H); LCMS: 490.1 (M+H)+.

Example 63

3-(4-Fluorophenyl)-4-methyl-2-(4-((S)-2-((R)-2-methylpyrrolidin-1-yl)propoxy)phenyl)-2H-chromen-6-ol

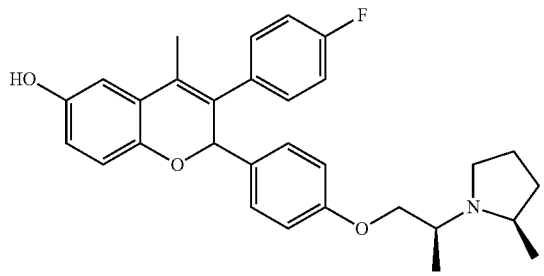 [SMILES: CC1=C(c2ccc(F)cc2)C(c2ccc(OC[C@H](C)N3CCC[C@H]3C)cc2)Oc2ccc(O)cc21]

The title compound was synthesized as described in Example 30 using 3-(4-fluorophenyl)-2-(4-iodophenyl)-4-methyl-6-((tetrahydro-2H-pyran-2-yl)oxy)-2H-chromene and Intermediate 24 as starting materials. $^1$H NMR (DMSO-$d_6$; HCl salt): δ 10.02 (br, 1H), 9.03 (br s, 1H), 7.36 (m, 2H), 7.25 (d, 2H), 7.18 (m, 2H), 6.87 (d, 2H), 6.77 (d, 1H), 6.50 (m, 2H), 5.92 (s, 1H), 4.18 (m, 2H), 3.85 (m, 1H), 3.70 (m, 1H), 3.42 (m, 1H), 3.27 (m, 1H), 2.15 (m, 1H), 2.02 (d, 3H), 1.90 (m, 2H), 1.63 (m, 1H), 1.35 (m, 6H); LCMS: 474.1 (M+H)+.

Example 64

2-(4-((S)-2-((R)-3-Fluoropyrrolidin-1-yl)propoxy)phenyl)-3-(3-hydroxyphenyl)-4-methyl-2H-chromen-6-ol

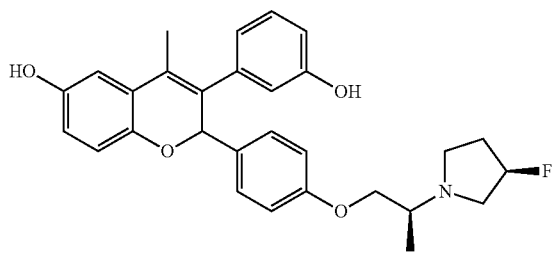 [SMILES: CC1=C(c2cccc(O)c2)C(c2ccc(OC[C@H](C)N3CC[C@@H](F)C3)cc2)Oc2ccc(O)cc21]

The title compound was synthesized as described in Example 2 using Intermediate 3 and Intermediate 39 as starting materials. $^1$H NMR (DMSO-$d_6$): δ 9.31 (s, 1H), 8.82 (s, 1H), 7.06 (d, 2H), 7.01 (t, 1H), 6.68 (d, 2H), 6.61 (m, 1H), 6.61-6.47 (m, 3H), 6.35 (m, 2H), 5.71 (s, 1H), 3.87 (m, 1H), 3.61 (m, 1H), 2.80-2.52 (m, 4H), 2.30 (m, 2H), 2.03-1.60 (m, 2H), 1.91 (s, 3H), 0.96 (d, 3H); LCMS: 476.1 (M+H)+.

Example 65

3-(4-Hydroxyphenyl)-2-(4-((S)-2-((R)-3-methylpyrrolidin-1-yl)propoxy)phenyl)-4-(trifluoromethyl)-2H-chromen-6-ol & 3-(4-hydroxyphenyl)-2-(4-((S)-2-((R)-3-methylpyrrolidin-1-yl)propoxy)phenyl)-4-(trifluoromethyl)-4H-chromen-6-ol

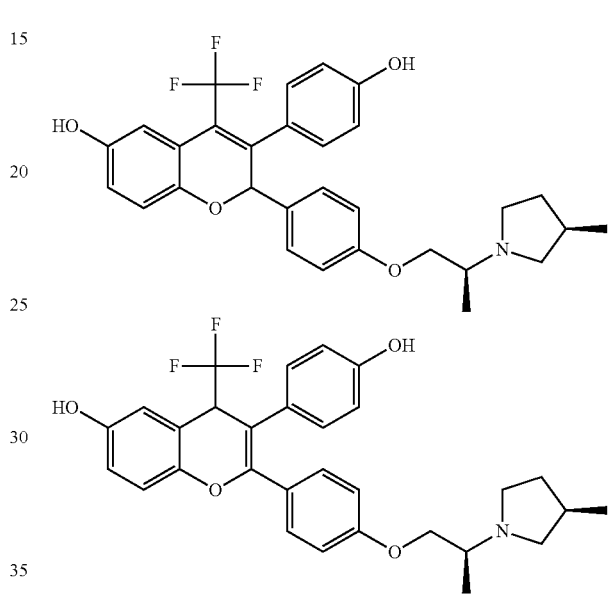

The title compounds were synthesized as described in Example 2 using Intermediate 41 and Intermediate 16 as starting materials. The compounds were isolated as a mixture because double bond isomerization occurred during the synthesis and the isomers were not separable by reverse-phase HPLC. LCMS: 526.1 (M+H)+.

Example 66

3-(3-Hydroxyphenyl)-2-(4-((S)-2-((R)-3-methylpyrrolidin-1-yl)propoxy)phenyl)-4-(trifluoromethyl)-2H-chromen-6-ol & 3-(3-hydroxyphenyl)-2-(4-((S)-2-((R)-3-methylpyrrolidin-1-yl)propoxy)phenyl)-4-(trifluoromethyl)-4H-chromen-6-ol

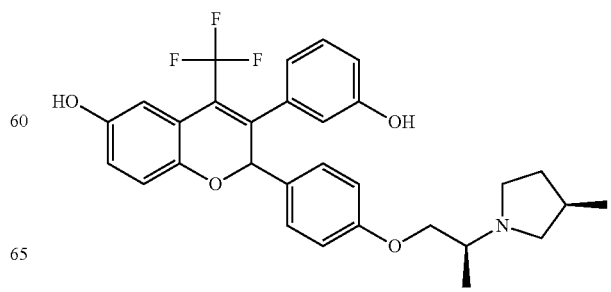

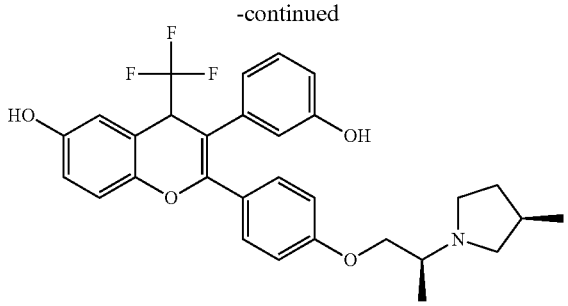

The title compounds were prepared from 2-(4-iodophenyl)-6-((tetrahydro-2H-pyran-2-yl)oxy)-3-(3-((tetrahydro-2H-pyran-2-yl)oxy)phenyl)chroman-4-one (intermediate in the synthesis of Intermediate 3) following the synthetic sequence outlined for Intermediate 41 and Example 2. The compounds were isolated as a mixture because double bond isomerization occurred during the synthesis and the isomers were not separable by reverse-phase HPLC. LCMS: 526.1 (M+H)⁺.

Example 67

2-(4-((S)-2-(7-Azabicyclo[2.2.1]heptan-7-yl)propoxy)phenyl)-3-(3-hydroxyphenyl)-4-methyl-2H-chromen-6-ol

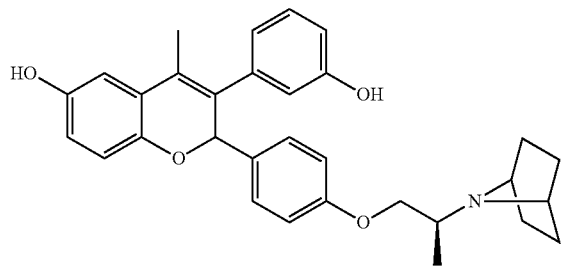 [SMILES: CC1=C(c2cccc(O)c2)C(c2ccc(OC[C@H](C)N3C4CCC3CC4)cc2)Oc2ccc(O)cc21]

The title compound was synthesized as described in Example 2 using Intermediate 3 and Intermediate 40 as starting materials. ¹H NMR (DMSO-d₆; HCl salt): δ 9.72 (br, 1H), 9.47 (s, 1H), 8.98 (s, 1H), 7.25 (d, 2H), 7.13 (t, 1H), 6.88 (d, 2H), 6.75 (m, 1H), 6.71-6.62 (m, 3H), 6.48 (m, 2H), 5.88 (s, 1H), 4.26 (m, 2H), 4.17 (m, 2H), 3.54 (m, 1H), 2.04 (s, 3H), 1.95 (m, 4H), 1.66 (m, 4H), 1.31 (d, 3H); LCMS: 484.2 (M+H)⁺.

Example 68

3-(3-Hydroxy-4-(trifluoromethyl)phenyl)-4-methyl-2-(4-((S)-2-((R)-3-methylpyrrolidin-1-yl)propoxy)phenyl)-2H-chromen-6-ol

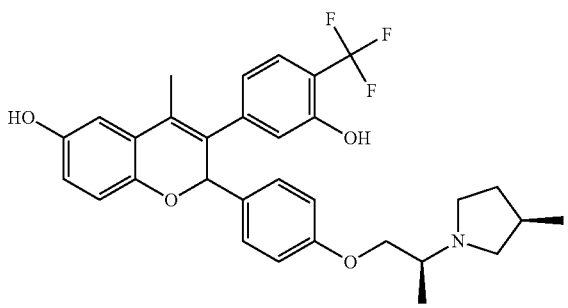 [SMILES: CC1=C(c2ccc(C(F)(F)F)c(O)c2)C(c2ccc(OC[C@H](C)N3CC[C@@H](C)C3)cc2)Oc2ccc(O)cc21]

The title compound was prepared from Intermediate 42 following the synthetic sequence outlined for Intermediate 2 (steps 2-3), Intermediate 3, and Example 2. ¹H NMR (DMSO-d₆; HCl salt): δ 10.65 (s, 1H), 10.25 (br, 1H), 9.04 (s, 1H), 7.47 (d, 1H), 7.25 (d, 2H), 7.40 (m, 3H), 6.83 (d, 1H), 6.79 (d, 1H), 6.52 (m, 2H), 5.88 (s, 1H), 4.17 (m, 2H), 3.67 (m, 1H), 3.48 (m, 2H), 3.20-2.90 (m, 1H), 2.73 (m, 1H), 2.45-2.20 (m, 1H), 2.11 (m, 1H), 2.05 (s, 3H), 1.54 (m, 1H), 1.34 (m, 3H), 1.03 (m, 3H); LCMS: 540.1 (M+H)⁺.

Example 69

3-(4-Hydroxy-3-(trifluoromethyl)phenyl)-4-methyl-2-(4-((S)-2-((R)-3-methylpyrrolidin-1-yl)propoxy)phenyl)-2H-chromen-6-ol

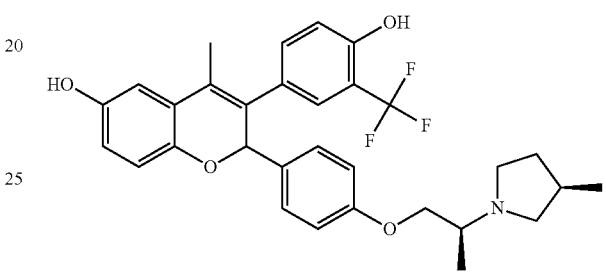

The title compound was synthesized as described in Example 68 using 2-(4-methoxy-3-(trifluoromethyl)phenyl)acetic acid as starting material. ¹H NMR (DMSO-d₆; HCl salt): δ 10.73 (s, 1H), 10.15 (br, 1H), 8.99 (s, 1H), 7.40 (d, 1H), 7.36 (s, 1H), 7.25 (d, 2H), 7.01 (d, 1H), 6.86 (d, 2H), 6.75 (s, 1H), 6.46 (m, 2H), 5.96 (s, 1H), 4.17 (m, 2H), 3.67 (m, 1H), 3.48 (m, 2H), 3.20-2.90 (m, 1H), 2.73 (m, 1H), 2.45-2.20 (m, 1H), 2.11 (m, 1H), 2.05 (s, 3H), 1.54 (m, 1H), 1.34 (m, 3H), 1.04 (m, 3H); LCMS: 540.1 (M+H)⁺.

Example 70

3-(4-Fluorophenyl)-4-methyl-2-(4-((S)-2-morpholinopropoxy)phenyl)-2H-chromen-6-ol

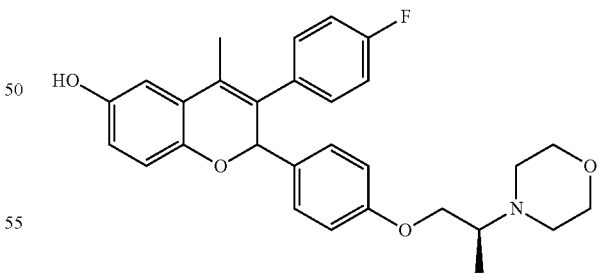

The title compound was synthesized as described in Example 30 using 3-(4-fluorophenyl)-2-(4-iodophenyl)-4-methyl-6-((tetrahydro-2H-pyran-2-yl)oxy)-2H-chromene and Intermediate 43 as starting materials. ¹H NMR (DMSO-d₆, TFA salt): δ 9.85 (br s, 1H), 8.99 (br s, 1H), 7.34 (m, 2H), 7.25 (d, 2H), 7.18 (t, 2H), 6.87 (d, 2H), 6.76 (m, 1H), 6.49 (m, 2H), 5.95 (s, 1H), 4.11-4.26 (m, 2H), 3.91-4.01 (m, 2H), 3.63-3.78 (m, 3H), 3.33-3.47 (m, 2H), 3.12-3.29 (m, 2H), 2.03 (s, 3H), 1.36 (d, 3H); LCMS: 476.1 (M+H)⁺.

Example 71

2-(4-(((2S)-2-(3-Azabicyclo[3.1.0]hexan-3-yl)propoxy)phenyl)-3-(4-fluorophenyl)-4-methyl-2H-chromen-6-ol

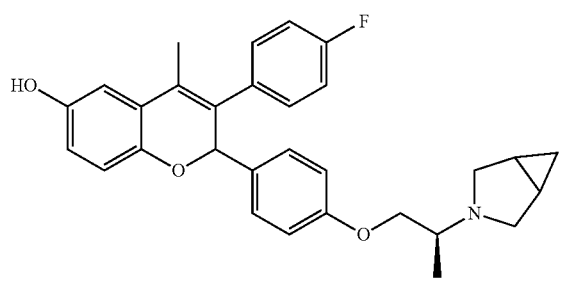 [SMILES: CC1=C(c2ccc(F)cc2)C(c2ccc(OC[C@H](C)N3CC4CC4C3)cc2)Oc2ccc(O)cc21]

The title compound was synthesized as described in Example 30 using 3-(4-fluorophenyl)-2-(4-iodophenyl)-4-methyl-6-((tetrahydro-2H-pyran-2-yl)oxy)-2H-chromene and Intermediate 44 as starting materials. $^1$H NMR (DMSO-$d_6$): δ 8.96 (s, 1H), 7.32 (m, 2H), 7.14-7.20 (m, 4H), 6.75-6.79 (m, 3H), 6.50 (m, 2H), 5.91 (s, 1H), 3.91 (m, 1H), 3.66 (m, 1H), 2.92 (d, 1H), 2.88 (d, 1H), 2.69 (m, 1H), 2.42 (m, 2H), 2.02 (s, 3H), 1.31 (m, 2H), 1.02 (d, 3H), 0.50 (m, 1H), 0.25 (m, 1H); LCMS: 472.1 (M+H)$^+$.

Example 72

3×ERE MCF-7 Reporter Assay

MCF7 cells were maintained in RPMI 1640 supplemented with 10% FCS. Transcriptional assays were performed by seeding 100 μL of cells at a density of 250,000 cells/mL into 96-well cell culture plates in RPMI 1640 supplemented with 10% charcoal stripped serum and allowed to attach overnight. Cells were transiently transfected using Lipofectin (Life Technologies) according to the manufacturer's protocol. Triplicate transfections were performed using 300 ng 3×ERE-TK-Luc (reporter vector), 50 ng CMVpRL (normalization vector), and 130 ng pCMX (filler DNA). Transfected cells were incubated overnight then treated with ligand. For ER agonist assays, the compounds were serially diluted and 50 μL of compound plus RPMI 1640 supplemented with charcoal stripped serum was added to the cells. For ER antagonist assays, the compounds were serially diluted and 50 μL of compound with RPMI plus 17β-estradiol supplemented with charcoal stripped serum were added to the cells. The final 17β-estradiol concentration used in the antagonist assays was 0.1 nM. Following 24 hour incubation the medium was removed and the cells were lysed in 40 μL of lysis buffer (25 mM Tris Phosphate, 2 mM CDTA, 10% Glycerol, 0.5% Triton X-100, 2 mM DTT). Firefly luciferase activity was measured immediately following the addition of 40 μL luciferase buffer (20 mM tricine, 0.1 mM EDTA, 1.07 mM (MgCo$_3$)$_4$Mg(OH)$_2$.5H$_2$O, 2.67 mM MgSO$_4$, 33.3 mM DTT, 270 μM Coenzyme A, 470 μM luciferin, 530 μM ATP). Renilla luciferase was measured following the addition of 40 μL colelenterazine buffer (1.1 M NaCl, 2.2 mM Na$_2$EDTA, 0.22 M K×PO$_4$ (pH 5.1), 0.44 mg/mL BSA, 1.3 mM NaN$_3$, 1.43 μM coelenterazine, final pH adjusted to 5.0).

Example 73

Breast Cancer Cell Viability Assays

MCF-7 cells were adjusted to a concentration of 20,000 cells per mL in RPMI containing 10% FBS and 20 mM HEPES. 16 microliters of the cell suspension (320 cells) was added to each well of a 384 well plate, and the cells were incubated overnight to allow the cells to adhere. The following day an eleven point, serial semilog dilution of each compound was added to the cells in 16 μL at a final concentration ranging from 0.3-0.000003 μM. After 5 days' compound exposure, 16 μL of CellTiter-GLo (Promega, Madison Wis.) was added to the cells the the relative luminescence units (RLUs) of each well was determined. CellTiter-Glo added to 32 μL of medium without cells was used to obtain a background value. The Percent viability of each sample was determined as follows: (RLU sample-RLU background/RLU untreated cells-RLU background)×100=% viability.

Viability effects in additional ER+ breast cancer cell lines, including BT474, CAMA1, MDA-MB-361, ZR-75-1, T47D, can be profiled in assays similar to Example 73.

Illustrative biological data for representative compounds disclosed herein is presented in the following table:

| Example | MCF7 Viability Assay IC$_{50}$ | MCF7 Viability Assay Max Response |
|---|---|---|
| 1 | A | ++ |
| 2 | A | ++ |
| 2a | A | ++ |
| 2b | B | ++ |
| 3 | A | ++ |
| 4 | B | + |
| 5 | A | ++ |
| 6 | A | ++ |
| 7 | A | + |
| 8 | A | ++ |
| 9 | A | ++ |
| 10 | A | + |
| 11 | A | ++ |
| 12 | A | ++ |
| 13 | A | ++ |
| 14 | A | + |
| 15 | A | ++ |
| 16 | A | + |
| 17 | A | + |
| 18 | A | ++ |
| 19 | A | ++ |
| 20 | A | ++ |
| 21 | A | ++ |
| 22 | A | + |
| 23 | A | ++ |
| 24 | A | + |
| 25 | A | + |
| 26 | A | ++ |
| 27 | A | ++ |
| 28 | A | ++ |
| 29 | A | ++ |
| 30 | A | ++ |
| 30a | A | ++ |
| 30b | B | ++ |
| 31 | A | ++ |
| 32 | A | + |
| 33 | A | ++ |
| 34 | A | ++ |
| 35 | A | ++ |
| 36 | A | ++ |
| 37 | A | ++ |
| 38 | A | ++ |
| 39 | B | ++ |
| 40 | A | ++ |
| 41 | A | ++ |
| 42 | A | ++ |
| 43 | A | ++ |
| 44 | B | ++ |
| 45 | A | ++ |
| 46 | B | ++ |
| 47 | A | ++ |
| 48 | B | ++ |
| 49 | A | ++ |
| 50 | A | ++ |

-continued

| Example | MCF7 Viability Assay IC$_{50}$ | MCF7 Viability Assay Max Response |
|---|---|---|
| 51 | A | ++ |
| 52 | A | ++ |
| 53 | A | ++ |
| 54 | B | ++ |
| 55 | B | ++ |
| 56 | A | ++ |
| 57 | A | ++ |
| 58 | B | ++ |
| 59 | B | ++ |
| 60 | A | ++ |
| 61 | A | ++ |
| 62 | A | ++ |
| 63 | A | ++ |
| 64 | A | ++ |
| 65 | A | ++ |
| 66 | A | ++ |
| 67 | A | ++ |
| 68 | B | ++ |
| 69 | B | ++ |
| 70 | B | ++ |
| 71 | B | ++ |

A = single IC$_{50}$ ≤1 nM;
B = single IC$_{50}$ >1 nM;
+ = a single % value <50%;
++ = a single % value ≥50%

Example 74

ER-α In Cell Western Assay (ER1D5)

MCF-7 cells were adjusted to a concentration of 200,000 cells per mL in RPMI containing 10% charcoal-stripped FBS and 20 mM HEPES. 16 microliters of the cell suspension (3200 cells) was added to each well of a poly-D-lysine 384 well plate, and the cells were incubated overnight to allow the cells to adhere. The following day an eleven point, serial semilog dilution of each compound was added to the cells in 16 μL at a final concentration ranging from 0.3-0.000003 μM. At 4 or 24 hr post compound addition, the cells were fixed (10% formalin in PBS) for 20 minutes. Cells were permeabalized in PBS 0.1% Triton and blocked with LICOR blocking buffer (50 μl/well, 90'). The wells were then incubated overnight at 4° C. with ER1D5 (Santa Cruz Biotechnology) diluted 1:100 in LICOR blocking buffer/0.1% Tween-20. Wells which were treated with blocking buffer with Tween but no antibody were used as a background control. Wells were washed with 0.1% Tween-20/PBS and then incubated in goat anti-mouse IRDye™ 800CW (LICOR Inc.; 1:1000) and DRAQ5 DNA dye (1:2000 for 2 mM stock) diluted in LICOR blocking buffer containing 0.1% Tween-20 and 0.01% SDS for 60 minutes. Cells were washed (50 μl/well, 5' each) in 0.1% Tween-20/PBS. Plates were scanned on a LICOR Odyssey infrared imaging system. Integrated intensities in the 800 nm channel and 700 nm channel were measured to determine levels of ER and DNA respectively. Percent ER levels were determined as follows: (Integrated intensity 800 nm sample/integrated intensity 700 nm sample)/(Integrated intensity 800 nm untreated cells/integrated intensity 700 nm untreated cells)×100=% ER levels.

Effects on steady state levels of ER-α in additional ER+ breast cancer cell lines, including BT474, CAMA1, MDA-MB-361, ZR-75-1, T47D, can be profiled in assays similar to Examples 74 & 75.

Illustrative biological data for representative compounds disclosed herein is presented in the following table:

| Example | ER In-Cell Western Assay (ER1D5); IC$_{50}$ | ER In-Cell Western Assay (ER1D5); Max Response |
|---|---|---|
| 1 | A | ++ |
| 2 | A | +++ |
| 2a | A | +++ |
| 2b | B | +++ |
| 3 | A | + |
| 4 | B | + |
| 5 | B | + |
| 6 | A | +++ |
| 7 | B | + |
| 8 | A | +++ |
| 9 | A | ++ |
| 10 | A | + |
| 11 | A | ++ |
| 12 | A | ++ |
| 13 | A | + |
| 14 | A | ++ |
| 15 | A | ++ |
| 16 | B | + |
| 17 | A | ++ |
| 18 | A | +++ |
| 19 | A | +++ |
| 20 | A | ++ |
| 21 | A | ++ |
| 22 | B | ++ |
| 23 | A | +++ |
| 24 | A | ++ |
| 25 | A | + |
| 26 | A | ++ |
| 27 | A | +++ |
| 28 | A | +++ |
| 29 | A | +++ |
| 30 | A | +++ |
| 30a | — | — |
| 30b | — | — |
| 31 | A | +++ |
| 32 | A | +++ |
| 33 | A | +++ |
| 34 | A | ++ |
| 35 | A | +++ |
| 36 | A | ++ |
| 37 | A | ++ |
| 38 | A | ++ |
| 39 | B | +++ |
| 40 | — | — |
| 41 | — | — |
| 42 | — | — |
| 43 | — | — |
| 44 | — | — |
| 45 | — | — |
| 46 | — | — |
| 47 | — | — |
| 48 | — | — |
| 49 | — | — |
| 50 | — | — |
| 51 | — | — |
| 52 | — | — |
| 53 | A | ++ |
| 54 | B | +++ |
| 55 | B | ++ |
| 56 | A | +++ |
| 57 | A | +++ |
| 58 | B | +++ |
| 59 | B | ++ |
| 60 | — | — |
| 61 | — | — |
| 62 | — | — |
| 63 | — | — |
| 64 | — | — |
| 65 | — | — |
| 66 | — | — |

-continued

| Example | ER In-Cell Western Assay (ER1D5); IC$_{50}$ | ER In-Cell Western Assay (ER1D5); Max Response |
|---|---|---|
| 67 | — | — |
| 68 | — | — |
| 69 | — | — |
| 70 | — | — |
| 71 | — | — |

A = single IC$_{50}$ ≤1 nM;
B = single IC$_{50}$ >1 nM
+ = a single % value that is <40%;
++ = a single % value that is % ≥40% to <65%;
+++ = a single % value that is ≥65%.

Example 75

ER-α in Cell Western Assay (SP1)

MCF-7 cells were adjusted to a concentration of 200,000 cells per mL in RPMI containing 10% charcoal-stripped FBS and 20 mM HEPES. 16 microliters of the cell suspension (3200 cells) was added to each well of a poly-D-lysine 384 well plate, and the cells were incubated overnight to allow the cells to adhere. The following day an eleven point, serial semilog dilution of each compound was added to the cells in 16 μL at a final concentration ranging from 0.3-0.000003 μM. At 4 or 24 hr post compound addition, the cells were fixed (10% formalin in PBS) for 20 minutes. Cells were permeabalized in PBS 0.1% Triton and blocked with LICOR blocking buffer (50 μl/well, 90'). The wells were then incubated overnight at 4° C. with SP1 rabbit monoclonal Ab (Thermo Scientific) diluted 1:1000 in LICOR blocking buffer/0.1% Tween-20. Wells which were treated with blocking buffer with Tween but no antibody were used as a background control. Wells were washed with 0.1% Tween-20/PBS and then incubated in goat anti-rabbit IRDye™ 800CW (LICOR Inc.; 1:1000) and DRAQ5 DNA dye (1:2000 for 2 mM stock) diluted in LICOR blocking buffer containing 0.1% Tween-20 and 0.01% SDS for 60 minutes. Cells were washed (50 μl/well, 5' each) in 0.1% Tween-20/PBS. Plates were scanned on a LICOR Odyssey infrared imaging system. Integrated intensities in the 800 nm channel and 700 nm channel were measured to determine levels of ER and DNA respectively. Percent ER levels were determined as follows:

(Integrated intensity 800 nm sample/integrated intensity 700 nm sample)/(Integrated intensity 800 nm untreated cells/integrated intensity 700 nm untreated cells)×100=% ER levels.

Illustrative biological data for representative compounds disclosed herein is presented in the following table:

| Example | ER In-Cell Western Assay (SP1); IC$_{50}$ | ER In-Cell Western Assay (SP1); Max Response |
|---|---|---|
| 1 | A | ++ |
| 2 | A | +++ |
| 2a | A | +++ |
| 2b | B | +++ |
| 3 | A | + |
| 4 | B | + |
| 5 | A | + |
| 6 | A | ++ |
| 7 | A | + |
| 8 | A | +++ |
| 9 | A | ++ |
| 10 | A | ++ |
| 11 | A | ++ |
| 12 | A | ++ |
| 13 | A | + |
| 14 | A | ++ |
| 15 | A | ++ |
| 16 | A | + |
| 17 | A | ++ |
| 18 | A | ++ |
| 19 | A | ++ |
| 20 | A | ++ |
| 21 | A | ++ |
| 22 | A | ++ |
| 23 | A | +++ |
| 24 | A | + |
| 25 | A | + |
| 26 | A | ++ |
| 27 | A | +++ |
| 28 | A | +++ |
| 29 | A | ++ |
| 30 | A | ++ |
| 30a | A | ++ |
| 30b | B | ++ |
| 31 | A | +++ |
| 32 | A | +++ |
| 33 | A | +++ |
| 34 | A | ++ |
| 35 | A | +++ |
| 36 | A | ++ |
| 37 | A | ++ |
| 38 | A | ++ |
| 39 | B | ++ |
| 40 | A | ++ |
| 41 | A | ++ |
| 42 | A | +++ |
| 43 | A | +++ |
| 44 | B | ++ |
| 45 | A | +++ |
| 46 | B | ++ |
| 47 | A | +++ |
| 48 | A | +++ |
| 49 | A | +++ |
| 50 | A | ++ |
| 51 | A | ++ |
| 52 | A | ++ |
| 53 | A | ++ |
| 54 | B | ++ |
| 55 | A | ++ |
| 56 | A | ++ |
| 57 | A | +++ |
| 58 | A | ++ |
| 59 | B | ++ |
| 60 | A | +++ |
| 61 | A | +++ |
| 62 | A | +++ |
| 63 | A | ++ |
| 64 | A | +++ |
| 65 | A | ++ |
| 66 | A | +++ |
| 67 | A | + |
| 68 | B | ++ |
| 69 | A | ++ |
| 70 | A | ++ |
| 71 | A | ++ |

A = single IC$_{50}$ ≤1 nM;
B = single IC$_{50}$ >1 nM
+ = a single % value that is <60%;
++ = a single % value that is % ≥60% to <85%;
+++ = a single % value that is ≥85%.

Example 76

Ishikawa Uterine Cell Alkaline Phosphatase Assay

Subconfuent Ishikawa cells in a T225 are incubated 24 hours in an estrogen free basal medium (EFBM) consisting of DMEM:Ham's F-12 50:50 phenol red free basal medium containing 5% Charcoal Dextran treated FBS and 20 mM HEPES. Cells are plated the following day in EFBM in clear 384 well plates at a concentration of 2.5×105 cells per mL, 16 µL per well (4000 cells per well). A 12 point semilog dilution of each compound is carried out in DMSO and subsequently diluted in EFBM. An equal volume of compound in EFBM is added immediately after plating cells, and the cells are incubated for 3 days. The cells are fixed with 5% formalin, and rinsed with PBS. Alkaline Phosphatase substrate 4-Nitrophenyl phosphate disodium salt hexahydrate is added to a solution containing 2 mM $MgCl_2$, 1 M diethanolamine, and adjusted to pH 9.0. The substrate solution is added to the cell cultures (16 µL per well), and OD405 is measured in a multiwall plate spectrophotometer when the optical density at 405 nm wavelength of cells treated with 17β-estradiol in the concentration range of 1-30 nM reaches 1.0-1.2 absorbance units. Cells treated with DMSO alone serve as a background control. Percent activity in background subtracted samples is measured as follows: % activity=OD405 sample/OD405 max of 17β-estradiol treated cells×100.

Example 77

Ovarian Cancer Cell Viability Assays

BG-1, cells were adjusted to a concentration of 20,000 cells per mL in RPMI containing 10% FBS and 20 mM HEPES. 16 microliters of the cell suspension (320 cells) was added to each well of a 384 well plate, and the cells were incubated overnight to allow the cells to adhere. The following day an eleven point, serial semilog dilution of each compound was added to the cells in 16 µL at a final concentration ranging from 0.3-0.000003 µM. After 5 days' compound exposure, 16 µL of CellTiter-GLo (Promega, Madison Wis.) was added to the cells the relative luminescence units (RLUs) of each well was determined. CellTiter-Glo added to 32 µL of medium without cells was used to obtain a background value. The Percent viability of each sample was determined as follows: (RLU sample-RLU background/RLU untreated cells-RLU background)×100=% viability.

Viability effects in additional ER+ ovarian cancer cell lines, including A1847, SKOV3, SW626, A2780, can be profiled in assays similar to Example 77.

Example 78

Ovarian Cancer Cell ER-α in Cell Western Assay

BG-1 cells were adjusted to a concentration of 200,000 cells per mL in RPMI containing 10% charcoal-stripped FBS and 20 mM HEPES. 16 microliters of the cell suspension (3200 cells) was added to each well of a poly-D-lysine 384 well plate, and the cells were incubated overnight to allow the cells to adhere. The following day an eleven point, serial semilog dilution of each compound was added to the cells in 16 µL at a final concentration ranging from 0.3-0.000003 µM. At 4 or 24 hr post compound addition, the cells were fixed (10% formalin in PBS) for 20 minutes. Cells were permeabalized in PBS 0.1% Triton and blocked with LICOR blocking buffer (50 µl/well, 90'). The wells were then incubated overnight at 4° C. with ER1D5 (Santa Cruz Biotechnology) diluted 1:100 in LICOR blocking buffer/0.1% Tween-20. Wells which were treated with blocking buffer with Tween but no antibody were used as a background control. Wells were washed with 0.1% Tween-20/PBS and then incubated in goat anti-mouse IRDye™ 800CW (LICOR Inc.; 1:1000) and DRAQ5 DNA dye (1:2000 for 2 mM stock) diluted in LICOR blocking buffer containing 0.1% Tween-20 and 0.01% SDS for 60 minutes. Cells were washed (50 µl/well, 5' each) in 0.1% Tween-20/PBS. Plates were scanned on a LICOR Odyssey infrared imaging system. Integrated intensities in the 800 nm channel and 700 nm channel were measured to determine levels of ER and DNA respectively. Percent ER levels were determined as follows:

(Integrated intensity 800 nm sample/integrated intensity 700 nm sample)/(Integrated intensity 800 nm untreated cells/integrated intensity 700 nm untreated cells)×100=% ER levels.

Effects on steady state levels of ER-α in additional ER+ ovarian cancer cell lines, including A1847, SKOV3, SW626, A2780, can be profiled in assays similar to Example 78.

Other cancer cell lines contemplated for testing compounds described herein include: ER-positive endometrial cell lines (Ishikawa, ECC1, HEC-1, EnCa-101) and ER-positive cervical cell lines (Caski, HeLa, SiHa).

Example 79

Xenograft Assay (MCF-7)

Time release pellets containing 0.72 mg 17-P3 Estradiol were subcutaneously implanted into nu/nu mice. MCF-7 cells were grown in RPMI containing 10% FBS at 5% $CO_2$, 37° C. Cells were spun down and re-suspended in 50% RPMI (serum free) and 50% Matrigel at 1×10$^7$ cells/mL. MCF-7 cells were subcutaneously injected (100 L/animal) on the right flank 2-3 days post pellet implantation. Tumor volume (length×width$^2$/2) was monitored bi-weekly. When tumors reached an average volume of ~200 mm$^3$ animals were randomized and treatment was started. Animals were treated with Vehicle or test compound daily for 4 weeks. Tumor volume and body weight were monitored bi-weekly throughout the study. At the conclusion of the treatment period, plasma and tumor samples were taken for pharmacokinetic and pharmacodynamic analyses, respectively.

Example 80

Xenograft Assay (MCF-7 Derivative)

Female nu/nu mice (with supplemental 17-P3 Estradiol pellets; 0.72 mg; 60 day slow release) bearing MCF-7 tumors (mean tumor volume 200 mm$^3$) were treated with Tamoxifen (citrate) by oral gavage. Tumor volume (length×width$^2$/2) and body weight were monitored twice weekly. Following a significant anti-tumor response in which tumor volume remained static, evident tumor growth was first observed at approximately 100 days of treatment. At 120 days of treatment, tamoxifen dose was increased. Rapidly growing tumors were deemed tamoxifen resistant and selected for in vivo passage into new host animals. Tumor Fragments (~100 mm$^3$/animal) from the tamoxifen resistant tumors were subcutaneously implanted into the right flank of female nu/nu mice (with 17-P3 Estradiol pellets (0.72 mg; 60 day slow release)). Passaged tumors were maintained under constant Tamoxifen selection and Tumor volume (length×width$^2$/2) monitored weekly. When tumor volume reached ~150-250 mm$^3$, animals were randomized into treatment groups (mean tumor volume 200 mm$^3$) and tamoxifen treatment was terminated (except for a tamoxifen control arm). Animals were treated with Vehicle or test compound daily for 4 weeks. Tumor volume and body weight were monitored twice weekly for the duration of the study. At the conclusion of the treatment period; plasma and tumor samples were taken for pharmacokinetic and pharmacodynamic analyses, respectively.

Example 81

Xenograft Assay (BG-1)

Time release pellets (0.72 mg 17-β Estradiol/60 days) were subcutaneously implanted into female nu/nu mice. BG-1 cells were grown in DMEM Ham's F-12 50/50 containing 10% FBS, 10 mM Sodium Pyruvate, 10 mM Non-Essential Amino Acids at 5% $CO_2$, 37° C. Cells were spun down and re-suspended in 50% DMEM Ham's F-12 (serum free) and 50% Matrigel at $5 \times 10^7$ cells/mL. BG-1 cells were subcutaneously injected (100 µL/animal) on the right flank 2-3 days post pellet implantation. Tumor volume (length×width$^2$/2) was monitored bi-weekly. When tumors reached an average volume of ~250 mm$^3$ animals were randomized and treatment was started. Animals were treated with Vehicle or test compound daily for 4 weeks. Tumor volume and body weight were monitored bi-weekly throughout the study. At the conclusion of the treatment period; plasma and tumor samples were taken for pharmacokinetic and pharmacodynamic analyses, respectively.

Example 82

Immature Uterine Wet Weight-Antagonist Mode

Female immature CD-IGS rats (21 days old upon arrival) were treated for three days. Animals were dosed daily for three days. Vehicle or test compound was administered orally by gavage followed 15 minutes later by an oral dose of 0.1 mg/kg Ethynyl Estradiol. On the fourth day 24 hours after dose, plasma was collected for pharmacokinetic analysis. Immediately following plasma collection, the animals were euthanized and the uterus was removed and weighed.

Example 83

Immature Uterine Wet Weight-Agonist Mode

Female immature CD-IGS rats (21 days old upon arrival) were treated for three days. Animals were dosed daily for three days. Vehicle or test compound was administered orally by gavage followed 15 minutes later by a second oral dose of vehicle. On the fourth day 24 hours after dose, plasma was collected for pharmacokinetic analysis. Immediately following plasma collection, the animals were euthanized and the uterus was removed and weighed.

Example 84

Parenteral Pharmaceutical Composition

To prepare a parenteral pharmaceutical composition suitable for administration by injection (subcutaneous, intravenous), 100 mg of a compound or a water-soluble salt of a compound of Formula (I), (II), (III), (IV), (V), (VI), (VII), (VIII), (IX), (X), (XI), (XII), or (XIII) is dissolved in sterile water and then mixed with 10 mL of 0.9% sterile saline. The mixture is incorporated into a dosage unit form suitable for administration by injection In another embodiment, the following ingredients are mixed to form an injectable formulation: 1.2 g of a compound of Formula (I), (II), (III), (IV), (V), (VI), (VII), (VIII), (IX), (X), (XI), (XII), or (XIII), or a pharmaceutically acceptable salt thereof, 2.0 mL of sodium acetate buffer solution (0.4 M), HCl (1 N) or NaOH (1 M) (q.s. to suitable pH), water (distilled, sterile) (q.s. to 20 mL). All of the above ingredients, except water, are combined and stirred and if necessary, with slight heating if necessary. A sufficient quantity of water is then added.

Example 85

Oral Solution

To prepare a pharmaceutical composition for oral delivery, an aqueous 20% propylene glycol solution is prepared. To this is added a sufficient amount of compound of Formula (I), (II), (III), (IV), (V), (VI), (VII), (VIII), (IX), (X), (XI), (XII), or (XIII), or a pharmaceutically acceptable salt thereof, to provide a 20 mg/mL solution.

Example 86

Oral Capsule

To prepare a pharmaceutical composition for oral delivery, 100-500 mg of a compound of Formula (I), (II), (III), (IV), (V), (VI), (VII), (VIII), (IX), (X), (XI), (XII), or (XIII), or a pharmaceutically acceptable salt thereof, is mixed with starch. The mixture is incorporated into an oral dosage unit such as a hard gelatin capsule, which is suitable for oral administration.

In another embodiment, 100-500 mg of a compound of Formula (I), (II), (III), (IV), (V), (VI), (VII), (VIII), (IX), (X), (XI), (XII), or (XIII), or a pharmaceutically acceptable salt thereof, is placed into Size 4 capsule, or size 1 capsule (hypromellose or hard gelatin) and the capsule is closed.

Example 87

Oral Tablet

A tablet is prepared by mixing 48% by weigh of a compound of Formula (I), (II), (III), (IV), (V), (VI), (VII), (VIII), (IX), (X), (XI), (XII), or (XIII), or a pharmaceutically acceptable salt thereof, 45% by weight of microcrystalline cellulose, 5% by weight of low-substituted hydroxypropyl cellulose, and 2% by weight of magnesium stearate. Tablets are prepared by direct compression. The total weight of the compressed tablets is maintained at 250-500 mg.

Example 88

Topical Gel Composition

To prepare a pharmaceutical topical gel composition, a compound of Formula (I), (II), (III), (IV), (V), (VI), (VII), (VIII), (IX), (X), (XI), (XII), or (XIII), or a pharmaceutically acceptable salt thereof, is mixed with hydroxypropyl cellulose, propylene glycol, isopropyl myristate and purified alcohol USP. The resulting gel mixture is then incorporated into containers, such as tubes, which are suitable for topical administration.

The examples and embodiments described herein are for illustrative purposes only and various modifications or changes suggested to persons skilled in the art are to be included within the spirit and purview of this application and scope of the appended claims.

What is claimed is:

1. A method of treating cancer in a mammal comprising administering to the mammal a therapeutically effective amount of a compound of Formula (VI), or a pharmaceutically acceptable salt thereof:

Formula (VI)

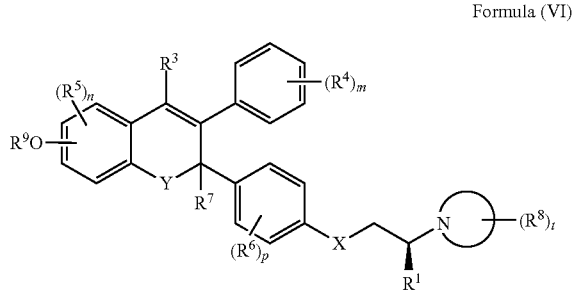

wherein, $R^1$ is H, F, $C_1$-$C_4$alkyl, or $C_1$-$C_4$fluoroalkyl;

$R^3$ is H, halogen, $C_1$-$C_4$alkyl, $C_3$-$C_6$cycloalkyl, or $C_1$-$C_4$fluoroalkyl;

each $R^4$ is independently selected from H, halogen, —CN, —OH, —$OR^9$, —$SR^9$, —S(=O)$R^{10}$, —S(=O)$_2R^{10}$, —C(=O)$R^{10}$, —C(=O)OH, —C(=O)$OR^{10}$, —C(=O)NH$R^{10}$, —C(=O)N($R^{10}$)$_2$, substituted or unsubstituted $C_1$-$C_6$alkyl, substituted or unsubstituted $C_1$-$C_6$fluoroalkyl, substituted or unsubstituted $C_1$-$C_6$fluoroalkoxy, substituted or unsubstituted $C_1$-$C_6$alkoxy, and substituted or unsubstituted $C_1$-$C_6$heteroalkyl;

each $R^5$ is independently selected from H, halogen, —CN, —OH, —$OR^9$, —$SR^9$, —S(=O)$R^{10}$, —S(=O)$_2R^{10}$, substituted or unsubstituted $C_1$-$C_6$alkyl, substituted or unsubstituted $C_1$-$C_6$fluoroalkyl, substituted or unsubstituted $C_1$-$C_6$fluoroalkoxy, substituted or unsubstituted $C_1$-$C_6$alkoxy, and substituted or unsubstituted $C_1$-$C_6$heteroalkyl;

each $R^6$ is independently selected from H, halogen, —CN, —OH, —$OR^9$, —$SR^9$, —S(=O)$R^{10}$, —S(=O)$_2R^{10}$, substituted or unsubstituted $C_1$-$C_6$alkyl, substituted or unsubstituted $C_1$-$C_6$fluoroalkyl, substituted or unsubstituted $C_1$-$C_6$fluoroalkoxy, substituted or unsubstituted $C_1$-$C_6$alkoxy, and substituted or unsubstituted $C_1$-$C_6$heteroalkyl;

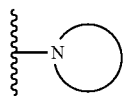

is azetidinyl or pyrrolidinyl;

$R^7$ is H or $C_1$-$C_4$alkyl;

each $R^8$ is independently selected from F, Cl, —CN, —OH, —$OR^9$, —$SR^9$, —S(=O)$R^{10}$, —S(=O)$_2R^{10}$, substituted or unsubstituted $C_1$-$C_6$alkyl, substituted or unsubstituted $C_1$-$C_6$fluoroalkyl, substituted or unsubstituted $C_1$-$C_6$fluoroalkoxy, substituted or unsubstituted $C_1$-$C_6$alkoxy, and substituted or unsubstituted $C_1$-$C_6$heteroalkyl;

or 1 $R^8$ is taken together with $R^1$ along with the intervening atoms joining $R^8$ to $R^1$ to form a 5-, 6-, or 7-membered ring;

each $R^9$ is independently selected from H, —C(=O)$R^{10}$, —C(=O)$OR^{10}$, —C(=O)NH$R^{10}$, substituted or unsubstituted $C_1$-$C_6$alkyl, substituted or unsubstituted $C_1$-$C_6$heteroalkyl, substituted or unsubstituted $C_1$-$C_6$fluoroalkyl, substituted or unsubstituted $C_3$-$C_{10}$cycloalkyl, substituted or unsubstituted $C_2$-$C_{10}$heterocycloalkyl, substituted or unsubstituted aryl, substituted or unsubstituted heteroaryl, —$C_1$-$C_2$alkylene-(substituted or unsubstituted $C_3$-$C_{10}$cycloalkyl), —$C_1$-$C_2$alkylene-(substituted or unsubstituted $C_2$-$C_{10}$heterocycloalkyl), —$C_1$-$C_2$alkylene-(substituted or unsubstituted aryl), and —$C_1$-$C_2$alkylene-(substituted or unsubstituted heteroaryl); or each $R^{10}$ is independently selected from substituted or unsubstituted $C_1$-$C_6$alkyl, substituted or unsubstituted $C_1$-$C_6$heteroalkyl, substituted or unsubstituted $C_1$-$C_6$fluoroalkyl, substituted or unsubstituted $C_3$-$C_{10}$cycloalkyl, substituted or unsubstituted $C_2$-$C_{10}$heterocycloalkyl, substituted or unsubstituted aryl, substituted or unsubstituted heteroaryl, —$C_1$-$C_2$alkylene-(substituted or unsubstituted $C_3$-$C_{10}$cycloalkyl), —$C_1$-$C_2$alkylene-(substituted or unsubstituted $C_2$-$C_{10}$heterocycloalkyl), —$C_1$-$C_2$alkylene-(substituted or unsubstituted aryl), and —$C_1$-$C_2$alkylene-(substituted or unsubstituted heteroaryl);

Y is —O—, —S—, or —NR$^{11}$—; $R^{11}$ is H, —C(=O)$R^{10}$, substituted or unsubstituted $C_1$-$C_6$alkyl, substituted or unsubstituted $C_1$-$C_6$fluoroalkyl, or substituted or unsubstituted $C_1$-$C_6$heteroalkyl;

X is —O—, —S—, —CH$_2$—, —NH— or —N($C_1$-$C_6$alkyl)-;

m is 0, 1, 2, 3 or 4;

n is 0, 1, 2, or 3;

p is 0, 1, 2, 3 or 4; and t is 1, 2, 3 or 4;

wherein the cancer is a hormone dependent cancer or a cancer resistant to anti-hormonal treatment; and wherein the cancer is selected from bone, breast, lung, colorectal, endometrial, prostate, ovarian, uterine, and cervical.

2. The method of claim 1, further comprising administering to the mammal at least one additional anti-cancer agent.

3. The method of claim 1, wherein:

$R^1$ is H or $C_1$-$C_4$alkyl;

$R^3$ is $C_1$-$C_4$alkyl or $C_1$-$C_4$fluoroalkyl;

each $R^4$ is independently selected from H, halogen, —CN, —OH, —$OR^9$, —$SR^9$, —S(=O)$R^{10}$, —S(=O)$_2R^{10}$, $C_1$-$C_4$alkyl, $C_1$-$C_4$fluoroalkyl, $C_1$-$C_4$fluoroalkoxy, $C_1$-$C_4$alkoxy, and $C_1$-$C_4$heteroalkyl;

each $R^5$ is independently selected from H, halogen, —OH, $C_1$-$C_4$alkyl, $C_1$-$C_4$fluoroalkyl, $C_1$-$C_4$fluoroalkoxy, $C_1$-$C_4$alkoxy, and $C_1$-$C_4$heteroalkyl;

each $R^6$ is independently selected from H, halogen, —OH, $C_1$-$C_4$alkyl, $C_1$-$C_4$fluoroalkyl, $C_1$-$C_4$fluoroalkoxy, and $C_1$-$C_4$alkoxy;

$R^7$ is H or —CH$_3$;

Y is —O— or —S—;

X is —O—, —S—, —CH$_2$—, —NH— or —N(CH$_3$)—;

p is 0, 1, or 2.

4. The method of claim 3, wherein:

each $R^5$ is independently selected from H, F, Cl, —OH, —CH$_3$, —CF$_3$, —OCF$_3$ and —OCH$_3$;

each $R^6$ is independently selected from H, F, Cl, —OH, —CH$_3$, —CF$_3$, —OCF$_3$ and —OCH$_3$;

$R^7$ is H;

each R⁸ is independently selected from F, Cl, —OH, C₁-C₄alkyl, C₁-C₄fluoroalkyl, C₁-C₄fluoroalkoxy, C₁-C₄alkoxy, and C₁-C₄heteroalkyl.

5. The method of claim 4, wherein:

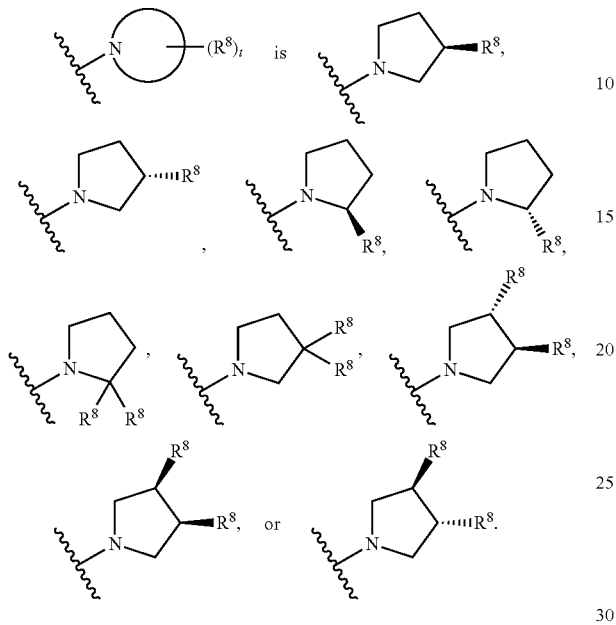

6. The method of claim 1, wherein the compound of Formula (VI) has the structure of Formula (VIII):

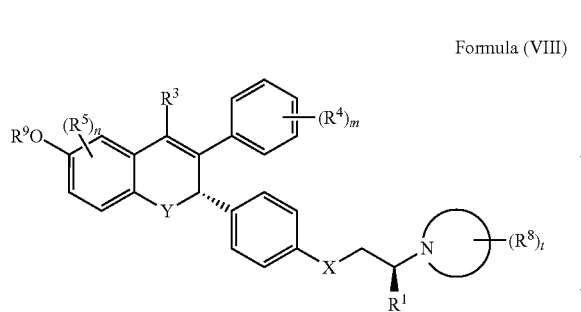

Formula (VIII)

or a pharmaceutically acceptable salt thereof.

7. The compound of claim 1, wherein the compound of Formula (VI) has the structure of Formula (X):

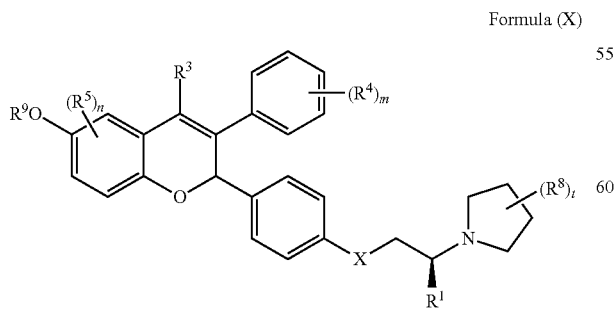

Formula (X)

or a pharmaceutically acceptable salt thereof.

8. The method of claim 7, wherein:
R¹ is H or —CH₃;
R³ is —CH₃ or —CF₃;

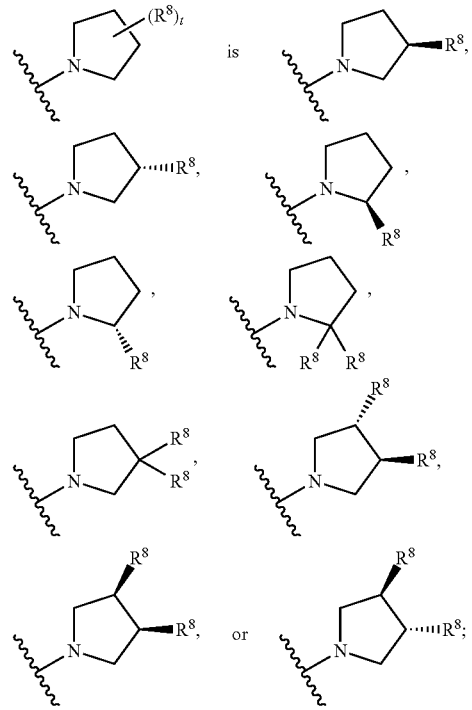

each R⁸ is independently selected from F, Cl, —OH, —CH₃, —CH₂CH₃, —CH(CH₃)₂, —CF₃, —CH₂CF₃, —OCF₃, —OCH₂CF₃, —OCH₃, —OCH₂CH₃, —CH₂OCH₃, —CH₂OCH₂CH₃, and —CH₂OH;

R⁹ is H;

X is —O—.

9. The method of claim 1, wherein the compound is:
3-(3-Hydroxyphenyl)-4-methyl-2-(4-((S)-2-((R)-3-methylpyrrolidin-1-yl)propoxy)phenyl)-2H-chromen-6-ol;
(S)-3-(3-Hydroxyphenyl)-4-methyl-2-(4-((S)-2-((R)-3-methylpyrrolidin-1-yl)propoxy)phenyl)-2H-chromen-6-ol;
(R)-3-(3-Hydroxyphenyl)-4-methyl-2-(4-((S)-2-((R)-3-methylpyrrolidin-1-yl)propoxy)phenyl)-2H-chromen-6-ol;
3-(3-Hydroxyphenyl)-4-methyl-2-(4-(2-((R)-3-methylpyrrolidin-1-yl)ethoxy)phenyl)-2H-chromen-6-ol;
3-(3-Hydroxyphenyl)-4-methyl-2-(4-((R)-2-((R)-3-methylpyrrolidin-1-yl)propoxy)phenyl)-2H-chromen-6-ol;
3-(3-Hydroxyphenyl)-4-methyl-2-(4-(2-((S)-3-methylpyrrolidin-1-yl)ethoxy)phenyl)-2H-chromen-6-ol;
3-(3-hydroxyphenyl)-4-methyl-2-(4-((S)-2-((S)-3-methylpyrrolidin-1-yl)propoxy)phenyl)-2H-chromen-6-ol;
3-(3-hydroxyphenyl)-4-methyl-2-(4-((R)-2-((S)-3-methylpyrrolidin-1-yl)propoxy)phenyl)-2H-chromen-6-ol;
2-(4-((S)-2-(3,3-Dimethylpyrrolidin-1-yl)propoxy)phenyl)-3-(3-hydroxyphenyl)-4-methyl-2H-chromen-6-ol;
2-(4-(2-(3,3-Dimethylpyrrolidin-1-yl)ethoxy)phenyl)-3-(3-hydroxyphenyl)-4-methyl-2H-chromen-6-ol;
3-(3-Hydroxyphenyl)-4-methyl-2-(4-(2-((R)-2-methylpyrrolidin-1-yl)ethoxy)phenyl)-2H-chromen-6-ol;
3-(3-Hydroxyphenyl)-4-methyl-2-(4-((S)-2-((R)-2-methylpyrrolidin-1-yl)propoxy)phenyl)-2H-chromen-6-ol;

3-(3-Hydroxyphenyl)-4-methyl-2-(4-((S)-2-((S)-2-methylpyrrolidin-1-yl)propoxy)phenyl)-2H-chromen-6-ol;
3-(3-Hydroxyphenyl)-4-methyl-2-(4-((S)-2-((R)-3-methylpyrrolidin-1-yl)propoxy)phenyl)-2H-chromen-7-ol;
3-(4-Hydroxyphenyl)-4-methyl-2-(4-((S)-2-((R)-3-methylpyrrolidin-1-yl)propoxy)phenyl)-2H-chromen-7-ol;
4-Methyl-2-(4-((S)-2-((R)-3-methylpyrrolidin-1-yl)propoxy)phenyl)-3-phenyl-2H-chromen-6-ol;
3-(4-Fluorophenyl)-4-methyl-2-(4-((S)-2-((R)-3-methylpyrrolidin-1-yl)propoxy)phenyl)-2H-chromen-6-ol;
(S)-3-(4-Fluorophenyl)-4-methyl-2-(4-((S)-2-((R)-3-methylpyrrolidin-1-yl)propoxy)phenyl)-2H-chromen-6-ol;
(R)-3-(4-Fluorophenyl)-4-methyl-2-(4-((S)-2-((R)-3-methylpyrrolidin-1-yl)propoxy)phenyl)-2H-chromen-6-ol;
3-(4-Hydroxyphenyl)-4-methyl-2-(4-((S)-2-((R)-3-methylpyrrolidin-1-yl)propoxy)phenyl)-2H-chromen-6-ol;
3-(3-Fluorophenyl)-4-methyl-2-(4-((S)-2-((R)-3-methylpyrrolidin-1-yl)propoxy)phenyl)-2H-chromen-6-ol;
3-(3-Fluoro-4-hydroxyphenyl)-4-methyl-2-(4-((S)-2-((R)-3-methylpyrrolidin-1-yl)propoxy)phenyl)-2H-chromen-6-ol;
2-(2-Fluoro-4-((S)-2-((R)-3-methylpyrrolidin-1-yl)propoxy)phenyl)-3-(3-hydroxyphenyl)-4-methyl-2H-chromen-6-ol;
3-(3-Hydroxy-4-methylphenyl)-4-methyl-2-(4-((S)-2-((R)-3-methylpyrrolidin-1-yl)propoxy)phenyl)-2H-chromen-6-ol;
3-(3-Hydroxy-2-methylphenyl)-4-methyl-2-(4-((S)-2-((R)-3-methylpyrrolidin-1-yl)propoxy)phenyl)-2H-chromen-6-ol;
3-(4-Hydroxy-2-methylphenyl)-4-methyl-2-(4-((S)-2-((R)-3-methylpyrrolidin-1-yl)propoxy)phenyl)-2H-chromen-6-ol;
3-(4-Hydroxy-3-methylphenyl)-4-methyl-2-(4-((S)-2-((R)-3-methylpyrrolidin-1-yl)propoxy)phenyl)-2H-chromen-6-ol;
3-(3-Fluoro-5-hydroxyphenyl)-4-methyl-2-(4-((S)-2-((R)-3-methylpyrrolidin-1-yl)propoxy)phenyl)-2H-chromen-6-ol;
3-(4-Chlorophenyl)-4-methyl-2-(4-((S)-2-((R)-3-methylpyrrolidin-1-yl)propoxy)phenyl)-2H-chromen-6-ol;
3-(2-Fluoro-4-hydroxyphenyl)-4-methyl-2-(4-((S)-2-((R)-3-methylpyrrolidin-1-yl)propoxy)phenyl)-2H-chromen-6-ol;
3-(3,4-Difluorophenyl)-4-methyl-2-(4-((S)-2-((R)-3-methylpyrrolidin-1-yl)propoxy)phenyl)-2H-chromen-6-ol;
3-(3,5-Difluoro-4-hydroxyphenyl)-4-methyl-2-(4-((S)-2-((R)-3-methylpyrrolidin-1-yl)propoxy)phenyl)-2H-chromen-6-ol;
3-(2,4-Difluoro-3-hydroxyphenyl)-4-methyl-2-(4-((S)-2-((R)-3-methylpyrrolidin-1-yl)propoxy)phenyl)-2H-chromen-6-ol;
3-(3,4-Difluoro-5-hydroxyphenyl)-4-methyl-2-(4-((S)-2-((R)-3-methylpyrrolidin-1-yl)propoxy)phenyl)-2H-chromen-6-ol;
3-(2-Chloro-4-fluorophenyl)-4-methyl-2-(4-((S)-2-((R)-3-methylpyrrolidin-1-yl)propoxy)phenyl)-2H-chromen-6-ol;
3-(2,4-Difluorophenyl)-4-methyl-2-(4-((S)-2-((R)-3-methylpyrrolidin-1-yl)propoxy)phenyl)-2H-chromen-6-ol;
3-(4-Bromophenyl)-4-methyl-2-(4-((S)-2-((R)-3-methylpyrrolidin-1-yl)propoxy)phenyl)-2H-chromen-6-ol;
4-Methyl-2-(4-((S)-2-((R)-3-methylpyrrolidin-1-yl)propoxy)phenyl)-3-(o-tolyl)-2H-chromen-6-ol;
3-(4-Fluoro-3-hydroxyphenyl)-4-methyl-2-(4-((S)-2-((R)-3-methylpyrrolidin-1-yl)propoxy)phenyl)-2H-chromen-6-ol;
3-(4-Ethynylphenyl)-4-methyl-2-(4-((S)-2-((R)-3-methylpyrrolidin-1-yl)propoxy)phenyl)-2H-chromen-6-ol;
4-Methyl-2-(4-((S)-2-((R)-3-methylpyrrolidin-1-yl)propoxy)phenyl)-3-(4-(methylsulfonyl)phenyl)-2H-chromen-6-ol;
3-(2-Fluoro-3-hydroxyphenyl)-4-methyl-2-(4-((S)-2-((R)-3-methylpyrrolidin-1-yl)propoxy)phenyl)-2H-chromen-6-ol;
5-Fluoro-3-(3-hydroxyphenyl)-4-methyl-2-(4-((S)-2-((R)-3-methylpyrrolidin-1-yl)propoxy)phenyl)-2H-chromen-6-ol;
3-(2-Fluoro-5-hydroxyphenyl)-4-methyl-2-(4-((S)-2-((R)-3-methylpyrrolidin-1-yl)propoxy)phenyl)-2H-chromen-6-ol;
3-(4-Fluorophenyl)-4-methyl-2-(4-((S)-2-((R)-2-methylpyrrolidin-1-yl)propoxy)phenyl)-2H-chromen-6-ol;
2-(4-((S)-2-((R)-3-Fluoropyrrolidin-1-yl)propoxy)phenyl)-3-(3-hydroxyphenyl)-4-methyl-2H-chromen-6-ol;
3-(4-Hydroxyphenyl)-2-(4-((S)-2-((R)-3-methylpyrrolidin-1-yl)propoxy)phenyl)-4-(trifluoromethyl)-2H-chromen-6-ol;
3-(3-Hydroxyphenyl)-2-(4-((S)-2-((R)-3-methylpyrrolidin-1-yl)propoxy)phenyl)-4-(trifluoromethyl)-2H-chromen-6-ol;
3-(3-Hydroxy-4-(trifluoromethyl)phenyl)-4-methyl-2-(4-((S)-2-((R)-3-methylpyrrolidin-1-yl)propoxy)phenyl)-2H-chromen-6-ol; or
3-(4-Hydroxy-3-(trifluoromethyl)phenyl)-4-methyl-2-(4-((S)-2-((R)-3-methylpyrrolidin-1-yl)propoxy)phenyl)-2H-chromen-6-ol;
or a pharmaceutically acceptable salt thereof.

10. The method of claim 1, wherein the compound of Formula (VI) has the structure of Formula (IX):

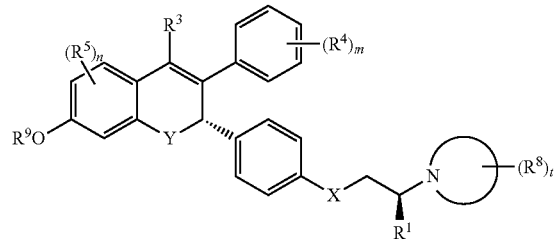

Formula (IX)

or a pharmaceutically acceptable salt thereof.

11. The method of claim 10, wherein:
$R^1$ is H or —CH$_3$;
$R^3$ is —CH$_3$;
$R^4$ is —OH;

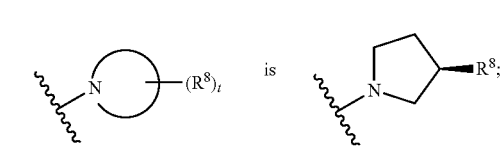

R[8] is —CH₃;
R[9] is H;
X is —O—;
Y is —O—;
n is 0;
m is 1.

12. The method of claim 6, wherein:
R[1] is H or —CH₃;
R[3] is —CH₃;
R[4] is —OH;

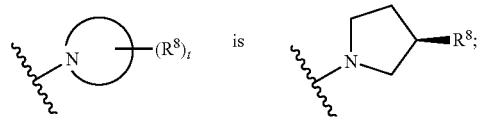

R[8] is —CH₃;
R[9] is H;
X is —O—;
Y is —O—;
n is 0;
m is 1.

13. The method of claim 1, wherein the compound of Formula (VI) has the following structure:

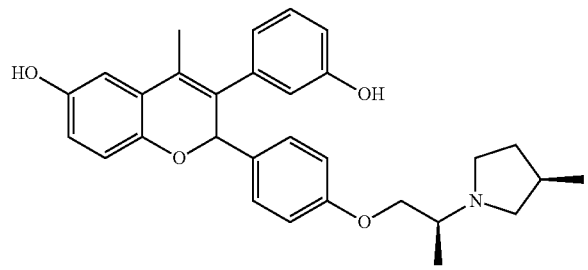 [SMILES: CC1=C(c2cccc(O)c2)C(c2ccc(OC[C@H](C)N3CC[C@@H](C)C3)cc2)Oc2ccc(O)cc21]

or a pharmaceutically acceptable salt thereof.

14. The method of claim 6, wherein the compound of Formula (VIII) has the following structure:

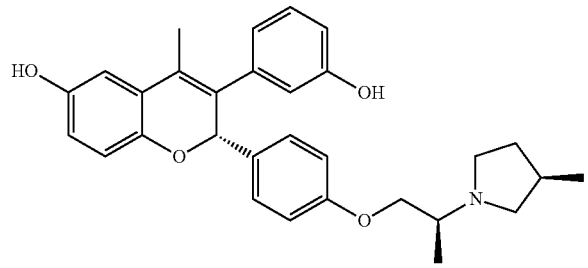

or a pharmaceutically acceptable salt thereof.

15. The method of claim 1, wherein the compound of Formula (VI) has the following structure:

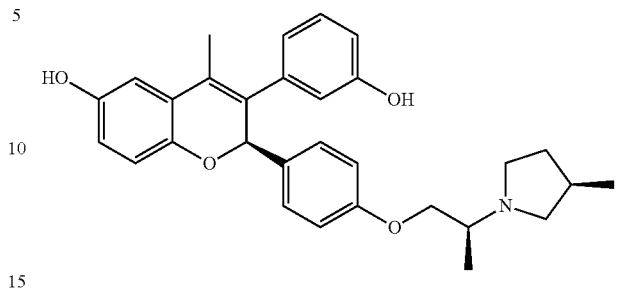

or a pharmaceutically acceptable salt thereof.

16. The method of claim 1, wherein the compound of Formula (VI) has the following structure:

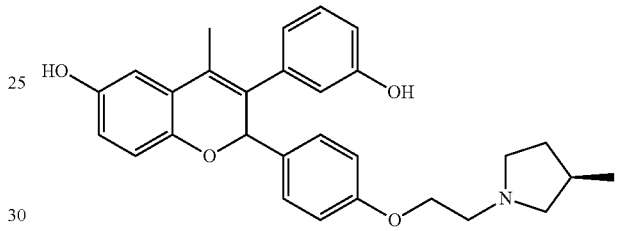

or a pharmaceutically acceptable salt thereof.

17. The method of claim 1, wherein the compound of Formula (VI) has the following structure:

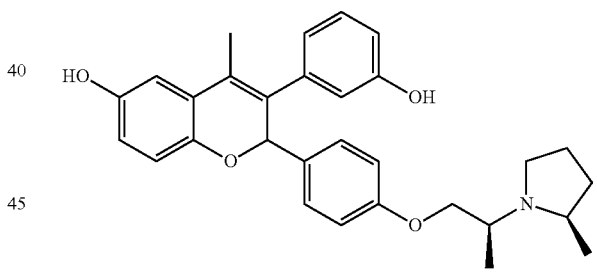

or a pharmaceutically acceptable salt thereof.

18. The method of claim 1, wherein the compound of Formula (VI) has the following structure:

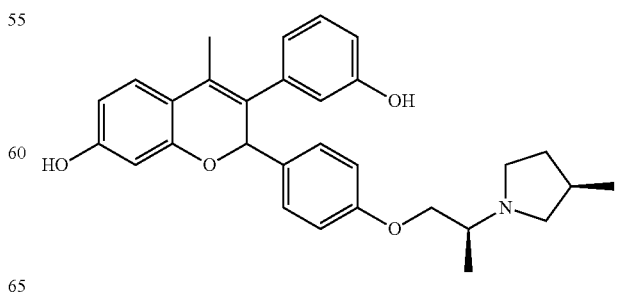

or a pharmaceutically acceptable salt thereof.

19. The method of claim 1, wherein the compound of Formula (VI) has the following structure:

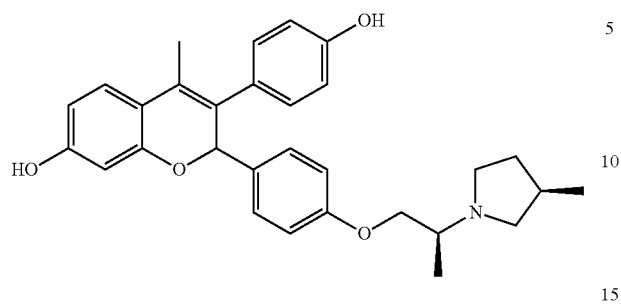

or a pharmaceutically acceptable salt thereof.

20. The method of claim 1, wherein the anti-hormonal treatment includes treatment with at least one agent selected from tamoxifen, fulvestrant, steroidal aromatase inhibitors, and non-steroidal aromatase inhibitors.

21. The method of claim 1 wherein the cancer is hormone receptor positive metastatic breast cancer.

22. The method of claim 21 wherein the compound of Formula (VI), or a pharmaceutically acceptable salt thereof is administered to a postmenopausal woman with disease progression following anti-estrogen therapy.

* * * * *